US008741573B2

(12) United States Patent
Sjoblom et al.

(10) Patent No.: US 8,741,573 B2
(45) Date of Patent: Jun. 3, 2014

(54) CONSENSUS CODING SEQUENCES OF HUMAN BREAST AND COLORECTAL CANCERS

(75) Inventors: Tobias Sjoblom, Baltimore, MD (US); Sian Jones, Baltimore, MD (US); D. Williams Parsons, Baltimore, MD (US); Laura D. Wood, Baltimore, MD (US); Jimmy Lin, Baltimore, MD (US); Thomas Barber, Baltimore, MD (US); Diana Mandelker, Baltimore, MD (US); Bert Vogelstein, Baltimore, MD (US); Kenneth W. Kinzler, Baltimore, MD (US); Victor E. Velculesu, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1371 days.

(21) Appl. No.: 12/377,073

(22) PCT Filed: Aug. 13, 2007

(86) PCT No.: PCT/US2007/017866
§ 371 (c)(1),
(2), (4) Date: Jul. 12, 2010

(87) PCT Pub. No.: WO2008/021288
PCT Pub. Date: Feb. 21, 2008

(65) Prior Publication Data
US 2010/0316995 A1 Dec. 16, 2010

Related U.S. Application Data

(60) Provisional application No. 60/836,944, filed on Aug. 11, 2006, provisional application No. 60/842,363, filed on Sep. 6, 2006.

(51) Int. Cl.
*C12Q 1/68* (2006.01)
*G01N 33/53* (2006.01)

(52) U.S. Cl.
USPC .......... 435/6.14; 435/6.11; 435/6.12; 435/7.1

(58) Field of Classification Search
None
See application file for complete search history.

(56) References Cited

U.S. PATENT DOCUMENTS

| 5,605,799 | A | 2/1997 | White |
| 2001/0021502 | A1 | 9/2001 | Swift et al. |

FOREIGN PATENT DOCUMENTS

| EP | 0 785 216 A1 | 7/1997 |
| WO | 92/13103 A1 | 8/1992 |
| WO | 00/42436 A1 | 7/2000 |
| WO | 01/42504 | 6/2001 |
| WO | 2004/082458 | 9/2004 |
| WO | 2005/113824 A2 | 12/2005 |

OTHER PUBLICATIONS

Strausberg et al, in Microarrays and Cancer Research, 2002, Warrington et al (eds.), Eaton Publishing, Westborough, MA, pp. xi-xvi.*
Notterman et al, in Microarrays and Cancer Research, 2002, Warrington et al (eds.), Eaton Publishing, Westborough, MA, pp. 81-111.*
Sjoblom et. al. "The Consensus Coding Sequences of Human Breast and Colorectal Cancers," Science, vol. 314, Oct. 13, 2006, pp. 268-274.
Wu, et al., "Somatic Mutation and Gain of Copy Number of PIK3CA in Human Breast Cancer," Breast Cancer Research, vol. 7 No. 5, pp. 609-613.
Lin, et. al., "Discovery of Estrogen Receptor Alpha Target Genes and Response Elements in Breast Tumor Cells," Genome Biology 2004, vol. 5, Issue 9, Article R66, Aug. 12, 2004, 18 pages.
Steinbach, et. al., "ABCA3 as a Possible Cause of Drug Resistance in Childhood Acute Myeloid Leukemia," Clinical Cancer Research, vol. 12, No. 14, Jul. 15, 2006, pp. 4357-4663.
Hirshman-Jax, et. al., "A Distinct Side Population of Cells with High Drug Efflux Capacity in Human Tumor Cells," Proceedings of the National Academy of Sciences of USA, National Academy of Science, Washington, DC, vol. 101, No. 39, Sep. 28, 2004, pp. 14228-14233.
Wajapeyee, et. al., "Pharmacogenomics in Breast Cancer: Current Trends and Future Directions," Current Opinion in Molecular Therapeutics, Jun. 2004, vol. 6, No. 3, pp. 296-601.
Pusztai, et. al., "Development of Pharmacogenomic Markers to Select Preoperative Chemotherapy for Breast Cancer," Breast Cancer (Tokyo, Japan) 2005, vol. 12, No. 2, pp. 73-85.
Van Putten, "Of Tumours in Mice and Men the Different Roles of Somatic Mutation in Treatment Failure," European Journal of Cancer and Clinical Oncology, Oxford, GB, vol. 22, No. 2, Jul. 1, 1986, pp. 753-755.
Forbes, et. al., "COSMIC 2005," British Journal of Cancer, vol. 94, No. 2, Jan. 2006, pp. 318-322.

(Continued)

Primary Examiner — James Martinell
(74) Attorney, Agent, or Firm — Banner & Witcoff, Ltd.

(57) ABSTRACT

Analysis of 13,023 genes in 11 breast and 11 colorectal cancers revealed that individual tumors accumulate an average of ~90 mutant genes but that only a subset of these contribute to the neoplastic process. Using stringent criteria to delineate this subset, we identified 189 genes (average of 11 per tumor) that were mutated at significant frequency. The vast majority of these genes were not known to be genetically altered in tumors and are predicted to affect a wide range of cellular functions, including transcription, adhesion, and invasion. These data define the genetic landscape of two human cancer types, provide new targets for diagnostic and therapeutic intervention and monitoring.

26 Claims, 36 Drawing Sheets

(56) References Cited

OTHER PUBLICATIONS

Bamford, et. al., "The COSMIC (Catalog of Somatic Mutations in Cancer) Database and Website," British Journal of Cancer, vol. 91, No. 2, Jul. 19, 2004, pp. 355-358.
Merajver, et. al., "Somatic Mutations in the BRCA1 Gene in Sporadic Ovarian Tumours," Nature Genetics, Nature Publishing Group, New York, US, vol. 9, No. 4, Apr. 1, 1995, pp. 439-443.
Gillet, et. al., "Macroarray-based Detection of Multidrug Resistance in Human Tumor Cells by Expression Profiling of ATP-binding Cassette Transporter Genes," Cancer Research, American Association for Cancer Research, Baltimore, MD, US, vol. 64, Dec. 15, 2004, pp. 8987-8993.
Extended European Search Report dated Mar. 23, 2010 in Application No. 07811279.4.
Partial European Search Report issued in related European Application No. 12176467.4, dated Nov. 29, 2012.
Bardelli et al., "Mutational analysis of gene families in human cancer," Current Opinion in Genetics & Development, Current Biology Ltd, XX, vol. 15, No. 1, Feb. 1, 2005, pp. 5-12.
Benvenuti et al., "Identification of cancer genes by mutational profiling of tumor genomes," Febs Letters, Elsevier, Amsterdam, NL, vol. 579, No. 8, Mar. 21, 2005, pp. 1884-1890.
Fang et al., "The MAPK signalling pathways and colorectal cancer," Lancet Oncology, Lancet Publishing Group, London, GB, vol. 6, No. 5, May 1, 2005, pp. 322-327.
Kim et al., "Absence of FES exon 16 and 17 mutation in the colorectal carcinomas in Korean patients," Digestive and Liver Disease, W.B., Saunders, GB, vol. 38, No. 3, Mar. 1, 2006, pp. 213-214.
Soung et al., "Kinase domain mutation of MLK4 gene is uncommon in gastric and hepatocellular carcinomas," Digestive and Liver Disease, W.B., Saunders, GB, vol. 38, No. 4, Apr. 1, 2006, p. 283.
Hafner et al., "Differential gene expression of Eph receptors and ephrins in benign human tissues and cancers," Clinical Chemistry, American Associate for Clinical Chemistry, Washington, DC, vol. 50, No. 3, Mar. 1, 2004, pp. 490-499.
Lin et al., "A multidimensional analysis of genes mutated in rbeast and colorectal cancers," Genome Research, vol. 17, No. 9, Jul. 25, 2007, pp. 1304-1318.
Higinbotham et al., "Activating Point Mutation in Ki-ras Codon 63 in a Chemically Induced Rat Renal Tumor," Molecular Carcinogenesis, 5:136-139, (1992).
Orita et al., "A Novel Point Mutation at Codon 146 of the K-ras Gene in a Human Colorectal Cancer Identified by the Polymerase Chain Reaction," Virus Genes, 5:1, 75-79, 1991.
Stanely, "Molecular aspects of chemical carcinogenes: The roles of oncogenes and tumour suppressor genes," Toxicology, 96:173-194, (1995).
Pauly et al., "Ki-ras Oncogene and p53 Tumour Suppressor Gene Mutations in Colorectal Carcinomas from the European Saar-Luxembourg Region are Less Frequent than Predicted by the Classic Adenoma-Carcinoma Sequence Model," European Journal of Cancer, vol. 33, No. 13, pp. 2265-2272, 1997.
Castagnola et al., "Mutant KRAS, chromosomal instability and prognosis in colorectal cancer," Biochimica et Biophysica Acta, 1756:115-125, (2005).
Allen et al., "The role of molecular markers in the adjuvant treatment of colorectal cancer," European Journal of Cancer. Supplement, Pergamon, Oxfor, GB, vol. 3, No. 3, Oct. 1, 2005.
Conlin et al., "The prognostic significance of K-ras, p53, and APC mutations in colorectal carcinoma," Gut, 54:1283-1286, 2005.
Edkins et al, "Recurrent KRAS Codon 146 Mutations in Human Colorectal Cancer," Cancer Biology & Therapy, 5:8, pp. 928-936, Aug. 2006.
Extended European Search Report issued in related European Application No. 12176466.6, dated Dec. 11, 2012.
Stephens et al. A screen of the complete protein kinase family identifies diverse patterns of somatic mutations in human breast cancer. Nature Genetics. Jun. 2005, vol. 37, No. 6, pp. 590-592, see entire reference particularly p. 590, right column, and Supplementary Table 1.

\* cited by examiner

Fig. 5. Table 1. Summary of somatic mutations*

| Screen | Tumor | Number of mutated genes | Number of mutations | Nonsynonymous mutations in coding sequences ||||| Mutations in non-coding sequences ||| Nucleotides successfully analyzed (Mb)° | Mutation frequency (mutations/Mb) |
|---|---|---|---|---|---|---|---|---|---|---|---|---|
| | | | | Mis-sense | Non-sense | Insertion | Deletion | Duplication | Splice site† | UTR‡ | | |
| Discovery Screen§ | Colon | 519 | 574 | 482 (84.0) | 35 (6.1) | 3 (0.5) | 18 (3.1) | 17 (3.0) | 17 (3.0) | 2 (0.3) | 208.5 | 2.8 |
| | Breast | 673 | 733 | 600 (81.9) | 39 (5.3) | 3 (0.4) | 48 (6.5) | 2 (0.3) | 37 (5.0) | 4 (0.5) | 209.2 | 3.5 |
| | Total | 1149 | 1307 | 1082 (82.8) | 74 (5.7) | 6 (0.5) | 66 (5.0) | 19 (1.5) | 54 (4.1) | 6 (0.5) | 417.7 | 3.1 |
| Prevalence Screen# | Colon | 105 | 177 | 126 (71.2) | 26 (14.7) | 2 (1.1) | 10 (5.6) | 3 (1.7) | 9 (5.1) | 1 (0.6) | 28.7 | 6.2 |
| | Breast | 137 | 188 | 145 (77.1) | 8 (4.3) | 2 (1.1) | 13 (6.9) | 12 (6.4) | 8 (4.3) | 0 (0.0) | 34.3 | 5.5 |
| | Total | 236 | 365 | 271 (74.2) | 34 (9.3) | 4 (1.1) | 23 (6.3) | 15 (4.1) | 17 (4.7) | 1 (0.3) | 63.0 | 5.8 |
| Both screens combined | Colon | 519 | 751 | 608 (81.0) | 61 (8.1) | 5 (0.7) | 28 (3.7) | 20 (2.7) | 26 (3.5) | 3 (0.4) | 237.2 | 3.2 |
| | Breast | 673 | 921 | 745 (80.9) | 47 (5.1) | 5 (0.5) | 61 (6.6) | 14 (1.5) | 45 (4.9) | 4 (0.4) | 243.5 | 3.8 |
| | Total | 1149 | 1672 | 1353 (80.9) | 108 (6.5) | 10 (0.6) | 89 (5.3) | 34 (2.0) | 71 (4.2) | 7 (0.4) | 480.7 | 3.5 |

*Numbers in parentheses refer to percentage of total mutations. §Coding and adjacent non-coding regions of 13,023 CCDS genes were sequenced in 11 colorectal and 11 breast cancers. #Genes mutated in the discovery screen were sequenced in 24 additional tumor samples of the affected tumor type. †Intronic mutations within 4 bp of exon/intron boundary. ‡Mutations in untranslated regions (UTR) within 4 bp 5' of initiation codon or 4 bp 3' of termination codon. °Nucleotides with Phred quality score of at least 20.

Table 2. Spectrum of single base substitutions*

| Screen | Tumor | Total number of substitutions | Substitutions at C:G base pairs | | | | | | Substitutions at T:A base pairs | | | | | | Substitutions at specific dinucleotides[‡] | | | |
|---|---|---|---|---|---|---|---|---|---|---|---|---|---|---|---|---|---|---|
| | | | C:G→T:A | | C:G→G:C | | C:G→A:T | | T:A→C:G | | T:A→G:C | | T:A→A:T | | 5'-CpG-3' | | 5'-TpC-3' | |
| Discovery Screen | Colon | 535 | 325 | (60.7) | 36 | (6.7) | 70 | (13.1) | 42 | (7.9) | 38 | (7.1) | 24 | (4.5) | 254 | (47.5) | 54 | (10.1) |
| | Breast | 678 | 230 | (33.9) | 207 | (30.5) | 110 | (16.2) | 54 | (8.0) | 30 | (4.4) | 47 | (6.9) | 115 | (17.0) | 235 | (34.7) |
| | Total | 1213 | 555 | (45.8) | 243 | (20.0) | 180 | (14.8) | 96 | (7.9) | 68 | (5.6) | 71 | (5.9) | 369 | (30.4) | 289 | (23.8) |
| Prevalence Screen | Colon | 161 | 88 | (54.7) | 12 | (7.5) | 23 | (14.3) | 14 | (8.7) | 13 | (8.1) | 11 | (6.8) | 55 | (34.2) | 25 | (15.5) |
| | Breast | 160 | 59 | (36.9) | 32 | (20.0) | 38 | (23.8) | 18 | (11.3) | 5 | (3.1) | 8 | (5.0) | 24 | (15.0) | 22 | (13.8) |
| | Total | 321 | 147 | (45.8) | 44 | (13.7) | 61 | (19.0) | 32 | (10.0) | 18 | (5.6) | 19 | (5.9) | 79 | (24.6) | 47 | (14.6) |
| Both screens combined | Colon | 696 | 413[§] | (59.3) | 48[§] | (6.9) | 93 | (13.4) | 56 | (8.0) | 51 | (7.3) | 35 | (5.0) | 309[§] | (44.4) | 79[§] | (11.4) |
| | Breast | 838 | 289[§] | (34.5) | 239[§] | (28.5) | 148 | (17.7) | 72 | (8.6) | 35 | (4.2) | 55 | (6.6) | 139[§] | (16.6) | 257[§] | (30.7) |
| | Total | 1534 | 702 | (45.8) | 287 | (18.7) | 241 | (15.7) | 128 | (8.3) | 86 | (5.6) | 90 | (5.9) | 448 | (29.2) | 336 | (21.9) |

*Base substitutions in coding sequences resulting in nonsynonymous changes as well as substitutions in non-coding sequences are included (see Table 1). Numbers in parentheses indicate percentage of total mutations. [§] indicates that the values in this category were significantly different between breast and colorectal cancers (P <0.0001). [‡]Includes substitutions at the C or G of the 5'-CpG-3' dinucleotide, the C of the 5'-TpC-3' dinucleotide, or the G of the 5'-GpA-3' dinucleotide.

Fig. 6

Table 3. Functional classification of CAN-genes*

| Breast cancers | | | | | | Colorectal cancers | | | | | |
|---|---|---|---|---|---|---|---|---|---|---|---|
| CAN-genes and CaMP scores | | | | | | CAN-genes and CaMP scores | | | | | |
| Cellular adhesion and motility | | | | | | | | | | | |
| (examples: cytoskeletal protein binding GO:0008092, cell adhesion GO:0007155, metallopeptidase activity GO:0008237) | | | | | | | | | | | |
| FLNB | 3.4 | TMPRSS6 | 2.0 | RAPH1 | 1.4 | PKHD1 | 3.5 | CNTN4 | 1.6 | | |
| MYH1 | 2.7 | COL11A1 | 1.8 | PCDHB15 | 1.4 | ADAMTSL3 | 3.3 | CHL1 | 1.3 | | |
| SPTAN1 | 2.6 | DNAH9 | 1.7 | CMYA1 | 1.4 | OBSCN | 3.0 | HAPLN1 | 1.2 | | |
| DBN1 | 2.5 | OBSCN | 1.7 | MACF1 | 1.3 | ADAMTS18 | 2.7 | MGC33407 | 1.2 | | |
| TECTA | 2.4 | COL7A1 | 1.5 | SYNE2 | 1.3 | MMP2 | 2.3 | MAP2 | 1.0 | | |
| ADAM12 | 2.3 | MAGEE1 | 1.5 | NRCAM | 1.1 | TLL3 | 2.2 | | | | |
| GSN | 2.2 | CDH10 | 1.5C | OL19A1 | 1.1 | EVL | 2.0 | | | | |
| CDH20 | 2.2 | SULF2 | 1.5 | SEMA5B | 1.1 | ADAM29 | 2.0 | | | | |
| BGN | 2.1 | CNTN6 | 1.4 | ITGA9 | 1.1 | CSMD3 | 1.9 | | | | |
| ICAM5 | 2.1 | THBS3 | 1.4 | | | ADAMTS15 | 1.8 | | | | |
| Signal transduction | | | | | | | | | | | |
| (examples: intracellular signaling cascade GO:0007242, receptor activity GO:0004872, GTPase regulator GO:0030695) | | | | | | | | | | | |
| VEPH1 | 2.1 | PFC | 1.5 | PRPF4B | 1.3 | APC | >10 | PTPRD | 2.2 | | |
| SBNO1 | 2.1 | GAB1 | 1.5 | CENTG1 | 1.3 | KRAS | >10 | MCP | 2.1 | | |
| DNASE1L3 | 1.8 | ARHGEF4 | 1.4 | MAP3K6 | 1.3 | EPHA3 | 4.2 | NF1 | 1.9 | | |
| RAP1GA1 | 1.8 | NALP8 | 1.4 | APC2 | 1.3 | GUCY1A2 | 3.5 | PTPRU | 1.4 | | |
| EGFL6 | 1.8 | RGL1 | 1.4 | STARD8 | 1.2 | EPHB6 | 3.5 | CD109 | 1.3 | | |
| AMFR | 1.7 | PPM1E | 1.4 | PTPN14 | 1.1 | TGFBR2 | 2.9 | PHIP1.2 | | | |
| CENTB1 | 1.7 | PKDREJ | 1.4 | IRTA2 | 1.1 | GNAS | 2.8 | | | | |
| GPNMB | 1.7 | CNNM4 | 1.3 | RASGRF2 | 1.1 | RET | 2.3 | | | | |
| INHBE | 1.7 | ALS2CL | 1.3 | MTMR3 | 1.1 | P2RY14 | 2.2 | | | | |
| FLJ10458 | 1.6 | RASAL2 | 1.3 | | | LGR6 | 2.2 | | | | |
| Transcriptional regulation | | | | | | | | | | | |
| (examples: regulation of transcription GO:0045449, zinc finger C2H2-subtype IPR007085) | | | | | | | | | | | |
| TP53 | >10 | CHD5 | 1.8 | ZFP64 | 1.4 | TP53 | >10 | ZNF442 | 1.9 | | |
| FLJ13479 | 3.4 | CIC | 1.7 | ZNF569 | 1.4 | SMAD4 | 4.8 | SMAD3 | 1.9 | | |
| SIX4 | 2.5 | KEAP1 | 1.6 | EHMT1 | 1.3 | MLL3 | 3.7 | EYA4 | 1.5 | | |
| KIAA0934 | 2.5 | HOXA3 | 1.6 | ZFYVE26 | 1.2 | TBX22 | 3.3 | PKNOX1 | 1.4 | | |
| LRRFIP1 | 2.4 | TCF1 | 1.6 | BCL11A | 1.1 | SMAD2 | 3.1 | MKRN3 | 1.3 | | |
| GLI1 | 2.3 | HDAC4 | 1.6 | ZNF318 | 1.1 | TCF7L2 | 2.8 | | | | |
| RFX2 | 2.1 | MYOD1 | 1.5 | | | HIST1H1B | 2.5 | | | | |
| ZCSL3 | 1.8 | NCOA6 | 1.5 | | | RUNX1T1 | 2.4 | | | | |
| Transport | | | | | | | | | | | |
| (examples: ion transporter activity GO:0015075, ligand-gated ion channel activity GO:0015276, carrier activity GO:0005386) | | | | | | | | | | | |
| ATP8B1 | 3.1 | ABCB8 | 1.7 | ABCB10 | 1.4 | ABCA1 | 2.8 | C6orf29 | 1.1 | | |
| CUBN | 2.5 | KPNA5 | 1.7 | SCNN1B | 1.3 | SLC29A1 | 1.9 | | | | |
| GRIN2D | 2.4 | ABCA3 | 1.7 | NUP133 | 1.1 | SCN3B | 1.9 | | | | |
| HDLBP | 2.2 | SLC9A2 | 1.6 | | | P2RX7 | 1.3 | | | | |
| NUP214 | 1.8 | SLC6A3 | 1.5 | | | KCNQ5 | 1.2 | | | | |
| Cellular metabolism | | | | | | | | | | | |
| (examples: aromatic compound metabolism GO:0006725, generation of precursor metabolites GO:0016445, biosynthesis GO:0009058) | | | | | | | | | | | |
| ACADM | 2.0 | NCB5OR | 1.7 | PHACS | 1.4 | UQCRC2 | 1.9 | | | | |
| PRPS1 | 1.8 | ASL | 1.6 | XDH | 1.3 | ACSL5 | 1.6 | | | | |
| CYP1A1 | 1.7 | GALNT5 | 1.4 | | | GALNS | 1.2 | | | | |
| Intracellular trafficking | | | | | | | | | | | |
| (examples: endoplasmic reticulum targeting sequence IPR000886, membrane fusion GO:0006944) | | | | | | | | | | | |
| OTOF | 2.2 | PLEKHA8 | 1.8 | KTN1 | 1.5 | SYNE1 | 2.3 | PRKD1 | 1.9 | | |
| LRBA | 2.1 | LOC283849 | 1.7 | GGA1 | 1.4 | SEC8L1 | 2.2 | LRP2 | 1.2 | | |
| AEGP | 1.8 | SORL1 | 1.7 | | | SDBCAG84 | 2.2 | | | | |
| RNA metabolism | | | | | | | | | | | |
| (examples: RNA processing GO:0006353, RNA splice site selection GO:0006376) | | | | | | | | | | | |
| C14orf155 | 3.3 | RNU3IP2 | 1.7 | KIAA0427 | 1.5 | SFRS5 | 1.3 | | | | |
| SP110 | 1.8 | C22orf19 | 1.5 | DDX10 | 1.3 | | | | | | |
| Other | | | | | | | | | | | |
| (examples: response to DNA damage stimulus GO:0006974, protein ubiquitination GO:0016567) | | | | | | | | | | | |
| FLJ40869 | 2.1 | SERPINB1 | 1.4 | | | FBXW7 | 5.1 | K6IRS3 | 1.2 | | |
| BRCA1 | 2.0 | | | | | UHRF2 | 1.5 | CD248 | 1.2 | | |
| MRE11A | 1.8 | | | | | LMO7 | 1.3 | ERCC6 | 1.0 | | |
| Unknown | | | | | | | | | | | |
| KIAA1632 | 2.4 | KIAA0999 | 1.3 | | | C10orf137 | 2.7 | KIAA1409 | 1.6 | | |
| MGC24047 | 2.1 | | | | | LOC157697 | 2.0 | C15orf2 | 1.0 | | |

*CAN-genes were assigned to functional classes using Gene Ontology (GO) groups, INTERPRO domains and available literature. Representative GO groups and INTERPRO domains are listed for each class.

Fig. 7

Fig. 8
Table S1. Primers used for PCR amplification and sequencing*

| CCDS accession | Gene | Coding exon | | Forward primer | | Reverse primer | |
|---|---|---|---|---|---|---|---|
| | | Number | Genomic position | Relative position[b] | Sequence[d] | Relative position[c] | Sequence[d] |
| CCDS1.1 | FLJ22639 | 1 | chr1:801942-802434 | -89 | M13-GCCCTTCCACCCTAGTTCTTC | +77 | CCCACTACTGCTTGCTCAGG[e] |
| | | | | 254 | M13-CTGTTGGGTGTCTACCCTGCC | +60 | TTGGGAATTAGGCTTCTGCTG |
| CCDS2.1 | SAMD11 | 1 | chr1:914632-914963 | -75 | M13-GTGCCTGGAGAAACCTCTCAC | +59 | GCCTCAGCAACAGGAATGG |
| | | 2 | chr1:916666-916629 | -85 | CACCTCAGTGTTCTACGCCAG | +88 | M13-AGAAGCTGAACACAGTGCTTGG |
| | | 3 | chr1:917656-917774 | -183 | CGCCGCCGAGATTAATTG | +74 | M13-CCCCTACCCGGTCCGTCTC |
| | | 4 | chr1:917632-918011 | -84 | M13-GAGACGGACCGGGTAGGG | +192 | GGTTCAGCACCAGCAGGG[e] |
| | | 5 | chr1:918081-918581 | -93 | CTGCGGAAGCAGAACCTG | 486 | M13-GCCCACCTGTGTGGAAGTAG |
| | | | | 305 | CACAAGATGGCTCGGAAGAC | +121 | M13-CTCCTGACCGTCGTGTGC |
| | | 6 | chr1:918775-918900 | -177 | M13-CTAGATCCTTCCAGAAGGGCAC | +51 | CCATCCTTTCCAGGGAGGTAG |
| | | 7 | chr1:919220-919331 | -134 | M13-CCTGACACTCAAACCCAACAG | +199 | GACAAGGGCTGCTCTCCTG |
| | | 8 | chr1:919430-919676 | -88 | GAGTGAGGTCAGGGTCTCCAG | +71 | M13-ACCGAAAGAAATAAAGCGGTG |
| CCDS3.1 | DKFZP564C186 | 1 | chr1:934737-934763 | -131 | GAGAACCATAGAGCCACTCGG | +159 | M13-AAAGCCCGAAGCTAGGAACTC[e] |
| | | 2 | chr1:934451-934604 | -97 | M13-GTGGGTGTCTGTATCCAAGGG | +176 | CCTGCCTAGGACAGAGTTTGG |
| | | 3 | chr1:932821-932796 | -88 | M13-TGAAGGGAGTAGACTGACCCTG | +58 | CTTCCTGCACAGAAAGGCTG[e] |
| | | 4 | chr1:932416-932548 | -128 | CGACAGCTCTGAGGAGGAAGAG | +188 | M13-TTGTCCACTTGCGCTGAAGAAG |
| | | 5 | chr1:931617-931738 | -120 | M13-CCAACCTCTGCCCTATGTCTG | +52 | AAAGGGCTGGATGTACTCACG |
| | | 6 | chr1:931445-931536 | -121 | M13-AGTGCTGAGGCCAACAAATTC | +78 | TTGCCATGTCTCTGTCCTAGC |
| | | 7 | chr1:929535-929605 | -102 | AGTCGTAGAGGCTATGCTGGC | +114 | M13-GTCTCCCACAGACAGGACACC |
| | | 8 | chr1:929304-929415 | -123 | M13-TCGGCCATACAGGTGCTATTC | +164 | GACTGCCTGAGACAGAAACCC |
| | | 9 | chr1:928697-928611 | -123 | AGGTGCTTTGGGAAGAGCTG | +141 | M13-AGGTGCTCTGTGAGACATTCG |
| | | 10 | chr1:927634-928123 | -89 | M13-AAGGCCCAGGTGTTCACAG | +147 | GTCTCAACCCATCCACCCTTC[e] |
| | | 11 | chr1:927522-927662 | -90 | AGGAAATGATTCCTGTGCCG | +157 | M13-TCCAGAATCCAGAGCATCTCC |
| | | 12 | chr1:926649-926761 | -124 | M13-ACGTGCCTTGTCCTGCTTTAG | +113 | GTGACACCCGTGACAAGGAG |
| | | 13 | chr1:924012-924128 | -169 | TATCTCTTGTTTCGGGTTGGG | +85 | M13-GTCCATGCTTGAACTTGGAGG |
| | | 14 | chr1:923653-923755 | -158 | M13-ATGGACCTTCATGGTCTCCC | +70 | ACAAGGCACCTCCTACCAG |
| | | 15 | chr1:921824-922068 | -150 | M13-CAACAGCTATGCACTTGAGCC | +116 | GTCAGCTTCTCCCAGGCTTC |
| | | 16 | chr1:921605-921609 | -130 | GAGCAGCAGGCAGTGGTTAG | +83 | M13-CGCCCTGGTCTCAAGTCATAG[e] |
| | | 17 | chr1:921040-921178 | -161 | AACTTGCACCATGGCTTTGTG | +54 | M13-CTCGTGGCTGTGGGAAGTC |
| | | 18 | chr1:920579-920669 | -197 | M13-AGTGAAGGCCTACTGGGATTG | +122 | TGCCAGAGAACAGAGCATTTC[e] |
| | | 19 | chr1:920218-920323 | -137 | M13-GCCAAATGCTCTGTTCTCTGG | +109 | AAGCCTGTGCCGTGTCTACTG |
| CCDS4.1 | DKFZP434H2010 | 1 | chr1:941978-942061 | -136 | M13-CTCTTCCAGAAAGGCTCCACC | +155 | TAGTGGAAGAGCTTGTTGGCG |
| | | 2 | chr1:942160-942250 | -200 | M13-AGACTTGCCGACCTGTACGAC | +70 | GGAAGACCCTGAGCTGCAC |
| | | 3 | chr1:945723-945870 | -80 | GTCCTGTAGCTGTGTGGATGC | +94 | M13-GTAGCAGTCGCTGCACATCCTG |
| | | 4 | chr1:945967-946048 | -145 | M13-AAAGTTGTGCATTACGCCAAG | +141 | AACACCTGTGATCTGGAAGGC |
| | | 5 | chr1:946132-946205 | -154 | M13-CTGCTACCTGGACGCTATTCCC | +75 | ACACATACACACAGGTGCTCC |
| | | 6 | chr1:946325-946453 | -85 | CCTGACCCAGGACTTGGAG | +155 | M13-CTCGAGGCACAGACAGCAC |
| | | 7 | chr1:946559-946655 | -174 | TTTACCACCTGGAGAAGCAGAC | +76 | M13-CAGCGCGATGAGGGAACTG |
| | | 8 | chr1:946770-946851 | -185 | M13-GCAGTGCTGTCTGTGCCTC | +88 | CGAAATACAGGTTCCTCCTGC |
| | | 9 | chr1:947521-947597 | -112 | M13-CCAGCTCTCCAAGTACCCAG | +171 | TGACCGTAGTCCTCGTAGCTG |
| | | 10 | chr1:947734-947871 | -73 | GACGCCCGACTCTTTAGTGG | +139 | M13-ACGTCGGTCAGGCTGATCTC |
| | | 11 | chr1:948307-948457 | -118 | M13-GCGACAGAATAAGACTTCGTCC | +103 | AACTCTCTGAGGCTGCAAGG |
| | | 12 | chr1:948832-948773 | -92 | M13-AACTCAGACTGGAGGGAGCC | +116 | GCTAGAAACAGGCTAGGCCAC |
| | | 13 | chr1:948946-949087 | -99 | M13-CAGTTGTCCTGGAGCCACC | +89 | CTGAACAGACCTCAGGCTTGG |
| | | 14 | chr1:949278-949498 | -92 | M13-CAAGCCTGAGGTCTGTTCAGG | +84 | TCCCTCAGAGTCCCAAGAGG |
| | | 15 | chr1:949762-949811 | -126 | M13-CAGCTTGTGAGTAGCAGCC | +54 | M13-GGTACGGAAGGCAGAGATGTG |
| | | 16 | chr1:949888-950022 | -89 | M13-TGCCTCTGACAGGTGAGTAAGG | +78 | TGGGTTCAGACCCTGACTTG |
| CCDS5.1 | HES4 | 1 | chr1:974312-974420 | -167 | AGGCCTTAAATAGGGAAACGG | +76 | M13-ATGACCGCCTTGGAGGAC |
| | | 3 | chr1:974972-975050 | -145 | M13-CCGACCGCGTATTAACGAG | +84 | GACAGAGGAGGAGAGAGGTCGG |
| | | 4 | chr1:974505-974679 | -142 | GAGATGACCGTGAGACACCTG | +54 | M13-TCTGCTACAGTCTCGGCAAAG |
| CCDS6.1 | G1P2 | 1 | chr1:989020-989023 | -110 | M13-CTTATAATAGGGCCGGTGCTG | +182 | CTCCCTTTACCTGCTAGGGTG |
| | | 2 | chr1:989430-989923 | -224 | ACCCTAGCAGGTAAAGGGAGG | 351 | M13-GTCAGCCAGAACAGGTCGTC |
| | | | | 63 | ATGTCGGTGTCAGAGCTGAAG | +51 | M13-GAGGCGGCCATTTCTCTTTAC |
| CCDS7.1 | FLJ20584 | 1 | chr1:1062441-1062481 | -126 | M13-CTCGCTTTCATATTTCCGTCC | +200 | TACGCCCTTTAGAGATGTGG |
| | | 2 | chr1:1001180-1001315 | -110 | TCAGGCATGTTCAGAGAGCAG | +84 | M13-ACTCCAGTCTCAGGCCCATC |
| | | 3 | chr1:1059783-1059809 | -207 | M13-GAATGTGGCAGGACCGAG | +59 | CAGAGTGAGGACTCGGGATG |
| | | 4 | chr1:1059217-1059566 | -33 | CGAGTCCTCACTCTGCCTTTC | -126 | M13-CACTGAGCCTGTGTCTGG |
| | | | | 213 | TCTGGATCTCAGCTGGATTTG | +151 | M13-CTTGATGGGAGAACGGTCTGTC |
| | | 6 | chr1:1056195-1058200 | -138 | M13-CCCACCTGGTCAGAGTAAACAG | +62 | CAACACTTTGTGCTCGTTCCC |
| CCDS8.1 | FLJ38119 | 1 | chr1:1155356-1155643 | -69 | M13-AGTGGGCAGCTCCCGTAG | +135 | AGTAGGAGCTGATGCTGGGAG |
| | | 2 | chr1:1155785-1155904 | -118 | M13-TGGTCCCACTGAATACCCAC | +149 | GAGGAGCTTGTTGTTGGGAAG |
| | | 3 | chr1:1156033-1156163 | -74 | M13-CACAGGGCAGGTTGGAGG | +231 | TAAAGGACAGGTGGAAGGTGG |
| | | 4 | chr1:1157043-1157118 | -121 | M13-TCCTTCCACCCACAACTCACAG | +112 | TGGCTGAACCTCTGACTCTAGC |
| | | 5 | chr1:1157053-1157746 | -76 | M13-ACAGGCTGGGCCTCAAAC | +117 | CTTCCTGACCACCTCGTCTC |
| | | 6 | chr1:1158178-1158350 | -124 | AGGGCCAAGGTTGGAATG | +52 | M13-GCTGACTGCACCAGTGGG |
| | | 7 | chr1:1160222-1160394 | -125 | M13-GAGGTCACACCTGGGACAGAG | +119 | TACTTCCAGGCGTGAGACACC |
| | | 8 | chr1:1160271-1160445 | -30 | AGCCAGTCTCCAGGCACC | +79 | M13-CACACGGTCAGGTCACACTTC |
| CCDS9.1 | TNFRSF18 | 1 | chr1:1181687-1181874 | -127 | M13-CTCCTCACACGCACTTCACC | +83 | CCTTCCTTAGACCTCACCAACG |
| | | 2 | chr1:1180672-1180795 | -99 | M13-GAGAACGGACAACCTCACTCC | +177 | GAGAAAGCAGGGACAGGACAC |
| | | 3 | chr1:1179701-1179789 | -114 | TTCTACTCAGCACCCAGACCC | +154 | M13-AACTGGGTGCAGCTGGAATAC |
| | | 4 | chr1:1178693-1179263 | -124 | AGCTTGGACTGCACATCTGG | +82 | M13-AGCATGCATCCACTCAGGTC |
| CCDS10.1 | TNFRSF18 | 4 | chr1:1179336-1179539 | -112 | M13-GAGGAAGGGTCCTCTCCTGTC | +83 | AGCAGCAGCTGGGTCTCTG |
| | | 5 | chr1:1179146-1179271 | -104 | ACATCTGGCAGCTGAGGAGTC | +109 | M13-TCCTGCACCCACTTCTGC |
| CCDS11.1 | TNFRSF4 | 1 | chr1:1189285-1189430 | -98 | M13-CTCCTCTGCCCTCCTCCC | +256 | CGTCGTTGTAGAAGCCCG |
| | | 2 | chr1:1168965-1189066 | -88 | CCAAGCCTGGCAGAGGAG | +94 | M13-GTTTGAGGTTCGTTTCTGCG |
| | | 3 | chr1:1168294-1188336 | -84 | CAACCTGTCCTCCAGTGCC | +252 | M13-ACAAAGATAGGGTGGTCAGGG |
| | | 4 | chr1:1187840-1188007 | -117 | M13-AGAGGCCAAACCCACCAC | +154 | CAACCAGGTCCAGCACATAG |
| | | 5 | chr1:1187244-1187441 | -109 | TGTGGTAGATGCTGCCTGTG | +171 | M13-GTACACGGCCAGCAGGATG |
| | | 6 | chr1:1187006-1187135 | -76 | M13-CAACCCGAATAGGAGAAGGG | +128 | ATCTTGGCCAGGGTGCAG |
| | | 7 | chr1:1186857-1186928 | -263 | CAACCCGAATAGGAGAAGGG | +110 | M13-GCACCTAGAACGGTGCAGAG |

*When multiple CCDS entries are derived from the same gene, the primers for shared exons are listed under the CCDS entry with the lowest ordinal number. Coding exons larger than 350 bp were amplified and sequenced with multiple primer pairs. [b]Position of the 5' end of forward PCR primer relative to the first base of the exon. §M13 denotes the universal sequencing primer 5'-GTAAAACGACGGCCAGT-3'. [c]Unsigned numbers indicate position of the 3' end of the reverse PCR primer relative to the first base of the exon. Plus signs indicate position of the 3' end of the reverse PCR primer relative to the last base of the exon. [e]The primer pair did not meet our quality criteria that ≥90% of bases in the target region have a Phred quality score of at least 20 in three quarters of the tumor samples analyzed in the Discovery Screen.

Fig. 9. Table S2A. Characteristics of the colorectal cancer samples

| ID | Patient age (years) | Sex | Tissue derivation | Location of original tumor | Clinical Stage | Sample type | Screen |
|---|---|---|---|---|---|---|---|
| Co74 | 35 | F | Liver metastasis | Sigmoid | IV | Cell line | Discovery |
| Co92 | 46 | F | Liver metastasis | Right colon | IV | Cell line | Discovery |
| Co108 | 77 | F | Liver metastasis | Right colon | IV | Cell line | Discovery |
| Mx22 | 66 | F | Liver metastasis | Unknown | IV | Xenograft | Discovery |
| Mx27 | 74 | F | Liver metastasis | Right colon | IV | Xenograft | Discovery |
| Mx30 | 62 | F | Liver metastasis | Sigmoid | IV | Xenograft | Discovery |
| Mx32 | 56 | F | Liver metastasis | Right colon | IV | Xenograft | Discovery |
| Mx38 | 67 | M | Liver metastasis | Rectum | IV | Xenograft | Discovery |
| Mx41 | 57 | M | Liver metastasis | Right colon | IV | Xenograft | Discovery |
| Mx42 | 72 | M | Liver metastasis | Left colon | IV | Xenograft | Discovery |
| Mx43 | 72 | M | Liver metastasis | Sigmoid | IV | Xenograft | Discovery |
| Co79 | 81 | M | Lymph node metastasis | Right colon | IV | Cell line | Validation |
| Co82 | 80 | F | Primary colorectal tumor | Right colon | IV | Cell line | Validation |
| Co84 | 40 | M | Lymph node metastasis | Right colon | III | Cell line | Validation |
| Co94 | 46 | M | Lymph node metastasis | Rectum | IV | Cell line | Validation |
| Mx3 | 64 | M | Primary colorectal tumor | Right colon | IV | Xenograft | Validation |
| Mx8 | 65 | M | Primary colorectal tumor | rectal | IV | Xenograft | Validation |
| Mx26 | 45 | F | Liver metastasis | Right colon | IV | Xenograft | Validation |
| Mx29 | 51 | M | Liver metastasis | Left colon | IV | Xenograft | Validation |
| Mx31 | 50 | M | Liver metastasis | Rectum | IV | Xenograft | Validation |
| Mx34 | 82 | F | Lymph node metastasis | Right colon | IV | Xenograft | Validation |
| Mx35 | 57 | F | Lung metastasis | Rectum | IV | Xenograft | Validation |
| Mx40 | 75 | F | Lymph node metastasis | Right colon | III | Xenograft | Validation |
| Mx45 | 67 | F | Liver metastasis | Transverse colon | IV | Xenograft | Validation |
| Hx005 | 62 | F | Liver metastasis | Splenic flexure | IV | Xenograft | Validation |
| Hx169 | 68 | M | Liver metastasis | Rectum | IV | Xenograft | Validation |
| Hx172 | 69 | F | Liver metastasis | Unknown | IV | Xenograft | Validation |
| Hx174 | 73 | F | Liver metastasis | Sigmoid | IV | Xenograft | Validation |
| Hx185 | 39 | F | Liver metastasis | Rectosigmoid | IV | Xenograft | Validation |
| Hx188 | 60 | M | Liver metastasis | Left | IV | Xenograft | Validation |
| Hx189 | 72 | M | Liver metastasis | Left | IV | Xenograft | Validation |
| Hx190 | 73 | M | Liver metastasis | Right | IV | Xenograft | Validation |
| Hx206 | 54 | M | Liver metastasis | Rectum | IV | Xenograft | Validation |
| Hx218 | 56 | F | Liver metastasis | Left | IV | Xenograft | Validation |
| Hx219 | 69 | M | Liver metastasis | Cecum | IV | Xenograft | Validation |
| Hx220 | 83 | F | Liver metastasis | Right | IV | Xenograft | Validation |
| Hx223 | 45 | F | Liver metastasis | Rectosigmoid | IV | Xenograft | Validation |

Fig. 10. Table S2B. Characteristics of the breast cancer samples

| ID | Patient age (years) | Adenocarcinoma Type | Tissue derivation | Stage | ER status* | PR status* | Her-2/neu status* | Sample type | Screen |
|---|---|---|---|---|---|---|---|---|---|
| HCC1008 | 67 | Ductal | Lymph node | IIA | - | - | +++ | Cell line | Discovery |
| HCC1954 | 61 | Ductal | Primary breast tumor | IIA | - | - | N/A | Cell line | Discovery |
| HCC38 | 50 | Ductal | Primary breast tumor | IIB | - | - | - | Cell line | Discovery |
| HCC1143 | 52 | Ductal | Primary breast tumor | IIA | - | - | - | Cell line | Discovery |
| HCC1187 | 41 | Ductal | Primary breast tumor | IIA | - | - | - | Cell line | Discovery |
| HCC1395 | 43 | Ductal | Primary breast tumor | I | - | - | - | Cell line | Discovery |
| HCC1599 | 44 | Ductal | Primary breast tumor | IIIA | - | - | - | Cell line | Discovery |
| HCC1937 | 24 | Ductal | Primary breast tumor | IIB | - | - | - | Cell line | Discovery |
| HCC2157 | 48 | Ductal | Primary breast tumor | IIIA | - | + | ++ | Cell line | Discovery |
| HCC2218 | 38 | Ductal | Primary breast tumor | IIIA | - | - | +++ | Cell line | Discovery |
| Hs578T | 74 | Carcinosarcoma | Primary breast tumor | N/A | - | - | + | Cell line | Discovery |
| HCC2713 | 35 | Ductal | Primary breast tumor | I | - | N/A | ++ | Cell line | Validation |
| BB1T | 51 | Ductal | Primary breast tumor | IIIC | - | - | - | Microdissected tumor tissue | Validation |
| BB2T | 51 | Ductal | Primary breast tumor | IIA | - | - | ++ | Microdissected tumor tissue | Validation |
| BB3T | 56 | Ductal | Primary breast tumor | IIA | + | + | +++ | Microdissected tumor tissue | Validation |
| BB4T | 52 | Lobular | Primary breast tumor | IIIA | + | + | ++ | Microdissected tumor tissue | Validation |
| BB5T | 42 | Ductal | Primary breast tumor | IIIA | + | + | - | Microdissected tumor tissue | Validation |
| BB7T | 59 | Ductal | Primary breast tumor | IIA | + | + | +++ | Microdissected tumor tissue | Validation |
| BB9T | 47 | Ductal | Primary breast tumor | IIA | + | + | +++ | Microdissected tumor tissue | Validation |
| BB10T | 55 | Ductal | Primary breast tumor | IIB | + | + | + | Microdissected tumor tissue | Validation |
| BB12T | 58 | Ductal | Primary breast tumor | IIIA | - | - | + | Microdissected tumor tissue | Validation |
| BB13T | 63 | Ductal | Primary breast tumor | IIIC | - | - | - | Microdissected tumor tissue | Validation |
| BB14T | 74 | Ductal | Primary breast tumor | IIA | + | + | - | Microdissected tumor tissue | Validation |
| BB15T | 79 | Ductal | Primary breast tumor | IIB | + | + | + | Microdissected tumor tissue | Validation |
| BB16T | 40 | Ductal | Primary breast tumor | IIB | + | + | + | Microdissected tumor tissue | Validation |
| BB18T | 53 | Ductal | Primary breast tumor | IIA | + | + | - | Microdissected tumor tissue | Validation |
| BB20T | 83 | Ductal | Primary breast tumor | IIA | + | + | - | Microdissected tumor tissue | Validation |
| BB21T | 77 | Ductal | Primary breast tumor | IIIA | + | + | - | Microdissected tumor tissue | Validation |
| BB22T | 50 | Ductal | Primary breast tumor | IIIC | + | + | + | Microdissected tumor tissue | Validation |
| BB23T | 46 | Ductolubular | Primary breast tumor | IIIC | + | - | - | Microdissected tumor tissue | Validation |
| BB24T | 66 | Ductal | Primary breast tumor | IIA | - | - | + | Microdissected tumor tissue | Validation |
| BB27T | 46 | Ductal | Primary breast tumor | IIIA | + | - | - | Microdissected tumor tissue | Validation |
| BB28T | 47 | Ductal | Primary breast tumor | IIIA | - | + | - | Microdissected tumor tissue | Validation |
| BB29T | 54 | Ductal | Primary breast tumor | IIA | + | - | - | Microdissected tumor tissue | Validation |
| BB30T | 50 | Ductal | Primary breast tumor | IIB | - | - | + | Microdissected tumor tissue | Validation |
| BB31T | 56 | Ductal | Primary breast tumor | IIIA | - | - | - | Microdissected tumor tissue | Validation |
| BB32T | 52 | Ductal | Primary breast tumor | IIA | + | + | + | Microdissected tumor tissue | Validation |
| BB33T | 36 | Ductal | Primary breast tumor | IV | + | + | ++ | Microdissected tumor tissue | Validation |
| BB34T | 36 | Ductolubular | Primary breast tumor | IIA | + | + | +++ | Microdissected tumor tissue | Validation |
| BB35T | 67 | Ductal | Primary breast tumor | IV | + | + | N/A | Microdissected tumor tissue | Validation |
| BB36T | 60 | Ductal | Primary breast tumor | IIB | - | - | ++ | Microdissected tumor tissue | Validation |
| BB37T | 47 | Ductal | Primary breast tumor | IIA | + | - | - | Microdissected tumor tissue | Validation |
| BB38T | 39 | Ductal | Primary breast tumor | IIB | + | + | ++ | Microdissected tumor tissue | Validation |
| BB39T | 39 | Lobular | Primary breast tumor | IIB | + | - | +++ | Microdissected tumor tissue | Validation |
| BB40T | 43 | Ductal | Primary breast tumor | IIA | + | - | - | Microdissected tumor tissue | Validation |
| BB42T | 56 | Ductal | Primary breast tumor | IIB | - | - | - | Microdissected tumor tissue | Validation |
| BB43T | 54 | Ductolubular | Primary breast tumor | IIIA | + | + | +++ | Microdissected tumor tissue | Validation |
| BB44T | 46 | Ductolubular | Primary breast tumor | I | + | + | + | Microdissected tumor tissue | Validation |

*Estrogen receptor (ER) and progesterone receptor (PR) status as determined by immunohistochemistry. -, negative; +, positive; *Her-2/neu status: -, negative; +, low positive, ++, moderately positive or +++ strongly positive; N/A, data not available.

Fig. 11. Table S3. Distribution of mutations in individual cancers*

| Tumor name | Number of mutations | Number of mutated CAN-genes[b] | Base substitution mutations | | | | | | | | | | | Insertion | Deletion | Duplication | Nucleotides successfully sequenced (Kb)[¶] |
|---|---|---|---|---|---|---|---|---|---|---|---|---|---|---|---|---|---|
| | | | Substitutions at C:G base pairs | | | | Substitutions at T:A base pairs | | | | Substitutions at specific dinucleotides[§] | | | | | | |
| | | | C:G→T:A | C:G→G:C | C:G→A:T | T:A→C:G | T:A→G:C | T:A→A:T | | | CpG | TpC | | | | |
| *Colorectal cancers* | | | | | | | | | | | | | | | | | |
| Co74 | 77 | 18 | 24 (31.2) | 10 (13.0) | 16 (20.8) | 8 (10.4) | 10 (13.0) | 6 (7.8) | | | 16 (20.8) | 12 (15.6) | 0 (0.0) | 1 (1.3) | 2 (2.6) | 18,447 |
| Co92 | 58 | 11 | 35 (59.3) | 4 (6.8) | 8 (13.8) | 5 (8.5) | 4 (6.8) | 1 (1.7) | | | 28 (47.5) | 5 (8.5) | 0 (0.0) | 1 (1.7) | 1 (1.7) | 19,003 |
| Co106 | 44 | 4 | 30 (68.2) | 1 (2.3) | 1 (2.3) | 4 (9.1) | 4 (9.1) | 3 (6.8) | | | 25 (56.8) | 3 (6.8) | 1 (2.3) | 0 (0.0) | 0 (0.0) | 19,023 |
| Mx22 | 47 | 6 | 30 (63.8) | 4 (8.5) | 3 (6.4) | 1 (2.1) | 2 (4.3) | 3 (6.4) | | | 25 (53.2) | 2 (4.3) | 1 (2.1) | 4 (8.4) | 4 (8.5) | 19,031 |
| Mx27 | 47 | 6 | 28 (59.6) | 2 (4.3) | 7 (14.9) | 3 (6.4) | 4 (8.5) | 3 (6.4) | | | 26 (55.3) | 4 (8.4) | 1 (2.1) | 0 (0.0) | 2 (4.3) | 18,100 |
| Mx30 | 31 | 5 | 18 (58.1) | 2 (6.5) | 3 (9.7) | 3 (9.7) | 2 (6.5) | 2 (3.2) | | | 9 (29.0) | 5 (16.1) | 0 (0.0) | 3 (9.5) | 3 (9.7) | 19,094 |
| Mx32 | 47 | 10 | 28 (59.6) | 2 (4.3) | 4 (8.5) | 5 (10.6) | 5 (10.6) | 0 (0.0) | | | 24 (51.1) | 2 (4.3) | 0 (0.0) | 2 (4.3) | 1 (2.1) | 18,421 |
| Mx38 | 51 | 7 | 22 (43.1) | 4 (7.8) | 7 (13.7) | 7 (13.7) | 2 (3.9) | 3 (5.9) | | | 15 (29.4) | 6 (11.8) | 2 (3.9) | 2 (3.9) | 3 (5.9) | 19,158 |
| Mx41 | 70 | 15 | 42 (60.0) | 4 (5.7) | 11 (15.7) | 5 (7.1) | 3 (4.3) | 4 (4.3) | | | 34 (48.6) | 10 (14.3) | 0 (0.0) | 2 (2.9) | 0 (0.0) | 19,132 |
| Mx42 | 51 | 9 | 32 (62.7) | 2 (3.9) | 5 (9.8) | 2 (3.9) | 1 (2.0) | 7 (7.8) | | | 24 (47.1) | 3 (5.9) | 0 (0.0) | 4 (7.8) | 1 (2.0) | 19,162 |
| Mx43 | 50 | 10 | 36 (72.0) | 1 (2.0) | 5 (10.0) | 2 (4.0) | 2 (4.0) | 2 (4.0) | | | 28 (56.0) | 3 (6.0) | 0 (0.0) | 1 (2.0) | 1 (2.0) | 18,951 |
| Average | 52 | 9 | | | | | | | | | | | | | | |
| *Breast cancers* | | | | | | | | | | | | | | | | | |
| HCC1008 | 98 | 23 | 30 (30.6) | 30 (30.6) | 11 (11.2) | 4 (4.1) | 3 (3.1) | 11 (11.2) | | | 18 (18.3) | 30 (30.6) | 0 (0.0) | 9 (9.2) | 0 (0.0) | 19,041 |
| HCC1954 | 45 | 9 | 27 (60.0) | 3 (6.7) | 2 (4.4) | 7 (15.6) | 2 (4.4) | 1 (2.2) | | | 13 (28.9) | 4 (8.9) | 0 (0.0) | 2 (4.4) | 1 (2.2) | 19,070 |
| HCC38 | 44 | 11 | 12 (27.3) | 13 (29.5) | 5 (11.4) | 4 (9.1) | 2 (4.5) | 3 (6.8) | | | 4 (9.1) | 15 (34.1) | 0 (0.0) | 6 (13.6) | 0 (0.0) | 19,932 |
| HCC1143 | 55 | 8 | 21 (38.2) | 13 (23.6) | 5 (9.1) | 7 (12.7) | 4 (7.3) | 5 (9.1) | | | 10 (18.2) | 16 (29.1) | 0 (0.0) | 0 (0.0) | 4 (8.5) | 19,122 |
| HCC1187 | 56 | 11 | 15 (26.8) | 12 (21.4) | 14 (25.0) | 2 (3.6) | 3 (5.4) | 1 (1.8) | | | 18 (32.1) | 7 (12.5) | 2 (3.6) | 0 (0.0) | 0 (0.0) | 19,105 |
| HCC1395 | 127 | 23 | 37 (29.1) | 48 (37.8) | 17 (13.4) | 10 (7.9) | 2 (1.6) | 5 (6.5) | | | 17 (13.4) | 43 (33.8) | 0 (0.0) | 6 (4.7) | 0 (0.0) | 19,062 |
| HCC1599 | 54 | 10 | 11 (20.4) | 11 (20.4) | 16 (29.6) | 2 (3.7) | 2 (3.7) | 3 (6.3) | | | 10 (18.5) | 12 (22.2) | 1 (1.9) | 6 (11.1) | 0 (0.0) | 19,038 |
| HCC1937 | 48 | 5 | 13 (27.1) | 10 (20.8) | 10 (20.8) | 3 (6.3) | 3 (6.3) | 4 (8.3) | | | 4 (8.3) | 12 (25.0) | 0 (0.0) | 5 (10.4) | 0 (0.0) | 19,141 |
| HCC2157 | 70 | 18 | 19 (27.1) | 18 (25.7) | 14 (20.0) | 9 (12.9) | 3 (4.3) | 2 (2.9) | | | 8 (11.4) | 18 (25.7) | 0 (0.0) | 5 (7.1) | 0 (0.0) | 19,031 |
| HCC2218 | 109 | 19 | 39 (35.8) | 48 (44.0) | 13 (11.9) | 2 (1.8) | 0 (0.0) | 6 (5.5) | | | 13 (11.9) | 71 (65.1) | 0 (0.0) | 1 (0.9) | 0 (0.0) | 18,976 |
| Hs578T | 27 | 4 | 6 (22.2) | 1 (3.7) | 3 (11.1) | 6 (22.2) | 6 (22.2) | 2 (7.4) | | | 2 (7.4) | 1 (3.7) | 0 (0.0) | 3 (11.1) | 1 (3.7) | 18,979 |
| Average | 71 | 12 | | | | | | | | | | | | | | |

*Base substitutions in coding sequences resulting in nonsynonymous changes as well as substitutions in non-coding sequences are included (see Table 1). Numbers in parentheses indicate percentage of total mutations. [b]CAN-genes, candidate cancer genes. [¶]Includes substitutions at the C or G of the 5'-CpG-3' dinucleotide, the C of the 5'-TpC-3' dinucleotide, or the G of the 5'-GpA-3' dinucleotide. [§]Nucleotides with Phred quality score of at least 20.

Table S4. Somatic mutations identified in breast or colorectal cancers

| CCDS accession | Gene | Tumor Type | Tumor name | Nucleotide (genomic)[a] | Nucleotide (cDNA)[b] | Amino acid (protein)[c] |
|---|---|---|---|---|---|---|
| CCDS7.1 | FLJ20584 | Breast | HCC1008 | g.chr1:1056278_1056271delGCTACGTC | c.683_690delGCTACGTC | fs |
| CCDS8.1 | FLJ38119 | Colorectal | Co108 | g.chr1:1155325G>A | c.169G>A | p.A57T |
| CCDS12.1 | Cab45 | Colorectal | Mx41 | g.chr1:1199156G>A | c.442G>A | p.A148T |
| CCDS37.1 | PRKCZ | Colorectal | Mx30 | g.chr1:2138880C>T | c.1541C>T | p.S514F |
| CCDS42.1 | PANK4 | Colorectal | Mx22 | g.chr1:2478019G>A | c.1423G>A | p.E475K |
| CCDS51.1 | KIAA1185 | Colorectal | Mx42 | g.chr1:3735819A>T | c.578A>T | p.E193D |
| CCDS57.1 | CHD5 | Breast | BB29T | g.chr1:8182550G>A | c.133G>A | p.V45M |
| CCDS57.1 | CHD5 | Breast | HCC1008 | g.chr1:8153894G>A | c.355G>A | p.D119N |
| CCDS57.1 | CHD5 | Breast | BB23T | g.chr1:8128193A>G | c.1999A>G | p.R667G |
| CCDS71.1 | TNFRSF25 | Breast | HCC1143 | g.chr1:6458971G>T | c.370G>T | p.E124X |
| CCDS92.1 | TNFRSF9 | Colorectal | Co108 | g.chr1:7915180A>G | c.748A>G | p.E250G |
| CCDS142.1 | PLOD1 | Breast | HCC2157 | g.chr1:11944748G>T | c.368G>T | p.Q123H |
| CCDS164.1 | SPEN | Breast | BB7T | g.chr1:16001009G>C | c.2968G>C | p.D690H |
| CCDS164.1 | SPEN | Breast | HCC1187 | g.chr1:16002504G>T | c.4463G>T | p.R1488I |
| CCDS166.1 | MGC24047 | Breast | BB12T | g.chr1:18077791G>T | c.154G>T | p.G52W |
| CCDS166.1 | MGC24047 | Breast | HCC1395 | g.chr1:18077793G>T (homozygous) | c.298G>T | p.G100W |
| CCDS172.1 | LOC374955 | Breast | Hs 578T | g.chr1:18493737C>T | c.70C>T | p.P24S |
| CCDS179.1 | PADI3 | Breast | HCC1599 | g.chr1:17346647G>C (homozygous) | c.1525G>C | p.G509R |
| CCDS182.1 | FLJ10521 | Colorectal | Mx30 | g.chr1:17873957C>T | c.297C>T | p.A99V |
| CCDS184.1 | MGC15730 | Colorectal | Co92 | g.chr1:18450122C>T (homozygous) | c.1400C>T | p.T487M |
| CCDS189.1 | RBAF600 | Breast | HCC1187 | g.chr1:19237466G>A | c.4181G>A | p.R1394H |
| CCDS189.1 | RBAF600 | Breast | BB33T | g.chr1:19176501_19176501dupC (homozygous) | c.12261_dupC | fs |
| CCDS218.1 | RAP1GA1 | Breast | Hs 578T | g.chr1:21683325T>C | c.769T>C | p.C257R |
| CCDS218.1 | RAP1GA1 | Breast | BB20T | g.chr1:21670252A>G | c.1826A>G | p.Y609C |
| CCDS228.1 | C1QB | Breast | HCC1393 | g.chr1:22732790G>A (homozygous) | c.367G>A | p.A123T |
| CCDS233.1 | ZNF436 | Breast | Hs 578T | g.chr1:23434957G>C | c.586T>G | p.C196G |
| CCDS235.1 | DDEFL1 | Colorectal | Mx41 | g.chr1:23506155G>A | c.1849G>A | p.A617T |
| CCDS244.1 | FUCA1 | Breast | HCC1008 | g.chr1:23639885delG | c.203delG | fs |
| CCDS253.1 | LOC90529 | Breast | HCC1143 | g.chr1:24432814C>T | c.620C>T | p.S207F |
| CCDS282.1 | RHD | Breast | HCC 38 | g.chr1:25356539C>G | c.308C>G | p.S103C |
| CCDS293.1 | FLJ34833 | Colorectal | Mx32 | g.chr1:26982079G>A | c.835G>A | p.R312H |
| CCDS299.1 | MAP3K6 | Breast | BB13T | g.chr1:27371551G>A | IVS14+3G>A | sp |
| CCDS299.1 | MAP3K6 | Breast | HCC1008 | g.chr1:27369223C>A | c.2605C>A | p.P869T |
| CCDS310.1 | STX12 | Breast | HCC1395 | g.chr1:27804280C>G | c.263C>G | p.P88R |
| CCDS334.1 | PTPRU | Colorectal | Mx34 | g.chr1:29439138C>T | c.2488C>T | p.H830Y |
| CCDS334.1 | PTPRU | Colorectal | Mx38 | g.chr1:29439151C>T | c.2503C>T | p.R835W |
| CCDS334.1 | PTPRU | Colorectal | Mx41 | g.chr1:29451042C>T | c.2566C>T | p.R856C |
| CCDS347.1 | SPOCD1 | Breast | HCC1954 | g.chr1:31933153C>T | c.2011C>T | p.R671W |
| CCDS364.1 | ZBTB8 | Colorectal | Mx42 | g.chr1:32605859G>A (homozygous) | c.541G>A | p.E181K |
| CCDS389.1 | ZNF262 | Colorectal | Hx190 | g.chr1:35516051delA | c.1290delA | fs |
| CCDS389.1 | ZNF262 | Colorectal | Mx22 | g.chr1:35550327C>T | c.4228C>T | p.R1410W |
| CCDS392.1 | NCDN | Colorectal | Co74 | g.chr1:35697116G>T | c.1174G>T | p.V392L |
| CCDS392.1 | NCDN | Colorectal | Co74 | g.chr1:35697117T>A | c.1175T>A | p.V392E |
| CCDS398.1 | CLSPN | Breast | HCC1954 | g.chr1:35895299A>G | c.1318A>G | p.H439R |
| CCDS416.1 | GRIK3 | Colorectal | Mx34 | g.chr1:37006970G>A | c.644G>A | p.R215H |
| CCDS416.1 | GRIK3 | Breast | HCC1008 | g.chr1:36990350G>C | c.1171G>C | p.D391H |
| CCDS420.1 | DNAL1 | Colorectal | Co92 | g.chr1:37694153C>G | c.426C>G | p.I142M |
| CCDS435.1 | MACF1 | Breast | BB4T | g.chr1:39416255A>T | c.905A>T | p.E302V |
| CCDS435.1 | MACF1 | Breast | BB7T | g.chr1:39522138_39522139insA | c.8345_8346insA | fs |
| CCDS435.1 | MACF1 | Breast | HCC 38 | g.chr1:39582278G>C | c.13510G>C | p.E4504Q |
| CCDS435.1 | MACF1 | Breast | BB7T | g.chr1:39596705G>A | c.16404G>A | p.O3135E |
| CCDS455.1 | NFYC | Breast | HCC2218 | g.chr1:40892993G>C | c.495G>C | p.Q185R |
| CCDS463.1 | HIVEP3 | Colorectal | Co74 | g.chr1:41718112G>A | c.1450G>A | p.V484M |
| CCDS460.1 | MGC17299 | Breast | HCC1599 | g.chr1:43407666G>T | c.320G>T | p.R107L |
| CCDS505.1 | ATP6V0B | Breast | HCC1599 | g.chr1:44111853G>A | c.463G>A | p.V155M |
| CCDS533.1 | MUF1 | Breast | HCC1008 | g.chr1:45475314C>T | c.286C>T | p.Q100X |
| CCDS533.1 | FAAH | Breast | HCC1937 | g.chr1:46586233C>A | c.1034C>A | p.A345D |
| CCDS572.1 | SCP2 | Breast | HCC1395 | g.chr1:53139263C>A | c.464C>A | p.A155D |
| CCDS574.1 | SLC1A7 | Colorectal | Co74 | g.chr1:53320022C>T | c.121C>T | p.R41C |
| CCDS584.1 | DJ187A19.1 | Colorectal | Mx30 | g.chr1:54046072C>T | c.475C>T | p.R158X |
| CCDS595.1 | FLJ46354 | Breast | HCC1599 | g.chr1:54831168C>A | c.548C>A | p.S183Y |
| CCDS605.1 | PRKAA2 | Breast | HCC1187 | g.chr1:56881987C>A | c.1111C>A | p.P371T |
| CCDS605.1 | PRKAA2 | Breast | HCC2157 | g.chr1:56885315A>G | c.1567A>G | p.G523G |
| CCDS608.1 | OMA1 | Colorectal | Co74 | g.chr1:58714259C>G | c.675C>G | p.L225V |
| CCDS612.1 | HOOK1 | Breast | HCC1395 | g.chr1:60038178C>T | c.1298C>T | p.S433L |
| CCDS614.1 | MGC34637 | Breast | HCC2157 | g.chr1:60218718C>G | c.451C>G | p.Q151E |
| CCDS626.1 | ROR1 | Breast | HCC1008 | g.chr1:64355431G>T | c.1686G>T | p.E562D |
| CCDS843.1 | LRRC7 | Breast | HCC1937 | g.chr1:70163978C>A (homozygous) | c.703C>A | p.L235M |
| CCDS843.1 | LRRC7 | Breast | BB1T | g.chr1:70163924delA | c.719delA | fs |
| CCDS864.1 | TNN3DX | Colorectal | Co108 | g.chr1:74817201C>G | c.1685C>G | p.R829Q |
| CCDS868.1 | ACADM | Breast | HCC2218 | g.chr1:75902494A>G | c.1A>G | unknown |
| CCDS868.1 | ACADM | Breast | BB9T | g.chr1:75912504C>G | c.395C>G | p.P132R |
| CCDS877.1 | ZZZ3 | Colorectal | Co74 | g.chr1:77809685C>T | c.1366C>T | p.P456S |
| CCDS707.1 | FLJ20722 | Colorectal | Co74 | g.chr1:85035539T>A | c.1364T>A | p.L455H |
| CCDS708.1 | CLCA2 | Breast | HCC1395 | g.chr1:86531178G>A | c.2261G>A | p.Q754E |
| CCDS715.1 | GTF2B | Colorectal | Mx41 | g.chr1:89037854G>A | c.395G>A | p.R132Q |
| CCDS731.1 | ZNF644 | Breast | HCC2218 | g.chr1:91116775G>C | c.157G>C | p.E53Q |
| CCDS747.1 | ABCA4 | Breast | HCC1599 | g.chr1:94276468C>T | c.671C>T | p.T224M |
| CCDS748.1 | PARG1 | Breast | HCC2157 | g.chr1:94386440C>G | c.1655C>G | p.S552C |
| CCDS748.1 | PARG1 | Breast | HCC2157 | g.chr1:94386412T>C | IVS14+2T>C | sp |
| CCDS769.1 | CDC14A | Colorectal | Mx43 | g.chr1:100676581C>T | c.1477C>T | p.D493Y |
| CCDS778.1 | COL11A1 | Breast | BB9T | g.chr1:103091930C>T | c.3977C>T | p.A1326V |
| CCDS778.1 | COL11A1 | Breast | HCC2157 | g.chr1:103091294C>A | c.3982C>A | p.Q1328K |
| CCDS778.1 | COL11A1 | Breast | HCC2157 | g.chr1:103091293A>T | c.3983A>T | p.Q1328L |
| CCDS785.1 | VAV3 | Breast | HCC1143 | g.chr1:108010111C>T | c.1153C>T | p.Q385X |
| CCDS794.1 | KIAA1324 | Breast | HCC1008 | g.chr1:109453322A>C | c.2485A>C | p.S829R |
| CCDS804.1 | AMPD2 | Breast | HCC1187 | g.chr1:109685704G>A (homozygous) | c.2285G>A | p.R762H |

FIG 12A

| | | | | | | |
|---|---|---|---|---|---|---|
| CCDS805.1 | AMPD2 | Breast | HCC1395 | g.chr1:109875687C>A | c.10C>A | p.R4S |
| CCDS821.1 | KCHC4 | Colorectal | Mx43 | g.chr1:110468245_110466247delGAG | c.82_84delGAG | p.E28del |
| CCDS824.1 | HBXIP | Colorectal | Mx30 | g.chr1:110661008_110661007delCA | c.317_318delCA | fs |
| CCDS828.1 | KCNA10 | Colorectal | Co74 | g.chr1:110772853G>A | c.599G>A | p.R200H |
| CCDS834.1 | OVGP1 | Colorectal | Co108 | g.chr1:111669180T>A | c.1985T>A | p.L662H |
| CCDS839.1 | AD029 | Colorectal | Mx38 | g.chr1:111757706G>A | c.313G>A | p.A105T |
| CCDS843.1 | KCND0 | Colorectal | Mx43 | g.chr1:112237111G>A | c.280G>A | p.V94M |
| CCDS874.1 | BCA52 | Colorectal | Co92 | g.chr1:114830256A>G | c.416A>G | p.N139S |
| CCDS876.1 | AMPD1 | Colorectal | Mx42 | g.chr1:114926648C>A | c.1898C>A | p.P633H |
| CCDS889.1 | CD2 | Breast | HCC1187 | g.chr1:117019184G>A | c.650G>A | p.C217Y |
| CCDS899.1 | PF9 | Colorectal | Co92 | g.chr1:118249128T>G | c.5121T>G | p.D1707E |
| CCDS938.1 | HIST2H2AB | Breast | HCC1008 | g.chr1:146872383G>A | c.157G>A | p.A53T |
| CCDS969.1 | TCFL1 | Breast | HCC1008 | g.chr1:147962338A>G | c.952A>G | p.I315V |
| CCDS1071.1 | ADAR | Breast | HCC1395 | g.chr1:151375812A>T | c.2417A>T | p.E806V |
| CCDS1074.1 | PBXIP1 | Colorectal | Co108 | g.chr1:151733832C>T | c.493C>T | p.R165W |
| CCDS1098.1 | MUC1 | Colorectal | Mx42 | g.chr1:151972790G>A | c.731G>A | p.R244H |
| CCDS1099.1 | THB93 | Breast | HCC 38 | g.chr1:151976718_151976702delGGAAGGGTGTGAGGA (homozygous) | c.2860_2874delGGAAGGGTGTGAGGA | p.G954_X957del |
| CCDS1099.1 | THB93 | Breast | BB40T | g.chr1:151976713A>G | c.2863A>G | p.R955G |
| CCDS1103.1 | C1orf2 | Breast | HCC2218 | g.chr1:152033577C>T | c.1073C>T | p.S358F |
| CCDS1108.1 | HCN3 | Breast | HCC1143 | g.chr1:152066835C>T | IVS2-3C>T | sp |
| CCDS1165.1 | IRTA2 | Breast | HCC2157 | g.chr1:154307321C>G | c.2060C>G | p.S687C |
| CCDS1165.1 | IRTA2 | Breast | BB7T | g.chr1:154298631C>G | IVS16-4C>G | sp |
| CCDS1167.1 | FCRH3 | Breast | HCC2157 | g.chr1:154476270C>A | c.1333C>A | p.H445N |
| CCDS1196.1 | APC3 | Breast | HCC1143 | g.chr1:156371320G>A | c.421G>A | p.G141S |
| CCDS1190.1 | IGSF9 | Colorectal | Mx43 | g.chr1:156712774C>T | c.2081C>T | p.R611W |
| CCDS1207.1 | SLAMF9 | Breast | HCC1008 | g.chr1:157420228C>T | c.241C>T | p.L81F |
| CCDS1227.1 | FLJ12770 | Colorectal | Co108 | g.chr1:158010520G>A | c.2960>A | p.D109N |
| CCDS1259.1 | POU2F1 | Breast | HCC2218 | g.chr1:164072881C>T | c.263C>T | p.S88F |
| CCDS1281.1 | F5 | Colorectal | Mx32 | g.chr1:168243683T>G | c.2323T>G | p.S775A |
| CCDS1321.1 | RASAL2 | Colorectal | Co92 | g.chr1:175143548T>A | c.955T>A | p.C319S |
| CCDS1321.1 | RASAL2 | Breast | HCC1143 | g.chr1:175148408G>C | c.1527G>C | p.E509D |
| CCDS1321.1 | RASAL2 | Breast | BB33T | g.chr1:175152488A>T | c.1695A>T | p.K587X |
| CCDS1335.1 | LAP1B | Breast | HCC 38 | g.chr1:176590119G>A | c.568G>A | p.V190I |
| CCDS1351.1 | LAMC1 | Colorectal | Mx32 | g.chr1:176831202G>A | c.3347G>A | p.R1116H |
| CCDS1359.1 | RGL1 | Breast | HCC1385 | g.chr1:180581502A>C | c.626A>C | p.Y209S |
| CCDS1359.1 | RGL1 | Breast | BB12T | g.chr1:180623103G>A | c.2200G>A | p.V734M |
| CCDS1360.1 | QLT25D2 | Breast | HCC1187 | g.chr1:180641553G>A | c.1423G>A | p.V475I |
| CCDS1372.1 | PLA2G4A | Breast | HCC1187 | g.chr1:183851507C>G | c.1326C>G | p.H442Q |
| CCDS1384.1 | SLICK | Breast | HCC1954 | g.chr1:193193127G>A | c.97G>A | p.V33I |
| CCDS1387.1 | CFHL5 | Breast | HCC1395 | g.chr1:163696543A>G | c.647A>G | p.N216S |
| CCDS1390.1 | CRB1 | Colorectal | Mx32 | g.chr1:194128346C>T | c.2234C>T | p.T745M |
| CCDS1397.1 | PTPRC | Breast | HCC1143 | g.chr1:195407523A>C | c.683A>C | p.E228A |
| CCDS1397.1 | PTPRC | Breast | HCC1143 | g.chr1:195443049G>A | c.2587G>A | p.G863R |
| CCDS1402.1 | ZNF281 | Breast | HCC1954 | g.chr1:197108911T>C | c.1580T>C | p.I527T |
| CCDS1403.1 | DKFZP56461023 | Breast | HCC2218 | g.chr1:197387297C>A | c.229C>A | p.P77T |
| CCDS1404.1 | KIAA1078 | Colorectal | Mx43 | g.chr1:197545626T>A | c.1081T>A | p.L361I |
| CCDS1424.1 | LGR6 | Colorectal | Mx22 | g.chr1:198001881_199001989dupGAAGATCGG | c.734_742dupGAAGATCGG | Indel |
| CCDS1424.1 | LGR6 | Colorectal | Co82 | g.chr1:199019261G>T | c.2017G>T | p.G673C |
| CCDS1424.1 | LGR6 | Colorectal | Co79 | g.chr1:199019871C>A (homozygous) | c.2627C>A | p.P676H |
| CCDS1434.1 | ADORA1 | Colorectal | Co108 | g.chr1:199856212G>A | c.508G>A | p.E170K |
| CCDS1477.1 | C4BPA | Colorectal | Mx42 | g.chr1:200705658T>A | c.1545T>A | p.Y515X |
| CCDS1479.1 | MCP | Colorectal | Co92 | g.chr1:204328782G>A | c.683G>A | p.C228Y |
| CCDS1479.1 | MCP | Colorectal | Co79 | g.chr1:204346841C>T | c.968C>T | p.A323V |
| CCDS1487.1 | LAMB3 | Colorectal | Mx43 | g.chr1:208189260C>T | c.1348C>T | p.R450C |
| CCDS1489.1 | HSD11B1 | Breast | HCC 38 | g.chr1:208268794T>A | c.443T>A | p.V148E |
| CCDS1490.1 | T3JAM | Colorectal | Mx38 | g.chr1:208343817C>T | c.1525C>T | p.P509S |
| CCDS1504.1 | FLJ10874 | Breast | HCC2218 | g.chr1:208926997G>C | c.1008G>C | p.K336N |
| CCDS1514.1 | PTPN14 | Breast | HCC1008 | g.chr1:210973457C>G | c.475C>G | p.Q159E |
| CCDS1514.1 | PTPN14 | Breast | BB27T | g.chr1:210946514A>C | c.1076A>C | p.H360P |
| CCDS1554.1 | PARP1 | Breast | HCC1008 | g.chr1:222874438A>T | c.1463A>T | p.E488V |
| CCDS1570.1 | OBSCN | Breast | BB30T | g.chr1:224737790delG | c.3101delG | fs |
| CCDS1570.1 | OBSCN | Colorectal | Co84 | g.chr1:224738933C>T | c.3407C>T | p.A1136V |
| CCDS1570.1 | OBSCN | Colorectal | Hx200 | g.chr1:224768323G>A | c.5255G>A | p.W1752X |
| CCDS1570.1 | OBSCN | Colorectal | Co108 | g.chr1:224768443G>A | c.5375G>A | p.R1792H |
| CCDS1570.1 | OBSCN | Colorectal | Co108 | g.chr1:224769112G>A | c.5786G>A | p.V1930M |
| CCDS1570.1 | OBSCN | Colorectal | Hx174 | g.chr1:224770933G>A | c.6268G>A | p.E2090K |
| CCDS1570.1 | OBSCN | Breast | BB13T | g.chr1:224773206C>T | c.6941C>T | p.S2314F |
| CCDS1570.1 | OBSCN | Colorectal | Mx8 | g.chr1:224801358G>A | c.11948G>A | p.R3983Q |
| CCDS1570.1 | OBSCN | Colorectal | Mx41 | g.chr1:224812011G>A | c.13873G>A | p.R4558H |
| CCDS1570.1 | OBSCN | Breast | HCC2157 | g.chr1:224813617G>A | c.14429G>A | p.R4810Q |
| CCDS1570.1 | OBSCN | Breast | BB7T | g.chr1:224816488G>A | c.15211G>A | p.A5071T |
| CCDS1570.1 | OBSCN | Breast | BB32T | g.chr1:224833341C>T | c.17137C>T | p.Q5713X |
| CCDS1579.1 | NUP133 | Breast | BB14T | g.chr1:225938048G>T (homozygous) | c.977G>T | p.G326V |
| CCDS1579.1 | NUP133 | Breast | HCC2218 | g.chr1:225929948G>A | c.1342G>A | p.G448R |
| CCDS1580.1 | ABC810 | Breast | BB23T | g.chr1:225953238C>A | IVS4-4C>A | sp |
| CCDS1580.1 | ABC810 | Breast | HCC 38 | g.chr1:225974141G>C | c.1412G>C | p.R471T |
| CCDS1589.1 | ARV1 | Breast | HCC1954 | g.chr1:227436310_227438310dupA | c.518_dupA | fs |
| CCDS1592.1 | GNPAT | Breast | HCC1395 | g.chr1:277718412G>T | c.1612G>T | p.E538X |
| CCDS1606.1 | B3GALNT2 | Breast | HCC1509 | g.chr1:231969454A>G | c.608A>G | p.N203S |
| CCDS1608.1 | NID | Colorectal | Co74 | g.chr2:232471072T>C | c.3107T>C | p.F1036S |
| CCDS1825.1 | MGC33370 | Breast | HCC1599 | g.chr2:241071148C>T | c.1958C>T | p.T653I |
| CCDS1852.1 | TTC15 | Breast | HCC2218 | g.chr2:5021458G>C | c.2149G>C | p.E717Q |
| CCDS1864.1 | CPSF3 | Breast | HCC2218 | g.chr2:9550291G>A | c.1732G>A | p.D578N |
| CCDS1864.1 | CPSF3 | Breast | HCC 38 | g.chr2:9563743G>C | c.2054G>C | p.X685S |
| CCDS1877.1 | FLJ33334 | Colorectal | Mx27 | g.chr2:11211587G>A | c.380G>A | p.R127Q |
| CCDS1882.1 | LPIN1 | Colorectal | Mx30 | g.chr2:11856432G>A | c.167G>A | p.G56E |
| CCDS1890.1 | SMC6L1 | Breast | HCC2157 | g.chr2:17841217delG | c.243delG | fs |
| CCDS1890.1 | SMC6L1 | Breast | HCC1954 | g.chr2:17823905C>T | c.875C>T | p.A292V |
| CCDS1891.1 | FLJ40869 | Breast | BB9T | g.chr2:17874166_17874185delC | c.785_788delC | fs |
| CCDS1891.1 | FLJ40869 | Breast | HCC2157 | g.chr2:17875550G>T | c.824G>T | p.R275L |

| | | | | | | | |
|---|---|---|---|---|---|---|---|
| CCDS2460.1 | SERPINE2 | Breast | HCC1143 | g.chr2:224682093A>T | c.612A>T | | p.K204N |
| CCDS2465.1 | C2orf33 | Colorectal | Mx43 | g.chr2:226020693G>A | c.85G>A | | p.E29K |
| CCDS2470.1 | FLJ25955 | Breast | HCC1395 | g.chr2:228584084C>T | c.368C>T | | p.T129M |
| CCDS2474.1 | SP110 | Breast | BB43T | g.chr2:230907125T>C | c.237T>C | | p.M8T |
| CCDS2474.1 | SP110 | Breast | HCC1008 | g.chr2:230859388G>A | c.2047G>A | | p.G683S |
| CCDS2494.1 | CHRND | Breast | HCC1008 | g.chr2:233224292C>A | c.1194C>A | | p.D398E |
| CCDS2505.1 | UGT1A9 | Breast | HCC1187 | g.chr2:234462937G>T (homozygous) | c.1325G>T | | p.G442I |
| CCDS2516.1 | CMKOR1 | Colorectal | Mx27 | g.chr2:237271243C>A | c.135C>A | | p.Y45X |
| CCDS2521.1 | LRRFIP1 | Breast | BB5T | g.chr2:238399278A>G | IVS2+3A>G | | sp |
| CCDS2521.1 | LRRFIP1 | Breast | HCC2218 | g.chr2:238411419C>G | c.203C>G | | p.G68C |
| CCDS2521.1 | LRRFIP1 | Breast | BB35T | g.chr2:238454328C>T | c.1900C>T | | p.Q634X |
| CCDS2528.1 | PER2 | Breast | HCC 38 | g.chr2:238944197C>G | c.2467C>G | | p.L823V |
| CCDS2529.1 | HDAC4 | Breast | BB27T | g.chr2:239760784C>G | c.2180C>G | | p.P727R |
| CCDS2529.1 | HDAC4 | Breast | HCC1143 | g.chr2:239712698G>A | IVS24+1G>A | | sp |
| CCDS2534.1 | GPC1 | Breast | HCC1599 | p.chr2:241124149C>A (homozygous) | c.1010C>A | | p.A337D |
| CCDS2537.1 | RNPEPL1 | Colorectal | Mx41 | g.chr2:241234939G>A | c.739G>A | | p.V247M |
| CCDS2539.1 | CAPN10 | Colorectal | Mx41 | p.chr2:241253451A>G | c.827A>G | | p.E276G |
| CCDS2547.1 | HDLBP | Breast | BB31T | p.chr2:241916116_241916107delCAAAATCCAG | c.546_555delCAAAATCCAG | | fs |
| CCDS2547.1 | HDLBP | Breast | BB18T | p.chr2:241907435A>C | c.1704A>C | | p.K568N |
| CCDS2547.1 | HDLBP | Breast | HCC1008 | p.chr2:241896108A>T | c.2816A>T | | p.D639V |
| CCDS2556.1 | CHL1 | Colorectal | Mx29 | g.chr3:359718A>G | IVS8+4A>G | | sp |
| CCDS2556.1 | CHL1 | Colorectal | Mx43 | g.chr3:377080C>A | c.1279C>A | | p.L427I |
| CCDS2557.1 | CNTN6 | Breast | BB4T | g.chr3:1244841A>G | c.322A>G | | p.T106A |
| CCDS2557.1 | CNTN6 | Breast | HCC1143 | g.chr3:1389608A>T (homozygous) | c.1753A>T | | p.S585C |
| CCDS2558.1 | CNTN4 | Colorectal | Co84 | g.chr3:2942385A>C | c.278A>C | | p.K92N |
| CCDS2558.1 | CNTN4 | Colorectal | Co74 | g.chr3:3042809C>A | c.526C>A | | p.P176T |
| CCDS2572.1 | SRGAP3 | Breast | HCC1599 | g.chr3:9630473C>A | c.1667C>A | | p.L623I |
| CCDS2583.1 | TTLL3 | Colorectal | Mx22 | g.chr3:9845085G>A | c.724G>A | | p.G242S |
| CCDS2585.1 | TTLL3 | Colorectal | Co79 | g.chr3:9845953G>T | c.792G>T | | p.M264I |
| CCDS2604.1 | HRH1 | Colorectal | Mx41 | g.chr3:11278878T>A | c.1155T>A | | p.D385E |
| CCDS2636.1 | ZNF659 | Colorectal | Mx32 | g.chr3:21437742G>A | c.1156G>A | | p.A386T |
| CCDS2636.1 | ZNF659 | Colorectal | Mx22 | g.chr3:21437737C>G | c.1161C>G | | p.H387Q |
| CCDS2642.1 | RARB | Colorectal | Mx27 | g.chr3:25477777G>A | c.247G>A | | p.V83I |
| CCDS2643.1 | FLJ20504 | Breast | HCC1599 | p.chr3:25807831T>A | c.316T>A | | p.F106I |
| CCDS2646.1 | EOMES | Breast | HCC2218 | p.chr3:27733827G>C | c.1999G>C | | p.E667Q |
| CCDS2648.1 | TGFBR2 | Colorectal | Hx189 | g.chr3:30661365A>G | c.217A>G | | p.I73V |
| CCDS2648.1 | TGFBR2 | Colorectal | Mx34 | g.chr3:30707954G>A (homozygous) | a.1583G>A | | p.W521X |
| CCDS2648.1 | TGFBR2 | Colorectal | Co74 | g.chr3:30707974G>A (homozygous) | c.1583G>A | | p.R528H |
| CCDS2656.1 | FBXL2 | Colorectal | Mx42 | g.chr3:33391800G>A | c.676G>A | | p.V226M |
| CCDS2659.1 | ITGA9 | Breast | BB27T | g.chr3:37758238C>T | c.2248C>T | | p.R750C |
| CCDS2659.1 | ITGA9 | Breast | HCC1395 | g.chr3:37835449G>T (homozygous) | c.3073G>T | | p.E1025X |
| CCDS2672.1 | DLEC1 | Breast | HCC1599 | g.chr3:38079254C>G | c.1052C>G | | p.P331R |
| CCDS2683.1 | CMYA1 | Breast | HCC1395 | g.chr3:39204810T>A | c.1331T>A | | p.L444H |
| CCDS2683.1 | CMYA1 | Breast | BB16T | g.chr3:39202495G>A | c.3446G>A | | p.R1149K |
| CCDS2743.1 | ALS2CL | Breast | BB23T | g.chr3:48700490C>G | c.836C>G | | p.Q260E |
| CCDS2743.1 | ALS2CL | Breast | HCC2218 | g.chr3:48694784C>T | c.1726C>T | | p.L578F |
| CCDS2765.1 | PLXNB1 | Breast | HCC1599 | g.chr3:48426424A>T | c.5672A>T | | p.D1891V |
| CCDS2771.1 | PFKFB4 | Breast | HCC1008 | g.chr3:48551024C>G (homozygous) | c.543C>G | | p.N181K |
| CCDS2773.1 | COL7A1 | Breast | HCC1937 | g.chr3:48606045A>C | c.355A>C | | p.T119P |
| CCDS2773.1 | COL7A1 | Breast | BB7T | g.chr3:48596951C>A | c.4090C>A | | p.P1364T |
| CCDS2773.1 | COL7A1 | Breast | BB22T | g.chr3:48596945C>T | c.4096C>T | | p.R1366W |
| CCDS2837.1 | RNU3IP2 | Breast | HCC1187 | g.chr3:51950902C>G (homozygous) | c.22C>G | | p.R8G |
| CCDS2837.1 | RNU3IP2 | Breast | BB23T | g.chr3:51944262C>A | c.1025C>A | | p.A342E |
| CCDS2844.1 | ACY1 | Breast | HCC1599 | g.chr3:51998047G>C | c.1143G>C | | p.E381D |
| CCDS2848.1 | TLR9 | Colorectal | Mx34 | g.chr3:52233067G>A | c.2702G>A | | p.R901H |
| CCDS2848.1 | TLR9 | Colorectal | Mx30 | g.chr3:52230574C>T | c.2798C>T | | p.T933M |
| CCDS2854.1 | PHF7 | Breast | HCC2157 | g.chr3:52432334G>C | c.1107G>C | | p.K369N |
| CCDS2868.1 | MGC52022 | Colorectal | Co74 | p.chr3:52861755G>T | IVS2-1G>T | | sp |
| CCDS2882.1 | APPL | Breast | HCC2218 | g.chr3:57277499G>C | c.1927G>C | | p.E643Q |
| CCDS2885.1 | FLNB | Breast | BB13T | g.chr3:58065933G>A | c.1697G>A | | p.R566Q |
| CCDS2885.1 | FLNB | Breast | BB23T | g.chr3:58009272C>A | c.1989C>A | | p.N663K |
| CCDS2885.1 | FLNB | Breast | BB23T | g.chr3:58069990C>A | c.2103C>A | | p.T703K |
| CCDS2885.1 | FLNB | Breast | BB7T | g.chr3:58070834_58070830dupACG | c.2381_2383dupACG | | indel |
| CCDS2885.1 | FLNB | Breast | HCC2157 | g.chr3:58095469C>G | c.4601C>G | | p.A1534G |
| CCDS2886.1 | DNASE1L3 | Breast | HCC1395 | g.chr3:58171019C>G (homozygous) | c.55C>G | | p.L19V |
| CCDS2886.1 | DNASE1L3 | Breast | BB20T | g.chr3:58166314G>C | c.244G>C | | p.G82R |
| CCDS2886.1 | DNASE1L3 | Colorectal | Mx22 | g.chr3:58165619A>C | c.350A>C | | p.Y117S |
| CCDS2909.1 | TA-KRP | Breast | HCC1008 | g.chr3:67136673A>T (homozygous) | c.514A>T | | p.S172C |
| CCDS2909.1 | TA-KRP | Colorectal | Mx38 | g.chr3:67137295G>A | c.1136G>A | | p.R379K |
| CCDS2922.1 | EPHA3 | Colorectal | Mx41 | g.chr3:89259070C>A | c.110C>A | | p.T37K |
| CCDS2922.1 | EPHA3 | Colorectal | Co74 | g.chr3:89341800A>G | c.254A>G | | p.N85S |
| CCDS2922.1 | EPHA3 | Colorectal | Hx218 | g.chr3:89545079A>C | c.1561A>C | | p.I521L |
| CCDS2922.1 | EPHA3 | Colorectal | Co84 | g.chr3:89581134G>A | c.2416G>A | | p.D806N |
| CCDS2923.1 | PROS1 | Colorectal | Mx41 | p.chr3:95080707A>G | c.1634A>C | | p.E545G |
| CCDS2939.1 | TFG | Colorectal | Mx30 | g.chr3:101934071G>T | c.445G>T | | p.A149S |
| CCDS2971.1 | BOC | Breast | HCC1054 | g.chr3:114481477G>A | c.2137G>A | | p.V713M |
| CCDS2987.1 | TMEM39A | Breast | HCC1143 | g.chr3:120639476C>T | c.740C>T | | p.S247L |
| CCDS3004.1 | GOLGB1 | Breast | HCC2157 | g.chr3:122916503G>C | c.1044G>C | | p.Q348H |
| CCDS3004.1 | GOLGB1 | Breast | HCC1395 | g.chr3:122899214C>G (homozygous) | c.2831C>G | | p.A944G |
| CCDS3015.1 | DTX3L | Breast | HCC1937 | g.chr3:123770253G>C (homozygous) | c.627G>C | | p.K209N |
| CCDS3019.1 | SEMA5B | Breast | BB24T | g.chr3:124102677G>A | c.124G>A | | p.G42S |
| CCDS3019.1 | SEMA5B | Breast | HCC1395 | g.chr3:124129506C>G (homozygous) | c.669C>G | | p.I223M |
| CCDS3027.1 | HAPIP | Colorectal | Mx27 | g.chr3:125470466C>T | c.637C>T | | p.R213W |
| CCDS3028.1 | TRAD | Breast | Hs 578T | g.chr3:125852372A>T | c.598A>T | | p.S200C |
| CCDS3033.1 | OSBPL11 | Breast | HCC1143 | g.chr3:126777836C>T | c.551C>T | | p.S184L |
| CCDS3034.1 | ALDH1L1 | Colorectal | Mx43 | g.chr3:127333016C>T (homozygous) | c.1532C>T | | p.A511V |
| CCDS3007.1 | PIK3R4 | Breast | HCC2157 | g.chr3:131907228G>A | c.2807G>A | | p.R936Q |
| CCDS3112.1 | CL6TN2 | Colorectal | Co92 | g.chr3:141806247C>T (homozygous) | c.578G>T | | p.G193I |
| CCDS3112.1 | CL6TN2 | Colorectal | Mx40 | g.chr3:141784432C>A | c.2294G>A | | p.R765Q |
| CCDS3138.1 | CPA3 | Breast | HCC1937 | g.chr3:150055986G>T | c.100G>T | | p.E34X |
| CCDS3140.1 | HPS3 | Colorectal | Mx22 | g.chr3:150351110G>A | c.1190G>A | | p.R397Q |

FIG. 12D

| | | | | | |
|---|---|---|---|---|---|
| CCDS3156.1 | P2RY14 | Colorectal | Mx32 | g.chr3:152414384T>C | c.418T>C | p.L140P |
| CCDS3156.1 | P2RY14 | Colorectal | Co79 | g.chr3:152413893G>T | c.910G>T | p.E304X |
| CCDS3157.1 | GPR87 | Colorectal | Co92 | g.chr3:152495181G>T | c.571G>T | p.D191Y |
| CCDS3173.1 | SLC33A1 | Colorectal | Mx41 | g.chr3:157034026T>C | c.1199T>C | p.V400A |
| CCDS3179.1 | VEPH1 | Breast | BB9T | g.chr3:158581788delG | c.988delG | fs |
| CCDS3179.1 | VEPH1 | Breast | BB5T | g.chr3:158581778G>T | c.998G>T | p.S333I |
| CCDS3179.1 | VEPH1 | Breast | HCC1599 | g.chr3:158481684_158481883delAA | c.2443_2444delAA | fs |
| CCDS3189.1 | SMC4L1 | Breast | HCC1599 | g.chr3:161612037_161612043delATTATAT | c.974_980delATTATAT | fs |
| CCDS3201.1 | WDR49 | Colorectal | Mx32 | g.chr3:168804865G>A | c.29G>A | p.R10H |
| CCDS3204.1 | GOLPH4 | Breast | HCC2157 | g.chr3:169243946G>T | c.440G>T | p.S147I |
| CCDS3204.1 | GOLPH4 | Breast | HCC1187 | g.chr3:169233252G>C | c.934G>C | p.A312P |
| CCDS3204.1 | GOLPH4 | Breast | HCC1187 | g.chr3:169233251G>T | c.935G>T | p.A312V |
| CCDS3217.1 | FNDC3B | Breast | HCC1395 | g.chr3:173553556C>T | c.2779C>T | p.P927S |
| CCDS3220.1 | ECT2 | Breast | HCC 38 | g.chr3:174018192A>C | c.2404A>C | p.T802P |
| CCDS3228.1 | MFN1 | Colorectal | Mx27 | g.chr3:180577852G>C | c.1243G>C | p.D415H |
| CCDS3236.1 | PEX5L | Colorectal | Co74 | g.chr3:181074887G>A | c.676G>A | p.A226T |
| CCDS3238.1 | FXR1 | Breast | HCC2157 | g.chr3:182151854G>A | c.697G>A | p.A233T |
| CCDS3243.1 | MCF2L2 | Colorectal | Mx22 | g.chr3:184512255T>C | c.761T>C | p.L254P |
| CCDS3243.1 | MCF2L2 | Colorectal | Mx38 | g.chr3:184431505G>A | c.1865G>A | p.R522H |
| CCDS3243.1 | MCF2L2 | Breast | HCC1395 | g.chr3:184380173C>T | c.3115C>T | p.L1039F |
| CCDS3250.1 | HTR3C | Colorectal | Mx41 | g.chr3:185256789G>A | c.382G>A | p.V128M |
| CCDS3253.1 | DVL3 | Breast | HCC2218 | g.chr3:185385850G>A | c.647G>A | p.R216T |
| CCDS3259.1 | EIF4G1 | Colorectal | Mx27 | g.chr3:185523730C>T | c.2087C>T | p.P696L |
| CCDS3262.1 | MGC21688 | Breast | HCC1395 | g.chr3:185545231G>A | c.779G>A | p.S260N |
| CCDS3274.1 | DGKG | Breast | HCC1395 | g.chr3:187365489G>A | c.2116G>A | p.E706K |
| CCDS3275.1 | FLJ10560 | Colorectal | Mx42 | g.chr3:187757259T>A | IVS2-3T>A | sp |
| CCDS3282.1 | EIF4A2 | Breast | HCC2157 | g.chr3:187986676G>C | c.541G>C | p.V181L |
| CCDS3283.1 | RFC4 | Colorectal | Mx22 | g.chr3:187990717_187990706delTCAGCTCGTCAA | c.912_923delTCAGCTCGTCAA | indel |
| CCDS3283.1 | RFC4 | Breast | HCC1954 | g.chr3:187990492A>T | c.1060A>T | p.T354S |
| CCDS3287.1 | RTP1 | Breast | HCC1187 | g.chr3:188400138C>A (homozygous) | c.262C>A | p.R88S |
| CCDS3294.1 | LEPREL1 | Breast | HCC2218 | g.chr3:191183584C>G | c.1277C>G | p.S426X |
| CCDS3294.1 | LEPREL1 | Breast | HCC2157 | g.chr3:191171383G>A | c.1837G>A | p.D613N |
| CCDS3307.1 | GP5 | Breast | HCC2157 | g.chr3:195599293G>T | c.1016G>T | p.G339V |
| CCDS3318.1 | WDR53 | Breast | HCC1395 | g.chr3:197776478C>G | c.179C>G | p.S60C |
| CCDS3382.1 | EVC2 | Colorectal | Co74 | g.chr4:5745706G>T | c.1648G>T | p.A550S |
| CCDS3382.1 | EVC2 | Colorectal | Co108 | g.chr4:5704499T>G | c.2740T>G | p.L914V |
| CCDS3382.1 | EVC2 | Colorectal | Mx32 | g.chr4:5682699_5682695delAG (homozygous) | c.3635_3636delAG | fs |
| CCDS3384.1 | FLJ46481 | Breast | HCC1008 | g.chr4:6087222G>C (homozygous) | c.448C>G | p.A150P |
| CCDS3385.1 | MARLIN1 | Colorectal | Co92 | g.chr4:6200089C>T | c.1124C>T | p.A375V |
| CCDS3396.1 | SH3TC1 | Colorectal | Mx38 | g.chr4:8347648G>A | c.2156G>A | p.R719H |
| CCDS3399.1 | SH3TC1 | Colorectal | Hx218 | g.chr4:8355336G>A | c.3388G>A | p.A1130T |
| CCDS3411.1 | FAM44A | Breast | HCC1395 | g.chr4:13292526G>T | c.737G>T | p.S246I |
| CCDS3424.1 | HCAP-G | Colorectal | Mx38 | g.chr4:17495171T>C | c.794T>C | p.M265T |
| CCDS3434.1 | ANAPC4 | Colorectal | Co74 | g.chr4:25066827A>G | c.463A>G | p.I155V |
| CCDS3439.1 | TBC1D19 | Breast | HCC2218 | g.chr4:26420471C>T (homozygous) | c.1300C>T | p.R434X |
| CCDS3455.1 | UGDH | Colorectal | Mx22 | g.chr4:39324443_39324443dupT | IVS10-4_dupT | fs |
| CCDS3457.1 | N4BP2 | Breast | HCC2218 | g.chr4:39926878C>G | c.847C>G | p.P283A |
| CCDS3473.1 | GABRA4 | Breast | Hs 578T | g.chr4:46771289A>C | c.1546A>C | p.S516R |
| CCDS3497.1 | KDR | Colorectal | Mx27 | g.chr4:55820551G>T | c.824G>T | p.R275L |
| CCDS3497.1 | KDR | Colorectal | Mx38 | g.chr4:55803435G>A (homozygous) | c.2617G>A | p.G873R |
| CCDS3510.1 | C4orf14 | Breast | HCC1187 | g.chr4:57673742A>G (homozygous) | c.1736A>G | p.Q579R |
| CCDS3536.1 | APIN | Colorectal | Mx38 | g.chr4:71246391G>C | c.429G>C | p.E143D |
| CCDS3542.1 | UNQ669 | Colorectal | Mx43 | g.chr4:71571376G>A (homozygous) | c.232G>A | p.G78S |
| CCDS3564.1 | EREG | Breast | HCC2218 | g.chr4:75010257G>C | c.125G>C | p.G42A |
| CCDS3570.1 | CDKL2 | Breast | HCC2218 | g.chr4:76884283C>G | c.1421C>G | p.S474X |
| CCDS3571.1 | G3BP2 | Breast | HCC1143 | g.chr4:76938234G>C | IVS4-1G>C | sp |
| CCDS3571.1 | G3BP2 | Breast | HCC2157 | g.chr4:76927941C>T | c.1301C>T | p.P434L |
| CCDS3598.1 | THAP9 | Colorectal | Co74 | g.chr4:84196586G>A | c.2044G>A | p.V682I |
| CCDS3603.1 | HELSG8 | Breast | HCC2218 | g.chr4:84718310G>A | c.1693G>A | p.D565N |
| CCDS3608.1 | CDS1 | Breast | Hs 578T | g.chr4:85910181A>C | c.811A>C | p.K204T |
| CCDS3608.1 | CDS1 | Colorectal | Co74 | g.chr4:85913662_85913662dupT | c.789_dupT | fs |
| CCDS3610.1 | MLLT2 | Breast | HCC1937 | g.chr4:88414009C>A | c.3810C>A | p.Q1204K |
| CCDS3637.1 | GRID2 | Colorectal | Co74 | g.chr4:94389173C>A | c.626C>A | p.T209N |
| CCDS3650.1 | RGBMTD2 | Breast | HCC1599 | g.chr4:100836487C>A | c.245C>A | p.P82Q |
| CCDS3657.1 | NFKB1 | Breast | HCC2218 | g.chr4:103808177G>A | IVS1-1G>A | sp |
| CCDS3670.1 | FLJ20184 | Breast | HCC1008 | g.chr4:106888013G>C | c.201G>C | p.K67N |
| CCDS3679.1 | LEF1 | Colorectal | Mx41 | g.chr4:109442405G>A | c.337G>A | p.G113R |
| CCDS3681.1 | DC2 | Breast | HCC1395 | g.chr4:109929442C>G | c.27C>G | p.F9L |
| CCDS3691.1 | ENPEP | Breast | HCC1395 | g.chr4:111838424G>C | c.2660G>C | p.R887T |
| CCDS3702.1 | ANK2 | Breast | Hs 578T | g.chr4:114561607G>A | c.2054G>A | p.G685E |
| CCDS3702.1 | ANK2 | Colorectal | Mx38 | g.chr4:114617988G>A | c.3799G>A | p.G1267R |
| CCDS3702.1 | ANK2 | Colorectal | Co74 | g.chr4:114843888C>A | c.10958C>A | p.T3653K |
| CCDS3708.1 | NDST3 | Colorectal | Mx27 | g.chr4:119333460T>G | c.792T>G | p.H264Q |
| CCDS3759.1 | GAB1 | Breast | BB22T | g.chr4:144594410A>G | c.248A>G | p.Y83C |
| CCDS3759.1 | GAB1 | Breast | HCC1954 | g.chr4:144717323C>A | c.1160C>A | p.T387N |
| CCDS3763.1 | HSH1N1 | Breast | Hs 578T | g.chr4:148431394A>G | IVS5-2A>G | sp |
| CCDS3768.1 | EDNRA | Breast | Hs 578T | g.chr4:148764844A>C | c.406A>C | p.I136L |
| CCDS3772.1 | NR3C2 | Colorectal | Mx30 | g.chr4:149715597C>A | c.21C>A | p.H7Q |
| CCDS3773.1 | LRBA | Breast | BB34T | g.chr4:151869582G>T | c.6114G>T | p.Q2038H |
| CCDS3773.1 | LRBA | Breast | BB22T | g.chr4:151715615G>C | c.6820G>C | p.G2274R |
| CCDS3773.1 | LRBA | Breast | HCC2157 | g.chr4:151584740C>A (homozygous) | c.8102C>A | p.T2701K |
| CCDS3777.1 | FBXW7 | Colorectal | Co74 | g.chr4:153690260C>T | c.292C>T | p.Q98X |
| CCDS3777.1 | FBXW7 | Colorectal | Hx174 | g.chr4:153606989G>A | c.1394G>A | p.R465H |
| CCDS3777.1 | FBXW7 | Colorectal | Hx190 | g.chr4:153804893G>T | c.1514G>T | p.R505L |
| CCDS3777.1 | FBXW7 | Colorectal | Hx218 | g.chr4:153603051C>T (homozygous) | c.1745C>T | p.S582L |
| CCDS3800.1 | ETFDH | Colorectal | Co74 | g.chr4:159976452_159976485dupTTGTGGTAAGTTAT | c.968_IVS8+9dupTTGTGGTAAGTTAT | fs |
| CCDS3800.1 | ETFDH | Colorectal | Mx30 | g.chr4:159997123G>C | c.1693G>C | p.V565L |
| CCDS3802.1 | F6TL5 | Colorectal | Mx43 | g.chr4:163199296C>A (homozygous) | c.274C>A | p.L92I |
| CCDS3810.1 | CPE | Colorectal | Mx43 | g.chr4:166763276G>A (homozygous) | c.890G>A | p.R297Q |
| CCDS3811.1 | TLL1 | Breast | HCC1937 | g.chr4:167444494C>G | c.2062C>G | p.L688V |
| CCDS3820.1 | FBXO8 | Breast | HCC1599 | g.chr4:175533448C>A | c.605C>A | p.L269I |

| | | | | | | |
|---|---|---|---|---|---|---|
| CCDS4407.1 | HK3 | Breast | HCC1008 | g.chr5:176247162C>T (homozygous) | c.1496C>T | p.A499V |
| CCDS4420.1 | DBN1 | Breast | HCC1395 | g.chr5:176820163G>T | IVS9-1G>T | sp |
| CCDS4420.1 | DBN1 | Breast | HCC1395 | g.chr5:176820162G>A | c.832G>A | p.E278K |
| CCDS4420.1 | DBN1 | Breast | BB16T | g.chr5:176817072G>C | c.1918G>C | p.E640Q |
| CCDS4422.1 | PDLIM7 | Breast | HCC2157 | g.chr5:176843275G>C | c.1350G>C | p.K450N |
| CCDS4433.1 | GMCL1L | Breast | HCC1187 | g.chr5:177546106delA (homozygous) | c.741delA | fs |
| CCDS4433.1 | GMCL1L | Colorectal | Co108 | g.chr5:177546083T>C | c.824T>C | p.V275A |
| CCDS4442.1 | GRM6 | Breast | HCC1008 | g.chr5:176351623C>T | c.572C>T | p.S191F |
| CCDS4445.1 | RUFY1 | Breast | HCC1008 | g.chr5:176929004G>T | c.476G>T | p.C159F |
| CCDS4450.1 | KIAA0678 | Breast | HCC1008 | g.chr5:179223550C>A | c.3206C>A | p.P1069Q |
| CCDS4477.1 | SERPINB1 | Breast | BB5T | g.chr6:2785685_2785685dupG | c.137_dupG | fs |
| CCDS4477.1 | SERPINB1 | Breast | HCC1395 | g.chr6:2779246G>C | IVS5-1G>C | sp |
| CCDS4483.1 | MGC8685 | Colorectal | Co108 | g.chr6:3171485C>T | c.184C>T | p.R62W |
| CCDS4486.1 | C6orf145 | Breast | HCC1395 | g.chr6:3888941G>C | c.607G>C | p.E203Q |
| CCDS4488.1 | PRPF4B | Breast | HCC2218 | g.chr6:3994787C>G | c.1974C>G | p.F658L |
| CCDS4488.1 | PRPF4B | Breast | BB12T | g.chr6:3994317G>A | c.2004G>A | p.W688X |
| CCDS4503.1 | BMP6 | Colorectal | Co74 | g.chr6:7807554C>A | c.1028C>A | p.A343D |
| CCDS4503.1 | BMP6 | Colorectal | Mx42 | g.chr6:7825480C>T | c.1427C>T | p.P476L |
| CCDS4531.1 | RNF182 | Colorectal | Mx41 | g.chr6:14083457T>C | c.128T>C | p.V43A |
| CCDS4531.1 | RNF182 | Colorectal | Mx42 | g.chr6:14085502C>T | c.173C>T | p.P58L |
| CCDS4566.1 | HIST1H1E | Colorectal | Mx32 | g.chr6:26264980C>T | c.383C>T | p.A128V |
| CCDS4629.1 | HIST1H2BM | Colorectal | Mx32 | g.chr6:27891129C>T | c.328C>T | p.H110Y |
| CCDS4635.1 | HIST1H1B | Colorectal | Hx219 | g.chr6:27843208A>T | c.79A>T | p.K27X |
| CCDS4635.1 | HIST1H1B | Colorectal | Mx43 | g.chr6:27843030G>A | c.257G>A | p.G86D |
| CCDS4637.1 | HIST1H4L | Breast | HCC1599 | g.chr6:27949078G>C | c.190G>C | p.E64Q |
| CCDS4644.1 | ZNF435 | Colorectal | Mx43 | g.chr6:28202562G>A | c.410G>A | p.R137Q |
| CCDS4858.1 | OR12D3 | Breast | HCC1395 | g.chr6:29450294C>G | c.750C>G | p.F250L |
| CCDS4708.1 | BAT2 | Breast | BB20T | g.chr6:31707889C>T | c.3260C>T | p.T1087I |
| CCDS4708.1 | BAT2 | Breast | HCC1954 | g.chr6:31707684G>A | c.3455G>A | p.R1152H |
| CCDS4709.1 | BAT3 | Breast | HCC1395 | g.chr6:31714884C>G | IVS24+3C>G | UTR |
| CCDS4724.1 | C6orf29 | Colorectal | Co79 | g.chr6:31945392G>A | c.1039G>A | p.A347T |
| CCDS4724.1 | C6orf29 | Colorectal | Co92 | g.chr6:31944912C>T | c.1238C>T | p.T412M |
| CCDS4731.1 | SKIV2L | Breast | HCC1187 | g.chr6:32036799C>G | c.547C>G | p.L183V |
| CCDS4731.1 | SKIV2L | Colorectal | Co74 | g.chr6:32042557G>A | c.2295G>A | p.M765I |
| CCDS4739.1 | C6orf31 | Breast | HCC1187 | g.chr6:32228401G>A | c.280G>A | p.A94T |
| CCDS4769.1 | HSD17B8 | Breast | HCC1187 | g.chr6:33281286G>T | c.472G>T | p.V158L |
| CCDS4818.1 | MAPK13 | Breast | HCC1937 | g.chr6:36214738G>T | c.946G>T | p.E316X |
| CCDS4838.1 | DNAH8 | Colorectal | Co92 | g.chr6:38948760C>T | c.6677C>T | p.T2226M |
| CCDS4844.1 | C6orf102 | Breast | HCC2218 | g.chr6:39853834C>A | c.1157C>A | p.A386E |
| CCDS4851.1 | TREML1 | Breast | HCC1143 | g.chr6:41229689C>G | c.16C>G | p.L6V |
| CCDS4854.1 | TREM1 | Breast | HCC2157 | g.chr6:41358228C>A | c.289C>A | p.R97S |
| CCDS4858.1 | FOXP4 | Breast | HCC1143 | g.chr6:41666019G>A | c.1351G>A | p.A451T |
| CCDS4895.1 | ZNF318 | Breast | BB13T | g.chr6:43430815A>G | c.1895A>G | p.N632S |
| CCDS4895.1 | ZNF318 | Breast | HCC1395 | g.chr6:43415894G>C | c.3280G>C | p.G1094R |
| CCDS4902.1 | POLH | Breast | HCC1395 | g.chr6:43863172G>A | c.458G>A | p.G153D |
| CCDS4908.1 | SLC29A1 | Colorectal | Mx29 | g.chr6:44307725G>A | c.877G>A | p.A293T |
| CCDS4908.1 | SLC29A1 | Colorectal | Mx43 | g.chr6:44309235A>G | c.163A>G | p.H55V |
| CCDS4922.1 | GPR115 | Breast | HCC1143 | g.chr6:47793033C>T | c.2192C>T | p.S731L |
| CCDS4927.1 | RHAG | Breast | HCC1008 | g.chr6:49682819C>T | IVS8+3C>T | sp |
| CCDS4933.1 | TFAP2D | Breast | HCC2218 | g.chr6:50804580G>T | c.640G>T | p.V214F |
| CCDS4935.1 | PKHD1 | Colorectal | Mx22 | g.chr6:52056009G>A | c.58G>A | p.R19H |
| CCDS4935.1 | PKHD1 | Colorectal | Hx5 | g.chr6:52005910C>T | c.3241C>T | p.R1081C |
| CCDS4935.1 | PKHD1 | Colorectal | Mx31 | g.chr6:52005064T>G | c.3287T>G | p.L1096R |
| CCDS4935.1 | PKHD1 | Colorectal | Hx206 | g.chr6:51997697C>T | c.4870C>T | p.R1624W |
| CCDS4935.1 | PKHD1 | Colorectal | Hx169 | g.chr6:51980351G>A | c.5416G>A | p.E1806K |
| CCDS4957.1 | UNQ9358 | Breast | HCC1395 | g.chr6:55324222G>C | c.583G>C | p.D195H |
| CCDS4970.1 | COL19A1 | Breast | BB32T | g.chr6:70600859G>A | c.1082G>A | p.G361D |
| CCDS4970.1 | COL19A1 | Breast | HCC1395 | g.chr6:70656769G>C | c.3057G>C | p.K1019N |
| CCDS4975.1 | KCNQ5 | Colorectal | Mx32 | g.chr6:73808461T>G | c.571T>G | p.W191G |
| CCDS4976.1 | KCNQ5 | Colorectal | Mx34 | g.chr6:73843879C>T | c.730C>T | p.R244C |
| CCDS4982.1 | CD109 | Colorectal | Hx218 | g.chr6:74573346C>G | c.3019C>G | p.Q1007E |
| CCDS4982.1 | CD109 | Colorectal | Mx38 | g.chr6:74574532C>A | c.3195C>A | p.N1065K |
| CCDS4987.1 | PHIP | Colorectal | Mx41 | g.chr6:79781837G>A | c.1405G>A | p.V469I |
| CCDS4987.1 | PHIP | Colorectal | Co79 | g.chr6:79707295G>T | c.5300G>T | p.R1767I |
| CCDS4996.1 | KIAA1117 | Breast | HCC2157 | g.chr6:83903943C>C | c.3463G>C | p.D1155H |
| CCDS5000.1 | NCB5OR | Breast | HCC1187 | g.chr6:84708496G>T | c.1009G>T | p.D337Y |
| CCDS5000.1 | NCB5OR | Breast | BB38T | g.chr6:84708863C>A | c.1168C>A | p.L390M |
| CCDS5031.1 | EPHA7 | Colorectal | Mx27 | g.chr6:94123389C>T | c.1111C>T | p.R371W |
| CCDS5032.1 | MANEA | Breast | HCC2157 | g.chr6:66160605A>G | c.992A>G | p.Y331C |
| CCDS5048.1 | GRIK2 | Breast | HCC1008 | g.chr6:102231208G>C | c.559G>C | p.E187Q |
| CCDS5055.1 | APG5L | Colorectal | Mx42 | g.chr6:106862985A>T | c.173A>T | p.K58M |
| CCDS5076.1 | MICAL1 | Breast | HCC1395 | g.chr6:109879504C>A | c.925C>A | p.L309M |
| CCDS5076.1 | MICAL1 | Breast | HCC1599 | g.chr6:109875337G>C | IVS14-1G>C | sp |
| CCDS5082.1 | DDO | Breast | HCC2218 | g.chr6:110632604C>G | c.408C>G | p.F136L |
| CCDS5091.1 | REV3L | Colorectal | Mx27 | g.chr6:111803854_111803854dupT | c.2163_dupT | fs |
| CCDS5111.1 | KPNA5 | Breast | HCC2218 | g.chr6:117119919C>G | c.144C>G | p.F48L |
| CCDS5111.1 | KPNA5 | Breast | BB5T | g.chr6:117152189G>T | c.957G>T | p.R319S |
| CCDS5119.1 | C6orf204 | Breast | HCC1008 | g.chr6:118919630C>T | c.1043C>T | p.S348F |
| CCDS5138.1 | LAMA2 | Breast | HCC1599 | g.chr6:129077559C>G | c.3478C>G | p.P1160A |
| CCDS5163.1 | EYA4 | Colorectal | Co74 | g.chr6:133825183T>G | c.455T>G | p.L152R |
| CCDS5165.1 | EYA4 | Colorectal | Mx29 | g.chr6:133831493G>A | c.901G>A | p.D301N |
| CCDS5208.1 | FBXO30 | Colorectal | Co74 | g.chr6:146169212C>G | c.23C>G | p.S8C |
| CCDS5209.1 | GRM1 | Colorectal | Mx41 | g.chr6:146761954C>T | c.2086C>T | p.R696W |
| CCDS5228.1 | MTHFD1L | Colorectal | Mx27 | g.chr6:151350128T>G | c.1331T>G | p.L444R |
| CCDS5229.1 | AKAP12 | Colorectal | Co92 | g.chr6:151762358G>A | c.718G>A | p.E240K |
| CCDS5229.1 | AKAP12 | Colorectal | Mx28 | g.chr6:151765620A>C (homozygous) | c.3980A>C | p.K1327T |
| CCDS5236.1 | SYNE1 | Colorectal | Mx43 | g.chr6:152786609G>A | c.11011G>A | p.V3671M |
| CCDS5236.1 | SYNE1 | Colorectal | Co82 | g.chr6:152747421A>C | c.12630A>C | p.E4210D |
| CCDS5236.1 | SYNE1 | Colorectal | Mx32 | g.chr6:152747363G>A | c.12668G>A | p.R4223H |
| CCDS5236.1 | SYNE1 | Colorectal | Co74 | g.chr6:152731382T>G | c.16520T>G | p.L5507R |
| CCDS5237.1 | SYNE1 | Colorectal | Mx41 | g.chr6:152551254G>A | c.8975G>A | p.R2992H |

FIG. 12G

| | | | | | | |
|---|---|---|---|---|---|---|
| CCDS5248.1 | MAGI1 | Breast | HCC1008 | g.chr6:154848733_154848711delGAGGATAAAGTTTTAACTGTGGT | c.529_551delGAGGATAAAGTTTTAACTGTGGT | fs |
| CCDS5251.1 | ARID1B | Breast | HCC1395 | g.chr6:157546383G>C | c.2267G>C | p.G758A |
| CCDS5268.1 | TCP1 | Breast | HCC1008 | g.chr6:160180853G>C | c.19G>C | p.V7L |
| CCDS5278.1 | GLC22A2 | Breast | HCC2218 | g.chr6:160642148C>T | IVS2-3C>T | sp |
| CCDS5285.1 | QKI | Colorectal | Co92 | g.chr6:163958236G>A | c.1007G>A | p.R336Q |
| CCDS5331.1 | GNX8 | Colorectal | Co74 | g.chr7:2084826C>G | c.440C>G | p.A147G |
| CCDS5352.1 | ZDHHC4 | Breast | HCC1954 | g.chr7:6395082C>T | c.310C>T | p.P104S |
| CCDS5358.1 | RPA3 | Colorectal | Mx38 | g.chr7:7451964G>T | c.151G>T | p.G51X |
| CCDS5388.1 | FERD3L | Colorectal | Co92 | g.chr7:19058120G>A | c.106G>A | p.G36R |
| CCDS5371.1 | ABCB5 | Colorectal | Mx43 | g.chr7:20511283A>T | c.689A>T | p.E230V |
| CCDS5380.1 | GPNMB | Breast | BB27T | g.chr7:23067133C>A | c.329C>A | p.A110D |
| CCDS5380.1 | GPNMB | Breast | HCC1187 | g.chr7:23088856G>T | c.1556G>T | p.S519I |
| CCDS5404.1 | HOXA3 | Breast | HCC2218 | g.chr7:26923378G>A | c.124G>A | p.D42N |
| CCDS5404.1 | HOXA3 | Breast | BB26T | g.chr7:26923109G>A | c.391G>A | p.A131T |
| CCDS5405.1 | HOXA4 | Breast | HCC1395 | g.chr7:26943483G>A | c.110G>A | p.G37D |
| CCDS5415.1 | TAX1BP1 | Breast | HCC2218 | g.chr7:27806031A>G | c.1370A>G | p.Q457R |
| CCDS5424.1 | PLEKHA8 | Breast | HCC2713 | g.chr7:26885561G>A | IVS8-4G>A | sp |
| CCDS5424.1 | PLEKHA8 | Breast | HCC1008 | g.chr7:29874757T>A | c.1103T>A | p.V368E |
| CCDS5432.1 | GHRHR | Colorectal | Mx41 | g.chr7:30781764G>A | c.133G>A | p.A45T |
| CCDS5435.1 | LOC223075 | Colorectal | Co74 | g.chr7:31394960T>G | c.313T>G | p.L105V |
| CCDS5452.1 | TXNDC3 | Breast | HCC2157 | g.chr7:37689721T>C | c.860T>C | p.I289T |
| CCDS5463.1 | C7orf11 | Breast | HCC2218 | g.chr7:39947321G>A | c.86G>A | p.G29E |
| CCDS5465.1 | GLI3 | Colorectal | Co74 | g.chr7:41881503C>T | c.506C>T | p.P169L |
| CCDS5465.1 | GLI3 | Colorectal | Co84 | g.chr7:41778001T>C | c.3910T>C | p.S1304P |
| CCDS5467.1 | PSMA2 | Colorectal | Mx41 | g.chr7:42737560C>G | c.328C>G | p.L110V |
| CCDS5505.1 | IGFBP3 | Colorectal | Mx27 | g.chr7:45733960C>T | c.20C>T | p.T7M |
| CCDS5505.1 | IGFBP3 | Colorectal | Hx218 | g.chr7:45727781C>T | c.754C>T | p.R252C |
| CCDS5531.1 | ASL | Breast | HCC1037 | g.chr7:64985898C>G | c.542C>G | p.T181S |
| CCDS5531.1 | ASL | Breast | BB12T | g.chr7:64995955G>T | c.599G>T | p.G200V |
| CCDS5549.1 | BAZ1B | Breast | HCC1395 | g.chr7:72328817C>G | c.2747C>G | p.S918X |
| CCDS5590.1 | SEMA3A | Breast | HCC1954 | g.chr7:83384499G>A | c.391G>A | p.A131T |
| CCDS5608.1 | ABC81 | Colorectal | Mx41 | g.chr7:88805285G>T | c.2661G>T | p.K887N |
| CCDS5622.1 | AKAP9 | Colorectal | Co108 | g.chr7:91335299_91335300insGTCC | c.5678_5677insGTCC | fs |
| CCDS5622.1 | AKAP9 | Breast | BB5T | g.chr7:91344028_91344028dupA | c.6384_dupA | fs |
| CCDS5622.1 | AKAP9 | Colorectal | Mx41 | g.chr7:91353325G>T | c.7227G>T | p.M2409I |
| CCDS5622.1 | AKAP9 | Breast | HCC1008 | g.chr7:91370813G>C | c.9889G>C | p.E3297Q |
| CCDS5829.1 | LOC253012 | Breast | HCC1954 | g.chr7:92493404G>A | c.55G>A | p.G19R |
| CCDS5889.1 | GPC2 | Breast | HCC2218 | g.chr7:99417896G>A (homozygous) | c.598G>A | p.D200N |
| CCDS5895.1 | THG-1 | Breast | HCC1954 | g.chr7:99709436G>A | c.985G>A | p.V329M |
| CCDS5716.1 | ZNHIT1 | Colorectal | Mx42 | g.chr7:100460515C>T | c.400C>T | p.R134W |
| CCDS5720.1 | CUTL1 | Breast | HCC2157 | g.chr7:101511970A>G | c.1458A>G | p.S490G |
| CCDS5720.1 | CUTL1 | Colorectal | Mx41 | g.chr7:101518570C>T | c.1825C>T | p.R609C |
| CCDS5737.1 | PBEF1 | Colorectal | Co92 | g.chr7:105503630T>C | c.527T>C | p.L176S |
| CCDS5751.1 | NRCAM | Breast | BB23T | g.chr7:107393895C>A | c.3278C>A | p.P1093H |
| CCDS5751.1 | NRCAM | Breast | HCC1143 | g.chr7:107384511G>T | c.3347G>T | p.G1116V |
| CCDS5755.1 | ZNF277 | Breast | HCC1937 | g.chr7:111573878A>T | c.958A>T | p.I320L |
| CCDS5755.1 | ZNF277 | Breast | HCC1395 | g.chr7:111576717G>C | c.1299G>C | p.L433F |
| CCDS5759.1 | PPP1R3A | Breast | HCC1143 | g.chr7:113113437G>C | c.1661G>C | p.G554A |
| CCDS5760.1 | FOXP2 | Breast | HCC1599 | g.chr7:113883859C>T | c.445C>T | p.Q149X |
| CCDS5762.1 | TFEC | Colorectal | Mx42 | g.chr7:115188594C>G | c.438C>G | p.L146V |
| CCDS5771.1 | WNT2 | Breast | HCC1599 | g.chr7:116512381_116512338delCAACCTGACTTCCCGGGGCATGGA | c.882_905delCAACCTGACTTCCCGGGGCATGGA | Indel |
| CCDS5780.1 | WNT16 | Colorectal | Mx38 | g.chr7:120585712G>A | c.346G>A | p.V115M |
| CCDS5787.1 | FLJ35934 | Colorectal | Co108 | g.chr7:122888920G>A | c.2204G>A | p.R735H |
| CCDS5789.1 | LRRC4 | Breast | HCC1008 | g.chr7:127264047_127264036delTATCTGAACTTG | c.598_609delTATCTGAACTTG | p.Y200_L203del |
| CCDS5789.1 | LRRC4 | Colorectal | Mx42 | g.chr7:127282910A>G | c.1735A>G | p.T579A |
| CCDS5829.1 | SEC8L1 | Colorectal | Hx172 | g.chr7:132459295C>T | c.859C>T | p.S220F |
| CCDS5829.1 | SEC8L1 | Colorectal | Co84 | g.chr7:133037887G>A | c.1795G>A | p.A599T |
| CCDS5829.1 | SEC8L1 | Colorectal | Mx38 | g.chr7:133059608_133059626delAAGAAAAACTTGTCATCAG | c.1889_1907delAAGAAAAACTTGTCATCAG | fs |
| CCDS5837.1 | FLJ11000 | Colorectal | Mx42 | g.chr7:134306783C>A | c.335C>A | p.A112E |
| CCDS5838.1 | MGC5242 | Colorectal | Mx27 | g.chr7:134308847C>T | c.161C>T | p.P54L |
| CCDS5855.1 | TBXAS1 | Breast | HCC1187 | g.chr7:139064224C>T | c.256C>T | p.R86W |
| CCDS5883.1 | BRAF | Colorectal | Co108 | g.chr7:139906320T>A | c.1799T>A | p.V600E |
| CCDS5885.1 | MULK | Breast | HCC1008 | g.chr7:140794328_140794345delCTTTGTACAGGAGAATATTA | c.821_840delCTTTGTACAGGAGAATATTA | fs |
| CCDS5872.1 | PRSS1 | Colorectal | Mx42 | g.chr7:141946123C>T | c.410C>T | p.T137M |
| CCDS5873.1 | EPHB6 | Colorectal | Co108 | g.chr7:142080198G>A | c.1033G>A | p.D345N |
| CCDS5873.1 | EPHB6 | Colorectal | Hx169 | g.chr7:142082259G>C | c.1782G>C | p.A583P |
| CCDS5873.1 | EPHB6 | Colorectal | Mx3 | g.chr7:142083204G>A | c.2111G>A | p.R704Q |
| CCDS5873.1 | EPHB6 | Colorectal | Mx43 | g.chr7:142084985A>G | c.2744A>G | p.D915G |
| CCDS5881.1 | CLCN1 | Breast | HCC1937 | g.chr7:142555918G>A | c.1642G>A | p.E548K |
| CCDS5891.1 | EZH2 | Colorectal | Mx42 | g.chr7:147951992_147951891dupTA | c.1380_1381dupTA | fs |
| CCDS5897.1 | FLJ31413 | Breast | HCC1008 | g.chr7:148609590_148609588delAGC | c.1468_1470delAGC | p.S490del |
| CCDS5906.1 | GIMAP1 | Breast | HCC1599 | g.chr7:149855237T>A | c.4877T>A | p.V186E |
| CCDS5912.1 | NOS3 | Colorectal | Hx190 | g.chr7:150138153C>T | c.1420C>T | p.R474C |
| CCDS5912.1 | NOS3 | Colorectal | Co108 | g.chr7:150141215G>A | c.1805G>A | p.R502Q |
| CCDS5913.1 | ABCB8 | Breast | BB16T | g.chr7:150169042T>C | c.443T>C | p.I148T |
| CCDS5913.1 | ABCB8 | Breast | HCC1187 | g.chr7:150179645C>G | c.2018C>G | p.A673G |
| CCDS5927.1 | RHEB | Colorectal | Mx22 | g.chr7:150605352G>A | c.415G>A | p.E139K |
| CCDS5931.1 | MLL3 | Colorectal | Mx6 | g.chr7:151399916T>G | c.1039T>G | p.C347G |
| CCDS5931.1 | MLL3 | Colorectal | Co82 | g.chr7:151397850G>A | c.1198G>A | p.D400N |
| CCDS5931.1 | MLL3 | Colorectal | Co79 | g.chr7:151387315T>G | c.1433T>G | p.L478W |
| CCDS5931.1 | MLL3 | Colorectal | Mx26 | g.chr7:151339989_151339930delTTTTTGGATAGGTATTGGTGGATTT ATGGTGCGGCAAAGA | IVS24-11_3870delTTTTTGGATAGGTATTGGTGGATTTA TGGTGCGGCAAAGA | fs |
| CCDS5931.1 | MLL3 | Colorectal | Hx169 | g.chr7:151318877C>T | c.571BC>T | p.R1906X |
| CCDS5931.1 | MLL3 | Colorectal | Co74 | g.chr7:151297218A>T | c.11092A>T | p.T3698S |
| CCDS5938.1 | HTR3A | Colorectal | Co92 | g.chr7:154313555C>T | c.784C>T | p.R262C |
| CCDS5947.1 | PTPRN2 | Colorectal | Mx32 | g.chr7:156948575G>A | c.2148G>A | p.E716K |
| CCDS5953.1 | LOC157697 | Colorectal | Mx41 | g.chr8:6326185G>T | IVS2-4G>T | sp |
| CCDS5955.1 | LOC157697 | Colorectal | Co79 | g.chr8:6087630C>T | c.1093C>T | p.L365F |
| CCDS5961.1 | DEFA4 | Colorectal | Co92 | g.chr8:6781025G>A | c.221G>A | p.R74Q |

| | | | | | | |
|---|---|---|---|---|---|---|
| CCDS7010.1 | AEGP | Breast | BB21T | g.chr9:137030264C>T | c.3263C>T | p.R1095W |
| CCDS7034.1 | SSNA1 | Breast | HCC2218 | g.chr9:137359068G>C | c.51G>C | p.K17N |
| CCDS7050.1 | EHMT1 | Breast | BB13T | g.chr9:137886957C>T | c.35C>T | p.A12V |
| CCDS7050.1 | EHMT1 | Breast | HCC2218 | g.chr9:137988405A>T | c.3425A>T | p.Y1142F |
| CCDS7050.1 | KIAA0934 | Breast | BB27T | g.chr10:435084_435083insAGCACAGCTTGCTTTGGGGTCAAACGTGGATCAGCAGCCTCTTGGTCAGTAAA | c.1225_1226insAGCACAGCTTGCTTTGGGGTCAAACGTGGATCAGCAGCCTCTTGGTCAGTAAA | fs |
| CCDS7054.1 | KIAA0934 | Breast | HCC1599 | g.chr10:420086C>A | c.1757C>A | p.A586E |
| CCDS7054.1 | KIAA0934 | Colorectal | Mx32 | g.chr10:419979G>A | c.1864G>A | p.G622S |
| CCDS7054.1 | KIAA0934 | Breast | BB12T | g.chr10:398392delT | c.2632delT | fs |
| CCDS7054.1 | KIAA0934 | Breast | HCC1187 | g.chr10:363080G>A | c.3790G>A | p.V1264M |
| CCDS7058.1 | ADARB2 | Colorectal | Hx206 | g.chr10:1395871C>T | c.629C>T | p.T210M |
| CCDS7058.1 | ADARB2 | Colorectal | Co108 | g.chr10:12530390>A | c.1534G>A | p.V512I |
| CCDS7067.1 | NET1 | Breast | HCC1143 | g.chr10:54852220>A | c.442G>A | p.D148N |
| CCDS7099.1 | C10orf30 | Breast | HCC1395 | g.chr10:135830300G>C | c.782G>C | p.R261T |
| CCDS7102.1 | C10orf45 | Breast | HCC 38 | g.chr10:147486570>C (homozygous) | c.451G>C | p.E151Q |
| CCDS7103.1 | HSPA14 | Breast | HCC1599 | g.chr10:14930646C>T | c.254C>T | p.A85V |
| CCDS7104.1 | SUV39H2 | Breast | HCC2157 | g.chr10:14984431G>C | c.967G>C | p.D323H |
| CCDS7113.1 | CUBN | Breast | BB23T | g.chr10:17153920C>A | c.2358C>A | p.H786Q |
| CCDS7113.1 | CUBN | Breast | HCC2157 | g.chr10:17147645A>C | IVS21-2A>C | sp |
| CCDS7113.1 | CUBN | Colorectal | Mx43 | g.chr10:17002034C>T | c.6755C>T | p.A2252V |
| CCDS7113.1 | CUBN | Breast | BB29T | g.chr10:16972390C>T | c.8741C>T | p.A2914V |
| CCDS7113.1 | CUBN | Breast | BB13T | g.chr10:16933338A>G | c.9565A>G | p.I3189V |
| CCDS7120.1 | VIM | Colorectal | Mx30 | g.chr10:17311988G>T | c.559G>T | p.E187X |
| CCDS7122.1 | STAM | Colorectal | Mx32 | g.chr10:17777153G>A | c.635G>A | p.G212D |
| CCDS7124.1 | SLC39A12 | Breast | HCC1937 | g.chr10:18320227C>A | c.1411C>A | p.P471T |
| CCDS7125.1 | CACNB2 | Colorectal | Co74 | g.chr10:18730941C>G | c.296C>G | p.A99G |
| CCDS7139.1 | SPAG6 | Breast | HCC1599 | g.chr10:22697457G>T | c.319G>T | p.V108L |
| CCDS7159.1 | WAC | Colorectal | Co108 | g.chr10:28940844C>T | c.1424C>T | p.S475L |
| CCDS7168.1 | LOC220929 | Breast | HCC1143 | g.chr10:31178197G>C | c.1143G>C | p.K381N |
| CCDS7191.1 | CX40.1 | Colorectal | Hx218 | g.chr10:35937253G>A | c.806G>A | p.R269H |
| CCDS7191.1 | CX40.1 | Colorectal | Co108 | g.chr10:35937258G>A | c.811G>A | p.G271R |
| CCDS7193.1 | ANKRD30A | Breast | HCC1954 | g.chr10:37462911C>G | c.511C>G | p.Q171E |
| CCDS7195.1 | ZNF25 | Breast | HCC1143 | g.chr10:38286435G>A | c.61G>A | p.E21K |
| CCDS7195.1 | ZNF25 | Breast | HCC2157 | g.chr10:38286688A>G | c.242A>G | p.D81G |
| CCDS7200.1 | RET | Colorectal | Mx3 | g.chr10:42917892T>G | c.434T>G | p.V145G |
| CCDS7200.1 | RET | Colorectal | Hx218 | g.chr10:42924499C>T | c.1076C>T | p.R360W |
| CCDS7200.1 | RET | Colorectal | Mx41 | g.chr10:42929026G>A | c.1778G>A | p.G593E |
| CCDS7208.1 | RASSF4 | Colorectal | Mx32 | g.chr10:44798066C>T | c.229C>T | p.Q77X |
| CCDS7211.1 | ZNF22 | Breast | HCC1143 | g.chr10:44819208A>T | c.385A>T | p.H129L |
| CCDS7218.1 | RBP3 | Colorectal | Co92 | g.chr10:48009295G>A | c.1589G>A | p.R530H |
| CCDS7222.1 | FRMPD2 | Colorectal | Mx22 | g.chr10:49065328C>T | c.2104C>T | p.R702W |
| CCDS7226.1 | C10orf72 | Colorectal | Mx41 | g.chr10:49985803G>A | c.299G>A | p.R100H |
| CCDS7229.1 | ERCC6 | Colorectal | Mx38 | g.chr10:50371219C>G | c.1771C>G | p.P591A |
| CCDS7229.1 | ERCC6 | Colorectal | Mx3 | g.chr10:50381435G>T | c.1955G>T | p.R652L |
| CCDS7229.1 | ERCC6 | Breast | HCC2218 | g.chr10:50348899G>C | c.3113G>C | p.R1038T |
| CCDS7229.1 | ERCC6 | Breast | HCC2218 | g.chr10:50348857G>C | c.3355G>C | p.E1119Q |
| CCDS7229.1 | ERCC6 | Breast | HCC2218 | g.chr10:50348856A>T | c.3356A>T | p.E1119V |
| CCDS7230.1 | PGBD3 | Breast | HCC1143 | g.chr10:50393923A>G | c.1244A>G | p.D415G |
| CCDS7262.1 | CCAR1 | Colorectal | Mx22 | g.chr10:70186229G>A | c.1819G>A | p.E607K |
| CCDS7296.1 | PP | Breast | HCC1143 | g.chr10:71846532A>C | c.171A>C | p.K57N |
| CCDS7304.1 | NODAL | Colorectal | Mx38 | g.chr10:71865104G>A | c.835G>A | p.E279K |
| CCDS7305.1 | PRF1 | Colorectal | Mx38 | g.chr10:72030297G>A | c.368G>A | p.R123H |
| CCDS7329.1 | USP54 | Breast | HCC1008 | g.chr10:74946568C>G | c.886C>G | p.L296V |
| CCDS7343.1 | MYST4 | Breast | HCC1008 | g.chr10:78405548A>G (homozygous) | c.1447A>G | p.T483A |
| CCDS7357.1 | RAI17 | Breast | HCC2218 | g.chr10:80726328C>G | c.1651C>G | p.L551V |
| CCDS7359.1 | C10orf56 | Breast | HCC1599 | g.chr10:80816108G>C | c.725G>C | p.X242S |
| CCDS7378.1 | MMRN2 | Colorectal | Mx32 | g.chr10:88693179G>A | c.1342G>A | p.V448M |
| CCDS7386.1 | ATAD1 | Colorectal | Co108 | g.chr10:89540110G>A | c.319G>A | p.V107I |
| CCDS7426.1 | CYP26A1 | Breast | HCC1008 | g.chr10:94824611G>A | c.500G>A | p.W167X |
| CCDS7442.1 | SORBS1 | Breast | HCC1954 | g.chr10:97164372G>A | c.583G>A | p.A105T |
| CCDS7470.1 | AVPI1 | Breast | HCC1187 | g.chr10:99429558C>T (homozygous) | c.94C>T | p.Q32X |
| CCDS7483.1 | CUTC | Breast | HCC1954 | g.chr10:101492938C>T | c.230C>T | p.P77L |
| CCDS7494.1 | WNT8B | Colorectal | Co74 | g.chr10:102229675G>C | c.157G>C | p.E53Q |
| CCDS7501.1 | SEMA4G | Breast | HCC1143 | g.chr10:102729808C>T | c.1168C>T | p.H333Y |
| CCDS7507.1 | LZT82 | Colorectal | Mx30 | g.chr10:102752647G>A | c.362G>A | p.R121H |
| CCDS7507.1 | LZTS2 | Breast | HCC1954 | g.chr10:102753718G>C | c.871G>C | p.G291R |
| CCDS7528.1 | LDB1 | Colorectal | Co92 | g.chr10:103858885G>A | c.788G>A | p.R263Q |
| CCDS7545.1 | INA | Breast | HCC1008 | g.chr10:105027288G>C | c.328G>C | p.E110Q |
| CCDS7559.1 | SORCS1 | Breast | HCC1187 | g.chr10:108579378A>C | c.669A>C | p.K223N |
| CCDS7581.1 | ADD3 | Colorectal | Co92 | g.chr10:111882095C>G | c.1775C>G | p.S592X |
| CCDS7587.1 | PDCD4 | Breast | HCC1008 | g.chr10:112632762C>G | c.358C>G | p.G120R |
| CCDS7572.1 | ACSL5 | Colorectal | Mx42 | g.chr10:114168715A>G | c.1331A>G | p.K444R |
| CCDS7572.1 | ACSL5 | Colorectal | Hx185 | g.chr10:114187604G>A (homozygous) | c.1397G>A | p.G466D |
| CCDS7576.1 | TCF7L2 | Colorectal | Co82 | g.chr10:114907768A>G | IVS10-2A>G | sp |
| CCDS7576.1 | TCF7L2 | Colorectal | Hx172 | g.chr10:114907769C>C (homozygous) | IVS10-1C>C | sp |
| CCDS7576.1 | TCF7L2 | Colorectal | Mx41 | g.chr10:114915323C>T | c.1393C>T | p.R465C |
| CCDS7589.1 | AMACO | Colorectal | Mx41 | g.chr10:118022527T>G | c.410T>G | p.L137R |
| CCDS7590.1 | ABLIM1 | Breast | HCC 38 | g.chr10:116351713C>T | IVS1-3C>T | sp |
| CCDS7595.1 | PNLIPRP1 | Breast | HCC1008 | g.chr10:118344287C>G | c.388C>G | p.S129C |
| CCDS7620.1 | FGFR2 | Breast | HCC1143 | g.chr10:123300811C>T | c.607C>T | p.R203C |
| CCDS7626.1 | TACC2 | Breast | BB4T | g.chr10:123834397C>G | c.2392C>G | p.L798V |
| CCDS7626.1 | TACC2 | Breast | HCC1599 | g.chr10:123836044G>T | c.4039G>T | p.A1347S |
| CCDS7646.1 | C10orf137 | Colorectal | Co74 | g.chr10:127399788A>G | c.134A>G | p.N45S |
| CCDS7646.1 | C10orf137 | Colorectal | Mx3 | g.chr10:127399937C>T | c.283C>T | p.L95F |
| CCDS7646.1 | C10orf137 | Colorectal | Hx189 | g.chr10:127414442C>G | c.1635C>G | p.Y545X |
| CCDS7649.1 | BCCIP | Breast | HCC2218 | g.chr10:127505166G>T | c.1840>T | p.E62X |
| CCDS7652.1 | DHX32 | Breast | HCC1395 | g.chr10:127538385C>G (homozygous) | c.626C>G | p.P209R |
| CCDS7653.1 | ADAM12 | Breast | HCC1008 | g.chr10:127779650G>C | c.601G>C | p.D201H |
| CCDS7653.1 | ADAM12 | Breast | BB5T | g.chr10:127743547G>A | c.1436G>A | p.G479E |
| CCDS7653.1 | ADAM12 | Breast | HCC1599 | g.chr10:127714887G>T | c.2376G>T | p.L792F |

FIG. 12J

| CCDS ID | Gene | Tissue | Sample | Genomic change | cDNA change | Protein change |
|---|---|---|---|---|---|---|
| CCDS7682.1 | TCERG1L | Colorectal | Mx22 | g.chr10:132805137A>C | c.1187A>C | p.K396T |
| CCDS7684.1 | C10orf39 | Breast | HCC1395 | g.chr10:133828871C>G | c.865C>G | p.R289G |
| CCDS7686.1 | STK32C | Colorectal | Mx32 | g.chr10:133889093delG (homozygous) | c.700delG | fs |
| CCDS7686.1 | STK32C | Colorectal | Co79 | g.chr10:133888259G>A (homozygous) | c.1127G>A | p.R378H |
| CCDS7692.1 | PAOX | Colorectal | Co74 | g.chr10:135093868G>A | c.1406G>A | p.R469H |
| CCDS7721.1 | TM4SF7 | Breast | HCC1395 | g.chr11:852887C>G | c.201C>G | p.I67M |
| CCDS7748.1 | NUP98 | Breast | HCC1143 | g.chr11:3756783C>G | c.251C>G | p.S84X |
| CCDS7748.1 | NUP98 | Breast | HCC1187 | g.chr11:3857478C>T (homozygous) | c.4955G>T | p.G1852V |
| CCDS7764.1 | TRIM3 | Colorectal | Mx43 | g.chr11:6429202C>T | c.1576C>T | p.R526X |
| CCDS7771.1 | DCHS1 | Colorectal | Mx43 | g.chr11:6607654C>T | c.4747C>T | p.R1583W |
| CCDS7778.1 | NALP14 | Breast | HCC2218 | g.chr11:7035528C>G | c.2338C>G | p.S779C |
| CCDS7779.1 | BYT9 | Colorectal | Co74 | g.chr11:7395931G>A | c.1333G>A | p.D445N |
| CCDS7788.1 | RIC3 | Colorectal | Co74 | g.chr11:8088694G>T | c.1034G>T | p.G345V |
| CCDS7802.1 | AMPD3 | Colorectal | Mx38 | g.chr11:10429188T>C (homozygous) | IVS1+2T>C | sp |
| CCDS7808.1 | DKK3 | Breast | HCC1008 | g.chr11:11976888C>G | c.386C>G | p.S129X |
| CCDS7828.1 | MYOD1 | Breast | HCC1008 | g.chr11:17699452G>A | c.784G>A | p.E262K |
| CCDS7828.1 | MYOD1 | Breast | BB13T | g.chr11:17699594C>T | c.926C>T | p.A309V |
| CCDS7854.1 | SLC6A5 | Breast | HCC1395 | g.chr11:20616606T>A | c.1895T>A | p.V632E |
| CCDS7855.1 | NELL1 | Colorectal | Mx27 | g.chr11:21512508G>T | c.1658G>T | p.C553F |
| CCDS7856.1 | SLC17A6 | Breast | HCC1008 | g.chr11:22316681A>T (homozygous) | c.118A>T | p.T40S |
| CCDS7871.1 | FLJ46154 | Colorectal | Mx30 | g.chr11:30581646C>T | c.1706C>T | p.A569V |
| CCDS7873.1 | ZCSL3 | Breast | BB13T | g.chr11:31348938A>G | c.64A>G | p.N22D |
| CCDS7873.1 | ZCSL3 | Breast | HCC1187 | g.chr11:31404458_31404470delTCTTG | c.304_308delTCTTG | fs |
| CCDS7878.1 | RCN1 | Colorectal | Mx43 | g.chr11:32075382T>G | c.351T>G | p.F117L |
| CCDS7880.1 | GA17 | Breast | HCC1143 | g.chr11:32568779A>G | c.239A>G | p.E80G |
| CCDS7907.1 | PHACS | Breast | BB13T | g.chr11:44055978G>A | c.662G>A | p.G221E |
| CCDS7907.1 | PHACS | Breast | HCC2218 | g.chr11:44061361C>T | c.1178C>T | p.S393L |
| CCDS7848.1 | FOLH1 | Colorectal | Mx43 | g.chr11:49188471G>A | c.67G>A | p.A23T |
| CCDS7855.1 | PRG2 | Colorectal | Mx42 | g.chr11:56911878C>T | c.535C>T | p.R179C |
| CCDS7974.1 | OSBP | Colorectal | Co74 | g.chr11:59125877A>C | c.833A>C | p.D278A |
| CCDS7987.1 | MS4A5 | Colorectal | Co92 | g.chr11:59957642T>G | c.368T>G | p.L123R |
| CCDS8034.1 | ZBTB3 | Breast | HCC1143 | g.chr11:62276592A>T | c.1271A>T | p.H424L |
| CCDS8034.1 | ZBTB3 | Breast | HCC1395 | g.chr11:62276499C>T | c.1364C>T | p.S455F |
| CCDS8036.1 | STX5A | Breast | HCC1008 | g.chr11:62351868G>T | c.75G>T | p.Q25H |
| CCDS8043.1 | SLC22A9 | Breast | HCC1937 | g.chr11:62293084BC>T | c.1178C>T | p.A393V |
| CCDS8043.1 | SLC22A9 | Breast | HCC 38 | g.chr11:62932785A>G | c.1459A>G | p.M487V |
| CCDS8043.1 | SLC22A9 | Colorectal | Mx27 | g.chr11:62932889C>A | c.1563C>A | p.N521K |
| CCDS8069.1 | PRDX5 | Breast | HCC1395 | g.chr11:63844643T>C | c.469T>C | p.F157L |
| CCDS8094.1 | ZNHIT2 | Breast | HCC1187 | g.chr11:64841527G>C | c.175G>C | p.A59P |
| CCDS8134.1 | CD248 | Colorectal | Mx41 | g.chr11:85841057G>T | c.16G>T | p.L6F |
| CCDS8134.1 | CD248 | Colorectal | Co79 | g.chr11:85838848_65838848dupC (homozygous) | c.2229_dupG | fs |
| CCDS8150.1 | SPTBN2 | Colorectal | Mx27 | g.chr11:66229003G>A | c.2320G>A | p.E774K |
| CCDS8161.1 | RCE1 | Breast | HCC1143 | g.chr11:66370128C>G | c.976C>G | p.P326A |
| CCDS8164.1 | CORO1B | Colorectal | Mx43 | g.chr11:66962831G>A | c.1231G>A | p.V411M |
| CCDS8164.1 | MTL5 | Breast | HCC2218 | g.chr11:68274512C>T | c.193C>T | p.H65Y |
| CCDS8212.1 | FOLR2 | Breast | HCC1937 | g.chr11:71610392C>A | c.706C>A | p.H236N |
| CCDS8218.1 | PDE2A | Breast | HCC2157 | g.chr11:71980013G>A | c.525G>A | p.W175X |
| CCDS8235.1 | SLCO2B1 | Breast | HCC 38 | g.chr11:74552737G>A | c.229G>A | p.E77K |
| CCDS8278.1 | FZD4 | Colorectal | Mx38 | g.chr11:86340139A>C | c.1307A>C | p.K438T |
| CCDS8281.1 | RAB38 | Colorectal | Co74 | g.chr11:87522642A>C | c.332A>C | p.K111T |
| CCDS8298.1 | MRE11A | Breast | BB7T | g.chr11:93844523T>G | c.710T>G | p.F237C |
| CCDS8298.1 | MRE11A | Breast | HCC2218 | g.chr11:93843398C>T | c.904C>T | p.H302Y |
| CCDS8321.1 | MMP10 | Breast | HCC1008 | g.chr11:102155226G>A | c.424G>C | p.E142Q |
| CCDS8326.1 | PDGFD | Colorectal | Mx41 | g.chr11:103319558G>T | c.586G>T | p.D196Y |
| CCDS8335.1 | GUCY1A2 | Colorectal | Hx218 | g.chr11:106362016C>T | c.355C>T | p.Q119X |
| CCDS8335.1 | GUCY1A2 | Colorectal | Co84 | g.chr11:106063842A>T | c.2042A>T | p.E681V |
| CCDS8335.1 | GUCY1A2 | Colorectal | Mx41 | g.chr11:106063830A>C | c.2054A>C | p.N685T |
| CCDS8342.1 | DDX10 | Breast | HCC1008 | g.chr11:108099130C>G | c.1895C>G | p.L568V |
| CCDS8342.1 | DDX10 | Breast | BB23T | g.chr11:108099215_108099289del (homozygous) | c.1781_1855del | indel |
| CCDS8356.1 | FLJ10726 | Breast | HCC1143 | g.chr11:111457912A>C | IVS2-4A>C | sp |
| CCDS8374.1 | MGC13125 | Colorectal | Mx43 | g.chr11:116124408A>C | c.1880A>C | p.X620Y |
| CCDS8379.1 | KIAA0999 | Breast | Hs 578T | g.chr11:116251855A>T | c.992A>T | p.H331L |
| CCDS8379.1 | KIAA0999 | Breast | BB40T | g.chr11:116233765C>T | c.3308C>T | p.A1103V |
| CCDS8384.1 | DSCAML1 | Colorectal | Mx3 | g.chr11:116881486G>A | c.2155G>A | p.V719I |
| CCDS8384.1 | DSCAML1 | Colorectal | Mx42 | g.chr11:116808353G>A | c.5284G>A | p.V1762I |
| CCDS8402.1 | BLR1 | Breast | HCC1395 | g.chr11:118289583G>A | c.100G>A | p.E34K |
| CCDS8411.1 | DPAGT1 | Breast | HCC 38 | g.chr11:118477549G>A | c.27G>A | p.M9I |
| CCDS8417.1 | PDZK2 | Breast | HCC1937 | g.chr11:118584922A>C | IVS9-2A>C | sp |
| CCDS8426.1 | TRIM29 | Breast | HCC2218 | g.chr11:119494227C>T | c.1541C>T | p.S514F |
| CCDS8434.1 | TECTA | Breast | BB12T | g.chr11:120494285G>A | c.851G>A | p.R284H |
| CCDS8434.1 | TECTA | Breast | BB23T | g.chr11:120504092_120504092dupC | c.2106_dupC | fs |
| CCDS8434.1 | TECTA | Breast | HCC 38 | g.chr11:120504208T>A (homozygous) | c.2312T>A | p.I771N |
| CCDS8434.1 | TECTA | Breast | BB14T | g.chr11:120505627A>C | c.2438A>C | p.N813T |
| CCDS8436.1 | SORL1 | Breast | BB29T | g.chr11:120845999T>C | c.359T>C | p.L120S |
| CCDS8438.1 | SORL1 | Colorectal | Co108 | g.chr11:120965178A>T | IVS28-2A>T | sp |
| CCDS8438.1 | SORL1 | Breast | HCC 38 | g.chr11:120966029delCACTGCATCCCC (homozygous) | c.4138_4149delCACTGCATCCCC | p.H1380_P1383del |
| CCDS8438.1 | SORL1 | Breast | HCC2157 | g.chr11:120981121A>T | c.4741A>T | p.M1581L |
| CCDS8438.1 | SORL1 | Colorectal | MxB | g.chr11:120997007C>G (homozygous) | c.5914C>G | p.L1972V |
| CCDS8442.1 | SCN3B | Colorectal | Mx35 | g.chr11:123018543A>T | c.266A>T | p.Q89L |
| CCDS8442.1 | SCN3B | Colorectal | Mx43 | g.chr11:123014105G>A | c.583G>A | p.A195T |
| CCDS8457.1 | MGC39545 | Colorectal | Co92 | g.chr11:124871711G>T | c.385G>T | p.D129Y |
| CCDS8468.1 | CDON | Breast | HCC2218 | g.chr11:125380921G>A | c.1794G>A | p.W598X |
| CCDS8469.1 | RPUSD4 | Breast | HCC1937 | g.chr11:125560721T>C | IVS4-4T>C | sp |
| CCDS8476.1 | KCNJ1 | Breast | HCC1008 | g.chr11:128215062C>T (homozygous) | c.344C>T | p.S115F |
| CCDS8488.1 | ADAMTS15 | Colorectal | Co79 | g.chr11:128848382A>G | c.2309A>G | p.Q770R |
| CCDS8488.1 | ADAMTS15 | Colorectal | Mx41 | g.chr11:128848705T>G | c.2632T>G | p.C878G |
| CCDS8500.1 | WNK1 | Colorectal | Co74 | g.chr12:862928A>G | c.3596A>G | p.E1199G |
| CCDS8506.1 | WNK1 | Breast | HCC1395 | g.chr12:888597C>G | c.5395C>G | p.Q1799E |
| CCDS8531.1 | AKAP3 | Colorectal | Mx41 | g.chr12:4595237C>T | c.2491C>T | p.R831C |
| CCDS8538.1 | KCNA5 | Breast | HCC2157 | g.chr12:5024472G>A | c.898G>A | p.G300S |
| CCDS8539.1 | VWF | Breast | Hs 578T | g.chr12:5988136A>G | c.4709A>G | p.Y1570C |

FIG. 12K

| | | | | | | |
|---|---|---|---|---|---|---|
| CCDS8559.1 | MLF2 | Colorectal | Mx32 | g.chr12:6730171T>G | c.239T>G | p.F80C |
| CCDS8578.1 | CLSTN3 | Colorectal | Co74 | g.chr12:7201444C>T | c.2620G>T | p.H874Y |
| CCDS8595.1 | MFAP5 | Breast | HCC2218 | g.chr12:8698335T>A | c.182T>A | p.V61D |
| CCDS8597.1 | PHC1 | Breast | HCC1395 | g.chr12:8977158C>G | c.1838C>G | p.S613X |
| CCDS8600.1 | PZP | Colorectal | Mx41 | g.chr12:9201205G>A | c.3383G>A | p.R1128H |
| CCDS8628.1 | FLJ10292 | Breast | HCC 38 | g.chr12:10650233G>A | c.355G>A | p.E119K |
| CCDS8630.1 | CSDA | Colorectal | Mx38 | g.chr12:10781991A>G | IVS2-4A>G | sp |
| CCDS8633.1 | TAS2R13 | Breast | HCC1187 | g.chr12:10952719A>G | c.446A>G | p.N149S |
| CCDS8670.1 | FLJ32115 | Breast | HCC 38 | g.chr12:14959710_14959699delTTCCTAAGTGGA | c.754_765delTTCCTAAGTGGA | p.F252_G255del |
| CCDS8684.1 | SLCO1B3 | Colorectal | Co74 | g.chr12:20910584T>G | c.876T>G | p.I292M |
| CCDS8684.1 | SLCO1B3 | Colorectal | Mx38 | g.chr12:20960278A>T | c.1939A>T | p.M847L |
| CCDS8688.1 | SLCO1A2 | Colorectal | Co74 | g.chr12:21345402G>A | c.658G>A | p.V220I |
| CCDS8691.1 | LDHB | Breast | HCC1395 | g.chr12:21698743G>T | IVS1+1G>T | sp |
| CCDS8702.1 | KRAS | Colorectal | Co94 | g.chr12:25289552G>A | c.34G>A | p.G12S |
| CCDS8702.1 | KRAS | Colorectal | Co92 | g.chr12:25289551G>A | c.35G>A | p.G12D |
| CCDS8702.1 | KRAS | Colorectal | Hx189 | g.chr12:25289551G>A | c.35G>A | p.G12D |
| CCDS8702.1 | KRAS | Colorectal | Hx208 | g.chr12:25289551G>T (homozygous) | c.35G>T | p.G12V |
| CCDS8702.1 | KRAS | Colorectal | Hx210 | g.chr12:25289551G>T | c.35G>T | p.G12V |
| CCDS8702.1 | KRAS | Colorectal | Hx219 | g.chr12:25289551G>T | c.35G>T | p.G12V |
| CCDS8702.1 | KRAS | Colorectal | Mx30 | g.chr12:25289551G>C | c.35G>C | p.G12A |
| CCDS8702.1 | KRAS | Colorectal | Mx34 | g.chr12:25289551G>A (homozygous) | c.35G>A | p.G12D |
| CCDS8702.1 | KRAS | Colorectal | Mx41 | g.chr12:25289551G>A | c.35G>A | p.G12D |
| CCDS8702.1 | KRAS | Colorectal | Hx5 | g.chr12:25289548C>A | c.38G>A | p.G13D |
| CCDS8702.1 | KRAS | Colorectal | Mx22 | g.chr12:25289548G>A (homozygous) | c.38G>A | p.G13D |
| CCDS8702.1 | KRAS | Colorectal | Mx43 | g.chr12:25289548G>A | c.38G>A | p.G13D |
| CCDS8702.1 | KRAS | Colorectal | Mx27 | g.chr12:25271343A>G | c.182A>G | p.Q61R |
| CCDS8702.1 | KRAS | Colorectal | Co82 | g.chr12:25269914A>T | c.351A>T | p.K117N |
| CCDS8702.1 | KRAS | Colorectal | Mx26 | g.chr12:25269828G>A (homozygous) | c.436G>A | p.A146T |
| CCDS8702.1 | KRAS | Colorectal | Mx3 | g.chr12:25269828G>A | c.436G>A | p.A146T |
| CCDS8708.1 | C12orf11 | Colorectal | Mx32 | g.chr12:26968680T>C | c.678T>C | p.S227P |
| CCDS8715.1 | PTHLH | Breast | HCC2218 | g.chr12:28007567T>A | c.505T>A | p.S169T |
| CCDS8726.1 | BICD1 | Colorectal | Mx41 | g.chr12:32361768C>T | c.2341C>T | p.R781X |
| CCDS8737.1 | CNTN1 | Colorectal | Co92 | g.chr12:39696947C>A | c.2381C>A | p.P794H |
| CCDS8739.1 | PDZRN4 | Colorectal | Hx189 | g.chr12:40253198G>A | c.1576G>A | p.G526R |
| CCDS8741.1 | PPHLN1 | Breast | HCC1187 | g.chr12:41065014G>A (homozygous) | c.517G>A | p.V173M |
| CCDS8756.1 | HDAC7A | Breast | HCC1937 | g.chr12:46478849G>A | c.127G>A | p.V43M |
| CCDS8787.1 | MCRS1 | Colorectal | Mx22 | g.chr12:48236781G>A | c.1321G>A | p.V441I |
| CCDS8805.1 | SLC11A2 | Colorectal | Mx32 | g.chr12:49688587G>A | c.142G>A | p.A48T |
| CCDS8812.1 | ELA1 | Breast | HCC 38 | g.chr12:50022725G>C | c.227G>C | p.G76A |
| CCDS8834.1 | KSIRS3 | Colorectal | Co82 | g.chr12:51296244G>A | c.635G>A | p.R212H |
| CCDS8834.1 | KSIRS3 | Colorectal | Hx218 | g.chr12:51294708C>T | c.743C>T | p.T248M |
| CCDS8838.1 | HUMCYT2A | Breast | HCC1143 | g.chr12:51456841C>G | c.502C>G | p.L168V |
| CCDS8850.1 | RARG | Breast | HCC2157 | g.chr12:51891804G>A | c.1288G>A | p.G430S |
| CCDS8859.1 | HOXC9 | Colorectal | Mx27 | g.chr12:52680498G>A | c.259G>A | p.G87S |
| CCDS8915.1 | USP52 | Colorectal | Mx43 | g.chr12:54997687C>T | c.3590C>T | p.A1197V |
| CCDS8918.1 | TIMELESS | Breast | BB28T | g.chr12:55101865G>A | c.1288C>A | p.A429D |
| CCDS8918.1 | TIMELESS | Breast | HCC2218 | g.chr12:55101032C>G | c.3022C>G | p.Q1008E |
| CCDS8932.1 | LRP1 | Colorectal | Hx220 | g.chr12:55845929G>A | c.2605G>A | p.E869K |
| CCDS8932.1 | LRP1 | Colorectal | Co92 | g.chr12:55885243G>A | c.11279G>A | p.R3760H |
| CCDS8939.1 | INHBE | Breast | HCC1187 | g.chr12:56135771G>C | c.185G>C | p.R62T |
| CCDS8939.1 | INHBE | Breast | BB1T | g.chr12:56136480G>T | c.645G>T | p.Q215H |
| CCDS8940.1 | GLI1 | Breast | BB23T | g.chr12:56145841C>G | c.628C>G | p.P210A |
| CCDS8940.1 | GLI1 | Breast | BB9T | g.chr12:56149713C>T | c.1541C>T | p.T514I |
| CCDS8940.1 | GLI1 | Breast | HCC1008 | g.chr12:56151239G>C | c.2449G>C | p.E817Q |
| CCDS8943.1 | DDIT3 | Colorectal | Co108 | g.chr12:56197025C>T | c.344C>T | p.A115V |
| CCDS8949.1 | SLC26A10 | Colorectal | Mx38 | g.chr12:50305740T>C | c.554T>C | p.L165S |
| CCDS8951.1 | CENTG1 | Breast | BB40T | g.chr12:56411823G>A | c.1015G>A | p.A339T |
| CCDS8951.1 | CENTG1 | Breast | HCC1599 | g.chr12:56409500G>T | c.1438G>T | p.D480Y |
| CCDS9005.1 | KCNC2 | Breast | HCC1599 | g.chr12:73730863G>A | c.1389G>A | p.L463 |
| CCDS9018.1 | FLJ90379 | Breast | HCC1937 | g.chr12:79274124G>T | c.920G>T | p.C307F |
| CCDS9031.1 | DRIM | Breast | BB13T | g.chr12:100248350A>T | c.4934A>T | p.K1845I |
| CCDS9031.1 | DRIM | Breast | HCC1008 | g.chr12:100271900A>T | c.7354A>T | p.I2452F |
| CCDS9115.1 | PRDM4 | Breast | HCC1395 | g.chr12:106642516G>A (homozygous) | IVS5+1G>A | sp |
| CCDS9141.1 | FLJ40142 | Colorectal | Mx27 | g.chr12:108959628G>A | c.76G>A | p.A26T |
| CCDS9159.1 | FLJ13089 | Breast | HCC1395 | g.chr12:110943619T>G (homozygous) | c.2367T>G | p.S789R |
| CCDS9162.1 | RPL6 | Colorectal | Co108 | g.chr12:111306802A>C | c.298A>C | p.K100Q |
| CCDS9196.1 | MSI1 | Breast | HCC1143 | g.chr12:119258395G>C | c.478G>C | p.E160Q |
| CCDS9209.1 | TCF1 | Breast | Hs 578T | g.chr12:118894790A>G (homozygous) | c.817A>G | p.K273E |
| CCDS9209.1 | TCF1 | Breast | BB12T | g.chr12:119900103G>A | c.1721G>A | p.S574N |
| CCDS9213.1 | P2RX7 | Colorectal | Hx218 | g.chr12:120033587A>G | c.74A>G | p.N25S |
| CCDS9213.1 | P2RX7 | Colorectal | Mx32 | g.chr12:120085258G>T | c.1721G>T | p.R574L |
| CCDS9220.1 | ANAPC5 | Breast | HCC1143 | g.chr12:120218842G>T | c.1851G>T | p.Q617H |
| CCDS9232.1 | RSN | Breast | HCC2218 | g.chr12:121297924G>A | c.3806G>A | p.M1202I |
| CCDS9236.1 | GPR81 | Breast | HCC1187 | g.chr12:121739602_121739601insA (homozygous) | c.165_166insA | fs |
| CCDS9236.1 | GPR81 | Breast | Hs 578T | g.chr12:121738783_121738782delTA (homozygous) | c.984_985delTA | fs |
| CCDS9237.1 | TSP-NY | Colorectal | Mx27 | g.chr12:121788972C>G | c.91C>G | p.Q31E |
| CCDS9246.1 | SBNO1 | Breast | BB23T | g.chr12:122335002A>T | c.1897A>T | p.T833S |
| CCDS9246.1 | SBNO1 | Breast | HCC2218 | g.chr12:122329861G>A | c.2662G>A | p.E888K |
| CCDS9246.1 | SBNO1 | Breast | HCC 38 | g.chr12:122325033C>G | c.2987C>G | p.S996C |
| CCDS9275.1 | PUS1 | Breast | HCC 38 | g.chr12:131080043G>A (homozygous) | c.313G>A | p.D105N |
| CCDS9283.1 | ZNF10 | Breast | HCC2218 | g.chr12:132342436C>G | IVS3-3C>G | sp |
| CCDS9300.1 | SACS | Colorectal | Mx41 | g.chr13:22810630G>A | c.4944G>A | p.M1648I |
| CCDS9312.1 | FLJ25477 | Colorectal | Co92 | g.chr13:24642389G>A | c.1012G>A | p.A338T |
| CCDS9344.1 | BRCA2 | Breast | HCC1395 | g.chr13:31811269G>T | c.4777G>T | p.E1593X |
| CCDS9347.1 | KL | Colorectal | Co108 | g.chr13:32536145C>T | c.2861C>T | p.P954L |
| CCDS9363.1 | CSNK1A1L | Colorectal | Co92 | g.chr13:38577332G>A | c.62G>A | p.R21Q |
| CCDS9365.1 | TRPC4 | Breast | HCC1395 | g.chr13:37218559G>A | c.412G>A | p.E138K |
| CCDS9375.1 | WBP4 | Breast | HCC1143 | g.chr13:40340772A>G (homozygous) | c.338A>G | p.K113R |
| CCDS9398.1 | COG3 | Breast | HCC2218 | g.chr13:44888327C>T (homozygous) | c.1858C>T | p.R620C |
| CCDS9438.1 | PCDH8 | Breast | HCC2218 | g.chr13:52317041G>C (homozygous) | c.2668G>C | p.K956N |
| CCDS9442.1 | PCDH20 | Breast | HCC1937 | g.chr13:60884666G>A | c.1486G>A | p.V496M |

FIG. 12L

| | | | | | |
|---|---|---|---|---|---|
| CCDS9448.1 | KLF5 | Colorectal | Mx38 | g.chr13:72534839C>T | c.901C>T | p.P301S |
| CCDS9454.1 | LMO7 | Colorectal | Mx41 | g.chr13:75276868A>G | c.1060A>G | p.T354A |
| CCDS9454.1 | LMO7 | Colorectal | Hx206 | g.chr13:75291862C>A | c.1351C>A | p.L451M |
| CCDS9472.1 | ITR | Breast | HCC1187 | g.chr13:94052277C>A | c.95C>A | p.T32N |
| CCDS9487.1 | FARP1 | Breast | HCC1395 | g.chr13:97881533G>T (homozygous) | c.2141G>T | p.R714L |
| CCDS9497.1 | FLJ14824 | Breast | HCC1954 | g.chr13:100062697A>G | c.1177A>G | p.M393V |
| CCDS9498.1 | VGCNL1 | Breast | HCC1143 | g.chr13:100518289G>A | c.4428G>A | p.M1478I |
| CCDS9500.1 | FGF14 | Colorectal | Co74 | g.chr13:101851898G>T | c.132G>T | p.W44C |
| CCDS9510.1 | IRS2 | Colorectal | Mx38 | g.chr13:109233296_109233294dupCCG | c.3106_3108dupCCG | p.P1036dup |
| CCDS9524.1 | LOC122258 | Colorectal | Mx38 | g.chr13:112078773C>T | c.73C>T | p.R25W |
| CCDS9584.1 | NDRG2 | Breast | HCC1008 | g.chr14:20556453C>T | IVS11+3C>T | sp |
| CCDS9574.1 | SLC7A7 | Breast | HCC1954 | g.chr14:22313411C>T | c.1237C>T | p.P413S |
| CCDS9587.1 | ACIN1 | Colorectal | Co92 | g.chr14:22600468G>A | c.3478G>A | p.R1160Q |
| CCDS9595.1 | EFS | Colorectal | Mx32 | g.chr14:22898444G>T | c.1083G>T | p.M361I |
| CCDS9604.1 | DHRS2 | Colorectal | Co108 | g.chr14:23184274C>T | c.815C>T | p.A272V |
| CCDS9624.1 | C14orf21 | Breast | HCC2218 | g.chr14:23843166C>A | c.1490C>A | p.S497Y |
| CCDS9624.1 | C14orf21 | Breast | HCC1954 | g.chr14:23844107G>A | c.1877G>A | p.R626Q |
| CCDS9637.1 | PRKD1 | Colorectal | Co74 | g.chr14:29205115C>T | c.454C>T | p.H152Y |
| CCDS9637.1 | PRKD1 | Colorectal | Hx174 | g.chr14:29116365G>A | c.2569G>A | p.E857K |
| CCDS9644.1 | AKAP6 | Breast | HCC1395 | g.chr14:32139748A>T | c.2729A>T | p.K910M |
| CCDS9644.1 | AKAP6 | Breast | HCC1395 | g.chr14:32312838G>T | c.3576G>T | p.M1192I |
| CCDS9644.1 | AKAP6 | Colorectal | Mx32 | g.chr14:32361162C>A | c.4412C>A | p.S1471X |
| CCDS9644.1 | AKAP6 | Breast | HCC 38 | g.chr14:32361874G>C | c.5104G>C | p.E1702Q |
| CCDS9644.1 | AKAP6 | Colorectal | Mx34 | g.chr14:32362285C>A | c.5515C>A | p.P1839T |
| CCDS9649.1 | CFL2 | Breast | HCC1954 | g.chr14:34252381A>G | c.141A>G | p.I47M |
| CCDS9651.1 | BAZ1A | Breast | HCC1008 | g.chr14:34297779delG (homozygous) | c.4268delG | fs |
| CCDS9656.1 | NFKBIA | Breast | HCC1187 | g.chr14:34942227_34942228insC (homozygous) | c.427_428insC | fs |
| CCDS9672.1 | MIA2 | Breast | HCC1395 | g.chr14:38768838G>C (homozygous) | c.1309G>C | p.D437H |
| CCDS9679.1 | C14orf155 | Breast | BB23T | g.chr14:44045158C>G | c.785C>G | p.T262R |
| CCDS9679.1 | C14orf155 | Breast | BB22T | g.chr14:44043851C>A | c.2290C>A | p.Q784K |
| CCDS9679.1 | C14orf155 | Breast | HCC1187 | g.chr14:44043617C>T | c.2324C>T | p.G775L |
| CCDS9682.1 | PRPF39 | Breast | HCC2218 | g.chr14:44047364C>G | IVS4-4C>G | sp |
| CCDS9702.1 | C14orf29 | Breast | HCC1937 | g.chr14:50438338A>G (homozygous) | c.613A>G | p.I205V |
| CCDS9706.1 | NID2 | Breast | HCC 38 | g.chr14:51596592_51596589delAGTA | c.767_IVS3+3delAGTA | fs |
| CCDS9706.1 | NID2 | Breast | HCC1937 | g.chr14:51547354C>T | c.3712C>T | p.P1238S |
| CCDS9725.1 | KTN1 | Breast | BB23T | g.chr14:55154450C>G | c.677C>G | p.P226R |
| CCDS9725.1 | KTN1 | Breast | HCC1008 | g.chr14:55214913A>C | c.3946A>C | p.T1316P |
| CCDS9727.1 | C14orf101 | Breast | HCC2218 | g.chr14:56118536G>T | c.151G>T | p.G51X |
| CCDS9736.1 | DACT1 | Colorectal | Mx38 | g.chr14:58177231G>T | c.370G>T | p.G124C |
| CCDS9736.1 | DACT1 | Colorectal | Mx38 | g.chr14:58183139C>T | c.2045C>T | p.S682L |
| CCDS9749.1 | SIX4 | Breast | HCC1395 | g.chr14:60260479C>G (homozygous) | c.4G>C | p.E2Q |
| CCDS9749.1 | SIX4 | Breast | HCC1954 | g.chr14:60256443G>A | c.1274G>A | p.G425D |
| CCDS9749.1 | SIX4 | Breast | BB28T | g.chr14:60249884C>A | c.2277C>A | p.D759E |
| CCDS9761.1 | SYNE2 | Breast | BB9T | g.chr14:63725126G>A | c.8973G>A | p.V2325I |
| CCDS9761.1 | SYNE2 | Breast | HCC1599 | g.chr14:63748471A>G (homozygous) | c.7754A>G | p.Y2585C |
| CCDS9761.1 | SYNE2 | Breast | BB22T | g.chr14:83755768_83755798dupA | c.8883_dupA | fs |
| CCDS9788.1 | ZFYVE26 | Breast | BB22T | g.chr14:87321561C>A | c.3491C>A | p.A1164E |
| CCDS9788.1 | ZFYVE26 | Breast | HCC1954 | g.chr14:87302874C>A | c.5834G>A | p.R1945Q |
| CCDS9800.1 | SLC8A3 | Breast | HCC 38 | g.chr14:89597380G>C (homozygous) | c.1834G>C | p.E612Q |
| CCDS9807.1 | SIPA1L1 | Breast | HCC2218 | g.chr14:71208976G>C | c.2988G>C | p.E996D |
| CCDS9828.1 | ABCD4 | Colorectal | Co92 | g.chr14:73834385G>A | IVS4+1G>A | sp |
| CCDS9830.1 | C14orf115 | Colorectal | Mx43 | g.chr14:73893836G>A | c.397G>A | p.V133M |
| CCDS9830.1 | C14orf115 | Colorectal | Mx28 | g.chr14:73894222_73894222dupG | c.983_dupG | fs |
| CCDS9870.1 | NRXN3 | Breast | HCC 38 | g.chr14:79003451delC | c.2278delC | fs |
| CCDS9873.1 | OTF2A1 | Breast | HCC2218 | g.chr14:80752554C>G | c.88C>G | p.L30V |
| CCDS9911.1 | KIAA1409 | Colorectal | Co74 | g.chr14:93013738C>T | IVS0-2C>T | UTR |
| CCDS9911.1 | KIAA1409 | Colorectal | Hx216 | g.chr14:93149184T>C | IVS24+2T>C | sp |
| CCDS9911.1 | KIAA1409 | Colorectal | Mx42 | g.chr14:93158358G>A | c.4645G>A | p.V1549I |
| CCDS9912.1 | PRIMA1 | Colorectal | Mx41 | g.chr14:93323753C>T | c.65C>T | p.A22V |
| CCDS9949.1 | BCL11B | Colorectal | Co92 | g.chr14:98711722C>T | c.991C>T | p.P331S |
| CCDS9955.1 | EVL | Colorectal | Co76 | g.chr14:99664690C>T (homozygous) | c.569C>T | p.P190L |
| CCDS9955.1 | EVL | Colorectal | Mx32 | g.chr14:99665831C>T | c.746C>T | p.P249L |
| CCDS9960.1 | WARS | Breast | HCC1187 | g.chr14:99871016G>C | c.1385G>C | p.E455D |
| CCDS9972.1 | CINP | Colorectal | Mx41 | g.chr14:101884757G>A | c.529G>A | p.D177N |
| CCDS9980.1 | EIF5 | Breast | HCC1143 | g.chr14:102877099A>T | c.1253A>T | p.K418M |
| CCDS10001.1 | BRF1 | Colorectal | Co74 | g.chr14:104755074G>A | c.1624G>A | p.V542M |
| CCDS10013.1 | MKRN3 | Colorectal | Co74 | g.chr15:21382456C>T (homozygous) | c.434C>T | p.T145M |
| CCDS10013.1 | MKRN3 | Colorectal | Hx189 | g.chr15:21362738G>C | c.716G>C | p.S239T |
| CCDS10015.1 | C15orf2 | Colorectal | Mx42 | g.chr15:22472127G>A | c.110G>A | p.R37Q |
| CCDS10015.1 | C15orf2 | Colorectal | Hx190 | g.chr15:22472447G>A (homozygous) | c.340G>A | p.V114I |
| CCDS10020.1 | OCA2 | Breast | HCC1954 | g.chr15:25770144G>A | c.2317G>A | p.A773T |
| CCDS10028.1 | ARHGAP11A | Breast | HCC2218 | g.chr15:30716079G>A | c.1813G>A | p.E605K |
| CCDS10054.1 | PAK6 | Colorectal | Mx42 | g.chr15:38344266G>A | c.8G>A | p.R3H |
| CCDS10055.1 | FLJ43339 | Colorectal | Co108 | g.chr15:38415060A>G | c.568A>G | p.E189G |
| CCDS10069.1 | VPS18 | Colorectal | Co108 | g.chr15:38982648G>T | c.2737G>T | p.A913S |
| CCDS10079.1 | RPAP1 | Colorectal | Mx41 | g.chr15:39606950G>A | c.1574G>A | p.R525Q |
| CCDS10096.1 | TP53BP1 | Colorectal | Mx41 | g.chr15:41495826C>T | c.4747C>T | p.R1583X |
| CCDS10134.1 | HDC | Colorectal | Mx41 | g.chr15:48342782A>T | c.146A>T | p.E49V |
| CCDS10134.1 | HDC | Colorectal | Mx27 | g.chr15:48332198G>A | c.853G>A | p.E285K |
| CCDS10135.1 | GABPB2 | Colorectal | Mx38 | g.chr15:48389197C>G (homozygous) | c.91C>G | p.P31A |
| CCDS10150.1 | NEDD4 | Breast | HCC1008 | g.chr15:53995400C>T | c.922C>T | p.H308Y |
| CCDS10178.1 | RORA | Colorectal | Mx43 | g.chr15:58708814C>T | c.52C>T | p.P18S |
| CCDS10222.1 | SMAD3 | Colorectal | Hx5 | g.chr15:65294257G>A (homozygous) | IVS7+1G>A | sp |
| CCDS10222.1 | SMAD3 | Colorectal | Mx30 | g.chr15:65269826C>T (homozygous) | c.1178C>T | p.P393L |
| CCDS10229.1 | CORO2B | Colorectal | Mx38 | g.chr15:66784690C>T | c.938C>T | p.P313L |
| CCDS10242.1 | BRUNOL6 | Colorectal | Mx38 | g.chr15:70389845C>T | c.400C>T | p.R134X |
| CCDS10260.1 | ISLR | Colorectal | Mx43 | g.chr15:72254799G>A | c.547G>A | p.D183N |
| CCDS10282.1 | SEMA7A | Breast | HCC2157 | g.chr15:72494142C>T | IVS9-3C>T | sp |
| CCDS10288.1 | CYP1A1 | Breast | BB29T | g.chr15:72622018C>A | c.474C>A | p.Y158X |
| CCDS10288.1 | CYP1A1 | Breast | HCC1008 | g.chr15:72799993C>T | c.1429C>T | p.R477W |
| CCDS10308.1 | CTSH | Colorectal | Mx42 | g.chr15:77014404G>A | c.376G>A | p.G126R |

FIG. 12M

| | | | | | | |
|---|---|---|---|---|---|---|
| CCDS10326.1 | ADAMTSL3 | Colorectal | Mx42 | g.chr15:82344864G>A | c.968G>A | p.V333M |
| CCDS10326.1 | ADAMTSL3 | Colorectal | Mx27 | g.chr15:82372907G>A | c.1750G>A | p.R587H |
| CCDS10326.1 | ADAMTSL3 | Colorectal | Mx40 | g.chr15:82430312C>T (homozygous) | c.2563C>T | p.R855C |
| CCDS10326.1 | ADAMTSL3 | Colorectal | Co82 | g.chr15:82450941C>A (homozygous) | c.3944C>A | p.A1315E |
| CCDS10381.1 | NEUGRIN | Colorectal | Mx38 | g.chr15:88615735_88615738dupCAGA | c.371_374dupCAGA | fs |
| CCDS10433.1 | UBE2I | Breast | HCC1395 | g.chr16:1310439G>C | IVS4-1G>C | sp |
| CCDS10468.1 | ABCA3 | Breast | BB1T | g.chr16:2309588C>A | c.888C>A | p.L290M |
| CCDS10468.1 | ABCA3 | Breast | HCC1395 | g.chr16:2285603G>C | c.2403G>C | p.E801D |
| CCDS10468.1 | ABCA3 | Breast | BB16T | g.chr16:2276767C>G | c.3207C>G | p.H1069Q |
| CCDS10471.1 | CGI-14 | Breast | HCC2218 | g.chr16:2517990G>A | IVS5+3G>A | sp |
| CCDS10471.1 | CGI-14 | Colorectal | Mx41 | g.chr16:2518471G>A | c.880G>A | p.D294N |
| CCDS10480.1 | MGC52282 | Colorectal | Mx41 | g.chr16:2829839G>A | c.250G>A | p.R87Q |
| CCDS10501.1 | ZNF75A | Breast | HCC1143 | g.chr16:3307861C>G | c.682C>G | p.Q228E |
| CCDS10515.1 | DNAJA3 | Breast | HCC1395 | g.chr16:4444857G>T | c.1384G>T | p.E482X |
| CCDS10333.1 | PRO0149 | Colorectal | Mx42 | g.chr16:9104399G>A (homozygous) | c.365G>A | p.R122Q |
| CCDS10584.1 | PDILT | Colorectal | Co74 | g.chr16:20303561G>C | c.316G>C | p.E106Q |
| CCDS10590.1 | MGC18943 | Colorectal | Co108 | g.chr16:20718806T>C | c.617T>C | p.I206T |
| CCDS10594.1 | DNAH3 | Colorectal | Hx169 | g.chr16:21040901A>T | c.1450A>T | p.I484L |
| CCDS10594.1 | DNAH3 | Colorectal | Mx27 | g.chr16:20956711C>T | c.4823C>T | p.S1608F |
| CCDS10601.1 | UQCRC2 | Colorectal | Mx41 | g.chr16:21875297C>G | c.176C>G | p.S59X |
| CCDS10601.1 | UQCRC2 | Colorectal | Hx174 | g.chr16:21887480T>A | c.623T>A | p.F208Y |
| CCDS10608.1 | SCNN1G | Colorectal | Mx22 | g.chr16:23105265G>A | c.172G>A | p.G58R |
| CCDS10609.1 | SCNN1B | Colorectal | Mx41 | g.chr16:23290172C>T | c.932C>T | p.A311V |
| CCDS10609.1 | SCNN1B | Breast | BB23T | g.chr16:23290161C>T | c.941C>T | p.A314V |
| CCDS10609.1 | SCNN1B | Breast | HCC2218 | g.chr16:23294566C>G | c.1159C>G | p.L387V |
| CCDS10628.1 | AQP8 | Breast | HCC1008 | g.chr16:25145974C>G | c.687C>G | p.I229M |
| CCDS10701.1 | FLJ13479 | Breast | BB5T | g.chr16:30983088G>A | c.196G>A | p.A66T |
| CCDS10701.1 | FLJ13479 | Breast | HCC1599 | g.chr16:30980894G>A | c.856G>A | p.G285S |
| CCDS10701.1 | FLJ13479 | Breast | BB12T | g.chr16:30980758C>G | c.992C>G | p.T331R |
| CCDS10701.1 | FLJ13479 | Breast | BB30T | g.chr16:30980083G>A | c.1667G>A | p.R556Q |
| CCDS10702.1 | ZNF646 | Breast | BB24T | g.chr16:30999158A>T | c.4010A>T | p.N1337I |
| CCDS10702.1 | ZNF646 | Breast | HCC2218 | g.chr16:31001789C>A | IVS1-1C>A | sp |
| CCDS10707.1 | FUS | Breast | HCC1599 | g.chr16:31108045A>C | c.934A>C | p.K312Q |
| CCDS10715.1 | FLJ13868 | Breast | HCC2157 | g.chr16:31427068G>A | c.128G>A | p.G43E |
| CCDS10720.1 | SHCBP1 | Breast | HCC1395 | g.chr16:45194949G>A | IVS8+3G>A | sp |
| CCDS10723.1 | LOC91807 | Colorectal | Co108 | g.chr16:45323915G>A | c.1096G>A | p.G366R |
| CCDS10729.1 | PHKB | Breast | HCC1143 | g.chr16:46260798T>G | c.2599T>G | p.L867V |
| CCDS10729.1 | PHKB | Colorectal | Mx22 | g.chr16:46260828G>A | c.2629G>A | p.G877R |
| CCDS10752.1 | MMP2 | Colorectal | Mx43 | g.chr16:54077040G>A | c.682G>A | p.A228T |
| CCDS10752.1 | MMP2 | Colorectal | Mx8 | g.chr16:54088359C>T | c.1493C>T | p.T498M |
| CCDS10752.1 | MMP2 | Colorectal | Co74 | g.chr16:54098803G>T | c.1931G>T | p.G644I |
| CCDS10768.1 | AMFR | Breast | HCC1395 | g.chr16:54858853A>G | IVS12+4A>G | sp |
| CCDS10759.1 | AMFR | Breast | BB10T | g.chr16:54854440A>T | c.1814A>T | p.D605V |
| CCDS10770.1 | SLC12A3 | Breast | HCC1008 | g.chr16:55475585_55475594delTCCTCCTGCT | c.1793_1802delTCCTCCTGCT | fs |
| CCDS10773.1 | NOD27 | Breast | HCC1143 | g.chr16:55817439G>A | c.1083G>A | p.M361I |
| CCDS10792.1 | MMP15 | Breast | HCC1395 | g.chr16:56836628A>G | c.1787A>G | p.D596G |
| CCDS10802.1 | CDH8 | Breast | HCC1599 | g.chr16:60305301C>A | c.1599C>A | p.Y533X |
| CCDS10827.1 | C8FB | Breast | HCC1008 | g.chr16:65858101C>A | c.298C>A | p.P100A |
| CCDS10832.1 | LOC283849 | Breast | HCC1395 | g.chr16:85780329T>A | c.223T>A | p.Y75N |
| CCDS10832.1 | LOC283849 | Breast | BB29T | g.chr16:85776850C>A | c.1541C>A | p.A514D |
| CCDS10834.1 | FHOD1 | Breast | Hs 578T | g.chr16:85825351delC | c.1756delC | fs |
| CCDS10877.1 | CGI-37 | Breast | HCC2218 | g.chr16:87833024G>C (homozygous) | c.511C>G | p.E171Q |
| CCDS10915.1 | BCAR1 | Breast | HCC1395 | g.chr16:73827078G>C | c.1220G>C | p.G407T |
| CCDS10926.1 | ADAMTS18 | Colorectal | Hx190 | g.chr16:75953574G>A | c.1145G>A | p.R382K |
| CCDS10926.1 | ADAMTS18 | Colorectal | Hx223 | g.chr16:75947434A>C | c.1364A>C | p.K455T |
| CCDS10926.1 | ADAMTS18 | Colorectal | Mx22 | g.chr16:75913812_75913812dupT | c.2085_dupT | fs |
| CCDS10946.1 | WFDC1 | Breast | HCC1395 | g.chr16:82909453G>A | c.412G>A | p.V138M |
| CCDS10950.1 | ZDHHC7 | Colorectal | Mx41 | g.chr16:83561506G>A | c.130G>A | p.D44N |
| CCDS10952.1 | KIAA0182 | Colorectal | Mx22 | g.chr16:84239798_84239798dupC | c.368_dupC | fs |
| CCDS10952.1 | KIAA0182 | Colorectal | Mx208 | g.chr16:84252491C>T | c.1879C>T | p.R627W |
| CCDS10956.1 | IRF8 | Breast | HCC1599 | g.chr16:84500184G>A | c.242G>A | p.R91K |
| CCDS10956.1 | IRF8 | Breast | Hs 578T | g.chr16:84505615G>A | c.589G>A | p.A197T |
| CCDS10961.1 | ZCCHC14 | Breast | HCC1395 | g.chr16:86006671C>G | c.888C>G | p.L290V |
| CCDS10970.1 | GALNS | Colorectal | Co74 | g.chr16:87436678C>T | c.181C>T | p.R61W |
| CCDS10970.1 | GALNS | Colorectal | Hx5 | g.chr16:87408389C>A | c.1528C>A | p.P510T |
| CCDS10972.1 | CBFA2T3 | Colorectal | Mx41 | g.chr16:87479155G>A | c.917G>A | p.R306H |
| CCDS10972.1 | CBFA2T3 | Colorectal | Mx43 | g.chr16:87473289G>A | c.1552G>A | p.E518K |
| CCDS10972.1 | CBFA2T3 | Colorectal | Mx41 | g.chr16:87473240C>T | c.1601C>T | p.A534V |
| CCDS10982.1 | DPEP1 | Colorectal | Co108 | g.chr16:86231256G>A | c.737G>A | p.R246H |
| CCDS10998.1 | NXN | Breast | HCC1008 | g.chr17:673651C>T | c.583C>T | p.H195Y |
| CCDS11004.1 | SKIP | Breast | HCC2157 | g.chr17:1347999C>T | c.944C>T | p.S315F |
| CCDS11026.1 | OR1E2 | Colorectal | Mx41 | g.chr17:3283384C>G | c.502C>G | p.H168D |
| CCDS11041.1 | ATP2A3 | Breast | HCC1395 | g.chr17:3781093G>A | c.2021G>A | p.R974H |
| CCDS11044.1 | MGC32124 | Colorectal | Mx41 | g.chr17:3993817C>G | c.19C>G | p.R7G |
| CCDS11044.1 | MGC32124 | Colorectal | Mx22 | g.chr17:3993818G>C | c.20G>C | p.R7P |
| CCDS11045.1 | MGC29671 | Colorectal | Mx22 | g.chr17:4337918G>A | c.1519G>A | p.A507T |
| CCDS11057.1 | PLD2 | Breast | HCC1395 | g.chr17:4888825_4888639delACAGAATCCTGAAGG | c.1988_2002delACAGAATCCTGAAGG | Indel |
| CCDS11057.1 | PLD2 | Breast | BB9T | g.chr17:4889800C>G | c.2419C>G | p.Q807E |
| CCDS11068.1 | ZNF232 | Colorectal | Mx22 | g.chr17:4953462C>T | c.449C>T | p.A150V |
| CCDS11089.1 | ASGR1 | Breast | HCC2218 | g.chr17:7018335C>G (homozygous) | IVS5-3C>G | sp |
| CCDS11101.1 | CENTB1 | Breast | BB3T | g.chr17:7185990G>C | IVS2-1G>C | sp |
| CCDS11101.1 | CENTB1 | Breast | HCC1954 | g.chr17:7186514A>G | c.341A>G | p.K114R |
| CCDS11101.1 | CENTB1 | Colorectal | Mx22 | g.chr17:7187463G>A | c.386G>A | p.R129Q |
| CCDS11118.1 | TP53 | Colorectal | Hx174 | g.chr17:7529246G>T | c.166G>T | p.E56X |
| CCDS11118.1 | TP53 | Breast | BB18T | g.chr17:7529091C>G | c.321C>G | p.Y107X |
| CCDS11118.1 | TP53 | Breast | HCC1187 | g.chr17:7520090_7520088delGGT (homozygous) | c.322_324delGGT | p.G108del |
| CCDS11118.1 | TP53 | Colorectal | Hx219 | g.chr17:7520047_7520046delTG (homozygous) | c.365_366delTG | fs |
| CCDS11118.1 | TP53 | Colorectal | Co74 | g.chr17:7519253T>G (homozygous) | c.402T>G | p.F134L |
| CCDS11118.1 | TP53 | Colorectal | Co84 | g.chr17:7519226C>T (homozygous) | c.430C>T | p.Q144X |
| CCDS11118.1 | TP53 | Breast | Hs 578T | g.chr17:7519168G>T (homozygous) | c.469G>T | p.V157F |
| CCDS11118.1 | TP53 | Breast | HCC1954 | g.chr17:7519187A>G (homozygous) | c.488A>G | p.Y163C |

FIG. 12N

| | | | | | | |
|---|---|---|---|---|---|---|
| CCDS11118.1 | TP53 | Breast | HCC1395 | g.chr17:7519131G>A (homozygous) | c.524C>A | p.R175H |
| CCDS11118.1 | TP53 | Colorectal | Hx172 | g.chr17:7519125C>G | c.530C>G | p.P177R |
| CCDS11118.1 | TP53 | Breast | BB28T | g.chr17:7519095G>C | IVS4+1G>C | sp |
| CCDS11118.1 | TP53 | Colorectal | Co82 | g.chr17:7518996A>G | c.578A>G | p.H193R |
| CCDS11118.1 | TP53 | Breast | BB30T | g.chr17:7518937C>T | c.637C>T | p.R213X |
| CCDS11118.1 | TP53 | Colorectal | Hx206 | g.chr17:7518937C>T (homozygous) | c.637C>T | p.R213X |
| CCDS11118.1 | TP53 | Colorectal | Mx8 | g.chr17:7518937C>T (homozygous) | c.637C>T | p.R213X |
| CCDS11118.1 | TP53 | Colorectal | Hx218 | g.chr17:7518936G>C (homozygous) | c.638G>C | p.R213P |
| CCDS11118.1 | TP53 | Breast | HCC1599 | g.chr17:7518335A>T (homozygous) | IVS5-2A>T | sp |
| CCDS11118.1 | TP53 | Breast | BB15T | g.chr17:7518284C>T | c.722C>T | p.S241F |
| CCDS11118.1 | TP53 | Breast | HCC2713 | g.chr17:7518283delC | c.723delC | fs |
| CCDS11118.1 | TP53 | Colorectal | Mx42 | g.chr17:7518283delC (homozygous) | c.723delC | fs |
| CCDS11118.1 | TP53 | Colorectal | Mx38 | g.chr17:7518281G>T (homozygous) | c.725G>T | p.C242F |
| CCDS11118.1 | TP53 | Breast | HCC2157 | g.chr17:7518264C>T (homozygous) | c.742C>T | p.R248W |
| CCDS11118.1 | TP53 | Breast | HCC1143 | g.chr17:7518263G>A (homozygous) | c.743G>A | p.R248Q |
| CCDS11118.1 | TP53 | Colorectal | Mx32 | g.chr17:7518259G>C (homozygous) | c.747G>C | p.R249S |
| CCDS11118.1 | TP53 | Breast | BB24T | g.chr17:7518237_7518230delCTGGAAGA (homozygous) | c.761_768delCTGGAAGA | fs |
| CCDS11118.1 | TP53 | Colorectal | Hx169 | g.chr17:7517864C>T (homozygous) | c.799C>T | p.R267W |
| CCDS11118.1 | TP53 | Colorectal | Hx174 | g.chr17:7517852G>A | c.811G>A | p.E271K |
| CCDS11118.1 | TP53 | Colorectal | Co2 | g.chr17:7517846C>T (homozygous) | c.817C>T | p.R273C |
| CCDS11118.1 | TP53 | Breast | HCC 38 | g.chr17:7517845G>T (homozygous) | c.818G>T | p.R273L |
| CCDS11118.1 | TP53 | Colorectal | Mx29 | g.chr17:7517845G>A (homozygous) | c.818G>A | p.R273H |
| CCDS11118.1 | TP53 | Breast | BB12T | g.chr17:7517831C>T | c.832C>T | p.P276S |
| CCDS11118.1 | TP53 | Breast | BB22T | g.chr17:7517831C>T | c.832C>T | p.P276S |
| CCDS11118.1 | TP53 | Colorectal | Mx31 | g.chr17:7517824G>T (homozygous) | c.839G>T | p.R280I |
| CCDS11118.1 | TP53 | Breast | HCC1008 | g.chr17:7517822G>C (homozygous) | c.841G>C | p.D281H |
| CCDS11118.1 | TP53 | Breast | HCC1937 | g.chr17:7517747C>T (homozygous) | c.916C>T | p.R306X |
| CCDS11118.1 | TP53 | Colorectal | Mx34 | g.chr17:7517853A>G (homozygous) | IVS7-2A>G | sp |
| CCDS11126.1 | LIP8 | Breast | Hs 578T | g.chr17:7792197T>G | IVS15-3T>G | sp |
| CCDS11131.1 | PER1 | Breast | HCC1008 | g.chr17:7990133G>C | c.2086G>C | p.E696Q |
| CCDS11131.1 | PER1 | Breast | HCC2157 | g.chr17:7987427A>G (homozygous) | c.2954A>G | p.N985S |
| CCDS11131.1 | PER1 | Colorectal | Mx32 | g.chr17:7986772C>T | c.3179C>T | p.S1060L |
| CCDS11147.1 | PIK3R5 | Colorectal | Mx22 | g.chr17:8755455C>T | c.82C>T | p.R28C |
| CCDS11155.1 | MYH1 | Breast | HCC1395 | g.chr17:10343083C>T (homozygous) | c.3917C>T | p.S1306L |
| CCDS11155.1 | MYH1 | Breast | BB29T | g.chr17:10341808G>A | c.4333G>A | p.A1445T |
| CCDS11155.1 | MYH1 | Breast | BB12T | g.chr17:10340456G>A | c.4792G>A | p.V1598M |
| CCDS11160.1 | DNAH9 | Breast | BB30T | g.chr17:11495325G>T | c.2312G>T | p.R771L |
| CCDS11160.1 | DNAH9 | Breast | HCC1395 | g.chr17:11628477G>C | c.7957G>C | p.D2653H |
| CCDS11160.1 | DNAH9 | Breast | BB38T | g.chr17:11730886C>A | c.10991C>A | p.T3664N |
| CCDS11180.1 | ZNF624 | Colorectal | Mx1 | g.chr17:16487631A>T | c.1294A>T | p.S432C |
| CCDS11223.1 | NOS2A | Breast | HCC1187 | g.chr17:23118990G>T (homozygous) | c.2035G>T | p.A679S |
| CCDS11235.1 | PIGS | Breast | HCC2218 | g.chr17:23912766G>A | c.477G>A | p.M159I |
| CCDS11264.1 | NF1 | Colorectal | Mx38 | g.chr17:26584208C>A | c.3559C>A | p.L1187I |
| CCDS11264.1 | NF1 | Colorectal | Hx190 | g.chr17:26877105_26877108delCTCT (homozygous) | c.4914_4917delCTCT | fs |
| CCDS11264.1 | NF1 | Colorectal | Co79 | g.chr17:26888021C>T | c.5789C>T | p.P1930L |
| CCDS11264.1 | NF1 | Breast | Hs 578T | g.chr17:26711703G>A | c.8170G>A | p.G2724R |
| CCDS11276.1 | ACCN1 | Colorectal | Mx42 | g.chr17:28463201C>A | IVS1-3C>A | sp |
| CCDS11284.1 | LIG3 | Colorectal | Mx38 | g.chr17:30350474G>A | c.1886G>A | p.D630N |
| CCDS11291.1 | FLJ10458 | Breast | HCC1599 | g.chr17:30487830G>C | IVS7-1G>C | sp |
| CCDS11291.1 | FLJ10458 | Breast | BB5T | g.chr17:30487503C>A | c.955C>A | p.Q319K |
| CCDS11292.1 | CMYA4 | Breast | HCC2218 | g.chr17:30521002G>C | c.1486G>C | p.D496H |
| CCDS11297.1 | RASL10B | Breast | HCC1187 | g.chr17:31088470G>A (homozygous) | c.154G>A | p.V52M |
| CCDS11299.1 | FLJ32830 | Breast | HCC2218 | g.chr17:31209592C>G (homozygous) | c.990C>G | p.I330M |
| CCDS11299.1 | FLJ32830 | Breast | HCC2218 | g.chr17:31209439C>G (homozygous) | IVS10-3C>G | sp |
| CCDS11317.1 | ACACA | Colorectal | Mx43 | g.chr17:32592688G>A | c.5060G>A | p.R1687Q |
| CCDS11334.1 | CACNB1 | Colorectal | Mx43 | g.chr17:34593526C>T | c.1151C>T | p.P384L |
| CCDS11354.1 | G6DML | Breast | HCC1937 | g.chr17:35318028A>G (homozygous) | c.683A>G | p.D228G |
| CCDS11368.1 | CTEN | Colorectal | Mx30 | g.chr17:35888413C>T | c.1924C>T | p.R642C |
| CCDS11379.1 | KRT20 | Colorectal | Co92 | g.chr17:36294954A>C (homozygous) | c.10A>C | p.S4R |
| CCDS11407.1 | JUP | Breast | HCC1395 | g.chr17:37181514_37181473delAGGGCATCATGGAGGAGGATGAGG CCTGCGGGCGCCAGTACA (homozygous) | c.119_160delAGGGCATCATGGAGGAGGATGAG GCCTGCGGGCGCCAGTACA | indel |
| CCDS11419.1 | RAB5C | Colorectal | Co92 | g.chr17:37535926G>A (homozygous) | c.119G>A | p.R40H |
| CCDS11420.1 | KCNH4 | Colorectal | Mx41 | g.chr17:37569238G>C | c.2389G>C | p.G797R |
| CCDS11425.1 | PTRF | Breast | HCC1937 | g.chr17:37828602C>A | c.40C>A | p.P14T |
| CCDS11448.1 | G6PC | Breast | HCC1954 | g.chr17:38313072C>T | c.347C>T | p.P116L |
| CCDS11453.1 | BRCA1 | Breast | HCC2157 | g.chr17:38521313G>T (homozygous) | c.90G>T | p.L30F |
| CCDS11453.1 | BRCA1 | Breast | BB23T | g.chr17:38488800G>C | c.2274G>C | p.L758F |
| CCDS11453.1 | BRCA1 | Breast | BB22T | g.chr17:38488742G>T | c.2332G>T | p.G778C |
| CCDS11509.1 | CDC27 | Breast | HCC2218 | g.chr17:42589311G>C (homozygous) | c.809G>C | p.G270A |
| CCDS11511.1 | ITGB3 | Colorectal | Mx22 | g.chr17:42724834G>A | IVS10+1G>A | sp |
| CCDS11512.1 | FLJ40342 | Breast | HCC2218 | g.chr17:42802854G>T | c.856G>T | p.Q286H |
| CCDS11544.1 | GALGT2 | Colorectal | Mx22 | g.chr17:44801142C>A | c.1376C>A | p.P459H |
| CCDS11590.1 | DGKE | Breast | HCC1954 | g.chr17:52267451T>G (homozygous) | c.298T>G | p.L99R |
| CCDS11591.1 | TRIM25 | Breast | BB22T | g.chr17:52338841A>T | c.901A>T | p.K301X |
| CCDS11600.1 | SFRS1 | Breast | HCC1143 | g.chr17:53438817C>T | c.265C>T | p.P89S |
| CCDS11604.1 | MPO | Colorectal | Mx41 | g.chr17:53707927G>A | c.1340G>A | p.R447Q |
| CCDS11613.1 | PPM1E | Breast | HCC2218 | g.chr17:54397951C>T | c.898C>T | p.S233L |
| CCDS11613.1 | PPM1E | Breast | BB9T | g.chr17:54401829C>G | c.931C>G | p.R311G |
| CCDS11621.1 | RPS6KB1 | Colorectal | Mx42 | g.chr17:55366663G>A | c.866G>A | p.G289E |
| CCDS11645.1 | PSMC5 | Colorectal | Mx32 | g.chr17:59260956G>A | c.179G>A | p.R60Q |
| CCDS11683.1 | ABCA8 | Colorectal | Mx38 | g.chr17:64643869_64643865dupT | c.419_dupT | fs |
| CCDS11702.1 | IREM2 | Colorectal | Mx27 | g.chr17:70125161A>G | c.79A>G | p.T27A |
| CCDS11708.1 | OTOP2 | Colorectal | Mx22 | g.chr17:70438500C>T | c.1175C>T | p.A302V |
| CCDS11716.1 | GGA3 | Breast | HCC1143 | g.chr17:70747110C>T (homozygous) | c.1622C>T | p.S541L |
| CCDS11805.1 | CSNK1D | Breast | HCC2218 | g.chr17:77606040C>G | c.290C>G | p.S97C |
| CCDS11810.1 | UTS2R | Breast | HCC1143 | g.chr17:77925927C>G (homozygous) | c.436C>G | p.S146R |
| CCDS11858.1 | C18orf19 | Breast | HCC1954 | g.chr18:13871832G>A | c.245G>A | p.R82H |
| CCDS11858.1 | C18orf19 | Breast | HCC1599 | g.chr18:13871658T>A | c.419T>A | p.V140E |
| CCDS11879.1 | ANKRD29 | Breast | HCC2218 | g.chr18:19472658G>A | c.283G>A | p.V95M |
| CCDS11901.1 | KIAA1012 | Breast | HCC2218 | g.chr18:27724814G>A | c.1610G>A | p.R537Q |
| CCDS11906.1 | DTNA | Breast | HCC1937 | g.chr18:30652196_30652199delGTGT (homozygous) | c.780_783delGTGT | fs |

FIG. 12O

| | | | | | | |
|---|---|---|---|---|---|---|
| CCDS11917.1 | P15RS | Breast | HCC1395 | g.chr18:31901303G>C | c.63G>C | p.Q21H |
| CCDS11918.1 | STATIP1 | Breast | HCC1187 | g.chr18:31994943_31994944delCT | c.1739_1740delCT | fs |
| CCDS11923.1 | SETBP1 | Colorectal | Mx22 | g.chr18:40786787C>T | c.3322C>T | p.R1108W |
| CCDS11926.1 | KIAA1632 | Breast | BB4T | g.chr18:41735074G>A | c.1027G>A | p.A343T |
| CCDS11926.1 | KIAA1632 | Breast | HCC1954 | g.chr18:41714111G>A | c.2090G>A | p.C697Y |
| CCDS11929.1 | KIAA1632 | Breast | BB13T | g.chr18:41704589C>T | c.2662C>T | p.R888W |
| CCDS11932.1 | TCEB3B | Colorectal | Mx30 | g.chr18:42814141G>A | c.1493G>A | p.R498Q |
| CCDS11934.1 | SMAD2 | Colorectal | Mx30 | g.chr18:43828842A>T (homozygous) | c.899A>T | p.D300V |
| CCDS11934.1 | SMAD2 | Colorectal | Hx5 | g.chr18:43822232G>A (homozygous) | IVS9-1G>A | sp |
| CCDS11934.1 | SMAD2 | Colorectal | Hx100 | g.chr18:43822215_43822209delGTTGCTC (homozygous) | c.1385_1391delGTTGCTC | fs |
| CCDS11935.1 | KIAA0427 | Breast | HCC1187 | g.chr18:44541852G>C | c.1165G>C | p.V389L |
| CCDS11935.1 | KIAA0427 | Breast | BB1T | g.chr18:44542001G>C | c.1314C>C | p.M438I |
| CCDS11950.1 | SMAD4 | Colorectal | Mx8 | g.chr18:46829192C>T (homozygous) | c.388C>T | p.P130S |
| CCDS11950.1 | SMAD4 | Colorectal | Co108 | g.chr18:46845886G>A (homozygous) | c.1051G>A | p.D351N |
| CCDS11950.1 | SMAD4 | Colorectal | Co92 | g.chr18:46845917G>A (homozygous) | c.1082G>A | p.R361H |
| CCDS11950.1 | SMAD4 | Colorectal | Hx206 | g.chr18:46845969_46845970delAG (homozygous) | c.1134_1135delAG | fs |
| CCDS11952.1 | DCC | Colorectal | Co92 | g.chr18:49191000T>C (homozygous) | c.3118T>C | p.F1039S |
| CCDS11965.1 | ATP8B1 | Breast | HCC1599 | g.chr18:53513387C>A | IVS9+4C>A | sp |
| CCDS11965.1 | ATP8B1 | Breast | BB9T | g.chr18:53488774C>A | IVS17-4C>A | sp |
| CCDS11965.1 | ATP8B1 | Breast | BB14T | g.chr18:53479454C>T | c.2657C>T | p.A886V |
| CCDS11965.1 | ATP8B1 | Breast | BB1T | g.chr18:53468940C>G | c.3534C>G | p.I1178M |
| CCDS11969.1 | ZNF532 | Breast | HCC1954 | g.chr18:54752763C>T | c.2465C>T | p.9822L |
| CCDS11977.1 | CDH20 | Breast | BB30T | g.chr18:57321158G>A | c.684G>A | p.M228I |
| CCDS11977.1 | CDH20 | Breast | BB23T | g.chr18:57346408C>A | c.1246C>A | p.P418T |
| CCDS11977.1 | CDH20 | Breast | HCC2157 | g.chr18:57372740G>T | c.2236G>T | p.G746H |
| CCDS11979.1 | KIAA1468 | Colorectal | Mx41 | g.chr18:58092218G>A | c.1718G>A | p.G573E |
| CCDS11995.1 | C18orf4 | Colorectal | Co92 | g.chr18:63329558A>G | c.3293A>G | p.K1100E |
| CCDS11998.1 | SOCS6 | Colorectal | Mx22 | g.chr18:66143138_66143139delAG | c.234_235delAG | fs |
| CCDS12013.1 | GALL3 | Colorectal | Co92 | g.chr18:74853407G>A (homozygous) | c.426G>A | p.R143H |
| CCDS12015.1 | NFATC1 | Colorectal | Mx42 | g.chr18:75272208G>A | c.943G>A | p.A315T |
| CCDS12020.1 | PQLC1 | Colorectal | Mx42 | g.chr18:75780256G>C | c.524G>C | p.G175A |
| CCDS12052.1 | C19orf8 | Breast | HCC2157 | g.chr19:9642826delC | c.585delC | fs |
| CCDS12065.1 | DAZAP1 | Breast | HCC1008 | g.chr19:1385828T>A | c.1141T>A | p.S381T |
| CCDS12068.1 | APC2 | Breast | BB22T | g.chr19:1413007G>T | c.1684G>T | p.A562S |
| CCDS12068.1 | APC2 | Breast | HCC2157 | g.chr19:1420307G>A | c.6007G>A | p.G2003S |
| CCDS12073.1 | UQCR | Breast | HCC1395 | g.chr19:1556356G>A (homozygous) | IVS1+3G>A | sp |
| CCDS12074.1 | TCF3 | Colorectal | Mx42 | g.chr19:1601225C>T | c.23C>T | p.A8V |
| CCDS12076.1 | LOC113179 | Breast | HCC2218 | g.chr19:1864088C>T | c.984C>T | p.R332C |
| CCDS12090.1 | LMNB2 | Colorectal | Co108 | g.chr19:2388148C>T | c.646C>T | p.R216W |
| CCDS12136.1 | TRIP | Breast | Hs 578T | g.chr19:4789252G>A | c.138G>A | p.M46I |
| CCDS12140.1 | PTPRS | Colorectal | Mx32 | g.chr19:5173816C>T | c.2821C>T | p.T974M |
| CCDS12157.1 | RFX2 | Breast | HCC1395 | g.chr19:5995274C>G (homozygous) | c.110C>G | p.A37G |
| CCDS12157.1 | RFX2 | Breast | BB28T | g.chr19:5991185G>A | c.328C>A | p.E110K |
| CCDS12157.1 | RFX2 | Breast | BB20T | g.chr19:5991045_5991045dupG | c.488_dupG | fs |
| CCDS12173.1 | SH2D3A | Breast | HCC1395 | g.chr19:6706029A>G (homozygous) | c.794A>G | p.E265G |
| CCDS12180.1 | MCOLN1 | Breast | HCC2157 | g.chr19:7499713G>C | c.991G>C | p.V331L |
| CCDS12207.1 | MGC33407 | Colorectal | Co79 | g.chr19:8669927C>A (homozygous) | c.125C>A | p.A42D |
| CCDS12207.1 | MGC33407 | Colorectal | Mx41 | g.chr19:8669058G>A | c.994G>A | p.A332T |
| CCDS12214.1 | ZNF560 | Colorectal | Mx38 | g.chr19:9440838G>A | c.557G>A | p.G186E |
| CCDS12221.1 | OLFM2 | Colorectal | Mx42 | g.chr19:9829494C>T | c.257C>T | p.T86M |
| CCDS12233.1 | ICAM5 | Breast | BB5T | g.chr19:10263230C>G (homozygous) | c.416C>G | p.L140V |
| CCDS12233.1 | ICAM5 | Breast | BB23T | g.chr19:10263374C>T | c.562C>T | p.R188W |
| CCDS12233.1 | ICAM5 | Breast | HCC1008 | g.chr19:10264919G>C | c.1482G>C | p.E488Q |
| CCDS12239.1 | KEAP1 | Breast | HCC1008 | g.chr19:10471642G>A | c.68G>A | p.C23Y |
| CCDS12239.1 | KEAP1 | Breast | BB20T | g.chr19:10461011C>T | c.1565C>T | p.A522V |
| CCDS12249.1 | TMED1 | Breast | HCC2157 | g.chr19:10808771G>A | c.304C>G | p.D102N |
| CCDS12258.1 | LPPR2 | Colorectal | Mx42 | g.chr19:11332965C>T | c.484C>T | p.T155M |
| CCDS12271.1 | ZNF442 | Colorectal | Hx220 | g.chr19:12322945C>T | c.454C>T | p.P152S |
| CCDS12271.1 | ZNF442 | Colorectal | Co92 | g.chr19:12322671G>C | c.728G>C | p.C243S |
| CCDS12329.1 | AKAP8 | Breast | HCC1008 | g.chr19:15326813A>T | c.1992A>T | p.Q664H |
| CCDS12338.1 | TPM4 | Breast | HCC1395 | g.chr19:18065509G>C | c.610G>C | p.E204Q |
| CCDS12242.1 | AP1M1 | Breast | HCC1008 | g.chr19:18200000G>A | c.908G>A | p.R303Q |
| CCDS12393.1 | FLJ20422 | Breast | HCC1187 | g.chr19:19104499G>T | c.253G>T | p.E85X |
| CCDS12393.1 | FLJ20422 | Breast | HCC1187 | g.chr19:19104498A>T | c.254A>T | p.E85V |
| CCDS12406.1 | PBX4 | Colorectal | Mx42 | g.chr19:19536519C>T | c.846C>T | p.T283M |
| CCDS12413.1 | ZNF43 | Colorectal | Mx27 | g.chr19:21783949C>T | c.712C>T | p.R238C |
| CCDS12429.1 | LOC126248 | Breast | HCC2218 | g.chr19:38330410G>C | c.499G>C | p.D166H |
| CCDS12433.1 | CHST8 | Colorectal | Mx22 | g.chr19:38955273G>A | c.740G>A | p.R247H |
| CCDS12463.1 | ZD52F10 | Colorectal | Mx41 | g.chr19:40696160C>A | c.38C>A | p.A13D |
| CCDS12503.1 | ZNF569 | Breast | HCC 38 | g.chr19:42609051C>G | c.85C>G | p.Q29E |
| CCDS12503.1 | ZNF569 | Breast | BB9T | g.chr19:42597140A>G | c.260A>G | p.E87G |
| CCDS12506.1 | ZNF540 | Colorectal | Co74 | g.chr19:42794845A>T | c.824A>T | p.K275I |
| CCDS12548.1 | ZNF548 | Breast | HCC2218 | g.chr19:45196116C>G | c.43C>G | p.L15V |
| CCDS12590.1 | ARHGEF1 | Colorectal | Co108 | g.chr19:47088594G>A | c.493G>A | p.V165M |
| CCDS12601.1 | CIC | Breast | HCC2218 | g.chr19:47463090G>A | c.310G>A | p.E104K |
| CCDS12601.1 | CIC | Breast | BB7T | g.chr19:47467140G>A | c.1954G>A | p.A652T |
| CCDS12601.1 | CIC | Breast | BB5T | g.chr19:47488433_47488433dupC | c.3150_dupC | fs |
| CCDS12607.1 | LIPE | Breast | HCC1599 | g.chr19:47622705C>A | c.437C>A | p.P146Q |
| CCDS12624.1 | XRCC1 | Colorectal | Mx30 | g.chr19:48748043C>T | c.1048C>T | p.R350W |
| CCDS12634.1 | ZNF155 | Colorectal | Mx32 | g.chr19:49183270A>G | c.1421A>G | p.H74R |
| CCDS12649.1 | APOC4 | Breast | HCC1187 | g.chr19:50140242C>A | c.224C>A | p.P75Q |
| CCDS12652.1 | GFRS16 | Breast | Hs 578T | g.chr19:50254390T>C | c.593T>C | p.L198S |
| CCDS12661.1 | AGE-1 | Colorectal | Mx22 | g.chr19:50603719_50603719dupA (homozygous) | c.653_dupA | fs |
| CCDS12670.1 | EML2 | Colorectal | Mx41 | g.chr19:50811818G>T | c.1450G>T | p.V484L |
| CCDS12703.1 | ZNF541 | Breast | HCC1008 | g.chr19:52738463C>T | c.473C>T | p.G158L |
| CCDS12706.1 | CRX | Breast | HCC1599 | g.chr19:53034558C>T | c.422C>T | p.S141F |
| CCDS12711.1 | LIG1 | Colorectal | Co79 | g.chr19:53348853A>G | c.454A>G | p.K152E |
| CCDS12711.1 | LIG1 | Colorectal | Mx27 | g.chr19:53323076C>T | c.1835C>T | p.S612L |
| CCDS12719.1 | GRIN2D | Breast | HCC1008 | g.chr19:53593670C>T | c.418C>T | p.P140S |
| CCDS12719.1 | GRIN2D | Breast | HCC 38 | g.chr19:53600193G>A | c.856G>A | p.G286R |
| CCDS12719.1 | GRIN2D | Breast | BB28T | g.chr19:53610100A>G | c.1580A>G | p.E527G |

| CCDS13713.1 | KRTAP10-8 | Breast | HCC1937 | g.chr21:44656921C>T | c.478C>T | p.S159F |
|---|---|---|---|---|---|---|
| CCDS13716.1 | ITGB2 | Breast | HCC1187 | g.chr21:45146037_45146013delTGAACACGCACCCTGATAAGCTGCG | c.539_563delTGAACACGCACCCTGATAAGCTGCG | fs |
| CCDS13734.1 | MCM3AP | Colorectal | Hs218 | g.chr21:46528175C>G | c.1225C>G | p.L409V |
| CCDS13734.1 | MCM3AP | Colorectal | Mx43 | g.chr21:46489481G>A | c.4726G>A | p.V1576I |
| CCDS13745.1 | ATP6V1E1 | Colorectal | Mx22 | g.chr22:18470592A>G | c.148A>G | p.R50G |
| CCDS13754.1 | PRODH | Breast | HCC 38 | g.chr22:17279020A>G | c.1463A>G | p.N488S |
| CCDS13765.1 | TBX1 | Breast | HCC1008 | g.chr22:18127178C>G (homozygous) | c.828C>G | p.Y278X |
| CCDS13765.1 | TBX1 | Colorectal | Mx43 | g.chr22:18144990G>A | c.1010G>A | p.G337E |
| CCDS13768.1 | GNB1L | Breast | HCC1954 | g.chr22:18150884G>A (homozygous) | c.886G>A | p.A296T |
| CCDS13774.1 | HTF9C | Breast | HCC1599 | g.chr22:18474708C>T | c.1810C>T | p.P604S |
| CCDS13775.1 | RANBP1 | Breast | HCC1937 | g.chr22:18481122G>C | c.48C>G | p.E16D |
| CCDS13779.1 | SCARF2 | Breast | HCC1937 | g.chr22:19108128C>T | c.1485C>T | p.R499C |
| CCDS13796.1 | PPM1F | Colorectal | Mx43 | g.chr22:20610078G>A | c.887G>A | p.R296Q |
| CCDS13796.1 | PPM1F | Breast | Hs 578T | g.chr22:20602135C>A | c.1249C>A | p.Q417K |
| CCDS13816.1 | MMP11 | Colorectal | Mx38 | g.chr22:22447338C>A (homozygous) | c.496G>A | p.D166N |
| CCDS13847.1 | XBP1 | Breast | HCC2218 | g.chr22:27521032A>T | c.35A>T | p.D12V |
| CCDS13859.1 | C22orf19 | Breast | BB14T | g.chr22:28248417C>A | c.1139C>A | p.T380K |
| CCDS13859.1 | C22orf19 | Breast | HCC1008 | g.chr22:28237904G>A | c.1495G>A | p.G499S |
| CCDS13861.1 | NF2 | Breast | HCC2218 | g.chr22:28305425C>A | c.1387G>A | p.E463K |
| CCDS13870.1 | MTMR3 | Breast | HCC1937 | g.chr22:28723526G>C | c.661G>C | p.V221L |
| CCDS13870.1 | MTMR3 | Breast | BB23T | g.chr22:28740882_28740882dupC | c.2680_dupC | fs |
| CCDS13875.1 | SF3A1 | Colorectal | Mx32 | g.chr22:29059544C>T | c.1531C>T | p.R511W |
| CCDS13888.1 | SMTN | Colorectal | Mx40 | g.chr22:29817321G>A | c.1910G>A | p.R837Q |
| CCDS13888.1 | SMTN | Colorectal | Mx42 | g.chr22:29819335C>T | c.2288C>T | p.A763V |
| CCDS13925.1 | APOL1 | Breast | HCC1937 | g.chr22:34985945T>C | c.611T>C | p.I204T |
| CCDS13927.1 | MYH9 | Breast | BB7T | g.chr22:35023183G>C | c.2430G>C | p.K810N |
| CCDS13927.1 | MYH9 | Breast | HCC1187 | g.chr22:35012676_35012674delGCA (homozygous) | c.4200_4202delGCA | indel |
| CCDS13941.1 | TMPRSS6 | Breast | BB14T | g.chr22:35823941_35823941dupC | c.44_dupC | fs |
| CCDS13941.1 | TMPRSS6 | Breast | HCC1599 | g.chr22:35810313G>A | c.666G>A | p.R223H |
| CCDS13941.1 | TMPRSS6 | Breast | BB33T | g.chr22:35810306C>A (homozygous) | c.675C>A | p.S225R |
| CCDS13945.1 | RAC2 | Breast | HCC1143 | g.chr22:35962148C>T | c.86C>T | p.P29L |
| CCDS13950.1 | LGALS2 | Breast | HCC1395 | g.chr22:36290775G>C | c.394G>C | p.E132Q |
| CCDS13951.1 | GGA1 | Breast | BB22T | g.chr22:36343939G>A | c.715G>A | p.G239S |
| CCDS13951.1 | GGA1 | Breast | HCC1395 | g.chr22:36351528C>G | c.1450C>G | p.P484A |
| CCDS13961.1 | MICAL-L1 | Breast | HCC2218 | g.chr22:38658278G>A | c.2449G>A | p.E817K |
| CCDS13963.1 | POLR2F | Breast | HCC2157 | g.chr22:36679940T>A | c.178T>A | p.Y60N |
| CCDS13978.1 | UNC84B | Colorectal | Mx42 | g.chr22:37459846G>A | IVS13+1G>A | sp |
| CCDS13988.1 | RPL3 | Breast | HCC2157 | g.chr22:38840102A>G | c.1A>G | unknown |
| CCDS14000.1 | LOC113828 | Breast | Hs 578T | g.chr22:38742267C>T | c.749C>T | p.A250V |
| CCDS14017.1 | ACO2 | Breast | HCC2157 | g.chr22:40248408C>A | c.2090C>A | p.T697N |
| CCDS14023.1 | SREBF2 | Breast | HCC2157 | g.chr22:40591489G>T | c.817G>T | p.A273S |
| CCDS14023.1 | SREBF2 | Breast | HCC1937 | g.chr22:40594475T>A | c.1041T>A | p.N347K |
| CCDS14042.1 | ARFGAP3 | Breast | HCC1954 | g.chr22:41538305A>G | c.869A>G | p.E290G |
| CCDS14073.1 | PKDREJ | Breast | BB23T | g.chr22:44977733C>G (homozygous) | c.2006C>G | p.A669G |
| CCDS14073.1 | PKDREJ | Breast | HCC1395 | g.chr22:44874115C>T | c.5824C>T | p.T1875I |
| CCDS14085.1 | PANX2 | Breast | HCC1395 | g.chr22:46916038C>T (homozygous) | c.410C>T | p.S137F |
| CCDS14093.1 | BC002942 | Breast | HCC1008 | g.chr22:49235500C>T (homozygous) | c.128C>T | p.P43L |
| CCDS14126.1 | NLGN4X | Colorectal | Co106 | g.chrX:5687002G>A | c.6040G>A | p.G2214S |
| CCDS14135.1 | APXL | Breast | HCC1395 | g.chrX:9715055G>C (homozygous) | c.3733G>C | p.D1245H |
| CCDS14152.1 | TLR8 | Colorectal | Mx41 | g.chrX:12966973C>T (homozygous) | c.157C>T | p.R53X |
| CCDS14155.1 | EGFL6 | Breast | BB13T | g.chrX:13405025G>T | c.1524C>T | p.L508F |
| CCDS14155.1 | EGFL6 | Breast | HCC1008 | g.chrX:13405025G>T | c.1524C>T | p.L508F |
| CCDS14164.1 | ASB11 | Breast | HCC2218 | g.chrX:15061320_15061315delGCCAGA | c.836_941delGCCAGA | indel |
| CCDS14181.1 | NHS | Breast | HCC1395 | g.chrX:17504476G>A (homozygous) | c.2530G>A | p.A844T |
| CCDS14182.1 | SCML1 | Breast | HCC2157 | g.chrX:17527859C>A | c.129C>A | p.Y43X |
| CCDS14186.1 | CDKL5 | Colorectal | Co106 | g.chrX:18381803A>C | c.1102A>C | p.N368H |
| CCDS14195.1 | FLJ14503 | Breast | HCC1599 | g.chrX:188945610>C | c.94G>C | p.A32P |
| CCDS14197.1 | RPS6KA3 | Breast | HCC1008 | g.chrX:16950628A>G | c.1246A>G | p.M416V |
| CCDS14198.1 | CNKSR2 | Colorectal | Mx32 | g.chrX:21204344G>A | c.137G>A | p.R46H |
| CCDS14202.1 | YY2 | Breast | HCC1008 | g.chrX:21634566G>A | c.307G>A | p.D103N |
| CCDS14233.1 | DMD | Colorectal | Mx41 | g.chrX:32422885G>T (homozygous) | c.1002G>T | p.L334F |
| CCDS14233.1 | DMD | Breast | BB32T | g.chrX:32226361G>C | c.3655G>C | p.E1219Q |
| CCDS14233.1 | DMD | Breast | HCC1395 | g.chrX:32167384G>A (homozygous) | c.4409G>A | p.R1470H |
| CCDS14233.1 | DMD | Colorectal | Co79 | g.chrX:31748238C>T | c.6491C>T | p.A2164V |
| CCDS14236.1 | FAM47B | Breast | HCC2218 | g.chrX:34721209C>T | c.604C>T | p.Q202X |
| CCDS14239.1 | PRRG1 | Breast | HCC1008 | g.chrX:37068559T>A | c.178T>A | p.F60I |
| CCDS14247.1 | OTC | Breast | HCC1395 | g.chrX:38024437A>G | c.809A>G | p.Q270R |
| CCDS14254.1 | CRSP2 | Breast | HCC1395 | g.chrX:40270564C>A (homozygous) | c.3975C>A | p.F1325L |
| CCDS14255.1 | DDX3X | Breast | HCC1395 | g.chrX:40659762G>C (homozygous) | c.881G>C | p.R294T |
| CCDS14260.1 | MAOA | Breast | HCC1395 | g.chrX:43271888C>A (homozygous) | c.45C>A | p.D15E |
| CCDS14264.1 | DUSP21 | Colorectal | Mx22 | g.chrX:44460131C>T | c.499C>T | p.R167C |
| CCDS14265.1 | UTX | Colorectal | Mx42 | g.chrX:44698991T>G (homozygous) | c.3317T>G | p.L1106R |
| CCDS14274.1 | RBM10 | Colorectal | Mx43 | g.chrX:46766098G>A (homozygous) | c.1187G>A | p.R396H |
| CCDS14282.1 | PFC | Breast | BB4T | g.chrX:47245400C>T | c.8C>T | p.T3I |
| CCDS14282.1 | PFC | Breast | HCC2218 | g.chrX:47245324C>G | c.80C>G | p.S27X |
| CCDS14309.1 | PQBP1 | Colorectal | Mx22 | g.chrX:48516481C>T | c.670C>T | p.R224W |
| CCDS14311.1 | SLC35A2 | Breast | HCC2157 | g.chrX:48516676G>T | c.756G>T | p.W252C |
| CCDS14320.1 | LMO6 | Breast | HCC1008 | g.chrX:48785567G>C | c.1874G>C | p.E558D |
| CCDS14331.1 | CCNB3 | Colorectal | Co74 | g.chrX:49885995A>C | c.1790A>C | p.K597T |
| CCDS14362.1 | MAGED2 | Breast | Hs 578T | g.chrX:54724215A>C | c.1372A>C | p.K458Q |
| CCDS14379.1 | MTMR8 | Breast | HCC1008 | g.chrX:63357767T>A | c.379T>A | p.W127R |
| CCDS14379.1 | MTMR8 | Breast | HCC1937 | g.chrX:63331794G>A | c.1360G>A | p.E454K |
| CCDS14381.1 | LAS1L | Colorectal | Mx30 | g.chrX:64534264C>T | c.508C>T | p.R170C |
| CCDS14390.1 | STARD8 | Breast | HCC1395 | g.chrX:67720579G>A (homozygous) | c.562G>A | p.G188S |
| CCDS14390.1 | STARD8 | Breast | BB32T | g.chrX:67720741G>A | c.724G>A | p.E242K |
| CCDS14394.1 | EDA | Colorectal | Mx22 | g.chrX:68619526C>T | c.353C>T | p.P118L |
| CCDS14399.1 | ARR3 | Colorectal | Mx30 | g.chrX:69280659_69280659dupA | c.682_dupA | fs |
| CCDS14403.1 | DLG3 | Colorectal | Co108 | g.chrX:69446190G>A | c.118G>A | p.G40R |
| CCDS14408.1 | GJB1 | Breast | HCC1395 | g.chrX:70226976G>A | c.398G>A | p.W133X |
| CCDS14412.1 | TAF1 | Breast | HCC1385 | g.chrX:70381158_70381163delAGATAT (homozygous) | c.1046_1051delAGATAT | indel |

FIG. 12R

| | | | | | | |
|---|---|---|---|---|---|---|
| CCDS14412.1 | TAF1 | Breast | BB15T | g.chrX:70457870delT | c.4940delT | fs |
| CCDS14426.1 | SLC18A2 | Breast | HCC 38 | g.chrX:73534403_73534407delAATCT | c.1836_1840delAATCT | fs |
| CCDS14433.1 | MAGEE1 | Breast | HCC2713 | g.chrX:75432642A>T | c.1919A>T | p.Y640F |
| CCDS14433.1 | MAGEE1 | Breast | HCC1008 | g.chrX:75433014C>A (homozygous) | c.1991C>A | p.T664N |
| CCDS14445.1 | TBX22 | Colorectal | Co79 | g.chrX:79083950T>C | c.47T>C | p.V16A |
| CCDS14445.1 | TBX22 | Colorectal | Mx26 | g.chrX:79084084C>A | c.151C>A | p.A51T |
| CCDS14445.1 | TBX22 | Colorectal | Mx43 | g.chrX:79089090G>A (homozygous) | c.919G>A | p.D307N |
| CCDS14481.1 | PCDH11X | Colorectal | Co74 | g.chrX:90996773A>G | c.125A>G | p.D42G |
| CCDS14481.1 | PCDH11X | Colorectal | Mx34 | g.chrX:91282537C>T | c.3052C>T | p.R1018X |
| CCDS14517.1 | IL1RAPL2 | Breast | HCC2218 | g.chrX:104817558C>G | c.1818C>G | p.F606L |
| CCDS14529.1 | PRPS1 | Breast | HCC2157 | g.chrX:106894628G>C | c.607G>C | p.D203H |
| CCDB14529.1 | PRPS1 | Breast | BB43T | g.chrX:106894677T>G | c.656T>G | p.V219G |
| CCDS14520.1 | PRPS1 | Colorectal | Mx22 | g.chrX:106894712C>G | c.691C>G | p.H231D |
| CCDS14541.1 | COL4A6 | Colorectal | Mx30 | g.chrX:107220091G>A | c.3389G>A | p.G1130E |
| CCDB14544.1 | IRS4 | Colorectal | Co108 | g.chrX:107785681C>T | c.59C>T | p.A20V |
| CCDS14544.1 | IRS4 | Breast | HCC2218 | g.chrX:107785078C>A | c.644C>A | p.G215E |
| CCDB14544.1 | IRS4 | Colorectal | Mx26 | g.chrX:107784051G>C | c.1869G>C | p.G557R |
| CCDS14545.1 | GUCY2F | Breast | HCC2157 | g.chrX:108525202G>C (homozygous) | c.29G>C | p.R10P |
| CCDS14548.1 | ACSL4 | Colorectal | Mx27 | g.chrX:108732225C>T | c.397C>T | p.R133C |
| CCDS14550.1 | FLJ22679 | Colorectal | Co92 | g.chrX:109222756T>C | c.709T>C | p.Y237H |
| CCDS14555.1 | CAPN6 | Colorectal | Co74 | g.chrX:110300376G>C | c.1072G>C | p.G358R |
| CCDS14558.1 | PLS3 | Breast | HCC1187 | g.chrX:114703779A>C | c.1454A>C | p.D485A |
| CCDS14575.1 | RNF127 | Breast | HCC1008 | g.chrX:117890990C>G | c.365C>G | p.A122G |
| CCDS14590.1 | NDUFA1 | Colorectal | Mx32 | g.chrX:118789203C>T | c.157C>T | p.R53C |
| CCDS14609.1 | ODZ1 | Breast | HCC 38 | g.chrX:123531210G>C | c.1026G>C | p.L342F |
| CCDS14609.1 | ODZ1 | Breast | HCC1008 | g.chrX:123356450G>A | c.3646G>A | p.V1216I |
| CCDS14609.1 | ODZ1 | Colorectal | Mx26 | g.chrX:123281663T>G | c.4444T>G | p.F1482V |
| CCDS14609.1 | ODZ1 | Breast | HCC1837 | g.chrX:123243590G>C | c.6705G>C | p.Q2235H |
| CCDS14609.1 | ODZ1 | Colorectal | Co78 | g.chrX:123243107G>T | c.7189G>T | p.L2396F |
| CCDS14618.1 | BCORL1 | Breast | HCC2218 | g.chrX:128874776G>A | c.2495G>A | p.G832D |
| CCDS14645.1 | MOSPD1 | Breast | HCC2218 | g.chrX:133758883G>A | c.187G>A | p.V63I |
| CCDS14663.1 | ZIC3 | Breast | HCC1008 | g.chrX:136375019C>G | c.649C>G | p.P217A |
| CCDS14684.1 | FGF13 | Colorectal | Co74 | g.chrX:137440688G>A | IVS4-1G>A | sp |
| CCDS14668.1 | ATP11C | Colorectal | Mx27 | g.chrX:138812244C>T | c.47C>T | p.T157I |
| CCDS14668.1 | ATP11C | Colorectal | Co108 | g.chrX:138557749A>C | c.2792A>C | p.Q931P |
| CCDS14878.1 | MAGEC2 | Breast | HCC1954 | g.chrX:141017276G>T | c.16G>T | p.G6C |
| CCDS14879.1 | SLITRK4 | Colorectal | Co108 | g.chrX:142443829G>A | c.616G>A | p.V206I |
| CCDS14697.1 | CD99L2 | Colorectal | Mx22 | g.chrX:149815214G>A | IVS6+1G>A | sp |
| CCDS14701.1 | CNGA2 | Breast | HCC1954 | g.chrX:150578688G>A (homozygous) | c.290G>A | p.R97H |
| CCDS14701.1 | CNGA2 | Breast | HCC1008 | g.chrX:150582739G>A | c.1196G>A | p.R399Q |
| CCDS14702.1 | MAGEA4 | Breast | HCC1008 | g.chrX:150763162G>A | c.458G>A | p.G153D |
| CCDS14720.1 | MAGEA1 | Breast | HCC1008 | g.chrX:151966378A>C | c.833A>C | p.K278T |
| CCDS14721.1 | BGN | Breast | BB4T | g.chrX:152293378C>G | c.797G>C | p.R266T |
| CCDS14721.1 | BGN | Breast | HCC1008 | g.chrX:152293445G>T | c.864G>T | p.K288N |
| CCDS14725.1 | PNCK | Breast | HCC2157 | g.chrX:152459082C>T | c.73C>T | p.P25S |
| CCDS14732.1 | PDZK4 | Breast | HCC1599 | g.chrX:152594843C>T | c.115C>T | p.R39C |
| CCDS14735.1 | AVPR2 | Breast | HCC1008 | g.chrX:152682547G>A | c.740G>A | p.R247H |
| CCDS14767.1 | CLIC2 | Colorectal | Mx41 | g.chrX:154070975G>A | c.665G>A | p.R222H |

*Genomic positions are coordinates in the May 2004, hg17 35.1 UCSC Santa Cruz release of the human genome. Genomic coordinates and sequences of mutations are on the coding strand. All changes are heterozygous unless marked as homozygous. g., genomic sequence; c., cDNA sequence; p., protein sequence; del, deletion; dup, duplication; ins, insertion. *chr, chromosome; †Mutations in non-coding sequences are annotated by intron number preceded by "IVS", with positive numbers starting from the G of the GT splice donor site and negative numbers starting from the G of the AG splice acceptor site. ‡fs, frameshift mutation; sp, splice site mutation; UTR, mutation in 5' or 3' untranslated region; indel, in frame insertion, deletion or duplication change affecting more than a single codon. The amino acid change resulting from mutations in the translation initiating methionine are indicated as "unknown".

FIG. 12S

Table S5. Breast CAN-genes

| Gene | CCDS accession | Gene name | Chromosome band | CaMP score | Estimated fraction of tumors containing mutation* | Total number of mutations | Homo-zygous | Hetero-zygous | Mis-sense | Non-sense | Insertion | Deletion | Dupli-cation | Splice site | UTR |
|---|---|---|---|---|---|---|---|---|---|---|---|---|---|---|---|
| ABCA3 | CCDS10466.1 | ATP-binding cassette, sub-family A (ABC1), member 3 | 16p13.3 | 1.55 | 9% | 3 | 0 | 3 | 3 | 0 | 0 | 0 | 0 | 0 | 0 |
| ABCB10 | CCDS1580.1 | ATP-binding cassette, sub-family B (MDR/TAP), member 10 | 1q42 | 1.39 | 8% | 2 | 0 | 2 | 1 | 0 | 0 | 0 | 0 | 1 | 0 |
| ABCB9 | CCDS9013.1 | ATP-binding cassette, sub-family B (MDR/TAP), member 8 | 7q36 | 1.67 | 6% | 2 | 0 | 2 | 2 | 0 | 0 | 0 | 0 | 0 | 0 |
| ACADM | CCDS668.1 | acyl-Coenzyme A dehydrogenase, C-4 to C-12 straight chain | 1p31 | 1.85 | 8% | 2 | 0 | 2 | 2 | 0 | 0 | 0 | 0 | 0 | 0 |
| ADAM12 | CCDS7653.1 | ADAM metallopeptidase domain 12 | 10q26.3 | 2.25 | 10% | 3 | 0 | 3 | 3 | 0 | 0 | 0 | 0 | 0 | 0 |
| AEGP | CCDS7010.1 | MAM domain containing 4 | 9q34.3 | 1.76 | 10% | 2 | 1 | 2 | 2 | 0 | 0 | 0 | 0 | 0 | 0 |
| ALS2CL | CCDS2743.1 | ALS2 C-terminal like | 3p21.31 | 1.33 | 6% | 2 | 0 | 2 | 2 | 0 | 0 | 0 | 0 | 0 | 0 |
| AMFR | CCDS10758.1 | autocrine motility factor receptor | 16q21 | 1.74 | 7% | 2 | 0 | 2 | 1 | 1 | 0 | 0 | 0 | 0 | 0 |
| APC2 | CCDS12068.1 | adenomatosis polyposis coli 2 | 19p13.3 | 1.25 | 8% | 2 | 0 | 2 | 2 | 0 | 0 | 0 | 0 | 0 | 0 |
| ARHGEF4 | CCDS2165.1 | Rho guanine nucleotide exchange factor (GEF) 4 | 2q22 | 1.43 | 6% | 2 | 0 | 2 | 2 | 0 | 0 | 0 | 0 | 0 | 0 |
| ASL | CCDS5531.1 | argininosuccinate lyase | 7cen-q11.2 | 1.59 | 7% | 2 | 0 | 2 | 1 | 0 | 0 | 1 | 0 | 0 | 0 |
| ATP6B1 | CCDS11965.1 | ATPase, Class I, type 8B, member 1 | 18q21.31 | 3.07 | 13% | 4 | 0 | 4 | 2 | 0 | 0 | 0 | 1 | 2 | 0 |
| BCL11A | CCDS1661.1 | B-cell CLL/lymphoma 11A | 2p16.1 | 1.11 | 8% | 2 | 0 | 2 | 2 | 0 | 0 | 0 | 0 | 0 | 0 |
| BGN | CCDS14721.1 | biglycan | Xq28 | 2.08 | 7% | 3 | 0 | 3 | 3 | 0 | 0 | 0 | 0 | 0 | 0 |
| BRCA1 | CCDS11453.1 | breast cancer 1, early onset | 17q21 | 2.02 | 9% | 2 | 0 | 2 | 2 | 0 | 0 | 0 | 0 | 0 | 0 |
| C14orf155 | CCDS9679.1 | chromosome 14 open reading frame 155 | 14q21.3 | 3.29 | 12% | 3 | 0 | 3 | 3 | 0 | 0 | 0 | 0 | 0 | 0 |
| C22orf19 | CCDS13859.1 | THO complex 5 | 22q12.2 | 1.46 | 6% | 2 | 0 | 2 | 2 | 0 | 0 | 0 | 0 | 0 | 0 |
| CDH10 | CCDS3892.1 | cadherin 10, type 2 (T2-cadherin) | 5p14-p13 | 1.45 | 9% | 2 | 0 | 2 | 2 | 0 | 0 | 0 | 0 | 0 | 0 |
| CDH20 | CCDS11977.1 | cadherin 20, type 2 | 18q22-q23 | 2.24 | 9% | 3 | 0 | 3 | 3 | 0 | 0 | 0 | 0 | 0 | 0 |
| CENTB1 | CCDS11101.1 | centaurin, beta 1 | 17p13.1 | 1.68 | 6% | 2 | 0 | 2 | 1 | 1 | 0 | 0 | 0 | 0 | 0 |
| CENTG1 | CCDS8951.1 | centaurin, gamma 1 | 12q14.1 | 1.29 | 7% | 2 | 0 | 2 | 2 | 0 | 0 | 0 | 0 | 0 | 0 |
| CHD5 | CCDS57.1 | chromodomain helicase DNA binding protein 5 | 1p36.31 | 1.75 | 10% | 3 | 0 | 3 | 2 | 1 | 0 | 0 | 0 | 0 | 0 |
| CIC | CCDS12601.1 | capicua homolog | 19q13.2 | 1.65 | 11% | 2 | 0 | 2 | 2 | 0 | 0 | 0 | 0 | 0 | 0 |
| CMYA1 | CCDS2683.1 | cardiomyopathy associated 1 | 3q22.2 | 1.38 | 8% | 2 | 0 | 2 | 2 | 0 | 0 | 0 | 0 | 0 | 0 |
| CNNM4 | CCDS2024.1 | cyclin M4 | 2p12-p11.2 | 1.34 | 7% | 2 | 0 | 2 | 2 | 0 | 0 | 0 | 0 | 0 | 0 |
| CNTN6 | CCDS2557.1 | contactin 6 | 3p26-p25 | 1.44 | 8% | 2 | 0 | 2 | 2 | 0 | 0 | 0 | 0 | 0 | 0 |
| COL11A1 | CCDS778.1 | collagen, type XI, alpha 1 | 1p21 | 1.75 | 8% | 3 | 0 | 3 | 3 | 0 | 0 | 0 | 0 | 0 | 0 |
| COL19A1 | CCDS4970.1 | collagen, type XIX, alpha 1 | 6q12-q13 | 1.06 | 7% | 2 | 0 | 2 | 2 | 0 | 0 | 0 | 0 | 0 | 0 |
| COL7A1 | CCDS2773.1 | collagen, type VII, alpha 1 | 3p21.1 | 1.46 | 8% | 2 | 0 | 2 | 2 | 0 | 0 | 0 | 0 | 0 | 0 |
| CUBN | CCDS7113.1 | cubilin (intrinsic factor-cobalamin receptor) | 10p12.31 | 2.45 | 15% | 4 | 0 | 4 | 4 | 0 | 0 | 0 | 0 | 0 | 0 |
| CYP1A1 | CCDS10268.1 | cytochrome P450, family 1, subfamily A, polypeptide 1 | 15q22-q24 | 1.69 | 8% | 2 | 0 | 2 | 2 | 0 | 0 | 0 | 0 | 0 | 0 |
| DBN1 | CCDS4420.1 | drebrin 1 | 5q35.3 | 2.53 | 8% | 3 | 1 | 3 | 3 | 0 | 0 | 0 | 0 | 0 | 0 |
| DDX10 | CCDS8342.1 | DEAD (Asp-Glu-Ala-Asp) box polypeptide 10 | 11q22-q23 | 1.29 | 6% | 2 | 0 | 2 | 2 | 0 | 0 | 0 | 0 | 0 | 0 |
| DNAH9 | CCDS11150.1 | dynein, axonemal, heavy polypeptide 9 | 17p12 | 1.67 | 10% | 3 | 0 | 3 | 2 | 0 | 0 | 1 | 0 | 0 | 0 |
| DNASE1L3 | CCDS2866.1 | deoxyribonuclease I-like 3 | 3p21.1-3p14.3 | 1.94 | 6% | 2 | 0 | 2 | 2 | 0 | 0 | 0 | 0 | 0 | 0 |
| EGFL6 | CCDS14155.1 | EGF-like-domain, multiple 6 | Xq22 | 1.79 | 6% | 2 | 0 | 2 | 2 | 0 | 0 | 0 | 0 | 0 | 0 |
| EHMT1 | CCDS7050.1 | euchromatic histone-lysine N-methyltransferase 1 | 9q34.3 | 1.26 | 7% | 2 | 0 | 2 | 2 | 0 | 0 | 0 | 0 | 0 | 0 |
| FLJ10458 | CCDS11291.1 | notchless homolog 1 | 17q12 | 1.57 | 6% | 2 | 0 | 2 | 1 | 0 | 0 | 1 | 0 | 0 | 0 |
| FLJ13479 | CCDS10701.1 | zinc finger protein 668 | 16p11.2 | 3.38 | 14% | 4 | 0 | 4 | 4 | 0 | 0 | 0 | 0 | 0 | 0 |
| FLJ40869 | CCDS1691.1 | hypothetical protein FLJ40869 | 2p24.2 | 2.12 | 11% | 3 | 0 | 3 | 3 | 0 | 0 | 0 | 0 | 0 | 0 |
| FLNB | CCDS2885.1 | filamin B, beta | 3p14.3 | 3.36 | 13% | 5 | 0 | 5 | 4 | 0 | 0 | 0 | 1 | 0 | 0 |
| GAB1 | CCDS3759.1 | GRB2-associated binding protein 1 | 4q31.21 | 1.45 | 5% | 2 | 0 | 2 | 2 | 0 | 0 | 0 | 0 | 0 | 0 |
| GALNT5 | CCDS2203.1 | UDP-N-acetyl-alpha-D-galactosamine:polypeptide N-acetylgalactosaminyltransferase 5 | 2q24.1 | 1.43 | 7% | 2 | 0 | 2 | 2 | 0 | 0 | 0 | 0 | 0 | 0 |
| GGA1 | CCDS13951.1 | golgi associated, gamma adaptin ear containing, ARF binding protein 1 | 22q13.31 | 1.38 | 8% | 2 | 0 | 2 | 2 | 0 | 0 | 0 | 0 | 0 | 0 |
| GLI1 | CCDS8940.1 | glioma-associated oncogene homolog 1 | 12q13.2-q13.3 | 2.30 | 15% | 3 | 0 | 3 | 2 | 0 | 0 | 0 | 0 | 1 | 0 |
| GPNMB | CCDS5380.1 | glycoprotein (transmembrane) nmb | 7p15 | 1.66 | 6% | 2 | 0 | 2 | 2 | 0 | 0 | 0 | 0 | 0 | 0 |
| GRIN2D | CCDS12719.1 | glutamate receptor, ionotropic, N-methyl D-aspartate 2D | 19q13.1-qter | 2.43 | 16% | 3 | 0 | 3 | 3 | 0 | 0 | 0 | 0 | 0 | 0 |
| GSN | CCDS6828.1 | gelsolin | 9q33 | 2.23 | 9% | 2 | 0 | 2 | 1 | 0 | 0 | 0 | 0 | 1 | 0 |
| HDAC4 | CCDS2529.1 | histone deacetylase 4 | 2q37.2 | 1.56 | 7% | 2 | 0 | 2 | 1 | 0 | 0 | 0 | 0 | 1 | 0 |
| HDLBP | CCDS2547.1 | high density lipoprotein binding protein | 2q37 | 2.21 | 10% | 3 | 0 | 3 | 2 | 0 | 0 | 0 | 0 | 1 | 0 |

| Gene | CCDS | Description | Locus | | % | | | | | | | | | |
|---|---|---|---|---|---|---|---|---|---|---|---|---|---|---|
| SPTAN1 | CCDS6905.1 | spectrin, alpha, non-erythrocytic 1 | 9q33-q34 | 2.61 | 16% | 5 | 0 | 5 | 4 | 0 | 1 | 0 | 0 | 0 |
| STARD8 | CCDS14390.1 | START domain containing 8 | Xq13.1 | 1.24 | 6% | 2 | 1 | 1 | 2 | 0 | 0 | 0 | 0 | 0 |
| SULF2 | CCDS13408.1 | sulfatase 2 | 20q12-q13.2 | 1.45 | 6% | 2 | 0 | 2 | 2 | 0 | 0 | 0 | 2 | 0 |
| SYNE2 | CCDS9761.1 | spectrin repeat containing, nuclear envelope 2 | 14q23.2 | 1.29 | 10% | 3 | 1 | 1 | 2 | 0 | 1 | 0 | 0 | 0 |
| TCF1 | CCDS9209.1 | transcription factor 1, hepatic | 12q24.2 | 1.56 | 6% | 2 | 1 | 1 | 2 | 0 | 0 | 0 | 0 | 0 |
| TECTA | CCDS8434.1 | tectorin alpha | 11q22-q24 | 2.41 | 13% | 4 | 1 | 3 | 3 | 0 | 0 | 0 | 0 | 0 |
| THBS3 | CCDS1059.1 | thrombospondin 3 | 1q21 | 1.42 | 11% | 3 | 1 | 1 | 1 | 0 | 1 | 0 | 0 | 0 |
| TMPRSS6 | CCDS13941.1 | transmembrane protease, serine 6 | 22q12.3 | 1.98 | 9% | 3 | 1 | 2 | 2 | 0 | 0 | 0 | 0 | 0 |
| TP53 | CCDS11118.1 | tumor protein p53 | 17p13.1 | >10 | 55% | 18 | 12 | 6 | 10 | 3 | 3 | 0 | 2 | 0 |
| VEPH1 | CCDS3179.1 | ventricular zone expressed PH domain homolog 1 | 3q24-q25 | 2.09 | 9% | 3 | 1 | 3 | 1 | 0 | 1 | 0 | 0 | 0 |
| XDH | CCDS1775.1 | xanthine dehydrogenase | 2q23.1 | 1.29 | 7% | 2 | 0 | 1 | 2 | 0 | 0 | 0 | 0 | 0 |
| ZCSL3 | CCDS7873.1 | zinc finger, CSL-type containing 3 | 11p13 | 1.82 | 6% | 2 | 0 | 2 | 1 | 0 | 0 | 0 | 0 | 0 |
| ZFP64 | CCDS13439.1 | zinc finger protein 64 homolog | 20q13.2 | 1.37 | 6% | 2 | 0 | 2 | 2 | 0 | 0 | 0 | 0 | 0 |
| ZFYVE26 | CCDS9788.1 | zinc finger, FYVE domain containing 26 | 14q24.1 | 1.15 | 8% | 2 | 0 | 2 | 2 | 0 | 0 | 0 | 0 | 0 |
| ZNF318 | CCDS4895.1 | zinc finger protein 318 | 6pter-p12.1 | 1.05 | 7% | 2 | 0 | 2 | 2 | 0 | 0 | 0 | 0 | 0 |
| ZNF569 | CCDS12503.1 | zinc finger protein 569 | 19q13.12 | 1.42 | 8% | 2 | 0 | 2 | 2 | 0 | 0 | 0 | 0 | 0 |

The fraction of the 35 breast tumors evaluated in the Discovery and Validation screens containing mutations of the gene divided by the number of bases successfully sequenced in that gene (i.e., bases with Phred quality score ≥ 20).

FIG. 13C

Table S6. Colorectal CAN-genes

| Gene | CCDS accession | Gene name | Chromosome band | CaMP score | Estimated fraction of tumors containing mutation | Total number of mutations | Homo-zygous | Hetero-zygous | Mis-sense | Non-sense | Insertion | Deletion | Dupli-cation | Splice site | UTR |
|---|---|---|---|---|---|---|---|---|---|---|---|---|---|---|---|
| ABCA1 | CCDS6762.1 | ATP-binding cassette, sub-family A (ABC1), member 1 | 9q31.1 | 2.82 | 12% | 4 | 0 | 4 | 4 | 0 | 0 | 0 | 0 | 0 | 0 |
| ACSL5 | CCDS7572.1 | acyl-CoA synthetase long-chain family member 5 | 10q25.1-q25.2 | 1.57 | 7% | 2 | 1 | 1 | 2 | 0 | 0 | 0 | 0 | 0 | 0 |
| ADAM29 | CCDS3823.1 | ADAM metallopeptidase domain 29 | 4q34 | 1.96 | 10% | 2 | 0 | 2 | 2 | 0 | 0 | 0 | 0 | 0 | 0 |
| ADAMTS15 | CCDS8468.1 | ADAM metallopeptidase with thrombospondin type 1 motif, 15 | 11q25 | 1.75 | 7% | 2 | 0 | 2 | 2 | 0 | 0 | 0 | 0 | 0 | 0 |
| ADAMTS18 | CCDS10926.1 | ADAM metallopeptidase with thrombospondin type 1 motif, 18 | 16q23 | 2.70 | 7% | 2 | 0 | 2 | 2 | 0 | 0 | 0 | 0 | 0 | 0 |
| ADAMTSL3 | CCDS10326.1 | ADAMTS-like 3 | 15q25.2 | 3.27 | 17% | 4 | 2 | 2 | 4 | 0 | 0 | 0 | 0 | 0 | 0 |
| APC | CCDS4107.1 | adenomatosis polyposis coli | 5q21-q22 | >10 | 92% | 31 | 16 | 15 | 2 | 18 | 3 | 7 | 1 | 0 | 0 |
| C10orf137 | CCDS7646.1 | chromosome 10 open reading frame 137 | 10q26.13-q26.2 | 2.87 | 10% | 3 | 0 | 3 | 2 | 1 | 0 | 0 | 0 | 0 | 0 |
| C15orf2 | CCDS10015.1 | chromosome 15 open reading frame 2 | 15q11-q13 | 1.04 | 7% | 2 | 1 | 1 | 2 | 0 | 0 | 0 | 0 | 0 | 0 |
| C6orf29 | CCDS4724.1 | solute carrier family 44, member 4 | 6p21.3 | 1.14 | 6% | 2 | 0 | 2 | 2 | 0 | 0 | 0 | 0 | 0 | 0 |
| CD109 | CCDS4982.1 | CD109 molecule | 6q13 | 1.33 | 7% | 2 | 0 | 2 | 2 | 0 | 0 | 0 | 0 | 0 | 0 |
| CD248 | CCDS8134.1 | CD248 molecule, endosialin | 11q13 | 1.17 | 8% | 2 | 0 | 2 | 2 | 0 | 0 | 0 | 0 | 0 | 0 |
| CHL1 | CCDS2556.1 | cell adhesion molecule with homology to L1CAM | 3p26.1 | 1.28 | 6% | 2 | 0 | 2 | 1 | 0 | 0 | 0 | 1 | 0 | 0 |
| CNTN4 | CCDS2558.1 | contactin 4 | 3p26-p25 | 1.58 | 6% | 2 | 0 | 2 | 2 | 0 | 0 | 0 | 0 | 0 | 0 |
| CSMD3 | CCDS6315.1 | CUB and Sushi multiple domains 3 | 8q23.3 | 1.85 | 11% | 3 | 1 | 2 | 3 | 0 | 0 | 0 | 0 | 0 | 0 |
| EPHA3 | CCDS2922.1 | EPH receptor A3 | 3p11.2 | 4.22 | 13% | 4 | 0 | 4 | 4 | 0 | 0 | 0 | 0 | 0 | 0 |
| EPHB6 | CCDS5873.1 | EPH receptor B6 | 7q33-q35 | 3.50 | 13% | 4 | 0 | 4 | 4 | 0 | 0 | 0 | 0 | 0 | 0 |
| ERCC6 | CCDS7229.1 | excision repair cross-complementing rodent repair deficiency, complementation group 6 | 10q11.23 | 1.02 | 8% | 5 | 0 | 5 | 5 | 0 | 0 | 0 | 0 | 0 | 0 |
| EVL | CCDS9955.1 | Enah/Vasp-like | 14q32.2 | 1.97 | 6% | 2 | 0 | 2 | 2 | 0 | 0 | 0 | 0 | 0 | 0 |
| EYA4 | CCDS5165.1 | eyes absent homolog 4 | 6q23 | 1.51 | 5% | 2 | 0 | 2 | 2 | 0 | 0 | 0 | 0 | 0 | 0 |
| FBXW7 | CCDS3777.1 | F-box and WD-40 domain protein 7 | 4q31.3 | 5.07 | 14% | 4 | 1 | 3 | 3 | 1 | 0 | 0 | 0 | 0 | 0 |
| GALNS | CCDS10970.1 | galactosamine (N-acetyl)-6-sulfate sulfatase | 16q24.3 | 1.19 | 6% | 2 | 0 | 2 | 2 | 0 | 0 | 0 | 0 | 0 | 0 |
| GNAS | CCDS13472.1 | GNAS complex locus | 20q13.3 | 2.64 | 10% | 3 | 0 | 3 | 3 | 0 | 0 | 0 | 0 | 0 | 0 |
| GUCY1A2 | CCDS8335.1 | guanylate cyclase 1, soluble, alpha 2 | 11q21-q22 | 3.51 | 12% | 3 | 0 | 3 | 2 | 1 | 0 | 0 | 0 | 0 | 0 |
| HAPLN1 | CCDS4081.1 | hyaluronan and proteoglycan link protein 1 | 5q14.3 | 1.22 | 6% | 2 | 0 | 2 | 2 | 0 | 0 | 0 | 0 | 0 | 0 |
| HIST1H1B | CCDS4635.1 | histone 1, H1b | 6p22-p21.3 | 2.47 | 8% | 2 | 0 | 2 | 2 | 0 | 0 | 0 | 0 | 0 | 0 |
| K6IRS3 | CCDS8834.1 | keratin 6 irs3 | 12q13.3 | 1.22 | 8% | 2 | 0 | 2 | 2 | 0 | 0 | 0 | 0 | 0 | 0 |
| KCNQ5 | CCDS4976.1 | potassium voltage-gated channel, KQT-like subfamily, member 5 | 6q14 | 1.17 | 9% | 3 | 0 | 3 | 2 | 1 | 0 | 0 | 0 | 0 | 0 |
| KIAA1409 | CCDS9911.1 | KIAA1409 | 14q32.13 | 1.60 | 9% | 3 | 0 | 3 | 3 | 0 | 0 | 0 | 0 | 0 | 0 |
| KRAS | CCDS8702.1 | v-Ki-ras2 Kirsten rat sarcoma viral oncogene homolog | 12p12.1 | >10 | 44% | 16 | 4 | 12 | 16 | 0 | 0 | 0 | 0 | 0 | 0 |
| LGR6 | CCDS1424.1 | leucine-rich repeat-containing G protein-coupled receptor 6 | 1q32.1 | 2.21 | 9% | 3 | 1 | 2 | 2 | 0 | 0 | 1 | 0 | 0 | 0 |
| LMO7 | CCDS9454.1 | LIM domain 7 | 13q22.2 | 1.29 | 6% | 2 | 0 | 2 | 2 | 0 | 0 | 0 | 0 | 0 | 0 |
| LOC157697 | CCDS9955.1 | glutamate-rich 1 | 8p23.3 | 1.97 | 7% | 2 | 0 | 2 | 2 | 0 | 0 | 0 | 0 | 0 | 0 |
| LRP2 | CCDS2232.1 | low density lipoprotein-related protein 2 | 2q24-q31 | 1.17 | 10% | 3 | 0 | 3 | 3 | 0 | 0 | 0 | 0 | 1 | 0 |
| MAP2 | CCDS2384.1 | microtubule-associated protein 2 | 2q34-q35 | 1.00 | 5% | 2 | 0 | 2 | 1 | 0 | 0 | 0 | 1 | 0 | 0 |
| MCP | CCDS1479.1 | CD46 molecule, complement regulatory protein | 1q32 | 2.14 | 6% | 2 | 0 | 2 | 2 | 0 | 0 | 0 | 0 | 0 | 0 |
| MGC33407 | CCDS12207.1 | hypothetical protein MGC33407 | 18p13.2 | 1.22 | 5% | 2 | 1 | 1 | 2 | 0 | 0 | 0 | 0 | 0 | 0 |
| MKRN3 | CCDS10013.1 | makorin, ring finger protein, 3 | 15q11-q13 | 1.29 | 6% | 2 | 0 | 2 | 2 | 0 | 0 | 0 | 0 | 0 | 0 |
| MLL3 | CCDS5931.1 | myeloid/lymphoid or mixed-lineage leukemia 3 | 7q36.1 | 3.69 | 21% | 6 | 0 | 6 | 4 | 1 | 0 | 1 | 0 | 0 | 0 |
| MMP2 | CCDS10752.1 | matrix metallopeptidase 2 | 16q13-q21 | 2.31 | 9% | 3 | 1 | 3 | 3 | 0 | 0 | 0 | 0 | 0 | 0 |
| NF1 | CCDS11264.1 | neurofibromin 1 | 17q11.2 | 1.90 | 10% | 3 | 0 | 3 | 2 | 0 | 0 | 0 | 1 | 0 | 0 |
| OBSCN | CCDS1570.1 | obscurin, cytoskeletal calmodulin and titin-interacting RhoGEF | 1q42.13 | 2.56 | 19% | 7 | 1 | 7 | 5 | 1 | 0 | 1 | 0 | 0 | 0 |
| P2RX7 | CCDS9213.1 | purinergic receptor P2X, ligand-gated ion channel, 7 | 12q24 | 1.27 | 6% | 2 | 0 | 2 | 2 | 0 | 0 | 0 | 0 | 0 | 0 |

FIG. 14A

| Gene | CCDS | Description | Locus | | % | | | | | | | | | |
|---|---|---|---|---|---|---|---|---|---|---|---|---|---|---|
| P2RY14 | CCDS3156.1 | purinergic receptor P2Y, G-protein coupled, 14 | 3q21-q25 | 2.22 | 9% | 2 | 0 | 2 | 1 | 0 | 0 | 0 | 0 | 0 |
| PHIP | CCDS4987.1 | pleckstrin homology domain interacting protein | 6q14 | 1.18 | 7% | 2 | 0 | 2 | 2 | 0 | 0 | 0 | 0 | 0 |
| PKHD1 | CCDS4935.1 | polycystic kidney and hepatic disease 1 | 6p12.2 | 3.46 | 16% | 5 | 0 | 5 | 5 | 0 | 0 | 0 | 0 | 0 |
| PKNOX1 | CCDS13692.1 | PBX/knotted 1 homeobox 1 | 21q22.3 | 1.44 | 7% | 2 | 0 | 2 | 1 | 0 | 0 | 0 | 1 | 0 |
| PRKD1 | CCDS9637.1 | protein kinase D1 | 14q11 | 1.50 | 9% | 2 | 0 | 2 | 2 | 0 | 0 | 0 | 0 | 0 |
| PTPRD | CCDS6472.1 | protein tyrosine phosphatase, receptor type, D | 9q23-p24.3 | 2.20 | 10% | 3 | 0 | 3 | 3 | 0 | 0 | 0 | 0 | 0 |
| PTPRU | CCDS334.1 | protein tyrosine phosphatase, receptor type, U | 1p35.3-p35.1 | 1.35 | 9% | 3 | 0 | 3 | 3 | 0 | 0 | 0 | 0 | 0 |
| RET | CCDS7200.1 | ret proto-oncogene | 10q11.2 | 2.29 | 10% | 3 | 0 | 3 | 3 | 0 | 0 | 0 | 0 | 0 |
| RUNX1T1 | CCDS6256.1 | runt-related transcription factor 1; translocated to, 1 | 8q22 | 2.42 | 9% | 3 | 0 | 3 | 2 | 0 | 1 | 0 | 0 | 0 |
| SCN3B | CCDS8442.1 | sodium channel, voltage-gated, type III, beta | 11q23.3 | 1.89 | 6% | 2 | 0 | 2 | 2 | 0 | 0 | 0 | 0 | 0 |
| SDBCAG84 | CCDS13257.1 | ERGIC and golgi 3 | 20p ter-q12 | 2.21 | 6% | 2 | 0 | 2 | 1 | 0 | 1 | 0 | 0 | 0 |
| SEC8L1 | CCDS5829.1 | exocyst complex component 4 | 7q31 | 2.24 | 9% | 3 | 0 | 3 | 2 | 1 | 0 | 0 | 0 | 0 |
| SFRS6 | CCDS13318.1 | splicing factor, arginine/serine-rich 6 | 20q12-q13.1 | 1.28 | 6% | 2 | 0 | 2 | 2 | 0 | 0 | 0 | 0 | 0 |
| SLC29A1 | CCDS4908.1 | solute carrier family 29 (nucleoside transporters), member 1 | 6p21.1-p21.2 | 1.90 | 6% | 2 | 3 | 2 | 1 | 1 | 0 | 0 | 0 | 0 |
| SMAD2 | CCDS11834.1 | SMAD, mothers against DPP homolog 2 (Drosophila) | 18q21.1 | 3.05 | 10% | 3 | 2 | 3 | 3 | 0 | 0 | 0 | 0 | 0 |
| SMAD3 | CCDS10222.1 | SMAD, mothers against DPP homolog 3 (Drosophila) | 15q22.33 | 1.90 | 7% | 2 | 2 | 2 | 2 | 0 | 0 | 0 | 0 | 0 |
| SMAD4 | CCDS11950.1 | SMAD, mothers against DPP homolog 4 (Drosophila) | 18q21.1 | 4.56 | 13% | 4 | 4 | 4 | 1 | 1 | 1 | 1 | 1 | 0 |
| SYNE1 | CCDS5236.1 | spectrin repeat containing, nuclear envelope 1 | 6q25 | 2.32 | 9% | 5 | 0 | 5 | 5 | 0 | 0 | 0 | 0 | 0 |
| TBX22 | CCDS14445.1 | T-box 22 | Xq21.1 | 3.27 | 12% | 3 | 1 | 3 | 2 | 1 | 0 | 0 | 0 | 0 |
| TCF7L2 | CCDS7576.1 | transcription factor 7-like 2 | 10q25.3 | 2.83 | 10% | 3 | 2 | 3 | 1 | 0 | 1 | 0 | 0 | 0 |
| TGFBR2 | CCDS2648.1 | transforming growth factor, beta receptor II (70/80kDa) | 3p22 | 2.65 | 9% | 3 | 1 | 3 | 2 | 1 | 0 | 0 | 2 | 0 |
| TP53 | CCDS11118.1 | tumor protein p53 | 17p13.1 | >10 | 51% | 18 | 15 | 11 | 3 | 4 | 0 | 0 | 0 | 0 |
| TTL3 | CCDS2585.1 | tubulin tyrosine ligase-like family, member 3 | 3p25.3 | 2.19 | 6% | 2 | 0 | 2 | 2 | 0 | 1 | 0 | 1 | 0 |
| UHRF2 | CCDS6469.1 | ubiquitin-like, containing PHD and RING finger domains, 2 | 9p24.1 | 1.48 | 6% | 2 | 0 | 2 | 1 | 1 | 0 | 0 | 0 | 0 |
| UQCRC2 | CCDS10801.1 | ubiquinol-cytochrome c reductase core protein II | 16p12 | 1.87 | 6% | 2 | 0 | 2 | 1 | 0 | 0 | 0 | 0 | 0 |
| ZNF442 | CCDS12271.1 | zinc finger protein 442 | 19p13.2 | 1.91 | 6% | 2 | 0 | 2 | 2 | 0 | 0 | 0 | 0 | 0 |

*The fraction of the 35 colorectal tumors evaluated in the Discovery and Validation screens containing mutations of the gene divided by the number of bases successfully sequenced in that gene (i.e., bases with Phred quality score ≥ 20).

FIG. 14B

SEQUENCE LISTING

```
<160> NUMBER OF SEQ ID NOS: 215

<210> SEQ ID NO 1
<211> LENGTH: 17
<212> TYPE: DNA
<213> ORGANISM: Homo sapiens

<400> SEQUENCE: 1
gtaaaacgac ggccagt                                                 17

<210> SEQ ID NO 2
<211> LENGTH: 20
<212> TYPE: DNA
<213> ORGANISM: Homo sapiens

<400> SEQUENCE: 2
cgcctttacc cggtttcatt                                              20

<210> SEQ ID NO 3
<211> LENGTH: 20
<212> TYPE: DNA
<213> ORGANISM: Homo sapiens

<400> SEQUENCE: 3
ccaattgtct cccctccttg                                              20
```

```
<210> SEQ ID NO 4
<211> LENGTH: 15
<212> TYPE: DNA
<213> ORGANISM: Homo sapiens

<400> SEQUENCE: 4
ggaagggtgt gagga                                                    15

<210> SEQ ID NO 5
<211> LENGTH: 15
<212> TYPE: DNA
<213> ORGANISM: Homo sapiens

<400> SEQUENCE: 5
ggaagggtgt gagga                                                    15

<210> SEQ ID NO 6
<211> LENGTH: 12
<212> TYPE: DNA
<213> ORGANISM: Homo sapiens

<400> SEQUENCE: 6
gaggaagaag ag                                                       12

<210> SEQ ID NO 7
<211> LENGTH: 12
<212> TYPE: DNA
<213> ORGANISM: Homo sapiens

<400> SEQUENCE: 7
gaggaagaag ag                                                       12

<210> SEQ ID NO 8
<211> LENGTH: 36
<212> TYPE: DNA
<213> ORGANISM: Homo sapiens

<400> SEQUENCE: 8
ggcggccgcg gcggcagtgg cggcggcggc ggcggc                             36

<210> SEQ ID NO 9
<211> LENGTH: 36
<212> TYPE: DNA
<213> ORGANISM: Homo sapiens

<400> SEQUENCE: 9
ggcggccgcg gcggcagtgg cggcggcggc ggcggc                             36

<210> SEQ ID NO 10
<211> LENGTH: 16
<212> TYPE: DNA
<213> ORGANISM: Homo sapiens

<400> SEQUENCE: 10
agtgttccca acatat                                                   16

<210> SEQ ID NO 11
<211> LENGTH: 16
<212> TYPE: DNA
<213> ORGANISM: Homo sapiens

<400> SEQUENCE: 11
agtgttccca acatat                                                   16
```

```
<210> SEQ ID NO 12
<211> LENGTH: 10
<212> TYPE: DNA
<213> ORGANISM: Homo sapiens

<400> SEQUENCE: 12
gacaaggaca                                                          10

<210> SEQ ID NO 13
<211> LENGTH: 10
<212> TYPE: DNA
<213> ORGANISM: Homo sapiens

<400> SEQUENCE: 13
gacaaggaca                                                          10

<210> SEQ ID NO 14
<211> LENGTH: 10
<212> TYPE: DNA
<213> ORGANISM: Homo sapiens

<400> SEQUENCE: 14
caaaatccag                                                          10

<210> SEQ ID NO 15
<211> LENGTH: 10
<212> TYPE: DNA
<213> ORGANISM: Homo sapiens

<400> SEQUENCE: 15
caaaatccag                                                          10

<210> SEQ ID NO 16
<211> LENGTH: 12
<212> TYPE: DNA
<213> ORGANISM: Homo sapiens

<400> SEQUENCE: 16
tcagctcgtc aa                                                       12

<210> SEQ ID NO 17
<211> LENGTH: 12
<212> TYPE: DNA
<213> ORGANISM: Homo sapiens

<400> SEQUENCE: 17
tcagctcgtc aa                                                       12

<210> SEQ ID NO 18
<211> LENGTH: 14
<212> TYPE: DNA
<213> ORGANISM: Homo sapiens

<400> SEQUENCE: 18
ttgtggtaag ttat                                                     14

<210> SEQ ID NO 19
<211> LENGTH: 14
<212> TYPE: DNA
<213> ORGANISM: Homo sapiens

<400> SEQUENCE: 19
ttgtggtaag ttat                                                     14
```

```
<210> SEQ ID NO 20
<211> LENGTH: 21
<212> TYPE: DNA
<213> ORGANISM: Homo sapiens

<400> SEQUENCE: 20
ttaacggtaa ggtgctgttg t                                              21

<210> SEQ ID NO 21
<211> LENGTH: 22
<212> TYPE: DNA
<213> ORGANISM: Homo sapiens

<400> SEQUENCE: 21
tttaacggta aggtgctgtt gt                                             22

<210> SEQ ID NO 22
<211> LENGTH: 23
<212> TYPE: DNA
<213> ORGANISM: Homo sapiens

<400> SEQUENCE: 22
gaggataaag ttttaactgt ggt                                            23

<210> SEQ ID NO 23
<211> LENGTH: 23
<212> TYPE: DNA
<213> ORGANISM: Homo sapiens

<400> SEQUENCE: 23
gaggataaag ttttaactgt ggt                                            23

<210> SEQ ID NO 24
<211> LENGTH: 24
<212> TYPE: DNA
<213> ORGANISM: Homo sapiens

<400> SEQUENCE: 24
caacctgact tcccggggca tgga                                           24

<210> SEQ ID NO 25
<211> LENGTH: 24
<212> TYPE: DNA
<213> ORGANISM: Homo sapiens

<400> SEQUENCE: 25
caacctgact tcccggggca tgga                                           24

<210> SEQ ID NO 26
<211> LENGTH: 12
<212> TYPE: DNA
<213> ORGANISM: Homo sapiens

<400> SEQUENCE: 26
tatctgaact tg                                                        12

<210> SEQ ID NO 27
<211> LENGTH: 12
<212> TYPE: DNA
<213> ORGANISM: Homo sapiens

<400> SEQUENCE: 27
tatctgaact tg                                                        12
```

```
<210> SEQ ID NO 28
<211> LENGTH: 19
<212> TYPE: DNA
<213> ORGANISM: Homo sapiens

<400> SEQUENCE: 28
aagaaaaact tgtcatcag                                                   19

<210> SEQ ID NO 29
<211> LENGTH: 19
<212> TYPE: DNA
<213> ORGANISM: Homo sapiens

<400> SEQUENCE: 29
aagaaaaact tgtcatcag                                                   19

<210> SEQ ID NO 30
<211> LENGTH: 20
<212> TYPE: DNA
<213> ORGANISM: Homo sapiens

<400> SEQUENCE: 30
ctttgtacag gagaatatta                                                  20

<210> SEQ ID NO 31
<211> LENGTH: 20
<212> TYPE: DNA
<213> ORGANISM: Homo sapiens

<400> SEQUENCE: 31
ctttgtacag gagaatatta                                                  20

<210> SEQ ID NO 32
<211> LENGTH: 40
<212> TYPE: DNA
<213> ORGANISM: Homo sapiens

<400> SEQUENCE: 32
tttttggata ggtattggtg gatttatggt gcggcaaaga                            40

<210> SEQ ID NO 33
<211> LENGTH: 40
<212> TYPE: DNA
<213> ORGANISM: Homo sapiens

<400> SEQUENCE: 33
tttttggata ggtattggtg gatttatggt gcggcaaaga                            40

<210> SEQ ID NO 34
<211> LENGTH: 24
<212> TYPE: DNA
<213> ORGANISM: Homo sapiens

<400> SEQUENCE: 34
cttgtacaat taatggcaca tgga                                             24

<210> SEQ ID NO 35
<211> LENGTH: 24
<212> TYPE: DNA
<213> ORGANISM: Homo sapiens

<400> SEQUENCE: 35
cttgtacaat taatggcaca tgga                                             24
```

```
<210> SEQ ID NO 36
<211> LENGTH: 53
<212> TYPE: DNA
<213> ORGANISM: Homo sapiens

<400> SEQUENCE: 36
agcacagctt gctttggggt caaacgtgga tcagcagcct cttggtcagt aaa          53

<210> SEQ ID NO 37
<211> LENGTH: 53
<212> TYPE: DNA
<213> ORGANISM: Homo sapiens

<400> SEQUENCE: 37
agcacagctt gctttggggt caaacgtgga tcagcagcct cttggtcagt aaa          53

<210> SEQ ID NO 38
<211> LENGTH: 12
<212> TYPE: DNA
<213> ORGANISM: Homo sapiens

<400> SEQUENCE: 38
cactgcatcc cc                                                       12

<210> SEQ ID NO 39
<211> LENGTH: 12
<212> TYPE: DNA
<213> ORGANISM: Homo sapiens

<400> SEQUENCE: 39
cactgcatcc cc                                                       12

<210> SEQ ID NO 40
<211> LENGTH: 12
<212> TYPE: DNA
<213> ORGANISM: Homo sapiens

<400> SEQUENCE: 40
ttcctaagtg ga                                                       12

<210> SEQ ID NO 41
<211> LENGTH: 12
<212> TYPE: DNA
<213> ORGANISM: Homo sapiens

<400> SEQUENCE: 41
ttcctaagtg ga                                                       12

<210> SEQ ID NO 42
<211> LENGTH: 10
<212> TYPE: DNA
<213> ORGANISM: Homo sapiens

<400> SEQUENCE: 42
tcctcctgct                                                          10

<210> SEQ ID NO 43
<211> LENGTH: 10
<212> TYPE: DNA
<213> ORGANISM: Homo sapiens

<400> SEQUENCE: 43
tcctcctgct                                                          10
```

```
<210> SEQ ID NO 44
<211> LENGTH: 15
<212> TYPE: DNA
<213> ORGANISM: Homo sapiens

<400> SEQUENCE: 44
acagaatcct gaagg                                                          15

<210> SEQ ID NO 45
<211> LENGTH: 15
<212> TYPE: DNA
<213> ORGANISM: Homo sapiens

<400> SEQUENCE: 45
acagaatcct gaagg                                                          15

<210> SEQ ID NO 46
<211> LENGTH: 42
<212> TYPE: DNA
<213> ORGANISM: Homo sapiens

<400> SEQUENCE: 46
agggcatcat ggaggaggat gaggcctgcg ggcgccagta ca                            42

<210> SEQ ID NO 47
<211> LENGTH: 42
<212> TYPE: DNA
<213> ORGANISM: Homo sapiens

<400> SEQUENCE: 47
agggcatcat ggaggaggat gaggcctgcg ggcgccagta ca                            42

<210> SEQ ID NO 48
<211> LENGTH: 12
<212> TYPE: DNA
<213> ORGANISM: Homo sapiens

<400> SEQUENCE: 48
gtgtttgtaa gc                                                             12

<210> SEQ ID NO 49
<211> LENGTH: 12
<212> TYPE: DNA
<213> ORGANISM: Homo sapiens

<400> SEQUENCE: 49
gtgtttgtaa gc                                                             12

<210> SEQ ID NO 50
<211> LENGTH: 19
<212> TYPE: DNA
<213> ORGANISM: Homo sapiens

<400> SEQUENCE: 50
ccatgatcct gtctgcggt                                                      19

<210> SEQ ID NO 51
<211> LENGTH: 19
<212> TYPE: DNA
<213> ORGANISM: Homo sapiens

<400> SEQUENCE: 51
ccatgatcct gtctgcggt                                                      19
```

```
<210> SEQ ID NO 52
<211> LENGTH: 15
<212> TYPE: DNA
<213> ORGANISM: Homo sapiens

<400> SEQUENCE: 52
tgctggacta accct                                                    15

<210> SEQ ID NO 53
<211> LENGTH: 15
<212> TYPE: DNA
<213> ORGANISM: Homo sapiens

<400> SEQUENCE: 53
tgctggacta accct                                                    15

<210> SEQ ID NO 54
<211> LENGTH: 11
<212> TYPE: DNA
<213> ORGANISM: Homo sapiens

<400> SEQUENCE: 54
ttttaatagc t                                                        11

<210> SEQ ID NO 55
<211> LENGTH: 11
<212> TYPE: DNA
<213> ORGANISM: Homo sapiens

<400> SEQUENCE: 55
ttttaatagc t                                                        11

<210> SEQ ID NO 56
<211> LENGTH: 25
<212> TYPE: DNA
<213> ORGANISM: Homo sapiens

<400> SEQUENCE: 56
tgaacacgca ccctgataag ctgcg                                         25

<210> SEQ ID NO 57
<211> LENGTH: 25
<212> TYPE: DNA
<213> ORGANISM: Homo sapiens

<400> SEQUENCE: 57
tgaacacgca ccctgataag ctgcg                                         25

<210> SEQ ID NO 58
<211> LENGTH: 38
<212> TYPE: DNA
<213> ORGANISM: Artificial Sequence
<220> FEATURE:
<223> OTHER INFORMATION: primer for pcr

<400> SEQUENCE: 58
gtaaaacgac ggccagtgcc cttccaccct agttcttc                           38

<210> SEQ ID NO 59
<211> LENGTH: 38
<212> TYPE: DNA
<213> ORGANISM: Artificial Sequence
<220> FEATURE:
<223> OTHER INFORMATION: primer for pcr
```

```
<400> SEQUENCE: 59
gtaaaacgac ggccagtctg ttgggtgtct accttccc                              38

<210> SEQ ID NO 60
<211> LENGTH: 38
<212> TYPE: DNA
<213> ORGANISM: Artificial Sequence
<220> FEATURE:
<223> OTHER INFORMATION: primer for pcr

<400> SEQUENCE: 60
gtaaaacgac ggccagtgtg cctggagaaa cctctcac                              38

<210> SEQ ID NO 61
<211> LENGTH: 21
<212> TYPE: DNA
<213> ORGANISM: Artificial Sequence
<220> FEATURE:
<223> OTHER INFORMATION: primer for pcr

<400> SEQUENCE: 61
cacctcagtg ttctacgcca g                                                21

<210> SEQ ID NO 62
<211> LENGTH: 18
<212> TYPE: DNA
<213> ORGANISM: Artificial Sequence
<220> FEATURE:
<223> OTHER INFORMATION: primer for pcr

<400> SEQUENCE: 62
cgccgccgag attaattg                                                    18

<210> SEQ ID NO 63
<211> LENGTH: 35
<212> TYPE: DNA
<213> ORGANISM: Artificial Sequence
<220> FEATURE:
<223> OTHER INFORMATION: primer for pcr

<400> SEQUENCE: 63
gtaaaacgac ggccagtgag acggaccggg taggg                                 35

<210> SEQ ID NO 64
<211> LENGTH: 18
<212> TYPE: DNA
<213> ORGANISM: Artificial Sequence
<220> FEATURE:
<223> OTHER INFORMATION: primer for pcr

<400> SEQUENCE: 64
ctgcggaagc agaacctg                                                    18

<210> SEQ ID NO 65
<211> LENGTH: 20
<212> TYPE: DNA
<213> ORGANISM: Artificial Sequence
<220> FEATURE:
<223> OTHER INFORMATION: primer for pcr

<400> SEQUENCE: 65
cacaagatgg ctcggaagac                                                  20

<210> SEQ ID NO 66
<211> LENGTH: 38
```

<210> SEQ ID NO 67
<211> LENGTH: 38
<212> TYPE: DNA
<213> ORGANISM: Artificial Sequence
<220> FEATURE:
<223> OTHER INFORMATION: primer for pcr

<400> SEQUENCE: 66
gtaaaacgac ggccagtcta gatccttcca gagggcac                38

<210> SEQ ID NO 67
<211> LENGTH: 38
<212> TYPE: DNA
<213> ORGANISM: Artificial Sequence
<220> FEATURE:
<223> OTHER INFORMATION: primer for pcr

<400> SEQUENCE: 67
gtaaaacgac ggccagtcct gacactcaaa cccaacag                38

<210> SEQ ID NO 68
<211> LENGTH: 21
<212> TYPE: DNA
<213> ORGANISM: Artificial Sequence
<220> FEATURE:
<223> OTHER INFORMATION: primer for pcr

<400> SEQUENCE: 68
gagtgaggtc agggtctcca g                                  21

<210> SEQ ID NO 69
<211> LENGTH: 21
<212> TYPE: DNA
<213> ORGANISM: Artificial Sequence
<220> FEATURE:
<223> OTHER INFORMATION: primer for pcr

<400> SEQUENCE: 69
gagaaccata gagccactcg g                                  21

<210> SEQ ID NO 70
<211> LENGTH: 38
<212> TYPE: DNA
<213> ORGANISM: Artificial Sequence
<220> FEATURE:
<223> OTHER INFORMATION: primer for pcr

<400> SEQUENCE: 70
gtaaaacgac ggccagtgtg ggtgtctgta tccaaggg                38

<210> SEQ ID NO 71
<211> LENGTH: 39
<212> TYPE: DNA
<213> ORGANISM: Artificial Sequence
<220> FEATURE:
<223> OTHER INFORMATION: primer for pcr

<400> SEQUENCE: 71
gtaaaacgac ggccagttga agggagtaga ctgaccctg               39

<210> SEQ ID NO 72
<211> LENGTH: 22
<212> TYPE: DNA
<213> ORGANISM: Artificial Sequence
<220> FEATURE:
<223> OTHER INFORMATION: primer for pcr

<400> SEQUENCE: 72
ggacagctct gaggaggaag ag                                 22

<210> SEQ ID NO 73
<211> LENGTH: 38
<212> TYPE: DNA
<213> ORGANISM: Artificial Sequence
<220> FEATURE:
<223> OTHER INFORMATION: primer for pcr

<400> SEQUENCE: 73
gtaaaacgac ggccagtcca acctctgccc tatgtctg                             38

<210> SEQ ID NO 74
<211> LENGTH: 38
<212> TYPE: DNA
<213> ORGANISM: Artificial Sequence
<220> FEATURE:
<223> OTHER INFORMATION: primer for pcr

<400> SEQUENCE: 74
gtaaaacgac ggccagtagt gctgaggcca acaaattc                             38

<210> SEQ ID NO 75
<211> LENGTH: 21
<212> TYPE: DNA
<213> ORGANISM: Artificial Sequence
<220> FEATURE:
<223> OTHER INFORMATION: primer for pcr

<400> SEQUENCE: 75
agtcgtagag gctatgctgg c                                               21

<210> SEQ ID NO 76
<211> LENGTH: 38
<212> TYPE: DNA
<213> ORGANISM: Artificial Sequence
<220> FEATURE:
<223> OTHER INFORMATION: primer for pcr

<400> SEQUENCE: 76
gtaaaacgac ggccagttcg gccatacagg tgctattc                             38

<210> SEQ ID NO 77
<211> LENGTH: 20
<212> TYPE: DNA
<213> ORGANISM: Artificial Sequence
<220> FEATURE:
<223> OTHER INFORMATION: primer for pcr

<400> SEQUENCE: 77
aggtgctttg ggaagagctg                                                 20

<210> SEQ ID NO 78
<211> LENGTH: 36
<212> TYPE: DNA
<213> ORGANISM: Artificial Sequence
<220> FEATURE:
<223> OTHER INFORMATION: primer for pcr

<400> SEQUENCE: 78
gtaaaacgac ggccagtaag gcccaggtgt tcacag                               36

<210> SEQ ID NO 79
<211> LENGTH: 20
<212> TYPE: DNA
<213> ORGANISM: Artificial Sequence
<220> FEATURE:
<223> OTHER INFORMATION: primer for pcr

<400> SEQUENCE: 79
aggaaatgat tcctgtgccg					20

<210> SEQ ID NO 80
<211> LENGTH: 38
<212> TYPE: DNA
<213> ORGANISM: Artificial Sequence
<220> FEATURE:
<223> OTHER INFORMATION: primer for pcr

<400> SEQUENCE: 80
gtaaaacgac ggccagtacg tgccttgtcc tgctttag					38

<210> SEQ ID NO 81
<211> LENGTH: 21
<212> TYPE: DNA
<213> ORGANISM: Artificial Sequence
<220> FEATURE:
<223> OTHER INFORMATION: primer for pcr

<400> SEQUENCE: 81
tatctcttgt ttcgggttgg g					21

<210> SEQ ID NO 82
<211> LENGTH: 37
<212> TYPE: DNA
<213> ORGANISM: Artificial Sequence
<220> FEATURE:
<223> OTHER INFORMATION: primer for pcr

<400> SEQUENCE: 82
gtaaaacgac ggccagtatg gaccttcatg gtctccc					37

<210> SEQ ID NO 83
<211> LENGTH: 38
<212> TYPE: DNA
<213> ORGANISM: Artificial Sequence
<220> FEATURE:
<223> OTHER INFORMATION: primer for pcr

<400> SEQUENCE: 83
gtaaaacgac ggccagtcaa cagctatgca cttgagcc					38

<210> SEQ ID NO 84
<211> LENGTH: 20
<212> TYPE: DNA
<213> ORGANISM: Artificial Sequence
<220> FEATURE:
<223> OTHER INFORMATION: primer for pcr

<400> SEQUENCE: 84
gagcagcagg cagtggttag					20

<210> SEQ ID NO 85
<211> LENGTH: 21
<212> TYPE: DNA
<213> ORGANISM: Artificial Sequence
<220> FEATURE:
<223> OTHER INFORMATION: primer for pcr

<400> SEQUENCE: 85
aacttggagg atggctttgt g					21

<210> SEQ ID NO 86
<211> LENGTH: 38

```
<212> TYPE: DNA
<213> ORGANISM: Artificial Sequence
<220> FEATURE:
<223> OTHER INFORMATION: primer for pcr

<400> SEQUENCE: 86
gtaaaacgac ggccagtagt gaaggcctac tgggattg                           38

<210> SEQ ID NO 87
<211> LENGTH: 38
<212> TYPE: DNA
<213> ORGANISM: Artificial Sequence
<220> FEATURE:
<223> OTHER INFORMATION: primer for pcr

<400> SEQUENCE: 87
gtaaaacgac ggccagtgcc aaatgctctg ttctctgg                           38

<210> SEQ ID NO 88
<211> LENGTH: 38
<212> TYPE: DNA
<213> ORGANISM: Artificial Sequence
<220> FEATURE:
<223> OTHER INFORMATION: primer for pcr

<400> SEQUENCE: 88
gtaaaacgac ggccagtctc ttccagaaag gctccacc                           38

<210> SEQ ID NO 89
<211> LENGTH: 38
<212> TYPE: DNA
<213> ORGANISM: Artificial Sequence
<220> FEATURE:
<223> OTHER INFORMATION: primer for pcr

<400> SEQUENCE: 89
gtaaaacgac ggccagtaga cttgccgacc tgtacgac                           38

<210> SEQ ID NO 90
<211> LENGTH: 21
<212> TYPE: DNA
<213> ORGANISM: Artificial Sequence
<220> FEATURE:
<223> OTHER INFORMATION: primer for pcr

<400> SEQUENCE: 90
gtcctgtagc tgtgtggatg c                                             21

<210> SEQ ID NO 91
<211> LENGTH: 38
<212> TYPE: DNA
<213> ORGANISM: Artificial Sequence
<220> FEATURE:
<223> OTHER INFORMATION: primer for pcr

<400> SEQUENCE: 91
gtaaaacgac ggccagtaaa gttgtgcatt acgccaag                           38

<210> SEQ ID NO 92
<211> LENGTH: 38
<212> TYPE: DNA
<213> ORGANISM: Artificial Sequence
<220> FEATURE:
<223> OTHER INFORMATION: primer for pcr

<400> SEQUENCE: 92
gtaaaacgac ggccagtctg ctacctggag ctattccc                           38
```

<210> SEQ ID NO 93
<211> LENGTH: 19
<212> TYPE: DNA
<213> ORGANISM: Artificial Sequence
<220> FEATURE:
<223> OTHER INFORMATION: primer for pcr

<400> SEQUENCE: 93
cctgacccag gacttggag                                        19

<210> SEQ ID NO 94
<211> LENGTH: 22
<212> TYPE: DNA
<213> ORGANISM: Artificial Sequence
<220> FEATURE:
<223> OTHER INFORMATION: primer for pcr

<400> SEQUENCE: 94
tttaccacct ggagaagcag ac                                    22

<210> SEQ ID NO 95
<211> LENGTH: 36
<212> TYPE: DNA
<213> ORGANISM: Artificial Sequence
<220> FEATURE:
<223> OTHER INFORMATION: primer for pcr

<400> SEQUENCE: 95
gtaaaacgac ggccagtgca gtgctgtctg tgcctc                     36

<210> SEQ ID NO 96
<211> LENGTH: 37
<212> TYPE: DNA
<213> ORGANISM: Artificial Sequence
<220> FEATURE:
<223> OTHER INFORMATION: primer for pcr

<400> SEQUENCE: 96
gtaaaacgac ggccagtcca gctctccaag tacccag                    37

<210> SEQ ID NO 97
<211> LENGTH: 20
<212> TYPE: DNA
<213> ORGANISM: Artificial Sequence
<220> FEATURE:
<223> OTHER INFORMATION: primer for pcr

<400> SEQUENCE: 97
gacgcccgac tctttagtgg                                       20

<210> SEQ ID NO 98
<211> LENGTH: 39
<212> TYPE: DNA
<213> ORGANISM: Artificial Sequence
<220> FEATURE:
<223> OTHER INFORMATION: primer for pcr

<400> SEQUENCE: 98
gtaaaacgac ggccagtgcg acagaataag acttcgtcc                  39

<210> SEQ ID NO 99
<211> LENGTH: 37
<212> TYPE: DNA
<213> ORGANISM: Artificial Sequence
<220> FEATURE:
<223> OTHER INFORMATION: primer for pcr

```
<400> SEQUENCE: 99
gtaaaacgac ggccagtaac tcagactgga gggagcc                             37

<210> SEQ ID NO 100
<211> LENGTH: 36
<212> TYPE: DNA
<213> ORGANISM: Artificial Sequence
<220> FEATURE:
<223> OTHER INFORMATION: primer for pcr

<400> SEQUENCE: 100
gtaaaacgac ggccagtcag ttgtcctgga gccacc                              36

<210> SEQ ID NO 101
<211> LENGTH: 38
<212> TYPE: DNA
<213> ORGANISM: Artificial Sequence
<220> FEATURE:
<223> OTHER INFORMATION: primer for pcr

<400> SEQUENCE: 101
gtaaaacgac ggccagtcaa gcctgaggtc tgttcagg                            38

<210> SEQ ID NO 102
<211> LENGTH: 21
<212> TYPE: DNA
<213> ORGANISM: Artificial Sequence
<220> FEATURE:
<223> OTHER INFORMATION: primer for pcr

<400> SEQUENCE: 102
ctcagcttgt gagtagcagc c                                              21

<210> SEQ ID NO 103
<211> LENGTH: 39
<212> TYPE: DNA
<213> ORGANISM: Artificial Sequence
<220> FEATURE:
<223> OTHER INFORMATION: primer for pcr

<400> SEQUENCE: 103
gtaaaacgac ggccagttgc ctctgacagg tgagtaagg                           39

<210> SEQ ID NO 104
<211> LENGTH: 21
<212> TYPE: DNA
<213> ORGANISM: Artificial Sequence
<220> FEATURE:
<223> OTHER INFORMATION: primer for pcr

<400> SEQUENCE: 104
aggccttaaa tagggaaacg g                                              21

<210> SEQ ID NO 105
<211> LENGTH: 36
<212> TYPE: DNA
<213> ORGANISM: Artificial Sequence
<220> FEATURE:
<223> OTHER INFORMATION: primer for pcr

<400> SEQUENCE: 105
gtaaaacgac ggccagtccg agcgcgtatt aacgag                              36

<210> SEQ ID NO 106
<211> LENGTH: 21
```

-continued

<212> TYPE: DNA
<213> ORGANISM: Artificial Sequence
<220> FEATURE:
<223> OTHER INFORMATION: primer for pcr

<400> SEQUENCE: 106
gagatgaccg tgagacacct g                                              21

<210> SEQ ID NO 107
<211> LENGTH: 38
<212> TYPE: DNA
<213> ORGANISM: Artificial Sequence
<220> FEATURE:
<223> OTHER INFORMATION: primer for pcr

<400> SEQUENCE: 107
gtaaaacgac ggccagtctt ataatagggc cggtgctg                            38

<210> SEQ ID NO 108
<211> LENGTH: 21
<212> TYPE: DNA
<213> ORGANISM: Artificial Sequence
<220> FEATURE:
<223> OTHER INFORMATION: primer for pcr

<400> SEQUENCE: 108
accctagcag gtaaagggag g                                              21

<210> SEQ ID NO 109
<211> LENGTH: 21
<212> TYPE: DNA
<213> ORGANISM: Artificial Sequence
<220> FEATURE:
<223> OTHER INFORMATION: primer for pcr

<400> SEQUENCE: 109
atgtcggtgt cagagctgaa g                                              21

<210> SEQ ID NO 110
<211> LENGTH: 38
<212> TYPE: DNA
<213> ORGANISM: Artificial Sequence
<220> FEATURE:
<223> OTHER INFORMATION: primer for pcr

<400> SEQUENCE: 110
gtaaaacgac ggccagtctc gctttcatat ttccgtcc                            38

<210> SEQ ID NO 111
<211> LENGTH: 21
<212> TYPE: DNA
<213> ORGANISM: Artificial Sequence
<220> FEATURE:
<223> OTHER INFORMATION: primer for pcr

<400> SEQUENCE: 111
tcaggcatgt tcagagagca g                                              21

<210> SEQ ID NO 112
<211> LENGTH: 35
<212> TYPE: DNA
<213> ORGANISM: Artificial Sequence
<220> FEATURE:
<223> OTHER INFORMATION: primer for pcr

<400> SEQUENCE: 112
gtaaaacgac ggccagtgaa tgtggcagga ccgag                               35

<210> SEQ ID NO 113
<211> LENGTH: 21
<212> TYPE: DNA
<213> ORGANISM: Artificial Sequence
<220> FEATURE:
<223> OTHER INFORMATION: primer for pcr

<400> SEQUENCE: 113
cgagtcctca ctctgccttt c                                         21

<210> SEQ ID NO 114
<211> LENGTH: 21
<212> TYPE: DNA
<213> ORGANISM: Artificial Sequence
<220> FEATURE:
<223> OTHER INFORMATION: primer for pcr

<400> SEQUENCE: 114
tctggatctc agctggattt g                                         21

<210> SEQ ID NO 115
<211> LENGTH: 39
<212> TYPE: DNA
<213> ORGANISM: Artificial Sequence
<220> FEATURE:
<223> OTHER INFORMATION: primer for pcr

<400> SEQUENCE: 115
gtaaaacgac ggccagtccc acctggtcag agtaaacag                      39

<210> SEQ ID NO 116
<211> LENGTH: 35
<212> TYPE: DNA
<213> ORGANISM: Artificial Sequence
<220> FEATURE:
<223> OTHER INFORMATION: primer for pcr

<400> SEQUENCE: 116
gtaaaacgac ggccagtagt gggcagctcc cgtag                          35

<210> SEQ ID NO 117
<211> LENGTH: 37
<212> TYPE: DNA
<213> ORGANISM: Artificial Sequence
<220> FEATURE:
<223> OTHER INFORMATION: primer for pcr

<400> SEQUENCE: 117
gtaaaacgac ggccagttgg tcccactgaa tacccac                        37

<210> SEQ ID NO 118
<211> LENGTH: 35
<212> TYPE: DNA
<213> ORGANISM: Artificial Sequence
<220> FEATURE:
<223> OTHER INFORMATION: primer for pcr

<400> SEQUENCE: 118
gtaaaacgac ggccagtcac agggcaggtt ggagg                          35

<210> SEQ ID NO 119
<211> LENGTH: 38
<212> TYPE: DNA
<213> ORGANISM: Artificial Sequence
<220> FEATURE:
<223> OTHER INFORMATION: primer for pcr

```
<400> SEQUENCE: 119
gtaaaacgac ggccagttcc ttccaccaca actcacag                              38

<210> SEQ ID NO 120
<211> LENGTH: 35
<212> TYPE: DNA
<213> ORGANISM: Artificial Sequence
<220> FEATURE:
<223> OTHER INFORMATION: primer for pcr

<400> SEQUENCE: 120
gtaaaacgac ggccagtaca ggctgggcct caaac                                 35

<210> SEQ ID NO 121
<211> LENGTH: 18
<212> TYPE: DNA
<213> ORGANISM: Artificial Sequence
<220> FEATURE:
<223> OTHER INFORMATION: primer for pcr

<400> SEQUENCE: 121
agggccaagg ttggaatg                                                    18

<210> SEQ ID NO 122
<211> LENGTH: 38
<212> TYPE: DNA
<213> ORGANISM: Artificial Sequence
<220> FEATURE:
<223> OTHER INFORMATION: primer for pcr

<400> SEQUENCE: 122
gtaaaacgac ggccagtgag gtcacacctg ggacagag                              38

<210> SEQ ID NO 123
<211> LENGTH: 18
<212> TYPE: DNA
<213> ORGANISM: Artificial Sequence
<220> FEATURE:
<223> OTHER INFORMATION: primer for pcr

<400> SEQUENCE: 123
agccagtctc caggcacc                                                    18

<210> SEQ ID NO 124
<211> LENGTH: 37
<212> TYPE: DNA
<213> ORGANISM: Artificial Sequence
<220> FEATURE:
<223> OTHER INFORMATION: primer for pcr

<400> SEQUENCE: 124
gtaaaacgac ggccagtctc ctcacacgca cttcacc                               37

<210> SEQ ID NO 125
<211> LENGTH: 38
<212> TYPE: DNA
<213> ORGANISM: Artificial Sequence
<220> FEATURE:
<223> OTHER INFORMATION: primer for pcr

<400> SEQUENCE: 125
gtaaaacgac ggccagtgag aacggacaac ctcactcc                              38

<210> SEQ ID NO 126
<211> LENGTH: 21
```

<212> TYPE: DNA
<213> ORGANISM: Artificial Sequence
<220> FEATURE:
<223> OTHER INFORMATION: primer for pcr

<400> SEQUENCE: 126
ttctactcag cacccagacc c                                     21

<210> SEQ ID NO 127
<211> LENGTH: 20
<212> TYPE: DNA
<213> ORGANISM: Artificial Sequence
<220> FEATURE:
<223> OTHER INFORMATION: primer for pcr

<400> SEQUENCE: 127
agcttggact gcacatctgg                                       20

<210> SEQ ID NO 128
<211> LENGTH: 38
<212> TYPE: DNA
<213> ORGANISM: Artificial Sequence
<220> FEATURE:
<223> OTHER INFORMATION: primer for pcr

<400> SEQUENCE: 128
gtaaaacgac ggccagtgag gaagggtcct ctcctgtc                   38

<210> SEQ ID NO 129
<211> LENGTH: 21
<212> TYPE: DNA
<213> ORGANISM: Artificial Sequence
<220> FEATURE:
<223> OTHER INFORMATION: primer for pcr

<400> SEQUENCE: 129
acatctggca gctgaggagt c                                     21

<210> SEQ ID NO 130
<211> LENGTH: 35
<212> TYPE: DNA
<213> ORGANISM: Artificial Sequence
<220> FEATURE:
<223> OTHER INFORMATION: primer for pcr

<400> SEQUENCE: 130
gtaaaacgac ggccagtctc ctctgccctc ctccc                      35

<210> SEQ ID NO 131
<211> LENGTH: 18
<212> TYPE: DNA
<213> ORGANISM: Artificial Sequence
<220> FEATURE:
<223> OTHER INFORMATION: primer for pcr

<400> SEQUENCE: 131
ccaagcctgg cagaggag                                         18

<210> SEQ ID NO 132
<211> LENGTH: 19
<212> TYPE: DNA
<213> ORGANISM: Artificial Sequence
<220> FEATURE:
<223> OTHER INFORMATION: primer for pcr

<400> SEQUENCE: 132
caacctgtcc tccagtgcc                                        19

<210> SEQ ID NO 133
<211> LENGTH: 35
<212> TYPE: DNA
<213> ORGANISM: Artificial Sequence
<220> FEATURE:
<223> OTHER INFORMATION: primer for pcr

<400> SEQUENCE: 133
gtaaaacgac ggccagtaga ggccaaaccc accac                              35

<210> SEQ ID NO 134
<211> LENGTH: 20
<212> TYPE: DNA
<213> ORGANISM: Artificial Sequence
<220> FEATURE:
<223> OTHER INFORMATION: primer for pcr

<400> SEQUENCE: 134
tgtggtagat gctgcctgtg                                               20

<210> SEQ ID NO 135
<211> LENGTH: 37
<212> TYPE: DNA
<213> ORGANISM: Artificial Sequence
<220> FEATURE:
<223> OTHER INFORMATION: primer for pcr

<400> SEQUENCE: 135
gtaaaacgac ggccagtcaa cccgaatagg agaaggg                            37

<210> SEQ ID NO 136
<211> LENGTH: 20
<212> TYPE: DNA
<213> ORGANISM: Artificial Sequence
<220> FEATURE:
<223> OTHER INFORMATION: primer for pcr

<400> SEQUENCE: 136
caacccgaat aggagaaggg                                               20

<210> SEQ ID NO 137
<211> LENGTH: 20
<212> TYPE: DNA
<213> ORGANISM: Artificial Sequence
<220> FEATURE:
<223> OTHER INFORMATION: primer for pcr

<400> SEQUENCE: 137
cccactactg cttgctcagg                                               20

<210> SEQ ID NO 138
<211> LENGTH: 21
<212> TYPE: DNA
<213> ORGANISM: Artificial Sequence
<220> FEATURE:
<223> OTHER INFORMATION: primer for pcr

<400> SEQUENCE: 138
ttgggaatta ggcttctgct g                                             21

<210> SEQ ID NO 139
<211> LENGTH: 19
<212> TYPE: DNA
<213> ORGANISM: Artificial Sequence
<220> FEATURE:
<223> OTHER INFORMATION: primer for pcr

```
<400> SEQUENCE: 139
gcctcagcaa caggaatgg                                                  19

<210> SEQ ID NO 140
<211> LENGTH: 38
<212> TYPE: DNA
<213> ORGANISM: Artificial Sequence
<220> FEATURE:
<223> OTHER INFORMATION: primer for pcr

<400> SEQUENCE: 140
gtaaaacgac ggccagtaga gctgaacaca gtgcttgg                             38

<210> SEQ ID NO 141
<211> LENGTH: 35
<212> TYPE: DNA
<213> ORGANISM: Artificial Sequence
<220> FEATURE:
<223> OTHER INFORMATION: primer for pcr

<400> SEQUENCE: 141
gtaaaacgac ggccagtccc tacccggtcc gtctc                                35

<210> SEQ ID NO 142
<211> LENGTH: 18
<212> TYPE: DNA
<213> ORGANISM: Artificial Sequence
<220> FEATURE:
<223> OTHER INFORMATION: primer for pcr

<400> SEQUENCE: 142
ggttcagcac cagcaggg                                                   18

<210> SEQ ID NO 143
<211> LENGTH: 37
<212> TYPE: DNA
<213> ORGANISM: Artificial Sequence
<220> FEATURE:
<223> OTHER INFORMATION: primer for pcr

<400> SEQUENCE: 143
gtaaaacgac ggccagtgcc cacctgtgtg gaagtag                              37

<210> SEQ ID NO 144
<211> LENGTH: 35
<212> TYPE: DNA
<213> ORGANISM: Artificial Sequence
<220> FEATURE:
<223> OTHER INFORMATION: primer for pcr

<400> SEQUENCE: 144
gtaaaacgac ggccagtctc ctgaccgtcg tgtgc                                35

<210> SEQ ID NO 145
<211> LENGTH: 21
<212> TYPE: DNA
<213> ORGANISM: Artificial Sequence
<220> FEATURE:
<223> OTHER INFORMATION: primer for pcr

<400> SEQUENCE: 145
ccatcctttc cagggaggta g                                               21

<210> SEQ ID NO 146
<211> LENGTH: 19
```

```
<212> TYPE: DNA
<213> ORGANISM: Artificial Sequence
<220> FEATURE:
<223> OTHER INFORMATION: primer for pcr

<400> SEQUENCE: 146
gacaagggct gctctcctg                                                19

<210> SEQ ID NO 147
<211> LENGTH: 38
<212> TYPE: DNA
<213> ORGANISM: Artificial Sequence
<220> FEATURE:
<223> OTHER INFORMATION: primer for pcr

<400> SEQUENCE: 147
gtaaaacgac ggccagtacc gaaagaaata aagcggtg                            38

<210> SEQ ID NO 148
<211> LENGTH: 38
<212> TYPE: DNA
<213> ORGANISM: Artificial Sequence
<220> FEATURE:
<223> OTHER INFORMATION: primer for pcr

<400> SEQUENCE: 148
gtaaaacgac ggccagtaaa gcccgaagct aggaactc                            38

<210> SEQ ID NO 149
<211> LENGTH: 21
<212> TYPE: DNA
<213> ORGANISM: Artificial Sequence
<220> FEATURE:
<223> OTHER INFORMATION: primer for pcr

<400> SEQUENCE: 149
cctgcctagg acagagtttg g                                              21

<210> SEQ ID NO 150
<211> LENGTH: 20
<212> TYPE: DNA
<213> ORGANISM: Artificial Sequence
<220> FEATURE:
<223> OTHER INFORMATION: primer for pcr

<400> SEQUENCE: 150
cttcctgcac agaaaggctg                                                20

<210> SEQ ID NO 151
<211> LENGTH: 38
<212> TYPE: DNA
<213> ORGANISM: Artificial Sequence
<220> FEATURE:
<223> OTHER INFORMATION: primer for pcr

<400> SEQUENCE: 151
gtaaaacgac ggccagtttg tcacttgcgc tgaagaag                            38

<210> SEQ ID NO 152
<211> LENGTH: 21
<212> TYPE: DNA
<213> ORGANISM: Artificial Sequence
<220> FEATURE:
<223> OTHER INFORMATION: primer for pcr

<400> SEQUENCE: 152
aaaggcctgg atgtactcac g                                              21
```

<210> SEQ ID NO 153
<211> LENGTH: 21
<212> TYPE: DNA
<213> ORGANISM: Artificial Sequence
<220> FEATURE:
<223> OTHER INFORMATION: primer for pcr

<400> SEQUENCE: 153
ttgccatgtc tctgtcctag c                                              21

<210> SEQ ID NO 154
<211> LENGTH: 38
<212> TYPE: DNA
<213> ORGANISM: Artificial Sequence
<220> FEATURE:
<223> OTHER INFORMATION: primer for pcr

<400> SEQUENCE: 154
gtaaaacgac ggccagtgtc tccgacagac aggacacc                            38

<210> SEQ ID NO 155
<211> LENGTH: 21
<212> TYPE: DNA
<213> ORGANISM: Artificial Sequence
<220> FEATURE:
<223> OTHER INFORMATION: primer for pcr

<400> SEQUENCE: 155
gactgcctga gacagaaacc c                                              21

<210> SEQ ID NO 156
<211> LENGTH: 38
<212> TYPE: DNA
<213> ORGANISM: Artificial Sequence
<220> FEATURE:
<223> OTHER INFORMATION: primer for pcr

<400> SEQUENCE: 156
gtaaaacgac ggccagtagg tgctctgtga gacattcg                            38

<210> SEQ ID NO 157
<211> LENGTH: 21
<212> TYPE: DNA
<213> ORGANISM: Artificial Sequence
<220> FEATURE:
<223> OTHER INFORMATION: primer for pcr

<400> SEQUENCE: 157
gtctcaaccc atccaccctt c                                              21

<210> SEQ ID NO 158
<211> LENGTH: 38
<212> TYPE: DNA
<213> ORGANISM: Artificial Sequence
<220> FEATURE:
<223> OTHER INFORMATION: primer for pcr

<400> SEQUENCE: 158
gtaaaacgac ggccagttcc agaatccaga gcatctcc                            38

<210> SEQ ID NO 159
<211> LENGTH: 20
<212> TYPE: DNA
<213> ORGANISM: Artificial Sequence
<220> FEATURE:
<223> OTHER INFORMATION: primer for pcr

```
<400> SEQUENCE: 159
gtgacacccg tgacaaggag                                              20

<210> SEQ ID NO 160
<211> LENGTH: 38
<212> TYPE: DNA
<213> ORGANISM: Artificial Sequence
<220> FEATURE:
<223> OTHER INFORMATION: primer for pcr

<400> SEQUENCE: 160
gtaaaacgac ggccagtgtc catgcttgaa cttggagg                          38

<210> SEQ ID NO 161
<211> LENGTH: 20
<212> TYPE: DNA
<213> ORGANISM: Artificial Sequence
<220> FEATURE:
<223> OTHER INFORMATION: primer for pcr

<400> SEQUENCE: 161
acaagggcac ctcctaccag                                              20

<210> SEQ ID NO 162
<211> LENGTH: 20
<212> TYPE: DNA
<213> ORGANISM: Artificial Sequence
<220> FEATURE:
<223> OTHER INFORMATION: primer for pcr

<400> SEQUENCE: 162
gtcagcttct cccaggcttc                                              20

<210> SEQ ID NO 163
<211> LENGTH: 38
<212> TYPE: DNA
<213> ORGANISM: Artificial Sequence
<220> FEATURE:
<223> OTHER INFORMATION: primer for pcr

<400> SEQUENCE: 163
gtaaaacgac ggccagtcgc cctggtctca agtcatag                          38

<210> SEQ ID NO 164
<211> LENGTH: 36
<212> TYPE: DNA
<213> ORGANISM: Artificial Sequence
<220> FEATURE:
<223> OTHER INFORMATION: primer for pcr

<400> SEQUENCE: 164
gtaaaacgac ggccagtctc gtggctctgg gaagtc                            36

<210> SEQ ID NO 165
<211> LENGTH: 21
<212> TYPE: DNA
<213> ORGANISM: Artificial Sequence
<220> FEATURE:
<223> OTHER INFORMATION: primer for pcr

<400> SEQUENCE: 165
tgccagagaa cagagcattt g                                            21

<210> SEQ ID NO 166
<211> LENGTH: 21
```

```
<212> TYPE: DNA
<213> ORGANISM: Artificial Sequence
<220> FEATURE:
<223> OTHER INFORMATION: primer for pcr

<400> SEQUENCE: 166
aagcctgtcc cgtgtctact g                                              21

<210> SEQ ID NO 167
<211> LENGTH: 21
<212> TYPE: DNA
<213> ORGANISM: Artificial Sequence
<220> FEATURE:
<223> OTHER INFORMATION: primer for pcr

<400> SEQUENCE: 167
tagtggaaga gcttgttggc g                                              21

<210> SEQ ID NO 168
<211> LENGTH: 19
<212> TYPE: DNA
<213> ORGANISM: Artificial Sequence
<220> FEATURE:
<223> OTHER INFORMATION: primer for pcr

<400> SEQUENCE: 168
ggaagaccct gagctgcac                                                 19

<210> SEQ ID NO 169
<211> LENGTH: 38
<212> TYPE: DNA
<213> ORGANISM: Artificial Sequence
<220> FEATURE:
<223> OTHER INFORMATION: primer for pcr

<400> SEQUENCE: 169
gtaaaacgac ggccagtgta gcagtcgctg acatcctg                            38

<210> SEQ ID NO 170
<211> LENGTH: 21
<212> TYPE: DNA
<213> ORGANISM: Artificial Sequence
<220> FEATURE:
<223> OTHER INFORMATION: primer for pcr

<400> SEQUENCE: 170
aacacctgtg atctggaagg c                                              21

<210> SEQ ID NO 171
<211> LENGTH: 21
<212> TYPE: DNA
<213> ORGANISM: Artificial Sequence
<220> FEATURE:
<223> OTHER INFORMATION: primer for pcr

<400> SEQUENCE: 171
acacatacac acacgtgctc c                                              21

<210> SEQ ID NO 172
<211> LENGTH: 36
<212> TYPE: DNA
<213> ORGANISM: Artificial Sequence
<220> FEATURE:
<223> OTHER INFORMATION: primer for pcr

<400> SEQUENCE: 172
gtaaaacgac ggccagtctc gaggcacaga cagcac                              36
```

<210> SEQ ID NO 173
<211> LENGTH: 35
<212> TYPE: DNA
<213> ORGANISM: Artificial Sequence
<220> FEATURE:
<223> OTHER INFORMATION: primer for pcr

<400> SEQUENCE: 173
gtaaaacgac ggccagtcag gcgatgaggg aactg                          35

<210> SEQ ID NO 174
<211> LENGTH: 21
<212> TYPE: DNA
<213> ORGANISM: Artificial Sequence
<220> FEATURE:
<223> OTHER INFORMATION: primer for pcr

<400> SEQUENCE: 174
cgaaatacag gttcctcctg c                                         21

<210> SEQ ID NO 175
<211> LENGTH: 21
<212> TYPE: DNA
<213> ORGANISM: Artificial Sequence
<220> FEATURE:
<223> OTHER INFORMATION: primer for pcr

<400> SEQUENCE: 175
tgaccgtagt cctcgtagct g                                         21

<210> SEQ ID NO 176
<211> LENGTH: 37
<212> TYPE: DNA
<213> ORGANISM: Artificial Sequence
<220> FEATURE:
<223> OTHER INFORMATION: primer for pcr

<400> SEQUENCE: 176
gtaaaacgac ggccagtacg tcggtcaggc tgatctc                        37

<210> SEQ ID NO 177
<211> LENGTH: 20
<212> TYPE: DNA
<213> ORGANISM: Artificial Sequence
<220> FEATURE:
<223> OTHER INFORMATION: primer for pcr

<400> SEQUENCE: 177
aactctctga ggctgcaagg                                           20

<210> SEQ ID NO 178
<211> LENGTH: 21
<212> TYPE: DNA
<213> ORGANISM: Artificial Sequence
<220> FEATURE:
<223> OTHER INFORMATION: primer for pcr

<400> SEQUENCE: 178
gctagaaaca gcctaggcca c                                         21

<210> SEQ ID NO 179
<211> LENGTH: 21
<212> TYPE: DNA
<213> ORGANISM: Artificial Sequence
<220> FEATURE:
<223> OTHER INFORMATION: primer for pcr

```
<400> SEQUENCE: 179
ctgaacagac ctcaggcttg g                                              21

<210> SEQ ID NO 180
<211> LENGTH: 20
<212> TYPE: DNA
<213> ORGANISM: Artificial Sequence
<220> FEATURE:
<223> OTHER INFORMATION: primer for pcr

<400> SEQUENCE: 180
tccctcagag tcccaagagg                                                20

<210> SEQ ID NO 181
<211> LENGTH: 38
<212> TYPE: DNA
<213> ORGANISM: Artificial Sequence
<220> FEATURE:
<223> OTHER INFORMATION: primer for pcr

<400> SEQUENCE: 181
gtaaaacgac ggccagtggt agggaaggca gagatgtg                            38

<210> SEQ ID NO 182
<211> LENGTH: 20
<212> TYPE: DNA
<213> ORGANISM: Artificial Sequence
<220> FEATURE:
<223> OTHER INFORMATION: primer for pcr

<400> SEQUENCE: 182
tgggttcaga ccctgacttg                                                20

<210> SEQ ID NO 183
<211> LENGTH: 35
<212> TYPE: DNA
<213> ORGANISM: Artificial Sequence
<220> FEATURE:
<223> OTHER INFORMATION: primer for pcr

<400> SEQUENCE: 183
gtaaaacgac ggccagtatg accggcttgg aggac                               35

<210> SEQ ID NO 184
<211> LENGTH: 20
<212> TYPE: DNA
<213> ORGANISM: Artificial Sequence
<220> FEATURE:
<223> OTHER INFORMATION: primer for pcr

<400> SEQUENCE: 184
gacacaggag gagaggtcgg                                                20

<210> SEQ ID NO 185
<211> LENGTH: 38
<212> TYPE: DNA
<213> ORGANISM: Artificial Sequence
<220> FEATURE:
<223> OTHER INFORMATION: primer for pcr

<400> SEQUENCE: 185
gtaaaacgac ggccagttct gctacagtct cggcaaag                            38

<210> SEQ ID NO 186
<211> LENGTH: 21
```

```
<212> TYPE: DNA
<213> ORGANISM: Artificial Sequence
<220> FEATURE:
<223> OTHER INFORMATION: primer for pcr

<400> SEQUENCE: 186
ctccctttac ctgctagggt g                                        21

<210> SEQ ID NO 187
<211> LENGTH: 37
<212> TYPE: DNA
<213> ORGANISM: Artificial Sequence
<220> FEATURE:
<223> OTHER INFORMATION: primer for pcr

<400> SEQUENCE: 187
gtaaaacgac ggccagtgtc agccagaaca ggtcgtc                       37

<210> SEQ ID NO 188
<211> LENGTH: 38
<212> TYPE: DNA
<213> ORGANISM: Artificial Sequence
<220> FEATURE:
<223> OTHER INFORMATION: primer for pcr

<400> SEQUENCE: 188
gtaaaacgac ggccagtgag gcggccattt ctctttac                      38

<210> SEQ ID NO 189
<211> LENGTH: 21
<212> TYPE: DNA
<213> ORGANISM: Artificial Sequence
<220> FEATURE:
<223> OTHER INFORMATION: primer for pcr

<400> SEQUENCE: 189
tacggccctt tagagatgtg g                                        21

<210> SEQ ID NO 190
<211> LENGTH: 37
<212> TYPE: DNA
<213> ORGANISM: Artificial Sequence
<220> FEATURE:
<223> OTHER INFORMATION: primer for pcr

<400> SEQUENCE: 190
gtaaaacgac ggccagtact ccagtctcag gcccatc                       37

<210> SEQ ID NO 191
<211> LENGTH: 20
<212> TYPE: DNA
<213> ORGANISM: Artificial Sequence
<220> FEATURE:
<223> OTHER INFORMATION: primer for pcr

<400> SEQUENCE: 191
cagagtgagg actcgggatg                                          20

<210> SEQ ID NO 192
<211> LENGTH: 37
<212> TYPE: DNA
<213> ORGANISM: Artificial Sequence
<220> FEATURE:
<223> OTHER INFORMATION: primer for pcr

<400> SEQUENCE: 192
gtaaaacgac ggccagtcac tcagcctgtg tctgtgg                       37
```

<210> SEQ ID NO 193
<211> LENGTH: 38
<212> TYPE: DNA
<213> ORGANISM: Artificial Sequence
<220> FEATURE:
<223> OTHER INFORMATION: primer for pcr

<400> SEQUENCE: 193
gtaaaacgac ggccagtctt gatggagaac ggtctgtc                    38

<210> SEQ ID NO 194
<211> LENGTH: 21
<212> TYPE: DNA
<213> ORGANISM: Artificial Sequence
<220> FEATURE:
<223> OTHER INFORMATION: primer for pcr

<400> SEQUENCE: 194
caacactttg tgctggttcc c                                      21

<210> SEQ ID NO 195
<211> LENGTH: 21
<212> TYPE: DNA
<213> ORGANISM: Artificial Sequence
<220> FEATURE:
<223> OTHER INFORMATION: primer for pcr

<400> SEQUENCE: 195
agtaggagct gatgctgcga g                                      21

<210> SEQ ID NO 196
<211> LENGTH: 21
<212> TYPE: DNA
<213> ORGANISM: Artificial Sequence
<220> FEATURE:
<223> OTHER INFORMATION: primer for pcr

<400> SEQUENCE: 196
gaggagcttg ttgttgggaa g                                      21

<210> SEQ ID NO 197
<211> LENGTH: 21
<212> TYPE: DNA
<213> ORGANISM: Artificial Sequence
<220> FEATURE:
<223> OTHER INFORMATION: primer for pcr

<400> SEQUENCE: 197
taaaggacag gtggaaggtg g                                      21

<210> SEQ ID NO 198
<211> LENGTH: 22
<212> TYPE: DNA
<213> ORGANISM: Artificial Sequence
<220> FEATURE:
<223> OTHER INFORMATION: primer for pcr

<400> SEQUENCE: 198
tggctgaacc tctgactcta gc                                     22

<210> SEQ ID NO 199
<211> LENGTH: 20
<212> TYPE: DNA
<213> ORGANISM: Artificial Sequence
<220> FEATURE:
<223> OTHER INFORMATION: primer for pcr

```
<400> SEQUENCE: 199
cttcctgacc acctcgtctc                                              20

<210> SEQ ID NO 200
<211> LENGTH: 35
<212> TYPE: DNA
<213> ORGANISM: Artificial Sequence
<220> FEATURE:
<223> OTHER INFORMATION: primer for pcr

<400> SEQUENCE: 200
gtaaaacgac ggccagtgct gactgcacca gtggg                             35

<210> SEQ ID NO 201
<211> LENGTH: 21
<212> TYPE: DNA
<213> ORGANISM: Artificial Sequence
<220> FEATURE:
<223> OTHER INFORMATION: primer for pcr

<400> SEQUENCE: 201
tacttccagg cctgagacac c                                            21

<210> SEQ ID NO 202
<211> LENGTH: 38
<212> TYPE: DNA
<213> ORGANISM: Artificial Sequence
<220> FEATURE:
<223> OTHER INFORMATION: primer for pcr

<400> SEQUENCE: 202
gtaaaacgac ggccagtcac acggtcaggt cacacttc                          38

<210> SEQ ID NO 203
<211> LENGTH: 21
<212> TYPE: DNA
<213> ORGANISM: Artificial Sequence
<220> FEATURE:
<223> OTHER INFORMATION: primer for pcr

<400> SEQUENCE: 203
cctccttaga cctcagcaac g                                            21

<210> SEQ ID NO 204
<211> LENGTH: 21
<212> TYPE: DNA
<213> ORGANISM: Artificial Sequence
<220> FEATURE:
<223> OTHER INFORMATION: primer for pcr

<400> SEQUENCE: 204
gagaaagcag ggacaggaca c                                            21

<210> SEQ ID NO 205
<211> LENGTH: 38
<212> TYPE: DNA
<213> ORGANISM: Artificial Sequence
<220> FEATURE:
<223> OTHER INFORMATION: primer for pcr

<400> SEQUENCE: 205
gtaaaacgac ggccagtaac tgggtgcagc tggaatac                          38

<210> SEQ ID NO 206
<211> LENGTH: 37
```

<212> TYPE: DNA
<213> ORGANISM: Artificial Sequence
<220> FEATURE:
<223> OTHER INFORMATION: primer for pcr

<400> SEQUENCE: 206
gtaaaacgac ggccagtagc atgcatccac tcaggtc          37

<210> SEQ ID NO 207
<211> LENGTH: 19
<212> TYPE: DNA
<213> ORGANISM: Artificial Sequence
<220> FEATURE:
<223> OTHER INFORMATION: primer for pcr

<400> SEQUENCE: 207
agcagcagct gggtctctg          19

<210> SEQ ID NO 208
<211> LENGTH: 35
<212> TYPE: DNA
<213> ORGANISM: Artificial Sequence
<220> FEATURE:
<223> OTHER INFORMATION: primer for pcr

<400> SEQUENCE: 208
gtaaaacgac ggccagttcc tgcacccact tctgc          35

<210> SEQ ID NO 209
<211> LENGTH: 18
<212> TYPE: DNA
<213> ORGANISM: Artificial Sequence
<220> FEATURE:
<223> OTHER INFORMATION: primer for pcr

<400> SEQUENCE: 209
cgtcgttgta gaagcccg          18

<210> SEQ ID NO 210
<211> LENGTH: 37
<212> TYPE: DNA
<213> ORGANISM: Artificial Sequence
<220> FEATURE:
<223> OTHER INFORMATION: primer for pcr

<400> SEQUENCE: 210
gtaaaacgac ggccagtgtt tgaggttcgt ttctgcg          37

<210> SEQ ID NO 211
<211> LENGTH: 38
<212> TYPE: DNA
<213> ORGANISM: Artificial Sequence
<220> FEATURE:
<223> OTHER INFORMATION: primer for pcr

<400> SEQUENCE: 211
gtaaaacgac ggccagtaca aagatagggt ggtcaggg          38

<210> SEQ ID NO 212
<211> LENGTH: 21
<212> TYPE: DNA
<213> ORGANISM: Artificial Sequence
<220> FEATURE:
<223> OTHER INFORMATION: primer for pcr

<400> SEQUENCE: 212
caaccaggtc cagccacata g          21

```
<210> SEQ ID NO 213
<211> LENGTH: 36
<212> TYPE: DNA
<213> ORGANISM: Artificial Sequence
<220> FEATURE:
<223> OTHER INFORMATION: primer for pcr

<400> SEQUENCE: 213
gtaaaacgac ggccagtgta cagggccagc aggatg                               36

<210> SEQ ID NO 214
<211> LENGTH: 18
<212> TYPE: DNA
<213> ORGANISM: Artificial Sequence
<220> FEATURE:
<223> OTHER INFORMATION: primer for pcr

<400> SEQUENCE: 214
atcttggcca gggtggag                                                   18

<210> SEQ ID NO 215
<211> LENGTH: 37
<212> TYPE: DNA
<213> ORGANISM: Artificial Sequence
<220> FEATURE:
<223> OTHER INFORMATION: primer for pcr

<400> SEQUENCE: 215
gtaaaacgac ggccagtgca cctagaacgg tgcagag                              37
```

CONSENSUS CODING SEQUENCES OF HUMAN BREAST AND COLORECTAL CANCERS

This invention was made using grant funds from the U.S. government. Under the term of the grants, the U.S. government retains certain rights in the invention. Grants used include NIH grants CA 121113, CA 43460, CA 57345, CA 62924, GM 07309, RR 017698, P30-CA43703, and CA109274, and Department of Defense grant DAMD17-03-1-0241.

TECHNICAL FIELD OF THE INVENTION

This invention is related to the area of cancer characterization. In particular, it relates to breast and colorectal cancers.

BACKGROUND OF THE INVENTION

It is widely accepted that human cancer is a genetic disease caused by sequential accumulation of mutations in oncogenes and tumor suppressor genes (1). These tumor-specific (that is, somatic) mutations provide clues to the cellular processes underlying tumorigenesis and have proven useful for diagnostic and therapeutic purposes. To date, however, only a small fraction of the genes has been analyzed and the number and type of alterations responsible for the development of common tumor types are unknown (2). In the past, the selection of genes chosen for mutational analyses in cancer has been guided by information from linkage studies in cancer-prone families, identification of chromosomal abnormalities in tumors, or known functional attributes of individual genes or gene families (2-4). The determination of the human genome sequence coupled with improvements in sequencing and bioinformatic approaches have now made it possible, in principle, to examine the cancer cell genome in a comprehensive and unbiased manner. Such an approach not only provides the means to discover other genes that contribute to tumorigenesis but can also lead to mechanistic insights that are only evident through a systems biological perspective. Comprehensive genetic analyses of human cancers could lead to discovery of a set of genes, linked together through a shared phenotype, that point to the importance of specific cellular processes or pathways.

There is a continuing need in the art to identify genes and patterns of gene mutations useful for identifying and stratifying individual patients' cancers.

SUMMARY OF THE INVENTION

According to one embodiment of the invention a method is provided for diagnosing breast cancer in a human. A somatic mutation in a gene or its encoded cDNA or protein is determined in a test sample relative to a normal sample of the human. The gene is selected from the group consisting of those listed in FIG. 13 (Table S5). The sample is identified as breast cancer when the somatic mutation is determined.

A method is provided for diagnosing colorectal cancer in a human. A somatic mutation in a gene or its encoded cDNA or protein is determined in a test sample relative to a normal sample of the human. The gene is selected from the group consisting of those listed in FIG. 14. (Table S6). The sample is identified as colorectal cancer if the somatic mutation is determined.

A method is provided for stratifying breast cancers for testing candidate or known anti-cancer therapeutics. A CAN-gene mutational signature for a breast cancer is determined by determining at least one somatic mutation in a test sample relative to a normal sample of a human. The at least one somatic mutation is in one or more genes selected from the group consisting of FIG. 13 (Table S5). A first group of breast cancers that have the CAN-gene mutational signature is formed. Efficacy of a candidate or known anti-cancer therapeutic on the first group is compared to efficacy on a second group of breast cancers that has a different CAN-gene mutational signature. A CAN gene mutational signature which correlates with increased or decreased efficacy of the candidate or known anti-cancer therapeutic relative to other groups is identified.

A method is provided for stratifying colorectal cancers for testing candidate or known anti-cancer therapeutics. A CAN-gene mutational signature for a colorectal cancer is determined by determining at least one somatic mutation in a test sample relative to a normal sample of the human. The at least one somatic mutation is in one or more genes selected from the group consisting of FIG. 14. (Table S6). A first group of colorectal cancers that have the CAN-gene mutational signature is formed. Efficacy of a candidate or known anti-cancer therapeutic on the first group is compared to efficacy on a second group of colorectal cancers that has a different CAN-gene mutational signature. A CAN gene mutational signature is identified which correlates with increased or decreased efficacy of the candidate or known anti-cancer therapeutic relative to other groups.

A method is provided for characterizing a breast cancer in a human. A somatic mutation in a gene or its encoded cDNA or protein is determined in a test sample relative to a normal sample of the human. The gene is selected from the group consisting of those listed in FIG. 13 (Table S5).

Another method provided is for characterizing a colorectal cancer in a human. A somatic mutation in a gene or its encoded cDNA or protein is determined in a test sample relative to a normal sample of the human. The gene is selected from the group consisting of those listed in FIG. 14 (Table S6).

These and other embodiments which will be apparent to those of skill in the art upon reading the specification provide the art with

BRIEF DESCRIPTION OF THE DRAWINGS

FIG. 5. (Table 1.) Summary of somatic mutations

FIG. 6. (Table 2) Spectrum of single base substitutions

FIG. 7. (Table 3.) Functional classification of CAN-genes*

FIG. 8. (Table S1.) Primers used for PCR amplification and sequencing (page 1 of 1333 only; all primer sequences are publicly available in a downloadable file (1133427_som_tables.zip) at the website of the journal Science (www.sciencemag.org) under Supporting Online Material located at the webpage /cgi/content/full/sci;1133427/DC1)

FIG. 9. (Table S2A.) Characteristics of the colorectal cancer samples.

FIG. 10. (Table S2B.) Characteristics of the breast cancer samples.

FIG. 11. (Table S3.) Distribution of mutations in individual cancers.

Figure 12C:
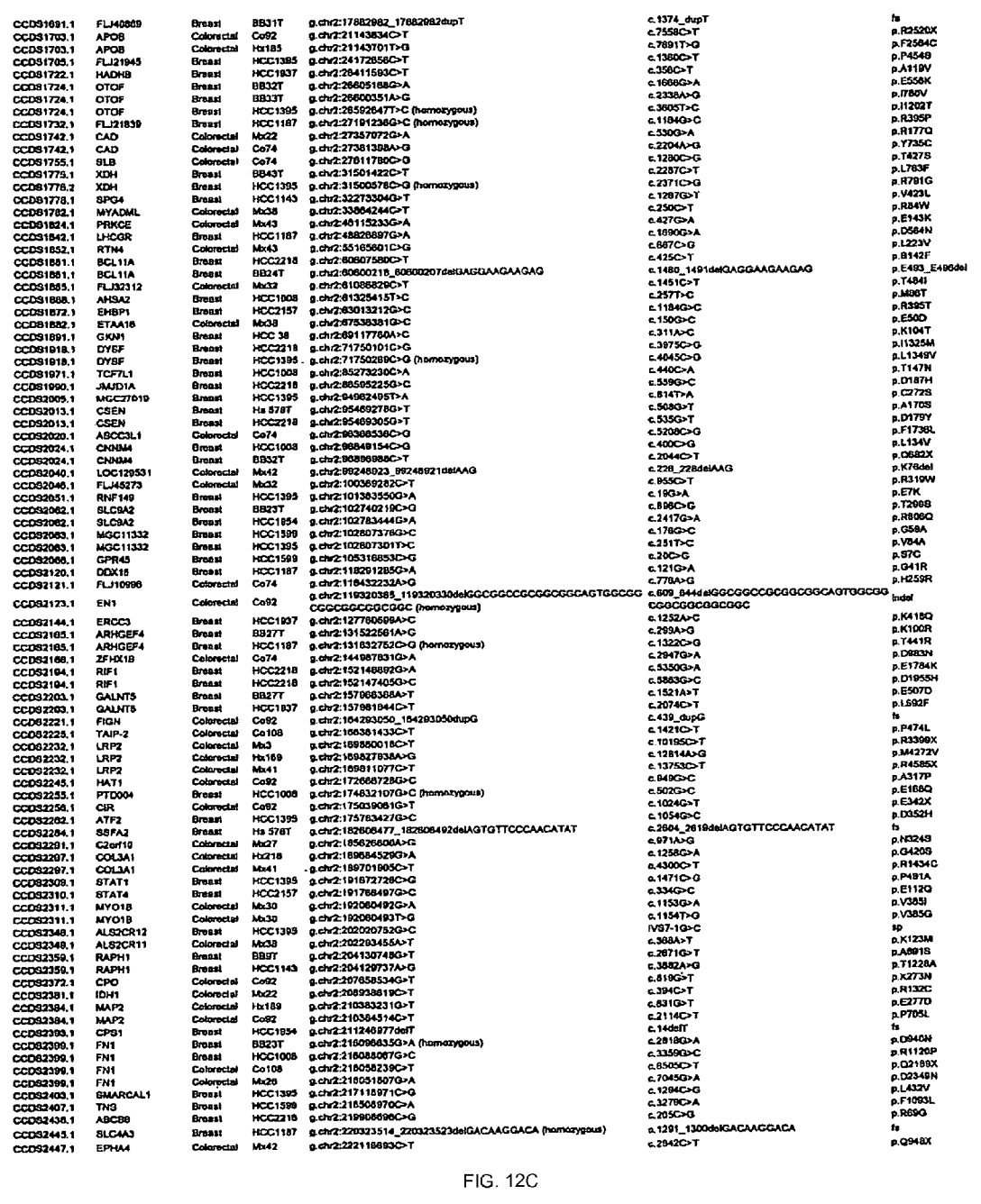
Figure 12F:
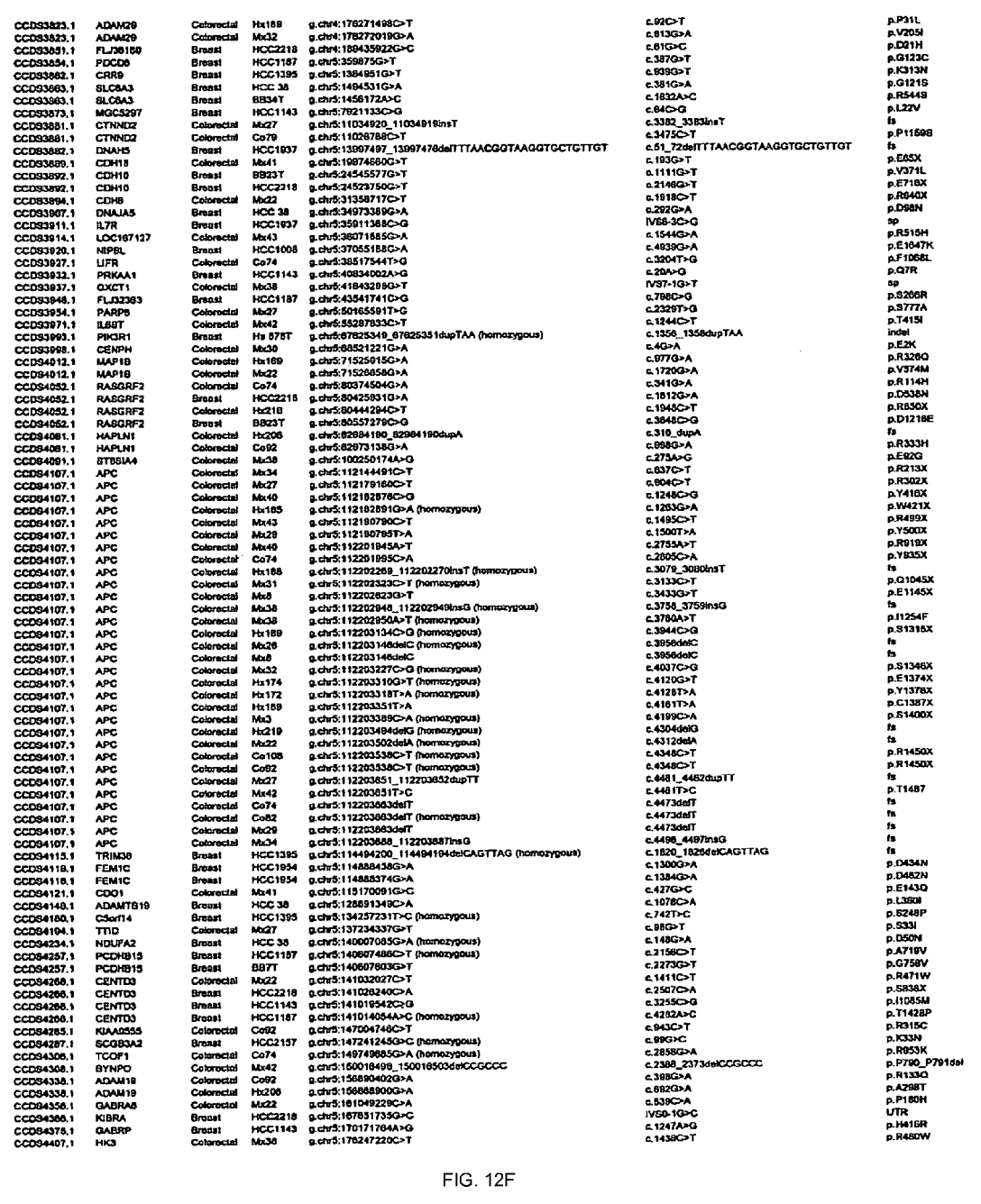
Figure 12I:
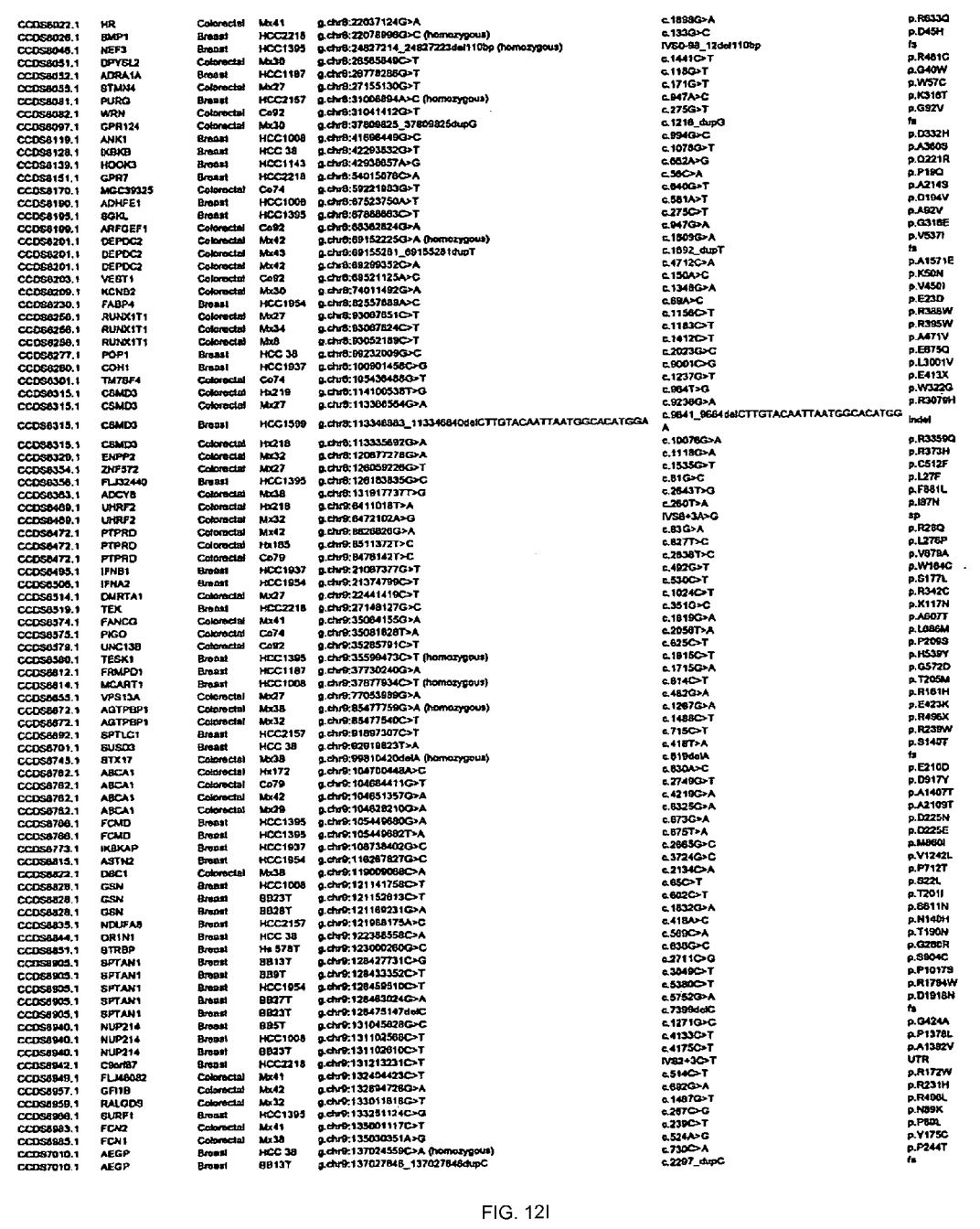
Figure 12Q:
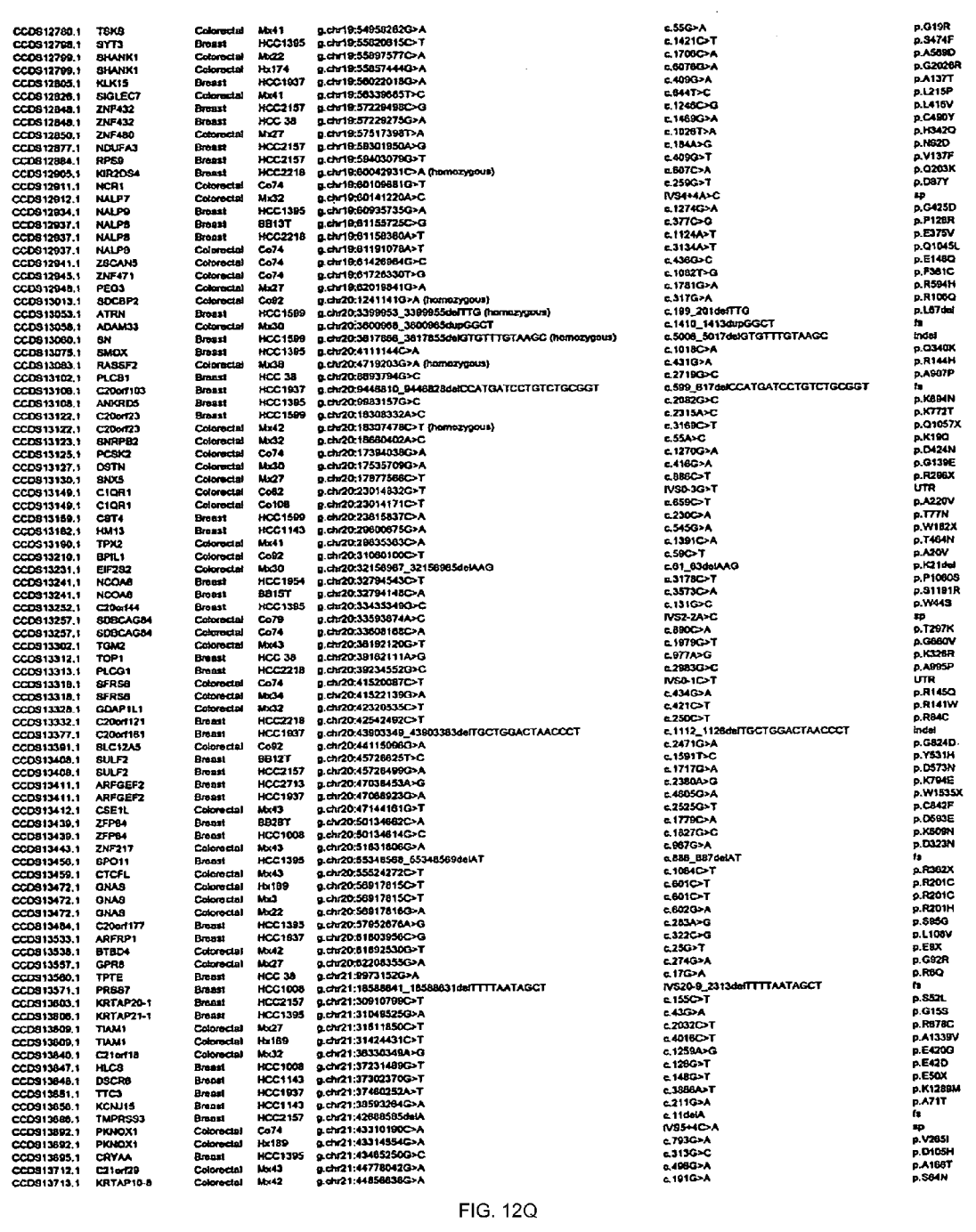

FIG. 12A-12S. (Table S4.) Somatic mutations identified in breast or colorectal cancers.

FIG. 13A-13C. (Table S5.) Breast CAN-genes.

FIG. 14A-14B. (Table S6.) Colorectal CAN-genes.

DETAILED DESCRIPTION OF THE INVENTION

Figure 1A:
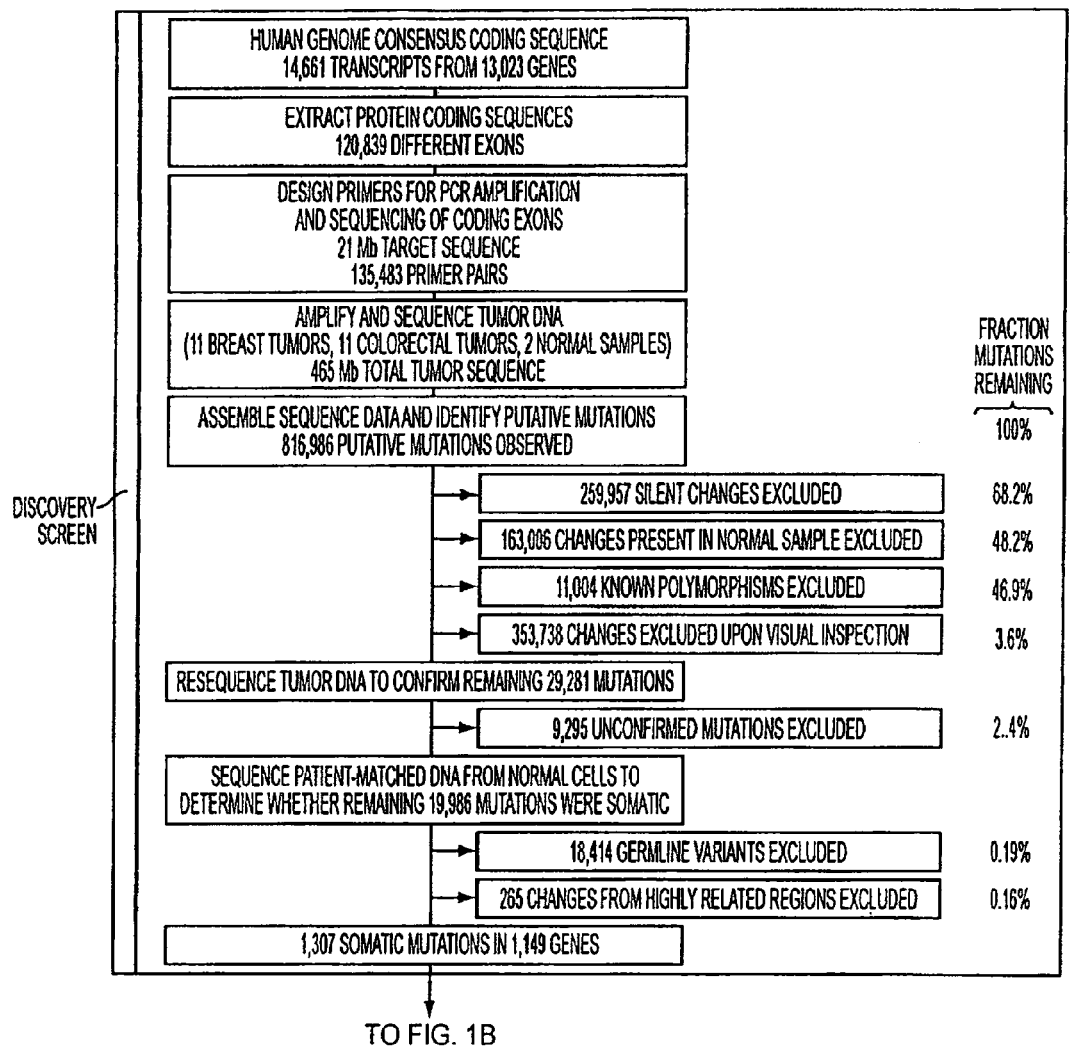
FIGS. 1A and 1B. Schematic of Mutation Discovery and Validation Screens.

The inventors have developed methods for characterizing breast and colorectal cancers on the basis of gene signatures. These signatures comprise one or more genes which are mutated in a particular cancer. The signatures can be used as a means of diagnosis, prognosis, identification of metastasis, stratification for drug studies, and for assigning an appropriate treatment.

According to the present invention a mutation, typically a somatic mutation, can be determined by testing either a gene, its mRNA (or derived cDNA), or its encoded protein. Any method known in the art for determining a somatic mutation can be used. The method may involve sequence determination of all or part of a gene, cDNA, or protein. The method may involve mutation-specific reagents such as probes, primers, or antibodies. The method may be based on amplification, hybridization, antibody-antigen reactions, primer extension, etc. Any technique or method known in the art for determining a sequence-based feature may be used.

Samples for testing may be tissue samples from breast or colorectal tissue or body fluids or products that contain sloughed off cells or genes or mRNA or proteins. Such fluids or products include breast milk, stool, breast discharge, intestinal fluid. Preferably the same type of tissue or fluid is used for the test sample and the normal sample. The test sample is, however, suspected of possible neoplastic abnormality, while the normal sample is not suspect.

Figure 13B:
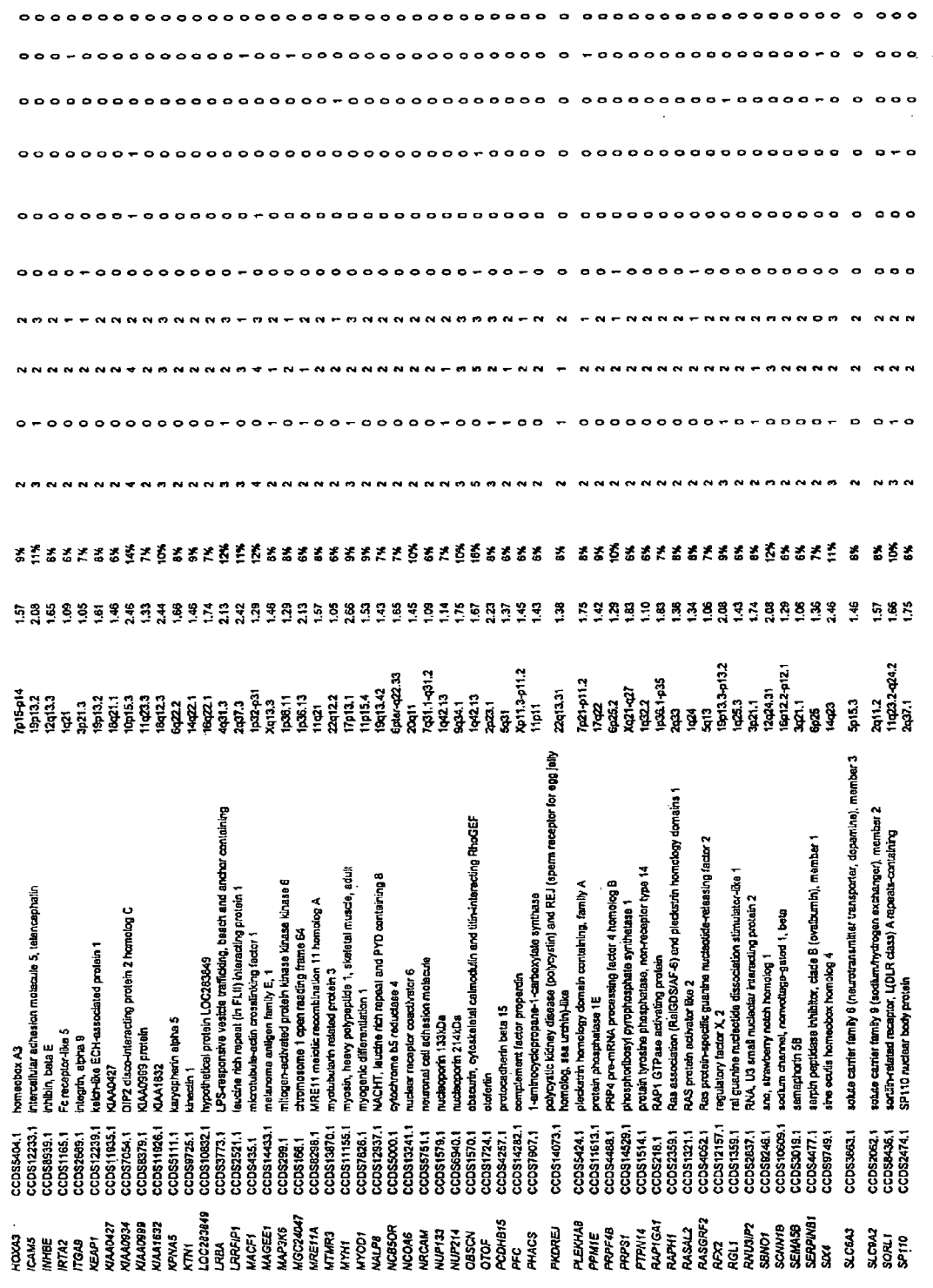

Somatic mutations are determined by finding a difference between a test sample and a normal sample of a human. This criterion eliminates the possibility of germ-line differences confounding the analysis. For breast cancer, the gene (or cDNA or protein) to be tested is any of those shown in FIG. 13 (Table S5). Particular genes which may be tested and useful are gelsolin GSN, cadherin genes CDH10 and CDH20, actin and SMAD binding protein filamin B FLNB, and autocrine motility factor receptor AMFR. Additional useful genes include ATP-dependent transporter ATP8B1, intrinsic factor-cobalamin receptor CUBN, actin binding protein DBN1, and tectorin alpha TECTA. For colorectal cancer, the gene (or cDNA or protein) to be tested is any of those shown in FIG. 14. (Table S6). Particular genes which may be tested and useful are ephrin receptor EPHB6, mixed lineage leukemia 3 gene (MLL3), and protein tyrosine phosphatase receptor PTPRD. Other genes which may be tested and useful are polycystic kidney and hepatic disease 1 gene PKHD1, guanylate cyclase 1 GUCY1A2, transcription factor TBX22, exocyst complex component SEC8L1, and tubulin tyrosine ligase TTLL3. Any somatic mutation may be informative. Particular mutations which may be used are shown in FIG. 12 (Table S4).

The number of genes or mutations that may be useful in forming a signature of a breast or colorectal cancer may vary from one to twenty-five. At least two, three, four, five, six, seven or more genes may be used. The mutations are typically somatic mutations and non-synonymous mutations. Those mutations described here are within coding regions. Other non-coding region mutations may also be found and may be informative.

In order to test candidate or already-identified therapeutic agents to determine which patients and tumors will be sensitive to the agents, stratification on the basis of signatures can be used. One or more groups with a similar mutation signature will be formed and the effect of the therapeutic agent on the group will be compared to the effect of patients whose tumors do not share the signature of the group formed. The group of patients who do not share the signature may share a different signature or they may be a mixed population of tumor-bearing patients whose tumors bear a variety of signatures.

Efficacy can be determined by any of the standard means known in the art. Any index of efficacy can be used. The index may be life span, disease free remission period, tumor shrinkage, tumor growth arrest, improvement of quality of life, decreased side effects, decreased pain, etc. Any useful measure of patient health and well-being can be used. In addition, in vitro testing may be done on tumor cells that have particular signatures. Tumor cells with particular signatures can also be tested in animal models.

Once a signature has been correlated with sensitivity or resistance to a particular therapeutic regimen, that signature can be used for prescribing a treatment to a patient. Thus determining a signature is useful for making therapeutic decisions. The signature can also be combined with other physical or biochemical findings regarding the patient to arrive at a therapeutic decision. A signature need not be the sole basis for making a therapeutic decision.

An anti-cancer agent associated with a signature may be, for example, docetaxel, paclitaxel, topotecan, adriamycin, etoposide, fluorouracil (5-FU), or cyclophosphamide. The agent may be an alkylating agent (e.g., nitrogen mustards), antimetabolites (e.g., pyrimidine analogs), radioactive isotopes (e.g., phosphorous and iodine), miscellaneous agents (e.g., substituted ureas) and natural products (e.g., vinca alkyloids and antibiotics). The therapeutic agent may be allopurinol sodium, dolasetron mesylate, pamidronate disodium, etidronate, fluconazole, epoetin alfa, levamisole HCL, amifostine, granisetron HCL, leucovorin calcium, sargramostim, dronabinol, mesna, filgrastim, pilocarpine HCL, octreotide acetate, dexrazoxane, ondansetron HCL, ondansetron, busulfan, carboplatin, cisplatin, thiotepa, melphalan HCL, melphalan, cyclophosphamide, ifosfamide, chlorambucil, mechlorethamine HCL, carmustine, lomustine, polifeprosan 20 with carmustine implant, streptozocin, doxorubicin HCL, bleomycin sulfate, daunirubicin HCL, dactinomycin, daunorucbicin citrate, idarubicin HCL, plimycin, mitomycin, pentostatin, mitoxantrone, valrubicin, cytarabine, fludarabine phosphate, floxuridine, cladribine, methotrexate, mercaptipurine, thioguanine, capecitabine, methyltestosterone, nilutamide, testolactone, bicalutamide, flutamide, anastrozole, toremifene citrate, estramustine phosphate sodium, ethinyl estradiol, estradiol, esterified estrogens, conjugated estrogens, leuprolide acetate, goserelin acetate, medroxyprogesterone acetate, megestrol acetate, levamisole HCL, aldesleukin, irinotecan HCL, dacarbazine, asparaginase, etoposide phosphate, gemcitabine HCL, altretamine, topotecan HCL, hydroxyurea, interferon alpha-2b, mitotane, procarbazine HCL, vinorelbine tartrate, E. coli L-asparaginase, Erwinia L-asparaginase, vincristine sulfate, denileukin diftitox, aldesleukin, rituximab, interferon alpha-2a, paclitaxel, docetaxel, BCG live (intravesical), vinblastine sulfate, etoposide, tretinoin, teniposide, porfimer sodium, fluorouracil, betamethasone sodium phosphate and betamethasone acetate, letrozole, etoposide citrororum factor, folinic acid, calcium leucouorin, 5-fluorouricil, adriamycin, cytoxan, or diamino-dichloro-platinum.

The signatures of CAN genes according to the present invention can be used to determine an appropriate therapy for an individual. For example, a sample of a tumor (e.g., a tissue obtained by a biopsy procedure, such as a needle biopsy) can be provided from the individual, such as before a primary therapy is administered. The gene expression profile of the tumor can be determined, such as by a nucleic acid array (or protein array) technology, and the expression profile can be compared to a database correlating signatures with treatment outcomes. Other information relating to the human (e.g., age, gender, family history, etc.) can factor into a treatment recommendation. A healthcare provider can make a decision to administer or prescribe a particular drug based on the comparison of the CAN gene signature of the tumor and information in the database. Exemplary healthcare providers include doctors, nurses, and nurse practitioners. Diagnostic laboratories can also provide a recommended therapy based on signatures and other information about the patient.

Following treatment with a primary cancer therapy, the patient can be monitored for an improvement or worsening of the cancer. A tumor tissue sample (such as a biopsy) can be taken at any stage of treatment. In particular, a tumor tissue sample can be taken upon tumor progression, which can be determined by tumor growth or metastasis. A CAN gene signature can be determined, and one or more secondary therapeutic agents can be administered to increase, or restore, the sensitivity of the tumor to the primary therapy.

Treatment predictions may be based on pre-treatment gene signatures. Secondary or subsequent therapeutics can be selected based on the subsequent assessments of the patient and the later signatures of the tumor. The patient will typically be monitored for the effect on tumor progression.

A medical intervention can be selected based on the identity of the CAN gene signature. For example, individuals can be sorted into subpopulations according to their genotype. Genotype-specific drug therapies can then be prescribed. Medical interventions include interventions that are widely practiced, as well as less conventional interventions. Thus, medical interventions include, but are not limited to, surgical procedures, administration of particular drugs or dosages of particular drugs (e.g., small molecules, bioengineered proteins, and gene-based drugs such as antisense oligonucleotides, ribozymes, gene replacements, and DNA- or RNA-based vaccines), including FDA-approved drugs, FDA-approved drugs used for off-label purposes, and experimental agents. Other medical interventions include nutritional therapy, holistic regimens, acupuncture, meditation, electrical or magnetic stimulation, osteopathic remedies, chiropractic treatments, naturopathic treatments, and exercise.

Four important points have emerged from our comprehensive mutational analysis of human cancer. First, a relatively large number of previously uncharacterized CAN-genes exist in breast and colorectal cancers and these genes can be discovered by unbiased approaches such as that used in our study. These results support the notion that large-scale mutational analyses of other tumor types will prove useful for identifying genes not previously known to be linked to human cancer.

Second, our results suggest that the number of mutational events occurring during the evolution of human tumors from a benign to a metastatic state is much larger than previously thought. We found that breast and colorectal cancers harbor an average of 52 and 67 non-synonymous somatic mutations in CCDS genes, of which an average of 9 and 12, respectively, were in CAN-genes. FIG. 11 (Table S3). These data can be used to estimate the total number of nonsynonymous mutations in coding genes that arise in a "typical" cancer through sequential rounds of mutation and selection. Assuming that the mutation prevalence in genes that have not yet been sequenced is similar to that of the genes so far analyzed, we estimate that there are 81 and 105 mutant genes (average, 93) in the typical colorectal or breast cancer, respectively. Of these, an average of 14 and 20, respectively, would be expected to be CAN-genes. In addition to the CAN-genes, there were other mutated CCDS genes that were likely to have been selected for during tumorigenesis but were not altered at a frequency high enough to warrant confidence in their interpretation.

A third point emerging from our study is that breast and colorectal cancers show substantial differences in their mutation spectra. In colorectal cancers, a bias toward C:G to T:A transitions at 5'-CpG-3' sites has been previously noted in TP53 (42). Our results suggest that this bias is genome-wide rather than representing a selection for certain nucleotides within TP53. This bias may reflect a more extensive methylation of 5'-CpG-3' dinucleotides in colorectal cancers than in breast cancers or the effect of dietary carcinogens (43, 44). In breast cancers, the fraction of mutations at 5'-TpC-3'sites was far higher in the CCDS genes examined in this study than previously reported for TP53 (37). It has been noted that a small fraction of breast tumors may have a defective repair system, resulting in 5'-TpC-3' mutations (15). Our studies confirm that some breast cancers have higher fractions of 5'-TpC-3' mutations than others, but also show that mutations at this dinucleotide are generally more frequent than in colorectal cancers (FIGS. 6 and 11; Tables 2 and S3).

Finally, our results reveal that there are substantial differences in the panel of CAN-genes mutated in the two tumor types (FIG. 7; Table 3). For example, metalloproteinase genes were mutated in a large fraction of colorectal but only in a small fraction of breast cancers (FIGS. 13 and 14; Tables S5 and S6). Transcriptional regulator genes were mutated in a high fraction of both breast and colorectal tumors, but the specific genes affected varied according to tumor type (FIG. 7; Table 3). There was also considerable heterogeneity among the CAN-genes mutated in different tumor specimens derived from the same tissue type (FIGS. 12-14; Tables S4, S5, and S6). It has been documented that virtually all biochemical, biological, and clinical attributes are heterogeneous within human cancers of the same histologic subtype (45). Our data suggest that differences in the CAN-genes mutated in various tumors could account for a major part of this heterogeneity. This might explain why it has been so difficult to correlate the behavior, prognosis, or response to therapy of common solid tumors with the presence or absence of a single gene alteration; such alterations reflect only a small component of each tumor's mutational composition. On the other hand, disparate genes contributing to cancer are often functionally equivalent, affecting net cell growth through the same molecular pathway (1). Thus, TP53 and MDM2 mutations exert comparable effects on cells, as do mutations in RB1, CDKN2A (p16), CCND1 and CDK4. It will be of interest to determine whether a limited number of pathways include most CAN-genes, a possibility consistent with the groupings in FIG. 2 and FIG. 7 (Table 3).

Like a draft version of any genome project, our study has limitations. First, only genes present in the current version of CCDS were analyzed. There are ~5000 genes for which excellent supporting evidence exists but are not yet included in the CCDS database (46). Second, we were not able to successfully sequence ~10% of the bases within the coding sequences of the 13,023 CCDS genes (equivalent to 1,302 unsequenced genes). Third, although our screen would be expected to identify the most common types of mutations found in cancers, some genetic alterations, including mutations in non-coding genes, mutations in non-coding regions of coding genes, relatively large deletions or insertions, amplifications, and translocations, would not be detectable by the methods we used. Future studies employing a combination of different technologies, such as those envisioned by The Cancer Genome Atlas Project (TCGA) (47), will be able to address these issues.

The results of this study inform future cancer genome sequencing efforts in several important ways.

Figure 1B:
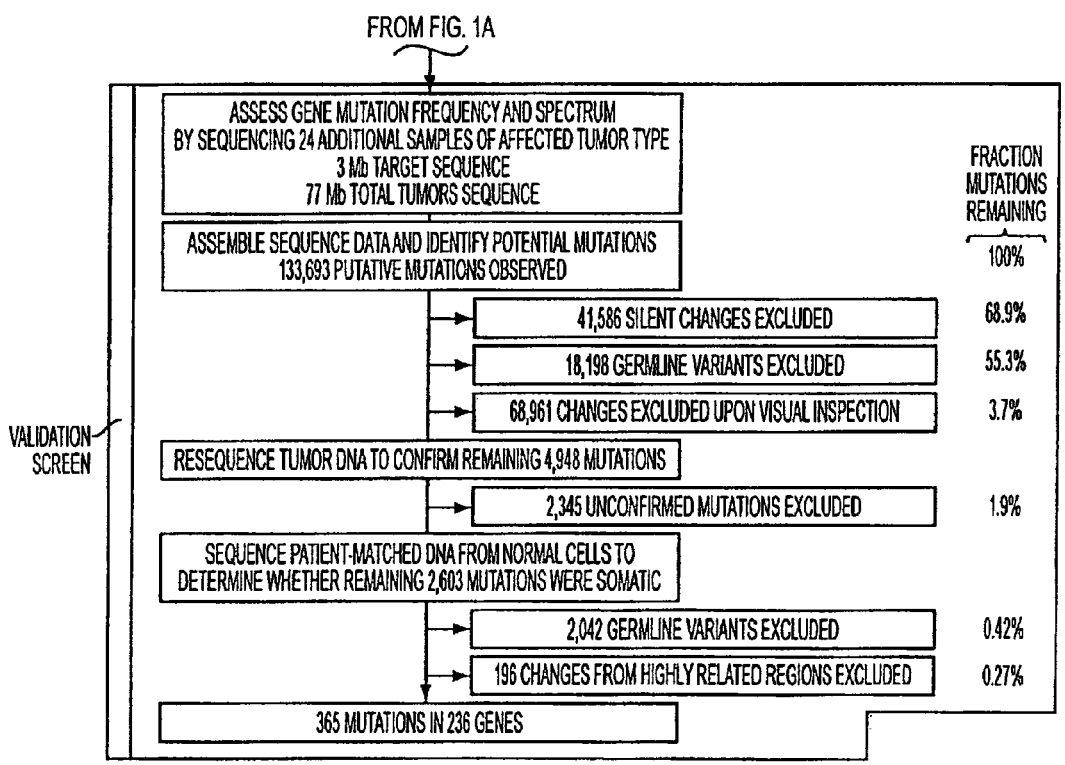

(i) A major technical challenge of such studies will be discerning somatic mutations from the large number of sequence alterations identified. In our study, 557,029 non-synonymous sequence alterations were detected in the Discovery Screen but after subsequent analyses only 0.23% of these were identified as legitimate somatic mutations (FIG. 1). Less than 10% of nonsynonymous alterations were known polymorphisms; many of the rest were uncommon germ-line variants or sequence artifacts that were not reproducible. Inclusion of matched normal samples and sequencing both strands of each PCR product would reduce false positives in the Discovery Screen but would increase the cost of sequencing by four-fold. Although recently developed sequencing methods could reduce the cost of such studies in the future (48), the higher error rates of these approaches may result in an even lower ratio of bona fide somatic mutations to putative alterations.

(ii) Another technical issue is that careful design of primers is important to eliminate sequence artifacts due to the inadvertent amplification and sequencing of related genes. The primer pairs that resulted in successful amplification and sequencing represent a valuable resource in this regard. Even with well-designed primers, it is essential to examine any observed mutation to ensure that it is not found as a normal variant in a related gene.

(iii) Although it is likely that studies of other solid tumor types will also identify a large number of somatic mutations, it will be important to apply rigorous approaches to identify those mutations that have been selected for during tumorigenesis. Statistical techniques, such as those used in this study or described by Greenman et al. (11), can provide strong evidence for selection of mutated genes. These approaches are likely to improve as more cancer genomic sequencing data is accumulated through The Cancer Genome Atlas Project (47) and other projects now underway.

(iv) There has been much discussion about which genes should be the focus of future sequencing efforts. Our results suggest that many genes not previously implicated in cancer are mutated at significant levels and may provide novel clues to pathogenesis. From these data, it would seem that large-scale unbiased screens of coding genes may be more informative than screens based on previously defined criteria.

(v) The results also raise questions about the optimum number of tumors of any given type that should be assessed in a cancer genome study. Our study was designed to determine the nature and types of alterations present in an "average" breast or colorectal cancer and to discover genes mutated at reasonably high frequencies. Our power to detect genes mutated in more than 20% of tumors of a given type was 90%, but only 50% of genes mutated in 6% of tumors would have been discovered. To detect genes mutated in 6% or 1% of tumors with >99% probability in a Discovery Screen would require sequence determination of at least 75 or 459 tumors, respectively. Though it will be impossible to detect all mutations that may occur in tumors, strategies that would identify the most important ones at an affordable cost can be envisioned on the basis of the data and analysis reported herein.

(vi) Ultimately, the sequences of entire cancer genomes, including intergenic regions, will be obtainable. Our studies demonstrate the inherent difficulties in determining the significance of somatic mutations, even those that alter the amino acid sequence of highly-annotated and well-studied genes. Establishing the significance of mutations in non-coding regions of the genome will likely be much more difficult. Until new tools for solving this problem become available, it is likely that gene-centric analyses of cancer will be more useful.

Our results provide a large number of future research opportunities in human cancer. For genetics, it will be of interest to elucidate the timing and extent of CAN-gene mutations in breast and colorectal cancers, whether these genes are mutated in other tumor types, and whether germline variants in CAN-genes are associated with cancer predisposition. For immunology, the finding that tumors contain an average of ~90 different amino acid substitutions not present in any normal cell can provide novel approaches to engender anti-tumor immunity. For epidemiology, the remarkable difference in mutation spectra of breast and colorectal cancers suggests the existence of organ-specific carcinogens. For cancer biology, it is clear that no current animal or in vitro model of cancer recapitulates the genetic landscape of an actual human tumor. Understanding and capturing this landscape and its heterogeneity may provide models that more successfully mimic the human disease. For epigenetics, it is possible that a subset of CAN-genes can also be dysregulated in tumors through changes in chromatin or DNA methylation rather than through mutation. For diagnostics, the CAN-genes define a relatively small subset of genes that could prove useful as markers for neoplasia. Finally, some of these genes, particularly those on the cell surface or those with enzymatic activity, may prove to be good targets for therapeutic development.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLES

To begin the systematic study of the cancer genome, we have examined a major fraction of human genes in two common tumor types, breast and colorectal cancers. These cancers were chosen for study because of their substantial clinical significance world-wide: together, they account for ~2.2 million cancer diagnoses (20% of the total) and ~940,000 cancer deaths each year (14% of the total) (5). For genetic evaluation of these tumors, we focused on a set of protein coding genes, termed the consensus coding sequences (CCDS) that represent the most highly curated gene set currently available (6). The CCDS database contains full-length protein coding genes that have been defined by extensive manual curation and computational processing and have gene annotations that are identical among reference databases.

The goals of this study were three-fold: (i) to develop a methodological strategy for conducting genome-wide analyses of cancer genes in human tumors; (ii) to determine the spectrum and extent of somatic mutations in human tumors of similar and different histologic types; and (iii) to identify new cancer genes and molecular pathways that could lead to improvements in diagnosis or therapy.

Example 1

Cancer Mutation Discovery Screen

The initial step toward achieving these goals was the development of methods for high-throughput identification of somatic mutations in cancers. These methods included those for primer design, polymerase chain reaction (PCR), sequencing, and mutational analysis (FIG. 1). The first component involved extraction of all protein coding sequences from the CCDS genes. A total of 120,839 non-redundant exons and adjacent intronic sequences were obtained from 14,661 different transcripts in CCDS. These sequences were used to design primers for PCR amplification and sequencing of exons and adjacent splice sites. Primers were designed using a number of criteria to ensure robust amplification and sequencing of template regions (7). While most exons could be amplified in a single PCR reaction, we found that exons larger than 350 bp were more effectively amplified as multiple overlapping amplicons. One member of every pair of PCR primers was tailed with a universal primer sequence for subsequent sequencing reactions. A total of 135,483 primer pairs encompassing ~21 Mb of genomic sequence were designed in this manner (FIG. 8; Table S1).

Eleven cell lines or xenografts of each tumor type (breast and colorectal carcinomas) were used in the Discovery Screen (FIGS. 9-10; Tables S2A and S2B). Two matching normal samples were used as controls to help identify normal sequence variations and amplicon-specific sequencing artifacts such as those associated with GC-rich regions. A total of ~3 million PCR products were generated and directly sequenced, resulting in 465 Mb of tumor sequence.

Sequence data were assembled for each amplicon and evaluated for quality within the target region using software specifically designed for this purpose (7). The target region of each exon included all coding bases as well as the four intronic bases at both the 5' and 3' ends that serve as the major splice recognition sites. In order for an amplicon to be considered successfully analyzed, we required that ≥90% of bases in the target region have a Phred quality score (defined as $-10[\log_{10}(\text{raw per-base error})]$) of at least 20 in at least three quarters of the tumor samples analyzed (8). This quality cutoff was chosen to provide high sensitivity for mutation detection while minimizing false positives. Using these criteria, 93% of the 135,483 amplicons and 91% of the total targeted bases in CCDS were successfully analyzed for potential alterations.

Examination of sequence traces from these amplicons revealed a total of 816,986 putative nucleotide changes. As the vast majority of changes that did not affect the amino acid sequence (i.e., synonymous or silent substitutions) were likely to be non-functional, these changes were not analyzed further. The remaining 557,029 changes could represent germline variants, artifacts of PCR or sequencing, or bona fide somatic mutations. Several bioinformatic and experimental steps were employed to distinguish among these possibilities. First, any alterations that were also present in either of the two normal samples included in the Discovery Screen were removed, as these were likely to represent common germline polymorphisms or sequence artifacts. Second, as these two normal control samples would be expected to contain only a subset of known variants, any change corresponding to a validated germline polymorphism found in single nucleotide polymorphism (SNP) databases was also removed (7). Finally, the sequence trace of each potential alteration was visually inspected in order to remove false positive calls in the automated analysis. The combination of these data analysis efforts was efficient, removing ~96% of the potential alterations and leaving 29,281 for further scrutiny (FIG. 1).

To ensure that the observed mutations did not arise artifactually during the PCR or sequencing steps, the regions containing them were independently re-amplified and re-sequenced in the corresponding tumors. This step removed 9,295 alterations. The regions containing the putative mutations were then sequenced in matched normal DNA samples to determine whether the mutations were truly somatic: 18,414 changes were observed to be present in the germline of these patients, representing variants not currently annotated in SNP databases, and were excluded. As a final step, the remaining 1,572 putative somatic mutations were carefully examined in silico to ensure that the alterations did not arise from mistargeted sequencing of highly related regions occurring elsewhere in the genome (7). Alterations in such duplicated regions may appear to be somatic when there is loss of one or both alleles of the target region in the tumor and when the selected primers closely match and therefore amplify similar areas of the genome. A total of 265 changes in closely related regions were excluded in this fashion, resulting in a total of 1,307 confirmed somatic mutations in 1,149 genes (FIG. 5; Table 1).

Example 2

Validation Screen

To evaluate the prevalence and spectrum of somatic mutations in these 1,149 genes, we determined their sequence in additional tumors of the same histologic type (FIGS. 1, 9, 10; Tables S2A and S2B). Genes mutated in at least one breast or colorectal tumor in the Discovery Screen were analyzed in 24 additional breast or colorectal tumors, respectively. This effort involved 453,024 additional PCR and sequencing reactions, encompassing 77 Mb of tumor DNA. A total of 133,693 putative changes were identified in the Validation Screen. Methods similar to those employed in the Discovery Screen were used to exclude silent changes, known and novel germline variants, false positives arising from PCR or sequencing artifacts, and apparent changes that were likely due to co-amplification of highly related genes. Additionally, any changes corresponding to germline variants not found in SNP databases but identified in the Discovery Screen were excluded. The regions containing the remaining 4,948 changes were re-amplified and re-sequenced in the corresponding tumors (to ensure reproducibility) and in matched normal tissue to determine if they were somatic. An additional 365 somatic mutations in 236 genes were identified in this manner. In total, 921 and 751 somatic mutations were identified in breast and colorectal cancers, respectively (FIGS. 1, 5, and 12; Tables 1 and S4).

Example 3

Mutation Spectrum

The great majority of the 1,672 mutations observed in the Discovery or Validation Screens were single base substitutions: 81% of the mutations were missense, 7% were nonsense, and 4% altered splice sites (FIG. 5; Table 1). The remaining 8% were insertions, deletions, and duplications ranging from one to 110 nucleotides in length. Though the fraction of mutations that were single base substitutions was similar in breast and colorectal cancers, the spectrum and nucleotide contexts of the substitution mutations were very different between the two tumor types. The most striking of these differences occurred at C:G base pairs: 59% of the 696 colorectal cancer mutations were C:G to T:A transitions while only 7% were C:G to G:C transversions (FIGS. 6 and 11; Tables 2 and S3). In contrast, only 35% of the mutations in breast cancers were C:G to T:A transitions, while 29% were C:G to G:C transversions. In addition, a large fraction (44%) of the mutations in colorectal cancers were at 5'-CpG-3' dinucleotide sites but only 17% of the mutations in breast cancers occurred at such sites. This 5'-CpG-3' preference led to an excess of nonsynonymous mutations resulting in changes of arginine residues in colorectal cancers though not in breast cancers (fig. S1). In contrast, 31% of mutations in breast cancers occurred at 5'-TpC-3' sites (or complementary 5'-GpA-3' sites), while only 11% of mutations in colorectal cancers occurred at these dinucleotide sites. The differences noted above were all highly significant (P<0.0001) (7) and have substantial implications for the mechanisms underlying mutagenesis in the two tumor types.

Example 4

Distinction Between Passenger and Non-Passenger Mutations

Somatic mutations in human tumors can arise either through selection of functionally important alterations via their effect on net cell growth or through accumulation of non-functional "passenger" alterations that arise during repeated rounds of cell division in the tumor or in its progenitor stem cell. In light of the relatively low rates of mutation in human cancer cells (9, 10), distinction between selected and passenger mutations is generally not required when the number of genes and tumors analyzed is small. In large-scale studies, however, such distinctions are of paramount importance (11, 12). For example, it has been estimated that non-synonymous passenger mutations are present at a frequency no higher than ~1.2 per Mb of DNA in cancers of the breast or colon (13-15). As we assessed 542 Mb of tumor DNA, we would therefore have expected to observe ~650 passenger mutations. We actually observed 1,672 mutations (FIG. 5; Table 1), many more than what would have been predicted to occur by chance (P<1×10$^{-10}$) (7). Moreover, the frequency of mutations in the Validation Screen was significantly higher than in the Discovery Screen (5.8 versus 3.1 mutations per Mb, P<1×10$^{-10}$, FIG. 5; Table 1). The mutations in the Validation Screen were also enriched for nonsense, insertion, deletion, duplication, and splice site changes compared to the Discovery Screen; each of these would be expected to have a functional effect on the encoded proteins.

To distinguish genes likely to contribute to tumorigenesis from those in which passenger mutations occurred by chance, we first excluded genes that were not mutated in the Validation Screen. We next developed statistical methods to estimate the probability that the number of mutations in a given gene was greater than expected from the background mutation rate. For each gene, this analysis incorporated the number of somatic alterations observed in either the Discovery or Validation Screen, the number of tumors studied, and the number of nucleotides that were successfully analyzed (as indicated by the number of bases with Phred quality scores≥20). Because the mutation frequencies varied with nucleotide type and context and were different in breast versus colorectal cancers (FIG. 6; Table 2), these factors were included in the calculations. The output of this analysis was a cancer mutation prevalence (CaMP) score for each gene analyzed. The CaMP score reflects the probability that the number of mutations actually observed in a gene is higher than that expected to be observed by chance given the background mutation rate; its derivation is based on principles described in the Supporting Online Material. The use of the CaMP score for analysis of somatic mutations is analogous to the use of the LOD score for linkage analysis in familial genetic settings. For example, 90% of the genes with CaMP scores>1.0 are predicted to have mutation frequencies higher than the background mutation frequency.

Example 5

Candidate Cancer Genes

A complete list of the somatic mutations identified in this study is provided in FIG. 12; Table S4. Validated genes with CaMP scores greater than 1.0 were considered to be candidate cancer genes (CAN-genes). The combination of experimental validation and statistical calculation thereby yielded four nested sets of genes: of 13,023 genes evaluated, 1,149 were mutated, 242 were validated, and 191 were CAN-genes. Among these, the CAN-genes were most likely to have been subjected to mutational selection during tumorigenesis. There were 122 and 69 CAN-genes identified in breast and colorectal cancers, respectively (FIGS. 13 and 14; Tables S5 and S6). Individual breast cancers examined in the Discovery Screen harbored an average of 12 (range 4 to 23) mutant CAN-genes while the average number of CAN-genes in colorectal cancers was 9 (range 3 to 18) (FIG. 11; Table S3). Interestingly, each cancer specimen of a given tumor type carried its own distinct CAN-gene mutational signature, as no cancer had more than six mutant CAN-genes in common with any other cancer (FIGS. 12-14; Tables S4, S5, and S6).

CAN-genes could be divided into three classes: (a) genes previously observed to be mutationally altered in human cancers; (b) genes in which no previous mutations in human cancers had been discovered but had been linked to cancer through functional studies; and (c) genes with no previous strong connections to neoplasia.

(a) The re-identification of genes that had been previously shown to be somatically mutated in cancers represented a critical validation of the approach used in this study. All of the CCDS genes previously shown to be mutated in >10% of either breast or colorectal cancers were found to be CAN-genes in the current study. These included TP53 (2), APC (2), KRAS (2), SMAD4 (2), and FBXW7 (CDC4) (16) (FIGS. 12-14; Tables S4, S5 and S6). In addition, we identified mutations in genes whose mutation prevalence in sporadic cancers was rather low. These genes included EPHA3 (17), MRE11A (18), NF1 (2), SMAD2 (19, 20), SMAD3 (21), TCF7L2 (TCF4) (22), BRCA1 (2) and TGFBRH (23). We also detected mutations in genes that had been previously found to be altered in human tumors but not in the same tumor type identified in this study. These included guanine nucleotide binding protein, alpha stimulating GNAS (24), kelch-like ECH-associated protein KEAP1 (25), RET proto-oncogene (2), and transcription factor TCF1 (26). Finally, we found mutations in a number of genes that have been previously identified as targets of translocation or amplification in human cancers. These included nucleoporin NUP214 (2), kinesin receptor KTN1 (27), DEAD box polypeptide 10 DDX10 (28), glioma-associated oncogene homolog 1 GLI1 (29), and the translocation target gene of the runt related transcription factor 1 RUNX1T1 (MTG8) (2). We conclude that if these genes had not already been demonstrated to play a causative role in human tumors, they would have been discovered through the approach taken in this study. By analogy, the 176 other CAN-genes in FIGS. 13 and 14 (Tables S5 and S6) are likely to play important roles in breast, colorectal, and perhaps other types of cancers.

(b) Although genetic alterations currently provide the most reliable indicator of a gene's importance in human neoplasia (1, 30), there are many other genes which are thought to play key roles on the basis of functional or expression studies. Our study provides genetic evidence supporting the importance of several of these genes in neoplasia. For example, we discovered intragenic mutations in the ephrin receptor EPHB6 (31), mixed-lineage leukemia 3 gene (MLL3) (32), gelsolin GSN (33), cadherin genes CDH10 and CDH20, actin and SMAD binding protein filamin B FLNB (34), protein tyrosine phosphatase receptor PTPRD (35), and autocrine motility factor receptor AMFR (36).

(c) In addition to the genes noted above, our study revealed a large number of genes that had not been strongly suspected to be involved in cancer. These included polycystic kidney and hepatic disease_1 gene PKHDI, guanylate cyclase 1 GUCY1A2, transcription factor TBX22, exocyst complex component SEC8L1, tubulin tyrosine ligase TTLL3, ATP-dependent transporter ATP8B1, intrinsic factor-cobalamin receptor CUBN, actin binding protein DBN1, and tectorin alpha TECTA. In addition, seven CAN-genes corresponded to genes for which no biologic role has yet been established.

We examined the distribution of mutations within CAN-gene products to see if clustering occurred in specific regions or functional domains. In addition to the well documented hotspots in TP53 (37) and KRAS (38), we identified three mutations in GNAS in colorectal cancers that affected a single amino acid residue (R201). Alterations of this residue have previously been shown to lead to constitutive activation of the encoded G protein $\alpha_s$ through inhibition of GTPase activity (24). Two mutations in the EGF-like gene EGFL6 in breast tumors affected the same nucleotide position and resulted in a L508F change in the MAM adhesion domain. A total of seven genes had alterations located within five amino acid residues of each other, and an additional 12 genes had clustering of multiple mutations within a specific protein domain (13 to 78 amino acids apart). Thirty-one of 40 of these changes affected residues that were evolutionarily conserved. Although the effects of these alterations are unknown, their clustering suggests specific roles for the mutated regions in the neoplastic process.

Example 6

CAN-Gene Groups

Figure 2:
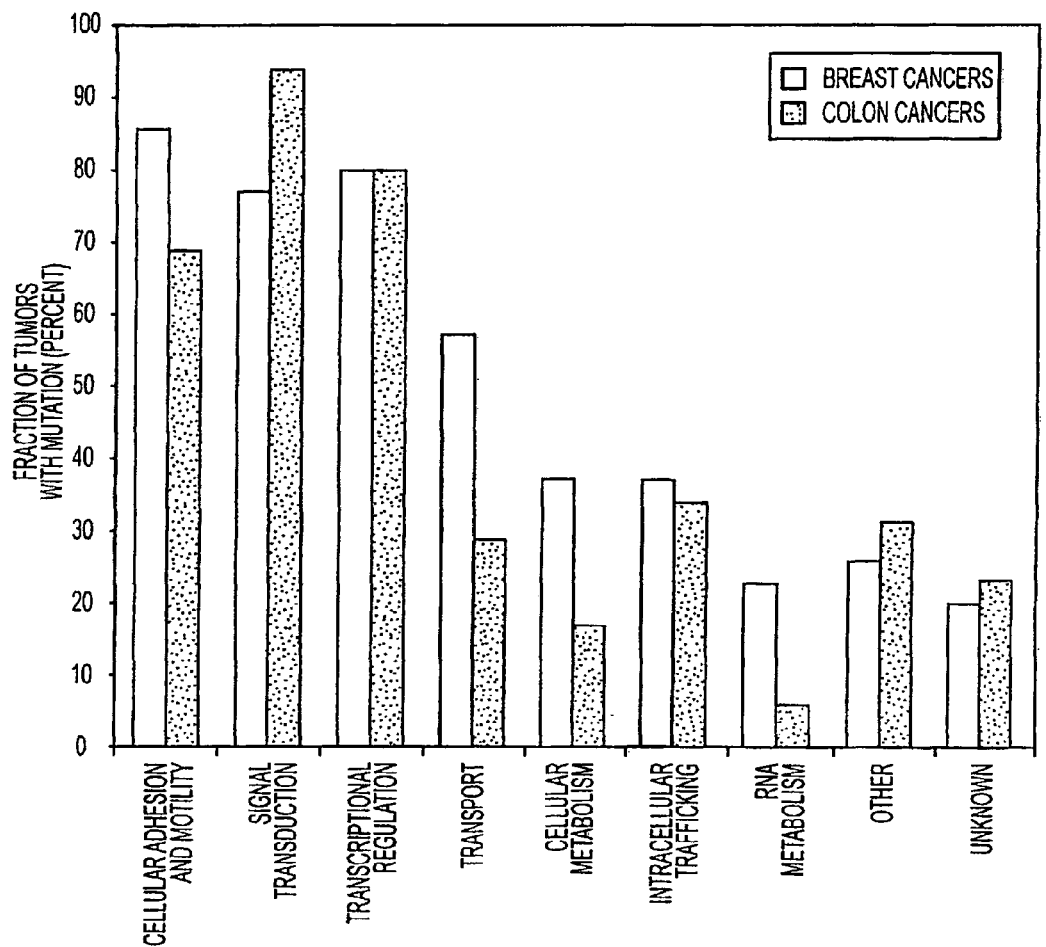
FIG. 2. Mutation frequency of CAN-gene groups. CAN-genes were grouped by function using Gene Ontology groups, INTERPRO domains, and available literature. Bars indicate the fraction of tumors (35 breast or 35 colorectal) with at least one mutated gene in the functional group.
Figure 3:
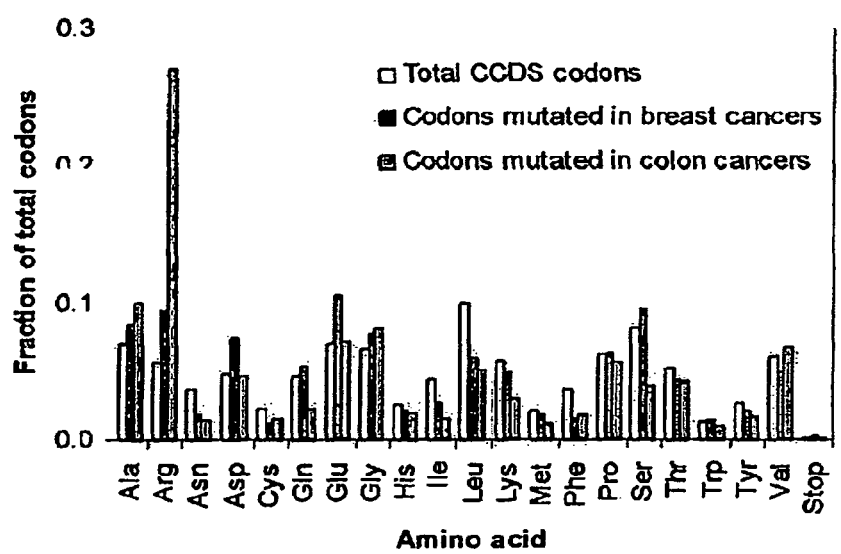
FIG. 3. (FIG. S1) Codon mutation frequencies. Open bars, CCDS codons (n=7,479,318 in 13,023 genes); red bars, codons affected by base substitution mutations in breast cancers (n=789); blue bars, codons affected by base substitution mutations in colorectal cancers (n=669).
Figure 4:
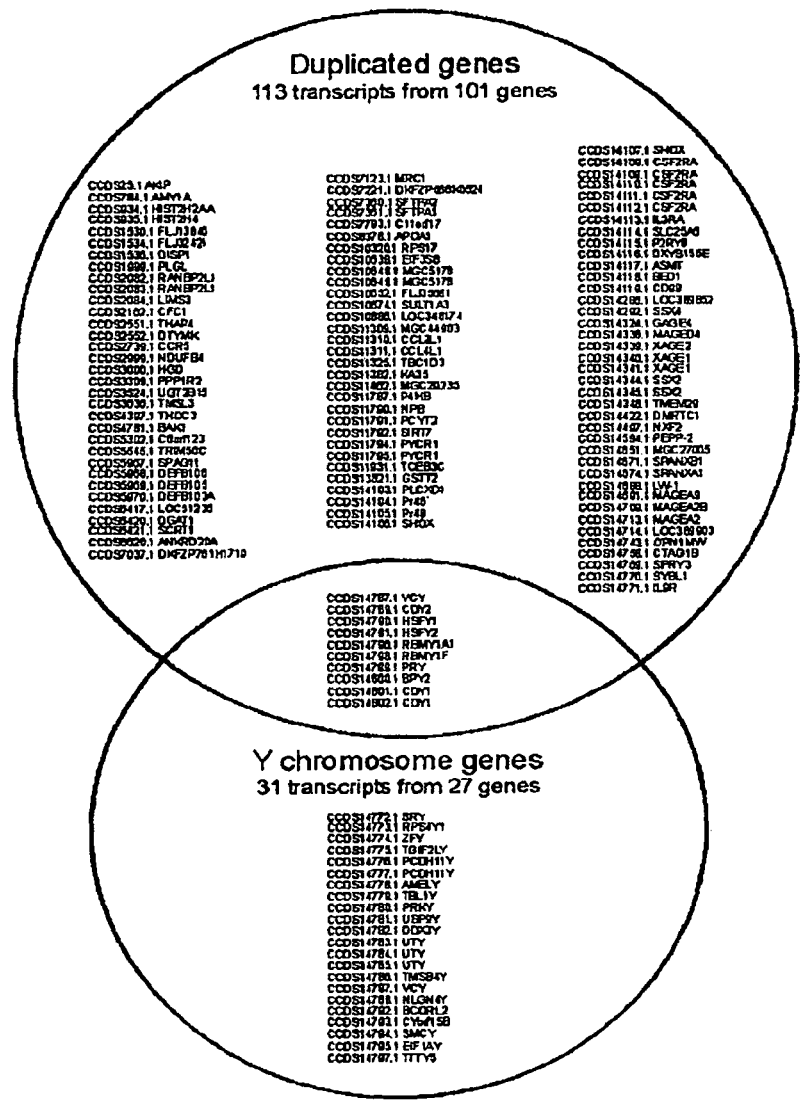
FIG. 4. (FIG. S2) CCDS genes excluded from analysis. One hundred thirty-four transcripts from 119 genes that closely matched more than one genomic locus (large circle), and/or were located won the Y chromosome (small circle), were excluded from analysis.

An unbiased screen of a large set of genes can provide insights into pathogenesis that would not be apparent through single gene mutational analysis. This has been exemplified by large scale mutagenesis screens in experimental organisms (39-41). We therefore attempted to assign each CAN-gene to a functional group based on Gene Ontology (GO) Molecular Function or Biochemical process groups, the presence of specific INTERPRO sequence domains, or previously published literature (FIG. 7; Table 3) and (FIG. 2). Several of the groups identified in this way were of special interest. For example, 22 of the 122 (18%) breast CAN-genes and 13 of the 69 (19%) colorectal CAN-genes were transcriptional regulators. At least one of these genes was mutated in more than 80% of the tumors of each type. Zinc-finger transcription factors were particularly highly represented (8 genes mutated collectively in 43% of breast cancer samples). Similarly, genes involved in cell adhesion represented ~22% of CAN-genes and affected more than two thirds of tumors of either type. Genes involved in signal transduction represented ~23% of CAN-genes and at least one such gene was mutated in 77% and 94% of the breast and colorectal cancer samples, respectively. Subsets of these groups were also of interest and included metalloproteinases (part of the cell adhesion and motility group and mutated in 37% of colorectal cancers), and G proteins and their regulators (part of the signal transduction group and altered in 43% of breast cancers). These data suggest that dysregulation of specific cellular processes are genetically selected during neoplasia and that distinct members of each group may serve similar roles in different tumors.

Example 7

Materials and Methods

Gene selection. The Consensus Coding DNA Sequence database (CCOS) represents a highly curated collection of 14,795 transcripts from 13,142 genes (www.ncbi.nlm.nih.gov/CCOSI). For inclusion in CCOS, genomic coordinates defining the transcript coding sequence must be identical in Ensembl and RefSeq databases. The transcripts must have canonical start and stop codons and consensus splice sites, not have in-frame stop codons, and be translatable from the reference genome sequence without frameshifts. Finally, CCOS transcripts must be supported by transcript and protein homology and inter-species conservation. We examined all CCOS transcripts and excluded those that were located at multiple locations in the genome through gene duplication (113 transcripts) or were present on the Y chromosome (21 additional transcripts) (fig. S1). The remaining 14,661 CCOS transcripts from 13,023 genes were selected for mutational analysis.

Bioinformatic resources. CCOS gene and transcript coordinates (release 1, Mar. 2, 2005), human genome sequences, and single nucleotide polymorphisms were obtained from the UCSC Santa Cruz Genome Bioinformatics Site (http://genome.ucsc.edu). Homology searches in the human and mouse genomes were performed using the BLAST-like alignment tool BLAT (S1) and In Silico PCR (http://genome.uc-sc.edu/cqi-bin/hqPcr). All genomic positions correspond to UCSC Santa Cruz hg17 build 35.1 human genome sequence. The ~3.4 M SNPs of dbSNP (release 125) that have been validated through the HapMap project (S2) were used for automated removal of known polymorphisms.

Primer design. For each transcript, genomic sequences comprising the entire coding region of each exon as well as flanking intronic sequences and 5' UTR and 3' UTR sequences were extracted. Primer pairs for PCR amplification and sequencing of each coding exon were generated using Primer3 (http://frodo.wi.mit.edu/cqi-bin/primer3/primer3 www.cqi) (S3). Forward and reverse PCR primers were required to be located no closer than 50 bp to the target exon boundaries, and genomic positions with known polymorphisms were avoided in the five 3'-most bases of the primers. Exons larger than 350 bp were analyzed as multiple overlapping amplicons. PCR products were designed to range in size from 300 to 600 bp, which was considered optimal for amplification, purification, and sequencing. To minimize amplification of homologous genomic sequences, primer pairs were filtered using UCSC In Silico PCR and only pairs yielding a single product were used. 0.33 Mb (~1.5%) of target genomic sequence was excluded from further analysis due to a lack of suitable amplification and sequencing primers. A total of 135,483 primer pairs encompassing ~21 Mb of target sequence were successfully designed. A universal sequencing primer (M13 forward, 5'-GTAAAACGACGGCCAGT-3'; SEQ ID NO: 1) was appended to the 5' end of the primer in the pair with the smallest number of mono- and dinucleotide repeats between itself and the target exon. Primer sequences are listed in FIG. 8; Table S1.

Tumor samples. DNA samples from ductal breast carcinoma cell lines and matched normal mammary tissue or peripheral blood lines were obtained from American Type Culture Collection (Manassas, Va.) or from A. Gazdar (S4, S5). Primary breast tumor and surrounding normal surgical tissue specimens isolated from node positive patients at Palmetto Health Richland or Baptist Hospitals were obtained through the South Carolina Cancer Center Tissue Bank. Each tissue sample was flash frozen within 30 minutes of excision, and stored at −80 °C. Surgically removed colorectal tumors were disaggregated and implanted into nude mice or into in vitro culture conditions as described previously (S6, 57). DNA was prepared within 3 passages after xenograft establishment. Characteristics of the tumor samples used in this study are listed in FIGS. 9-10; Tables S2A and S2B. No tumor used in this study was mismatch repair deficient as assessed with standard microsatellite markers (S8); such tumors were excluded because of their much higher background mutation rates. All samples were obtained in accordance with the Health Insurance Portability and Accountability Act (HIPAA).

Laser capture microdissection. 20 μm sections of snap frozen primary breast tumor tissues embedded in OCT were deposited on Sigma silane-prep™ slides and stained with hematoxylin and eosin. Tumor cells were separated from surrounding tissue and recovered on transfer film by laser-capture microdissection (PixCell® lie, Arcturus). Genomic DNA was purified from approximately 20 slides for each sample using the Qiagen™ QIAamp® DNA Micro kit according to the manufacturer's protocol.

Whole Genome Amplification. Whole genome amplification was used to provide sufficient quantities of DNA for the Validation Screen. Briefly, 5-20 ng template DNA was denatured with 5 M KOH, neutralized and incubated at 30° C. for 16-24 hours with 4×REPLI-g buffer and REPLI-g DNA polymerase according to the manufacturer's instructions (Qiagen, Valencia, Calif.). Samples were incubated at 65° C. for 3 min to inactivate the enzyme before storage at 20° C. For each sample, a minimum of 5 independent WGA reactions were pooled to reduce the effects of any allelic or locus bias that may have occurred during amplification.

Confirmation of sample identity. DNA sample identities were monitored throughout the Discovery and Validation Screens by PCR amplification and sequencing of exon 3 of the major histocompatibility complex gene HLA-A (forward primer 5'CGCCTTTACCCGGTTTCATT-3', SEQ ID NO: 2; reverse primer 5'-CCAATTGTCTCCCCTCCTTG-3', SEQ ID NO: 3). In addition, matching of all tumor-normal pairs was confirmed by typing nine STR loci (TPOX, chr 2p23-ter; D3S1358, chr3p; FGA, chr4q28; D8S1 179, chr8; TH01, chr11 p15.5; vWA, chr12p12-ter; Penta E, chr15q; D18S51, chr18q21.3; 021 S11, chr21 q11-21) using the PowerPlex 2.1 System (Promega, Madison, Wis.).

PCR amplification and sequencing. All primers were synthesized by Invitrogen (San Diego, Calif.). PCR was performed in 5 III reactions containing 1×PCR Buffer (67 mM TrisHCl, pH 8.8, 6.7 mM MgCb, 16.6 mM NH4SO4, 10 mM 2-mercaptoethanol), 1 mM dNTPs (Invitrogen, San Diego, Calif.), 1 11M forward and 1 11M reverse primers, 6% DMSO, 2 mM ATP, 0.25 U Platinum Taq (Invitrogen, San Diego, Calif.) and 3 ng DNA. Reactions were carried out in 384-well ABI9700 thermocyclers (Applied Biosystems, Foster City, Calif.) using a touchdown PCR protocol (1 cycle of 96° C. for 2 min; 3 cycles of 96° C. for 10 see, 64° C. for 10 see, 70° C. for 30 see; 3 cycles of 96° C. for 10 see, 61° C. for 10 see, 70° C. for 30 see; 3 cycles of 96° C. for 10 see, 58° C. for 10 see, 70° C. for 30 see; 41 cycles of 96° C. for 10 see, 57° C. for 10 see, 70° C. for 30 see; 1 cycle of 70° C. for 5 min). Templates were purified using AMPure (Agencourt Biosciences, Beverly, Mass.) and sequencing carried out with M13 forward primer (5'GTAAAACGACGGCCAGT-3; SEQ ID NO: 1) and Big Dye Terminator Kit v.3.1 (Applied Biosystems, Foster City, Calif.). 1% DMSO was included in sequencing reactions when the GC content of the template exceeded 65%. Dye terminators were removed using the CleanSEQ kit (Agencourt Biosciences, Beverly, Mass.) and sequence reactions were delineated on ABI PRISM 3730×1 sequencing apparatuses (Applied Biosystems, Foster City, Calif.).

Sequence assembly and analysis of mutations. Sequence traces from tumor and normal DNA samples were aligned to the genomic reference sequences. To consider an amplicon successfully sequenced, at least three quarters of the tumors were required to have 2':90% of the bases in the target region with a Phred quality score of 20 or better. Amplicons not meeting these criteria were not analyzed further. Mutational analysis was performed for all coding exonic sequences and the flanking 4 bp of intronic or UTR sequences using Mutation Surveyor (Softgenetics, State College, Pa.) coupled to a relational database (Microsoft SQL Server). For both Mutation Discovery and Validation Screens, the following basic steps were employed to identify mutations of interest. First, synonymous changes were identified and excluded from further analysis. Second, nonsynonymous changes in tumor samples were discarded if an identical change was present in a normal DNA sample. Third, known singlenucleotide polymorphisms were removed by comparison to a database of dbSNP entries previously validated by the Hap Map project. Finally, false positive artifacts were eliminated by visual inspection of chromatograms for each sample with a putative mutation. Additional steps are described below.

Mutation Discovery Screen. Primers designed above were used to amplify all known CCDS exons from 11 colorectal cancer samples, 11 breast cancer samples, and two matched normal DNA samples. This resulted in a total of ~3.25 million PCR reactions, comprising 465 Mb of tumor-derived sequences as well as a total of 42 Mb of normal sequences from the two matched normal DNA samples. Following sequence assembly and mutational analysis, each observed putative nonsynonymous change was confirmed in an independent PCR reaction using the same primer pair. Upon confirmation, DNA from a normal tissue of the same patient was used to determine whether the observed mutation was a true somatic event rather than a germ line variant. When the same putative mutation was observed in multiple tumor samples, only a single tumor and matched normal sample were initially used to confirm the mutation and its somatic mutation. If confirmed, DNA from the other tumors containing the same somatic mutation were similarly evaluated. To exclude the possibility that putative somatic mutations might be caused by amplification of homologous but non-identical sequences, BLAT (58) was used to search these sequences against the human genome. This examination ensured that the nucleotide change was not present in a highly related region in the human genome. For putative somatic mutations found in xenografted tumors, BLAT was used to similarly search the mouse genome to exclude the contribution of homologous mouse sequences.

Mutation Validation Screen. Every gene found mutated in the Discovery Screen was further analyzed by amplification and sequencing of 24 additional tumor samples of the same tissue type. Because of limiting amounts of sample DNA, the set of 24 tumors evaluated changed over time. All CCDS transcript variants of the gene of interest were investigated using primer pairs that yielded informative sequences in the Discovery Screen. Mutation detection, confirmation of alterations, and determination of somatic status was performed as above, with the exception that all germ line variants previously observed in the normal DNA samples of the Discovery Screen were considered to be known variants (FIG. 1).

Statistical Analyses

CaMP scores. To help identify genes that were mutated more frequently than would be expected in the absence of selection, we first computed the probability that a given gene was mutated the observed number of times given the background mutation frequency. The background mutation frequency in breast and colorectal cancers has been previously determined to be less than 1.2 mutations per Mb (59-511). Comparison of the prevalence of synonymous vs. non-synonymous mutations can be useful predictors of genes that had undergone selection, as it can be assumed that synonymous mutations are generally nonfunctional (511-515). However, relatively few mutations were detected in most genes in many of the tumors we studied, leading to wide confidence limits in this parameter. We therefore used a combination of experimental validation and an estimate of the background mutation rate to identify those genes most likely to have undergone selection.

To correct for the influence of nucleotide composition on the likelihood of mutation, we assumed that the mutation spectrum observed in the current study was no different from that of unselected background mutations and that both were a result of the same underlying processes and exposures to exogenous agents. The table below shows the background mutation frequency per Mb at each of the six nucleotide contexts and positions analyzed. For example, in our Discovery and Validation screens in colorectal cancers, we found that mutations at 5'-CpG-3' mutations were 6.44 more frequent than the mutation frequency at all positions combined. The expected background mutation frequency at 5'-CpG-3' sites was therefore calculated to be 6.44×1.2=7.73 mutations per million bp.

Estimated BackOround mutation frequencies per million bp.

|  | 5'-CpG-3' | 5'-TpC-3' | A | C | G | T | INS/DEL/DUP |
|---|---|---|---|---|---|---|---|
| Colorectal | 7.73 | 0.96 | 0.56 | 0.95 | 0.85 | 0.51 | 0.55 |
| Breast | 2.99 | 2.48 | 0.76 | 1.38 | 1.07 | 0.30 | 0.55 |

For each gene and tumor type, the number of successfully sequenced 5'-CpG-3' and 5'-TpC3' (or complementary 5'-GpA-3') dinucleotide sites and A, C, T, and G mononucleotide sites were designated NcpG, NTpC, NA, Nc, NG, and NT, respectively. $N_c$ did not include those C's within 5'-CpG or 5'-TpC dinucleotides and NG did not include those G's within 5'-CpG-3' or 5'GpA-3 dinucleotides. Note that mutations at 5'-TpC-3' sites were nearly always at the C residue and mutations at the complementary 5'-GpA-3' sites were nearly always at the G residue, explaining why the A's and T's did not need to be corrected for their presence within dinucleotides. The probability of a gene having the observed number of mutations at a particular site was then calculated with an exact binomial distribution. For example, the parameters for this calculation for the 5'-CpG-3' category used the observed number of mutations at 5'-CpG-3' sites as the number of positive events, NcpG as the number of independent trials, and the background mutation frequencies for NcpG listed in the table above (7.73×10−6 for colorectal cancers) as the probability of a positive result in each trial. The probabilities of a gene having the observed number of mutations at each of the other five dinucleotide or mononucleotides were similarly calculated. The probability of a gene containing the observed number of insertions, deletions, or duplications (INS/DEL/DUP) was calculated by using a binomial distribution with the following parameters: observed number of INS/DEL/DUP events as the number of positive events, total nucleotides successfully sequenced within the gene as the number of independent trials, and 0.55×10⁻⁶ as the probability of a positive result in each trial. Note that each of these seven probabilities was considered to be independent. The probability of a gene having the observed number of mutations at the observed positions was then calculated to be the product of the seven nucleotide context-specific probabilities.

As 13,023 genes were evaluated for mutations, it was necessary to correct these probabilities for multiple comparisons. For this purpose, we used the algorithm described by Benjamini and Hochberg (S16). The genes were ranked in ascending order, assigning a 1 to the gene with the lowest probability of having the observed number of mutations in it, a 2 to the gene with the next lowest probability, etc. The CaMP score for each gene was then defined as $-\log_{10}(13,023*\text{PROB}/\text{RANK})$, where PROB is the probability of its having the observed number of mutations and RANK represents its numerical position in the list. A Microsoft Excel™ spreadsheet that automatically calculates CaMP scores for individual or multiple genes is available from the authors upon request.

Statistical significance of data in FIGS. 5-6 (Tables 1 and 2) and FIG. 15 (fig. S1). To determine whether the observed number of mutations in the entire set of breast and colorectal cancers differed significantly from the expected number of mutations (FIG. 5; Table 1), a simple binomial distribution test was used, employing a probability of 1.2×10⁻⁶ as the background rate. The spectrum of mutations was compared in breast and colorectal cancers (FIG. 6; Table 2) using a Chi-Square test.

The spectrum of codons affected by mutation (FIG. 15; fig. S1) was also analyzed with a Chi-Square test.

Estimate of non-synonymous mutations in the cancer genome. The total number of genes containing non-synonymous mutations in a typical colorectal or breast cancer was estimated in the following way. Although the actual number of protein coding genes in the human genome is still a matter of debate, there are 5180 genes for which excellent supporting evidence exists and which are part of RefSeq (S17) but are not yet included in the CCOS database. We assumed that the mutation prevalence in genes that have not yet been sequenced is similar to that of the genes already sequenced. Additionally, we were not able to successfully sequence −10% of the bases within the coding sequences of the 13,023 CCOS genes (equivalent to 1,302 unsequenced genes). We thereby estimate that we have successfully sequenced 64% of the 18,203 protein-encoding genes in the human genome (13023-1302)/(13023+5180). As we identified an average of 60 mutated genes per tumor in the genes already sequenced, 93 genes (6010.64) would be predicted to be mutated in the entire compendium of protein encoding genes in a typical cancer.

References

The disclosure of each reference cited is expressly incorporated herein.

1. B. Vogelstein, K. W. Kinzler, Nature Med 10, 789 (2004).
2. P. A. Futreal et al., Nature Rev Cancer 4, 177 (2004).
3. A. Bardelli, V. E. Velculescu, Curr Opin Genet Dev 15, 5 (2005).
4. B. Vogelstein, K. W. Kinzler, The Genetic Basis of Human Cancer (McGraw-Hill, Toronto, 2002)
5. D. M. Parkin, F. Bray, J. Ferlay, P. Pisani, CA Cancer J Clin 55, 74 (2005).
6. world wide web domain: ncbi.nlm.nih.gov, database: CCDS.
7. Materials and methods are available as supporting material at Science Online.
8. B. Ewing, P. Green, Genome Res 8, 186 (1998).
9. C. Lengauer, K. W. Kinzler, B. Vogelstein, Nature 396, 643 (1998).
10. L. A. Loeb, Cancer Res 61, 3230 (2001).
11. C. Greenman, R. Wooster, P. A. Futreal, M. R. Stratton, D. F. Easton, Genetics 173, 2187 (2006).
12. S. E. Kern, J. M. Winter, Cancer Biol Ther 5, 349 (2006).
13. T. L. Wang et al., Proc Natl Acad Sci USA 99, 3076 (2002).
14. D. Shen et al., Submitted (2006).
15. P. Stephens et al., Nat Genet 37, 590 (2005).
16. H. Strohmaier et al., Nature 413, 316 (2001).
17. A. Bardelli et al., Science 300, 949 (2003).
18. Z. Wang et al., Cancer Res 64, 2998 (2004).
19. G. J. Riggins, et al. Nat Genet 13, 347 (1996).
20. K. Eppert et al., Cell 86, 543 (1996).
21. J. L. Ku et al., Cancer Lett (Jul 5, 2006).
22. A. Duval et al., Cancer Res 59, 4213 (1999).
23. S. Markowitz et al., Science 268, 1336 (1995).
24. C. A. Landis et al., Nature 340, 692 (1989).
25. B. Padmanabhan et al., Mol Cell 21, 689 (2006).
26. O. Bluteau et al., Nat Genet 32, 312 (2002).
27. K. Salassidis et al., Cancer Res 60, 2786 (2000).
28. Y. Arai et al., Blood 89, 3936 (1997).
29. K. W. Kinzler et al., Science 236, 70 (1987).
30. H. Varmus, Science 312, 1162 (2006).
31. X. X. Tang, G. M. Brodeur, B. G. Campling, N. Ikegaki, Clin Cancer Res 5, 455 (1999).
32. M. Ruault, M. E. Brun, M. Ventura, G. Roizes, A. De Sario, Gene 284, 73 (2002).
33. M. Tanaka et al., Cancer Res 55, 3228 (1995).
34. A. Sasaki, Y. Masuda, Y. Ohm, K. Ikeda, K. Watanabe, J Biol Chem 276, 17871 (2001).
35. M. Sato et al., Genes Chromosomes Cancer 44, 405 (2005).
36. Y. Onishi, K. Tsukada, J. Yokota, A. Raz, Clin Exp Metastasis 20, 51 (2003).
37. M. Hollstein, D. Sidransky, B. Vogelstein, C. C. Harris, Science 253, 49 (1991).
38. J. L. Bos et al., Nature 327, 293 (1987).
39. R. Brent, Cell 100, 169 (2000).
40. T. Ideker et al., Science 292, 929 (2001).
41. S. L. Ooi et al., Trends Genet 22, 56 (2006).
42. T. Soussi, G. Lozano, Biochem Biophys Res Commun 331, 834 (2005).
43. M. Olivier, S. P. Hussain, C. Caron de Fromentel, P. Hainaut, C. C. Harris, IARC Sci Publ, 247 (2004).
44. J. F. Costello et al., Nat Genet 24, 132 (2000).
45. A. H. Owens, Coffey, D. S., and Baylin, S. B., eds., Tumor Cell Heterogeneity. (Academic Press, New York, 1982), pp. pp. 441-460.
46. K. D. Pruitt, T. Tatusova, D. R. Maglott, Nucleic Acids Res 33, D501 (2005).
47. world wide web domain: cancergenome.nih.gov; document: index.asp
49. Y. H. Rogers, J. C. Venter. Nature 437, 326 (2005).

We claim:

1. A method of testing a human sample, comprising the steps of:
assaying a test colorectal sample or a suspected colorectal cancer metastasis relative to a normal sample of the human and determining a somatic K117 mutation in KRAS gene or its encoded cDNA or protein.

2. The method of claim wherein the normal sample is a colorectal tissue sample.

3. The method of claim 1 wherein the mutation is assayed and determined in the gene.

4. The method of claim 1 wherein the mutation is assayed and determined in the cDNA.

5. The method of claim 1 wherein the mutation is assayed and determined in the protein.

6. The method of claim 1 wherein the step of testing comprises sequencing all or part of the gene.

7. The method of claim 1 wherein the step of testing employs a mutation specific probe.

8. The method of claim 1 wherein the step of testing employs a mutation specific primer.

9. The method of claim 1 wherein the step of testing employs a mutation specific antibody.

10. The method of claim 1 wherein the step of testing employs an amplification reaction.

11. The method of claim 1 wherein the step of testing employs an antibody-antigen reaction.

12. The method of claim 1 wherein the step of testing employs a hybridization reaction.

13. The method of claim 1 wherein the step of testing employs a primer extension reaction.

14. A method of characterizing a colorectal cancer in a human, comprising the steps of:
assaying and determining in a test colorectal cancer sample or a suspected colorectal cancer metastasis relative to a normal sample of the human, a somatic K117 mutation in KRAS gene or its encoded cDNA or protein.

15. The method of claim 14 wherein the normal sample is a colorectal tissue sample.

16. The method of claim 14 wherein the mutation is assayed and determined in the gene.

17. The method of claim 14 wherein the mutation is assayed and determined in the cDNA.

18. The method of claim 14 wherein the mutation is assayed and determined in the protein.

19. The method of claim 14 wherein the step of testing comprises sequencing all or part of the gene.

20. The method of claim 14 wherein the step of testing employs a mutation specific probe.

21. The method of claim 14 wherein the step of testing employs a mutation specific primer.

22. The method of claim 14 wherein the step of testing employs a mutation specify antibody.

23. The method of claim 14 wherein the step of testing employs an amplification reaction.

24. The method of claim 14 wherein the step of testing employs an antibody-antigen reaction.

25. The method of claim 14 wherein the step of testing employs a hybridization reaction.

26. The method of claim 14 wherein the step of testing employs a primer extension reaction.

* * * * *